United States Patent
Takaishi et al.

(10) Patent No.: US 9,458,176 B2
(45) Date of Patent: Oct. 4, 2016

(54) TETRAHYDROIMIDAZO(1,5-D)[1,4] OXAZEPINE DERIVATIVE

(71) Applicant: Eisai R&D Management Co., Ltd., Tokyo (JP)

(72) Inventors: Mamoru Takaishi, Tsukuba (JP); Nobuhiro Sato, Tsukuba (JP); Tomoyuki Shibuguchi, Tsukuba (JP); Takafumi Motoki, Tsukuba (JP); Yoshinori Takahashi, Tsukuba (JP); Takeo Sasaki, Tsukuba (JP); Alan Braunton, Hatfield (GB)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 14/190,356

(22) Filed: Feb. 26, 2014

(65) Prior Publication Data

US 2014/0243316 A1 Aug. 28, 2014

Related U.S. Application Data

(60) Provisional application No. 61/770,469, filed on Feb. 28, 2013.

(51) Int. Cl.
*A61K 31/553* (2006.01)
*C07D 498/04* (2006.01)

(52) U.S. Cl.
CPC .................................. *C07D 498/04* (2013.01)

(58) Field of Classification Search
CPC ........................... A61K 31/553; C07D 498/04
USPC ......................................... 514/211.1; 540/552
See application file for complete search history.

(56) References Cited

U.S. PATENT DOCUMENTS

| | | | |
|---|---|---|---|
| 2012/0015930 A1 | 1/2012 | O'Connor et al. | |
| 2012/0159320 A1 | 6/2012 | Audet | |

FOREIGN PATENT DOCUMENTS

| | | |
|---|---|---|
| CN | 101273040 | 9/2008 |
| CN | 102232074 | 11/2011 |
| JP | 2008-534455 | 8/2008 |
| JP | 2009-510011 | 3/2009 |
| JP | 2012-510437 | 5/2012 |
| JP | 2012-513399 | 6/2012 |
| WO | WO 02/083665 | 10/2002 |
| WO | WO 2006/099972 | 9/2006 |
| WO | WO 2010/068520 | 6/2010 |
| WO | WO 2010/075203 | 7/2010 |

OTHER PUBLICATIONS

Doody, "Current treatments for Alzheimer's disease: cholinesterase inhibitors," J Clin Psychiatry, 2003, 64(suppl 9):11-17.

Eisai R&D Management Co., Ltd., "Experimental data," Aug. 21, 2014, 1 page.

Kavanagh et al., "Long-term response to galantamine in relation to short-term efficacy data: pooled analysis in patients with mild to moderate Alzheimer's disease," Current Alzheimer Res., 2011, 8:175-186.

Rogers et al., "Long-term efficacy and safety of donepezil in the treatment of Alzheimer's disease: final analysis of a US multicentre open-label study," European Neuropsychopharmacology, 2000, 10:195-203.

Vellas et al., "Endpoints for trials in Alzheimer's disease: a European task force consensus," Lancet Neurology, May 2008, 7:436-450.

International Search Report and Written Opinion in International Application No. PCT/JP2014/054724, dated Mar. 25, 2014, 8 pages.

Bespalov et al., "Habituation deficits induced by metabotropic glutamate receptors 2/3 receptor blockage in mice: Reversal by antipsychotic drugs," J Pharmacology and Experimental Therapeutics, 2007, 320(2):944-950.

Brookmeyer et al., "Forecasting the global burden of Alzheimer's disease," Johns Hopkins University, Dept. of Biostatistics Working Papers, 2007, 26 pages.

Campo et al., "Characterization of an mGluR2/3 Negative Allosteric Modulator in rodent models of depression," J Neurogenetics, 2001, 25(4):152-166.

Chaki et al., "mGlu2/3 and mGlu5 receptors: Potential targets for novel antidepressants," Neuropharmacol., 2013, 66:40-52.

Cheng and Pai, "Dissociation between recognition of familiar scenes and of faces in patients with very mild Alzheimer disease: An event-related potential study," Clinical Neurophysiology, 2010, 121:1519-1525.

Chin et al., "Awake rat pharmacological magnetic resonance imaging as a translational pharmacodynamics biomarker: metabotropic glutamate 2/3 agonist mokulation of ketamine-induced blood oxygenation level dependence signals," J of Pharmacology and Experimental Therapeutics, 2011, 336(3):709-715.

(Continued)

*Primary Examiner* — Brenda Coleman
(74) *Attorney, Agent, or Firm* — Fish & Richardson P.C.

(57) ABSTRACT

A compound represented by the following formula (I) or a pharmaceutically acceptable salt thereof works as an mGluR2 antagonist, and is applicable as a therapeutic agent for neurological disorders related to glutamate dysfunction and diseases involving the mGluR2, such as Alzheimer's disease:

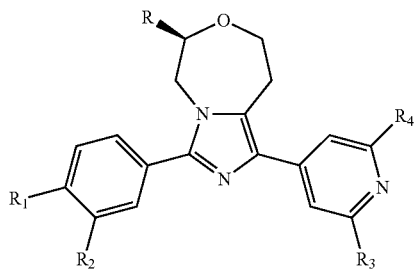

wherein R is a hydrogen atom, a $C_{1-6}$ alkyl group or the like, $R_1$ is a $C_{1-6}$ alkyl group, a $C_{1-6}$ alkoxy group or the like, $R_2$ is a halogen atom, a $C_{1-6}$ alkyl group, a $C_{1-6}$ alkoxy group or the like, $R_3$ is a hydrogen atom, a $C_{1-6}$ alkyl group or the like, and $R_4$ is a $C_{1-6}$ alkyl group or the like.

28 Claims, No Drawings

(56) References Cited

OTHER PUBLICATIONS

Conn et al., "Allosteric modulators of GPCRs: a novel approach for the treatment of CNS disorders," Nat Rev Drug Disc., 2009, 8:41-54.
Feinberg et al., "The metabotropic glutamate (mGLU)2/3 receptor antagonist LY341495 stimulates waking and fast electroencephalogram power and blocks the effects of mGLU2/3 receptor agonist LY379268 in rats," J Pharmacology and Experimental Therapeutics, 2005, 826:833.
Gomez-Isla et al., "Profound Loss of Layer II Entorhinal Cortex Neurons Occurs in Very Mild Alzheimer's Disease," J Neurosci., 1996, 16(14):4491-4500.
Higgins, "Pharmacological manipulation of mGlu2 receptors influences cognitive performance in the rodent," Neuropharmacol., 2004, 46(7):907-917.
Hyman et al., "A direct demonstration of the perforant pathway terminal zone in Alzheimer's disease using the monoclonal antibody Alz-50," Brain Res., 1988, 450:392-397.
Hyman et al., "Alzheimer's disease: Glutamate Depletion in the Hippocampal Perforant Pathway Zone," Ann Neurol., 1987, 22:37-40.
Hyman et al., "Perforant Pathway Changes and the Memory Impairment of Alzheimer's Disease," Ann Neurol., 1986, 20:472-481.
Iijima et al., "Effects of metabotropic glutamate 2/3 receptor antagonists in the stress-induced hyperthermia test in singly housed mice," Psychopharmacol., 2007, 190:233-239.
Kadono et al., "Quantitative prediction of intestinal metabolism in humans from a simplified intestinal availability model and empirical scaling factor," Drug Metab Dispos., 2010, 38:1230-1237.
Kew, "Positive and negative allosteric modulation of metabotropic glutamate receptors: emerging therapeutic potential," Pharmacol. Therapeutics, 2004, 104(3):233-244.
Kodama et al., "Release of neurotransmitters in the monkey frontal cortex is related to level attention," Psychiatry and Clinical Neuroscience, 2002, 56:341-342.
Kunishima et al., "Structural basis of glutamate recognition by a dimeric metabotropic glutamate receptor," Nature, 2000, 407:971-977.
Masliah et al., "Synaptic and neuritic alterations during the progression of Alzheimer's disease," Neurosci Lett., 1994, 174:67-72.
Nakanishi, "Molecular diversity of glutamate receptors and implications for brain function," Sci., 1992, 258:597-603.
Richards et al., "Distribution and abundance of metabotropic glutamate receptor subtype 2 in rat brain revealed by [3H]LY354740 binding in vitro and quantitative radioautography: Correlation with the sites of synthesis, expression, and agonist stimulation of [35S]GTPγs binding," J Comparative Neurol., 2005, 487:15-27.
Schoepp and Conn, "Metabotropic glutamate receptors in brain function and pathology," Trends Pharmacol. Sci., 1993, 14(1):13-20.
Shimazaki et al., "Anxiolytic-like activity of MGS0039, a potent group II metabotropic glutamate receptor antagonist, in a marble-burying behavior test," Eur J Pharmacol., 2004, 504:121-125.
Swanson et al., "Metabotropic glutamate receptors as novel targets for anxiety and stress disorders," Nat Rev Drug Disc., 2005, 4:131-146.
Takagi et al., "A provisional biopharmaceutical classification of the top 200 oral drug products in the United States, Great Britain, Spain, and Japan," Mol Pharmaceutics, 2006, 3:631-643.
Wakabayashi et al., "Synapse alterations in the hippocampal-entorhinal formation in Alzheimer's disease with and without Lewy body disease," Brain Res., 1994, 667:24-32.
Woltering et al., "Synthesis and characterization of 1,3-dihydro-benzo[b][1,4]diazepin-2-one derivatives: Part 3: New potent non-competitive metabotropic glutamate receptor 2/3 antagonists," Bioorg Med Chem Lett., 2008, 18:2725-2729.
Wright et al., "CNS distribution of metabotropic glutamate 2 and 3 receptors: Transgenic mice and [3H]LY459477 autoradiography," Neuropharmacol., 2013, 66:89-98.
Yasuhara et al., "Prodrugs of 3-(3,4-dichlorobenzyloxy)-2-amino-6-fluorobicyclo[3.1.0]hexane-2,6-dicarboxylic acid (MGS00339):a potent and orally active group II mGluR antagonist with antidepressant-like potential," Bioorg Med Chem Left., 2007, 14:4193-4207.
Yoshimizu et al., "An mGluR2/3 antagonist, MGS0039, exerts antidepressant and anxiolytic effects in behavioral models in rats," Psychopharmacol., 2006, 186:587-593.
Notice of Allowance in U.S. Appl. No. 13/126,201, dated May 6, 2014, 8 pages.
International Preliminary Report on Patentability in International Application No. PCT/JP2014/054724, dated Sep. 11, 2015, 6 pages.
Office Action in VN App. Ser. No. 1-2015-02612, dated Oct. 26, 2015, 2 pages (with English translation).
Major R&D Pipeline: In-House R&D Pipeline List (Oct. 30, 2015), 1 page.
Chemical Name and Chemical Structure of E2307 (Sep. 16, 2014), 2 pages (with English translation).
Amendment Filed in European Application No. 14756740.8, dated Apr. 5, 2016, 16 pages.
Amendment Filed in PH Application No. 1-2015-501878, dated Jan. 4, 2016, 9 pages.
Israeli Office Action in Application No. 240402, dated Jan. 19, 2016, 5 pages, including English translation.
Pakistani Office Action in Application No. 122/2014, dated Jan. 28, 2016, 2 pages.
Chinese Office Action in Application No. 201480009750.3, dated Apr. 6, 2016, 12 pages, with English translation.
European Search Report in Application No. 14756740.8, dated Jun. 16, 2016, 7 pages.
Israeli Submission Documents in Application No. 240402, dated May 18, 2016, 10 pages, with English translation.
South African Submission Documents in Application No. 2015/06027, dated Jul. 1, 2016, 21 pages.

TETRAHYDROIMIDAZO(1,5-D)[1,4]OXAZEPINE DERIVATIVE

CROSS-REFERENCE TO RELATED APPLICATION

This application claims the benefit of U.S. provisional application No. 61/770,469 filed on Feb. 28, 2013, the disclosure of which is herein incorporated by reference in its entirety.

BACKGROUND OF THE INVENTION

1. Field of the Invention

The present invention relates to a tetrahydroimidazo[1,5-d][1,4]oxazepine derivative having an antagonistic action against group II metabotropic glutamate receptor or a pharmaceutically acceptable acid addition salt thereof. The present invention also relates to a pharmaceutical composition comprising the compound as an active ingredient.

2. Related Background Art

Glutamic acid is known as one of principal excitatory neurotransmitters working for adjusting advanced functions of memory, learning and the like in a central nervous system of a mammal. Glutamate receptors are roughly classified into two types, that is, ionotropic glutamate receptors (iGlu receptors) and metabotropic glutamate receptors (mGlu receptors) coupled with G protein (see Non Patent Document 1).

The iGlu receptors are classified, on the basis of types of their agonists, into three types, that is, N-methyl-D-aspartate (NMDA) receptors, α-amino-3-hydroxy-5-methyl-4-isoxazolepropionic acid (AMPA) receptors and kainate receptors. On the other hand, the mGlu receptors have 8 subtypes (mGluR1 to 8) and are classified, on the basis of a signaling system to be conjugated and pharmacological characteristics, into group I (mGluR1, mGluR5), group II (mGluR2, mGluR3) and group III (mGluR4, mGluR6, mGluR7 and mGluR8). The group II and group III mGluRs are expressed as an autoreceptor or a heteroreceptor mainly at the nerve terminal, so as to suppress adenylate cyclase via Gi protein and regulate a specific $K^+$ or $Ca^{2+}$ channel activity (see Non Patent Document 2).

Antagonists against group II mGluRs, among these glutamate receptors, show an action to improve the cognitive function in animal models and also show an antidepressant action and an antianxiety action, and therefore, it is suggested that group II mGluR antagonists are effective as a novel cognitive function enhancer or antidepressant (see Non Patent Documents 3, 4 and 5).

CITATION LIST

[Non-Patent Literature 1] Science, 258, 597-603, 1992
[Non-Patent Literature 2] Trends Pharmacol. Sci., 14, 13 (1993)
[Non-Patent Literature 3] Neuropharmacol., 46 (7), 907-917 (2004)
[Non-Patent Literature 4] Pharmacol. Therapeutics, 104(3), 233-244 (2004)
[Non-Patent Literature 5] Neuropharmacol., 66, 40-52 (2013)

SUMMARY OF THE INVENTION

An object of the present invention is to provide a tetrahydroimidazo[1,5-d][1,4]oxazepine derivative or a pharmaceutically acceptable salt thereof having an antagonistic action against group II metabotropic glutamate receptors, and a pharmaceutical composition comprising the same.

The present invention relate to [1] to [22] below:
[1] A compound represented by the following formula (I) or a pharmaceutically acceptable acid addition salt thereof:

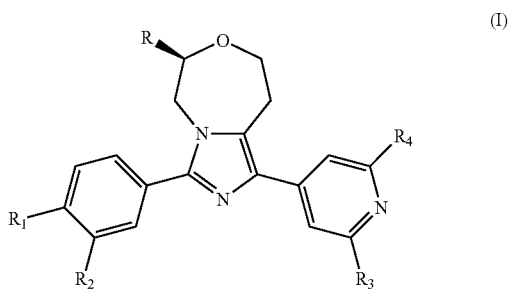

wherein R is a hydrogen atom or a $C_{1-6}$ alkyl group optionally substituted with 1 to 3 fluorine atoms, wherein
when R is a hydrogen atom,
$R_1$ is a chlorine atom, a bromine atom, a trifluoromethyl group, an ethyl group, a trifluoromethoxy group, a methoxy group substituted with a phenyl group, a methoxy group substituted with a $C_{3-8}$ cycloalkyl group, an ethoxy group optionally substituted with 1 to 3 fluorine atoms, or $C_{3-8}$ cycloalkyloxy group,
$R_2$ is a fluorine atom, a chlorine atom, a methyl group optionally substituted with 2 to 3 fluorine atoms, a methoxy group optionally substituted with 1 to 3 fluorine atoms, or an ethoxy group optionally substituted with 1 to 3 fluorine atoms,
$R_3$ is a hydrogen atom or a methyl group, and
$R_4$ is a fluorine atom or a methyl group optionally substituted with 1 to 3 fluorine atoms, or
when R is a $C_{1-6}$ alkyl group optionally substituted with 1 to 3 fluorine atoms,
$R_1$ is a hydrogen atom, a halogen atom, a $C_{1-6}$ alkyl group optionally substituted with 1 to 3 fluorine atoms, a $C_{1-6}$ alkoxy group optionally substituted with 1 to 3 substituents selected from a fluorine atom and a $C_{3-8}$ cycloalkyl group, a $C_{3-8}$ cycloalkyloxy group, or a 4- to 6-membered heterocycloalkyloxy group,
$R_2$ is a hydrogen atom, a cyano group, a halogen atom, a $C_{1-6}$ alkyl group optionally substituted with 1 to 3 substituents selected from a fluorine atom and a hydroxyl group, or a $C_{1-6}$ alkoxy group optionally substituted with 1 to 3 substituents selected from a fluorine atom, a $C_{3-8}$ cycloalkyl group and a 4- to 6-membered heterocycloalkyl group,
$R_3$ is a hydrogen atom or a $C_{1-6}$ alkyl group, and
$R_4$ is a $C_{1-6}$ alkyl group optionally substituted with 1 to 3 substituents selected from a fluorine atom and a hydroxyl group, or a $C_{1-6}$ alkoxy group.
[2] The compound or a pharmaceutically acceptable acid addition salt thereof according to [1], wherein
R is a $C_{1-6}$ alkyl group optionally substituted with 1 to 3 fluorine atoms,
$R_1$ is a hydrogen atom, a halogen atom, a $C_{1-6}$ alkyl group optionally substituted with 1 to 3 fluorine atoms, a $C_{1-6}$ alkoxy group optionally substituted with 1 to 3 substituents selected from a fluorine atom and a $C_{3-8}$ cycloalkyl group, a $C_{3-8}$ cycloalkyloxy group, or a 4- to 6-membered heterocycloalkyloxy group, R$_2$ is a hydrogen atom, a cyano group, a halogen atom, a C$_{1-6}$ alkyl group optionally substituted with 1 to 3 substituents selected from a fluorine atom and a hydroxyl group, or a C$_{1-6}$ alkoxy group optionally substituted with 1 to 3 substituents selected from a fluorine atom, a C$_{3-8}$ cycloalkyl group and a 4- to 6-membered heterocycloalkyl group, R$_3$ is a hydrogen atom or a C$_{1-6}$ alkyl group, and R$_4$ is a C$_{1-6}$ alkyl group optionally substituted with 1 to 3 substituents selected from a fluorine atom and a hydroxyl group, or a C$_{1-6}$ alkoxy group.

[3] The compound or a pharmaceutically acceptable acid addition salt thereof according to [2], wherein R is a methyl group, an ethyl group, a fluoromethyl group or a difluoromethyl group.

[4] The compound or a pharmaceutically acceptable acid addition salt thereof according to [3], wherein R$_1$ is a hydrogen atom, a fluorine atom, a chlorine atom, a methyl group, a fluoromethyl group, a difluoromethyl group, a trifluoromethyl group, an ethyl group, a 1,1-difluoroethyl group, a methoxy group, a fluoromethoxy group, a difluoromethoxy group, a trifluoromethoxy group, an ethoxy group, a 2-fluoroethoxy group, a 2-propyloxy group, a cyclopropylmethoxy group, a cyclopropyloxy group or an (oxetan-3-yl)oxy group.

[5] The compound or a pharmaceutically acceptable acid addition salt thereof according to [4], wherein R$_2$ is a hydrogen atom, a cyano group, a fluorine atom, a chlorine atom, a methyl group, a fluoromethyl group, a difluoromethyl group, a trifluoromethyl group, a hydroxymethyl group, an ethyl group, a methoxy group, a fluoromethoxy group, a difluoromethoxy group, a trifluoromethoxy group, an ethoxy group, a 2-fluoroethoxy group, a 2-propyloxy group, a cyclopropylmethoxy group, a cyclobutylmethoxy group or a (tetrahydro-2H-pyran-4-yl) methoxy group.

[6] The compound or a pharmaceutically acceptable acid addition salt thereof according to [5], wherein R$_3$ is a hydrogen atom or a methyl group.

[7] The compound or a pharmaceutically acceptable acid addition salt thereof according to [6], wherein R$_4$ is a methyl group, a fluoromethyl group, a difluoromethyl group, a hydroxymethyl group or a methoxy group.

[8] The compound or a pharmaceutically acceptable acid addition salt thereof according to [2], wherein R is a methyl group optionally substituted with 1 to 2 fluorine atoms, R$_1$ is a hydrogen atom, a chlorine atom, a methyl group optionally substituted with 1 to 3 fluorine atoms, an ethyl group, a C$_{1-6}$ alkoxy group optionally substituted with 1 to 3 fluorine atoms, or a C$_{3-6}$ cycloalkyloxy group, R$_2$ is a cyano group, a chlorine atom, a C$_{1-6}$ alkyl group optionally substituted with 1 to 3 fluorine atoms, or a C$_{1-6}$ alkoxy group optionally substituted with 1 to 3 fluorine atoms, R$_3$ is a hydrogen atom or a methyl group, and R$_4$ is a methyl group optionally substituted with 1 to 3 fluorine atoms.

[9] The compound or a pharmaceutically acceptable acid addition salt thereof according to [2], wherein R is a methyl group optionally substituted with 1 to 2 fluorine atoms, R$_1$ is a hydrogen atom, a halogen atom, a C$_{1-6}$ alkyl group optionally substituted with 1 to 3 fluorine atoms, a C$_{1-6}$ alkoxy group optionally substituted with 1 to 3 fluorine atoms, or a C$_{3-6}$ cycloalkyloxy group, R$_2$ is a cyano group, a halogen atom, a C$_{1-6}$ alkyl group optionally substituted with 1 to 3 fluorine atoms, or a C$_{1-6}$ alkoxy group optionally substituted with 1 to 3 fluorine atoms, R$_3$ is a methyl group, and R$_4$ is a methyl group optionally substituted with 1 to 3 fluorine atoms, with a proviso that when R$_1$ is an unsubstituted methoxy group, R$_2$ is not a fluorine atom.

[10] The compound or a pharmaceutically acceptable acid addition salt thereof according to [1], which is a compound selected from the following compounds or a pharmaceutically acceptable acid addition salt thereof:

(R)-3-(4-chloro-3-methoxyphenyl)-1-(2,6-dimethylpyridin-4-yl)-6-methyl-5,6,8,9-tetrahydroimidazo[1,5-d][1,4]oxazepine, (R)-1-(2,6-dimethylpyridin-4-yl)-3-(3-methoxy-4-(trifluoromethyl)phenyl)-6-methyl-5,6,8,9-tetrahydroimidazo[1,5-d][1,4]oxazepine, (R)-6-methyl-3-(3-methyl-4-(trifluoromethoxy)phenyl)-1-(2-methylpyridin-4-yl)-5,6,8,9-tetrahydroimidazo[1,5-d][1,4]oxazepine, (R)-3-(4-(difluoromethoxy)-3-methylphenyl)-1-(2,6-dimethylpyridin-4-yl)-6-methyl-5,6,8,9-tetrahydroimidazo[1,5-d][1,4]oxazepine, (R)-3-(4-(difluoromethoxy)-3-methylphenyl)-6-methyl-1-(2-methylpyridin-4-yl)-5,6,8,9-tetrahydroimidazo[1,5-d][1,4]oxazepine, (S)-1-(2,6-dimethylpyridin-4-yl)-6-(fluoromethyl)-3-(3-methoxy-4-(trifluoromethoxy)phenyl)-5,6,8,9-tetrahydroimidazo[1,5-d][1,4]oxazepine, (S)-6-(fluoromethyl)-3-(3-methoxy-4-(trifluoromethoxy)phenyl)-1-(2-methylpyridin-4-yl)-5,6,8,9-tetrahydroimidazo[1,5-d][1,4]oxazepine, (R)-3-(3-chloro-4-cyclopropoxyphenyl)-1-(2,6-dimethylpyridin-4-yl)-6-methyl-5,6,8,9-tetrahydroimidazo[1,5-d][1,4]oxazepine, (R)-3-(4-cyclopropoxy-3-methylphenyl)-1-(2,6-dimethylpyridin-4-yl)-6-methyl-5,6,8,9-tetrahydroimidazo[1,5-d][1,4]oxazepine, (R)-3-(3-chloro-4-(difluoromethoxy)phenyl)-6-methyl-1-(2-methylpyridin-4-yl)-5,6,8,9-tetrahydroimidazo[1,5-d][1,4]oxazepine, (S)-3-(4-cyclopropoxy-3-methylphenyl)-1-(2,6-dimethylpyridin-4-yl)-6-(fluoromethyl)-5,6,8,9-tetrahydroimidazo[1,5-d][1,4]oxazepine, (R)-3-(3-methoxy-4-(trifluoromethoxy)phenyl)-6-methyl-1-(2-methylpyridin-4-yl)-5,6,8,9-tetrahydroimidazo[1,5-d][1,4]oxazepine, (R)-1-(2,6-dimethylpyridin-4-yl)-3-(3-methoxy-4-(trifluoromethoxy)phenyl)-6-methyl-5,6,8,9-tetrahydroimidazo[1,5-d][1,4]oxazepine, (S)-3-(4-(difluoromethoxy)-3-methylphenyl)-1-(2,6-dimethylpyridin-4-yl)-6-(fluoromethyl)-5,6,8,9-tetrahydroimidazo[1,5-d][1,4]oxazepine, (S)-1-(2,6-dimethylpyridin-4-yl)-6-(fluoromethyl)-3-(3-methoxy-4-(trifluoromethyl)phenyl)-5,6,8,9-tetrahydroimidazo[1,5-d][1,4]oxazepine, (R)-3-(3-chloro-4-(difluoromethoxy)phenyl)-1-(2,6-dimethylpyridin-4-yl)-6-methyl-5,6,8,9-tetrahydroimidazo[1,5-d][1,4]oxazepine, (R)-3-(3-chloro-4-methoxyphenyl)-1-(2,6-dimethylpyridin-4-yl)-6-methyl-5,6,8,9-tetrahydroimidazo[1,5-d][1,4]oxazepine, (R)-3-(3-chloro-4-ethoxyphenyl)-1-(2,6-dimethylpyridin-4-yl)-6-methyl-5,6,8,9-tetrahydroimidazo[1,5-d][1,4]oxazepine, (R)-3-(3-chloro-4-isopropoxyphenyl)-1-(2,6-dimethylpyridin-4-yl)-6-methyl-5,6,8,9-tetrahydroimidazo[1,5-d][1,4]oxazepine, (S)-3-(3-chloro-4-methoxyphenyl)-1-(2,6-dimethylpyridin-4-yl)-6-(fluoromethyl)-5,6,8,9-tetrahydroimidazo[1,5-d][1,4]oxazepine, (S)-3-(3-chloro-4-ethoxyphenyl)-1-(2,6-dimethylpyridin-4-yl)-6-(fluoromethyl)-5,6,8,9-tetrahydroimidazo[1,5-d][1,4]oxazepine, (S)-3-(3-chloro-4-isopropoxyphenyl)-1-(2,6-dimethylpyridin-4-yl)-6-(fluoromethyl)-5,6,8,9-tetrahydroimidazo[1,5-d][1,4]oxazepine, (R)-3-(3-(fluoromethyl)-4-(trifluoromethoxy)phenyl)-6-methyl-1-(2-methyl pyridin-4-yl)-5,6,8,9-tetrahydroimidazo[1,5-d][1,4]oxazepine, (S)-3-(4-(difluoromethoxy)-3-methylphenyl)-6-(fluoromethyl)-1-(2-methyl pyridin-4-yl)-5,6,8,9-tetrahydroimidazo[1,5-d][1,4]oxazepine, and (S)-6-(fluoromethyl)-3-(3-methoxy-4-(trifluoromethyl)phenyl)-1-(2-methyl pyridin-4-yl)-5,6,8,9-tetrahydroimidazo[1,5-d][1,4]oxazepine.

[11] The compound or a pharmaceutically acceptable acid addition salt thereof according to [1], which is (R)-3-(4-chloro-3-methoxyphenyl)-1-(2,6-dimethylpyridin-4-yl)-6-methyl-5,6,8,9-tetrahydroimidazo[1,5-d][1,4]oxazepine represented by the following formula:

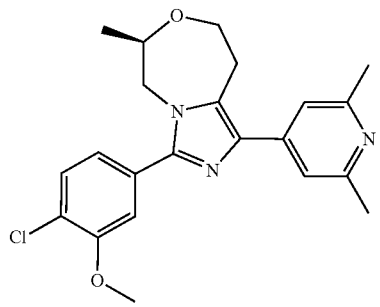 [SMILES: COc1cc(-c2nc(-c3cc(C)nc(C)c3)c3n2C[C@@H](C)OCC3)ccc1Cl]

or a pharmaceutically acceptable acid addition salt thereof.

[12] The compound or a pharmaceutically acceptable acid addition salt thereof according to [1], which is (R)-1-(2,6-dimethylpyridin-4-yl)-3-(3-methoxy-4-(trifluoromethyl)phenyl)-6-methyl-5,6,8,9-tetrahydroimidazo[1,5-d][1,4]oxazepine represented by the following formula:

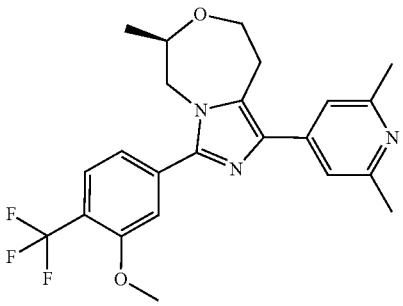 [SMILES: COc1cc(-c2nc(-c3cc(C)nc(C)c3)c3n2C[C@@H](C)OCC3)ccc1C(F)(F)F]

or a pharmaceutically acceptable acid addition salt thereof.

[13] The compound or a pharmaceutically acceptable acid addition salt thereof according to [1], which is (R)-3-(3-methoxy-4-(trifluoromethoxy)phenyl)-6-methyl-1-(2-methylpyridin-4-yl)-5,6,8,9-tetrahydroimidazo[1,5-d][1,4]oxazepine represented by the following formula:

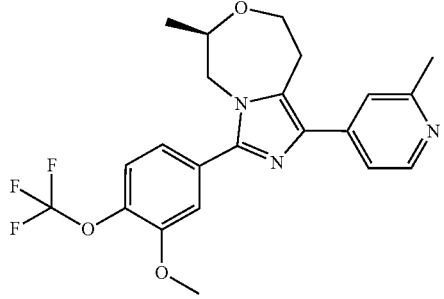 [SMILES: COc1cc(-c2nc(-c3ccnc(C)c3)c3n2C[C@@H](C)OCC3)ccc1OC(F)(F)F]

or a pharmaceutically acceptable acid addition salt thereof.

[14] The compound or a pharmaceutically acceptable acid addition salt thereof according to [1], which is (R)-3-(4-(difluoromethoxy)-3-methyl phenyl)-1-(2,6-dimethylpyridin-4-yl)-6-methyl-5,6,8,9-tetrahydroimidazo[1,5-d][1,4]oxazepine represented by the following formula:

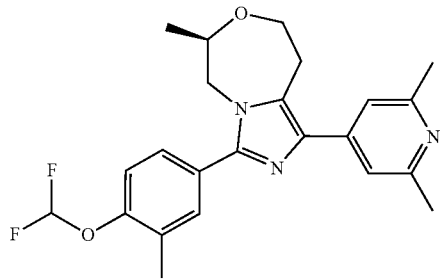 [SMILES: Cc1cc(-c2nc(-c3ccc(OC(F)F)c(C)c3)n3c2CCO[C@H](C)C3)cc(C)n1]

or a pharmaceutically acceptable acid addition salt thereof.

[15] The compound or a pharmaceutically acceptable acid addition salt thereof according to [1], which is (R)-3-(3-chloro-4-(difluoromethoxy)phenyl)-1-(2,6-dimethylpyridin-4-yl)-6-methyl-5,6,8,9-tetrahydroimidazo[1,5-d][1,4]oxazepine represented by the following formula:

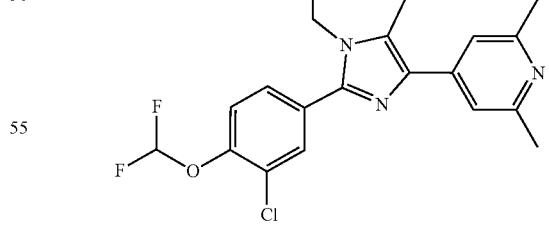

or a pharmaceutically acceptable acid addition salt thereof.

[16] The compound or a pharmaceutically acceptable acid addition salt thereof according to [1], which is (S)-3-(4-(difluoromethoxy)-3-methylphenyl)-1-(2,6-dimethylpyridin-4-yl)-6-(fluoromethyl)-5,6,8,9-tetrahydroimidazo[1,5-d][1,4]oxazepine represented by the following formula:

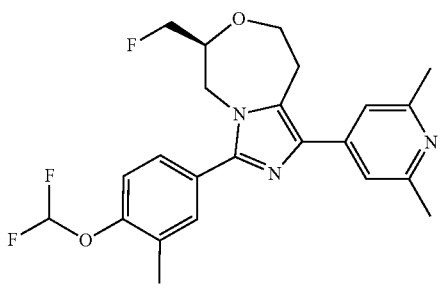 [SMILES: Cc1cc(-c2nc(-c3ccc(OC(F)F)c(C)c3)n3c2CCO[C@H](CF)C3)cc(C)n1]

or a pharmaceutically acceptable acid addition salt thereof.
[17] The compound or a pharmaceutically acceptable acid addition salt thereof according to [1], which is (S)-1-(2,6-dimethylpyridin-4-yl)-6-(fluoromethyl)-3-(3-methoxy-4-(trifluoromethyl)phenyl)-5,6,8,9-tetrahydroimidazo[1,5-d][1,4]oxazepine represented by the following formula:

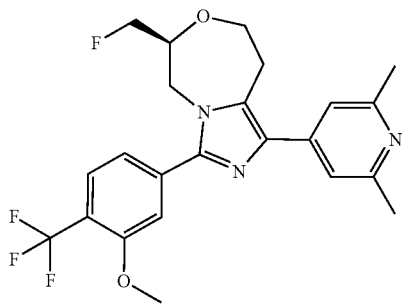 [SMILES: COc1cc(-c2nc(-c3cc(C)nc(C)c3)c3n2C[C@@H](CF)OCC3)ccc1C(F)(F)F]

or a pharmaceutically acceptable acid addition salt thereof.
[18] A pharmaceutical composition comprising the compounds or pharmaceutically acceptable acid addition salt according to any one of [1] to [17], and one or more pharmaceutically acceptable excipients.
[19] The pharmaceutical composition according to [18] for treatment of a disease or symptom in which an antagonistic action against a group II metabotropic glutamate receptor is effective.
[20] The pharmaceutical composition according to [19], the disease or symptom is Alzheimer's disease.
[21] A method for treating a disease or symptom in which an antagonistic action against a group II metabotropic glutamate receptor is effective, comprising administrating the compound or pharmaceutically acceptable acid addition salt according to any one of [1] to [17] to a subject in need thereof.
[22] The method for treating according to [21], wherein the disease or symptom is Alzheimer's disease.

Advantageous Effects of Invention

The compound of the present invention represented by formula (I) (hereinafter also referred to as the tetrahydroimidazo[1,5-d][1,4]oxazepine derivative) or a pharmaceutically acceptable acid addition salt thereof shows an antagonistic action against group II metabotropic glutamate receptors. Therefore, the tetrahydroimidazo[1,5-d][1,4]oxazepine derivative of the present invention or a pharmaceutically acceptable acid addition salt thereof has a potential use as a therapeutic agent for diseases or symptoms for which the antagonistic action against group II metabotropic glutamate receptors effectively works, such as Alzheimer's disease.

DESCRIPTION OF THE PREFERRED EMBODIMENTS

Hereinafter, the meanings of signs, terms and the like used herein will be explained, and the present invention will be described in details.

Herein, a structural formula of a compound may represent a given isomer for convenience, but a compound of the present invention includes isomers, such as all geometric isomers structurally formed from the compound, optical isomers based on asymmetric carbon, stereoisomers and tautomers, and the isomeric mixtures thereof. The compound is not limited to the formula given for convenience, and it may be any one of the isomers and mixtures. Accordingly, the compound of the present invention may have an asymmetric carbon atom in a molecule thereof and exist as an optically active substance and a racemic form. However, the present invention is not limited thereto, but it includes all cases. Incidentally, any one of isomers, racemic compounds and mixtures of isomers may show stronger activity than the other isomers. Furthermore, there may exist crystal polymorphisms, which also does not limit the present invention, and the compound may be any of single crystals or mixtures thereof, and may be a hydrate or a solvate as well as an anhydrate, all of which are included in the scope of the claims herein.

The present invention includes an isotopically-labeled compound of the compound of formula (I). The isotopically-labeled compound is equivalent to the compound of formula (I) except that one or more of atoms are replaced by atom(s) having an atomic mass or a mass number different from those usually found in nature. Examples of an isotope that can be incorporated into the compound of the present invention include isotopes of hydrogen, carbon, nitrogen, oxygen, fluorine, chlorine, phosphorus, sulfur and iodine, such as $^2H$, $^3H$, $^{11}C$, $^{14}C$, $^{13}N$, $^{15}O$, $^{18}F$, $^{32}P$, $^{35}S$, $^{123}I$ and $^{125}I$.

The compound of the present invention containing any of the aforementioned isotopes and/or another isotope, and a pharmaceutically acceptable derivative (such as a salt) thereof fall in the scope of the claims herein. The isotopically-labeled compound of the present invention, for example those to which radioactive isotopes such as $^3H$ and/or $^{14}C$ are incorporated, may be useful in drug and/or substrate tissue distribution assays. The isotopes $^3H$ and $^{14}C$ are regarded to be useful because these isotopes can be easily prepared and detected. The isotopes $^{11}C$ and $^{18}F$ are regarded to be useful in PET (positron emission tomography), the isotope $^{125}I$ is regarded to be useful in SPECT (single photon emission computed tomography), and these isotopes are all useful in brain imaging. Replacement by a heavier isotope such as $^2H$ causes, because of its higher metabolic stability, some types of advantages, in a treatment, of, for example, extension of half-life in vivo or reduction of a necessary dose, and therefore, is regarded useful under given circumstances. An isotopically-labeled compound of the compound of formula (I) of the present invention can be similarly prepared by using a readily available isotopically-labeled reagent instead of a nonisotopically-labeled reagent and by performing procedures disclosed in schemes and/or examples described below.

Herein, a "halogen atom" means a fluorine atom, a chlorine atom, a bromine atom, an iodine atom and the like, and is preferably a fluorine atom or a chlorine atom.

A "$C_{1-6}$ alkyl group" means a linear or branched alkyl group having 1 to 6 carbon atoms, and specific examples include a methyl group, an ethyl group, a n-propyl group, an isopropyl group, a n-butyl group, an isobutyl group, a tert-butyl group, a n-pentyl group, an isopentyl group, a neopentyl group, a n-hexyl group, a 1-methylpropyl group, a 1,2-dimethylpropyl group, a 1-ethylpropyl group, a 1-methyl-2-ethylpropyl group, a 1-ethyl-2-methylpropyl group, a 1,1,2-trimethylpropyl group, a 1-methylbutyl group, a 2-methylbutyl group, a 1,1-dimethylbutyl group, a 2,2-dimethylbutyl group, a 2-ethylbutyl group, a 1,3-dimethylbutyl group, a 2-methylpentyl group and a 3-methylpentyl group, and more preferable examples include a methyl group, an ethyl group and a n-propyl group.

A "$C_{1-6}$ alkoxy group" means an oxy group binding to the "$C_{1-6}$ alkyl group", and specific examples include a methoxy group, an ethoxy group, a 1-propyloxy group, a 2-propyloxy group, a 2-methyl-1-propyloxy group, a 2-methyl-2-propyloxy group, a 1-butyloxy group, a 2-butyloxy group, a 1-pentyloxy group, a 2-pentyloxy group, a 3-pentyloxy group, a 2-methyl-1-butyloxy group, a 3-methyl-1-butyloxy group, a 2-methyl-2-butyloxy group, a 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1-butyloxy group, a 2,2-dimethyl-1-butyloxy group, a 2-ethyl-1-butyloxy group, a 3,3-dimethyl-2-butyloxy group, and a 2,3-dimethyl-2-butyloxy group, and preferable examples include a methoxy group, an ethoxy group and a 1-propyloxy group.

A "$C_{3-8}$ cycloalkyl group" means a cyclic alkyl group having 3 to 8 carbon atoms, and specific examples include a cyclopropyl group, a cyclobutyl group, a cyclopentyl group, a cyclohexyl group, a cycloheptyl group and a cyclooctyl group.

A "$C_{1-6}$ alkyl group optionally substituted with 1 to 3 fluorine atoms" means the "$C_{1-6}$ alkyl group" unsubstituted or the "$C_{1-6}$ alkyl group" in which 1 to 3 hydrogen atoms are substituted with a fluorine atom. Specific examples of the $C_{1-6}$ alkyl group substituted with 1 to 3 fluorine atoms include a fluoromethyl group, a 1-fluoroethyl group, a 2-fluoroethyl group, a 3-fluoropropyl group, a difluoromethyl group, a 1,1-difluoroethyl group, a 2,2-difluoroethyl group, a trifluoromethyl group and a 2,2,2-trifluoroethyl group.

A "$C_{1-6}$ alkoxy group optionally substituted with 1 to 3 substituents selected from a fluorine atom and a $C_{3-8}$ cycloalkyl group" means the "$C_{1-6}$ alkoxy group" unsubstituted or the "$C_{1-6}$ alkoxy group" in which 1 to 3 hydrogen atoms are substituted with a fluorine atom or a $C_{3-8}$ cycloalkyl group. Specific examples of the $C_{1-6}$ alkoxy group substituted with one or more fluorine atoms include a fluoromethoxy group, a 1-fluoroethoxy group, a 2-fluoroethoxy group, a 3-fluoropropyloxy group, a difluoromethoxy group, a 1,1-difluoroethoxy group, a 2,2-difluoroethoxy group, a trifluoromethoxy group and a 2,2,2-trifluoroethoxy group. Specific examples of the $C_{1-6}$ alkoxy group substituted with a $C_{3-8}$ cycloalkyl group include a cyclopropylmethoxy group, a cyclobutylmethoxy group, a cyclopentylmethoxy group, a cyclohexylmethoxy group, a cyclopropylethoxy group, a cyclobutylethoxy group, a cyclopentylethoxy group and a cyclohexylethoxy group.

A "$C_{3-8}$ cycloalkyloxy group" means an oxy group binding to the "$C_{3-8}$ cycloalkyl group", and specific examples include a cyclopropyloxy group, a cyclobutyloxy group, a cyclopentyloxy group, a cyclohexyloxy group, a cycloheptyloxy group and a cyclooctyloxy group.

A "4- to 6-membered heterocycloalkyl group" means a 4- to 6-membered ring group containing one or more hetero atoms of nitrogen, oxygen, sulfur and the like, and specific examples include a 3-azetidinyl group, a 1-methyl-3-azetidinyl group, a 3-pyrrolidinyl group, a 1-methyl-3-pyrrolidinyl group, a 1-methyl-3-piperidinyl group, a 1-methyl-4-piperidinyl group, a 3-oxetanyl group, a 3-tetrahydrofuryl group, a 3-tetrahydropyranyl group, a 4-tetrahydropyranyl group, a 3-tetrahydrothienyl group and a 4-tetrahydrothiopyranyl group.

A "4- to 6-membered heterocycloalkyloxy group" means an oxy group binding to the "4- to 6-membered heterocycloalkyl group", and specific examples include a 3-azetidinyloxy group, a 1-methyl-3-azetidinyloxy group, a 3-pyrrolidinyloxy group, a 1-methyl-3-pyrrolidinyloxy group, a 1-methyl-3-piperidinyloxy group, a 1-methyl-4-piperidinyloxy group, a 3-oxetanyloxy group, a 3-tetrahydrofuryloxy group, a 3-tetrahydropyranyloxy group, a 4-tetrahydropyranyloxy group, a 3-tetrahydrothienyloxy group and a 4-tetrahydrothiopyranyloxy group.

The tetrahydroimidazo[1,5-d][1,4]oxazepine derivative of formula (I) of the present invention may be in the form of a pharmaceutically acceptable acid addition salt. Specific examples of the pharmaceutically acceptable acid addition salt include inorganic acid salts (such as a sulfate, a nitrate, a perchlorate, a phosphate, a carbonate, a bicarbonate, a hydrofluoride, a hydrochloride, a hydrobromide and a hydroiodide), organic carboxylates (such as an acetate, an oxalate, a maleate, a tartrate, a fumarate and a citrate), organic sulfonates (such as a methanesulfonate, a trifluoromethanesulfonate, an ethanesulfonate, a benzene sulfonate, a toluene sulfonate and a camphorsulfonate), and amino acid salts (such as an aspartate and a glutamate).

An embodiment of the present invention includes a compound represented by the following formula (I) or a pharmaceutically acceptable acid addition salt thereof:

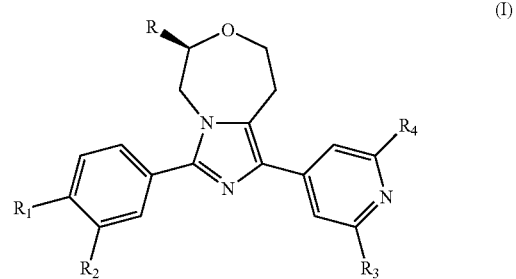

(I)

wherein R, $R_1$, $R_2$, $R_3$ and $R_4$ represent the same as defined in [1] above.

A preferred embodiment of the present invention provides a tetrahydroimidazo[1,5-d][1,4]oxazepine derivative or a pharmaceutically acceptable acid addition salt thereof, in which when R is a hydrogen atom in formula (I), $R_1$ is a chlorine atom, a bromine atom, a trifluoromethyl group, an ethyl group, a trifluoromethoxy group, a methyl group substituted with a phenyl group, a methoxy group substituted with a $C_{3-8}$ cycloalkyl group, an ethoxy group optionally substituted with 1 to 3 fluorine atoms, or a $C_{3-8}$ cycloalkyloxy group; $R_2$ is a fluorine atom, a chlorine atom, a methyl group optionally substituted with 2 to 3 fluorine atoms, a methoxy group optionally substituted with 1 to 3 fluorine atoms, or an ethoxy group optionally substituted with 1 to 3 fluorine atoms; $R_3$ is a hydrogen atom or a methyl group; and $R_4$ is a fluorine atom or a methyl group optionally substituted with 1 to 3 fluorine atoms.

Another preferable embodiment of the present invention is a tetrahydroimidazo[1,5-d][1,4]oxazepine derivative or a pharmaceutically acceptable acid addition salt thereof, in which when R is a $C_{1-6}$ alkyl group optionally substituted with 1 to 3 fluorine atoms in formula (I), $R_1$ is a hydrogen atom, a halogen atom, a $C_{1-6}$ alkyl group optionally substituted with 1 to 3 fluorine atoms, a $C_{1-6}$ alkoxy group optionally substituted with 1 to 3 substituents selected from a fluorine atom and a $C_{3-8}$ cycloalkyl group, a $C_{3-8}$ cycloalkyloxy group, or a 4- to 6-membered heterocycloalkyloxy group; $R_2$ is a hydrogen atom, a cyano group, a halogen atom, a $C_{1-6}$ alkyl group optionally substituted with 1 to 3 substituents selected from a fluorine atom and a hydroxyl group, or a $C_{1-6}$ alkoxy group optionally substituted with 1 to 3 substituents selected from a fluorine atom, a $C_{3-8}$ cycloalkyl group and a 4- to 6-membered heterocycloalkyl group; $R_3$ is a hydrogen atom or a $C_{1-6}$ alkyl group; and $R_4$ is a $C_{1-6}$ alkyl group optionally substituted with 1 to 3 substituents selected from a fluorine atom and a hydroxyl group, or a $C_{1-6}$ alkoxy group.

In formula (I), R preferably is a methyl group, an ethyl group, a fluoromethyl group or a difluoromethyl group; $R_1$ preferably is a hydrogen atom, a fluorine atom, a chlorine atom, a methyl group, a fluoromethyl group, a difluoromethyl group, a trifluoromethyl group, an ethyl group, a 1,1-difluoroethyl group, a methoxy group, a fluoromethoxy group, a difluoromethoxy group, a trifluoromethoxy group, an ethoxy group, a 2-fluoroethoxy group, a 2-propyloxy group, a cyclopropylmethoxy group, a cyclopropyloxy group or an (oxetan-3-yl)oxy group; $R_2$ preferably is a hydrogen atom, a cyano group, a fluorine atom, a chlorine atom, a methyl group, a fluoromethyl group, a difluoromethyl group, a trifluoromethyl group, a hydroxymethyl group, an ethyl group, a methoxy group, a fluoromethoxy group, a difluoromethoxy group, a trifluoromethoxy group, an ethoxy group, a 2-fluoroethoxy group, a 2-propyloxy group, a cyclopropylmethoxy group, a cyclobutylmethoxy group or a (tetrahydro-2H-pyran-4-yl)methoxy group; $R_3$ preferably is a hydrogen atom or a methyl group; and $R_4$ preferably is a methyl group, a fluoromethyl group, a difluoromethyl group, a hydroxymethyl group or a methoxy group.

In formula (I), a preferable combination of R, $R_1$, $R_2$, $R_3$ and $R_4$ is as follows: R is a methyl group optionally substituted with 1 to 2 fluorine atoms; $R_1$ is a hydrogen atom, a halogen atom, a $C_{1-6}$ alkyl group optionally substituted with 1 to 3 fluorine atoms, a $C_{1-6}$ alkoxy group optionally substituted with 1 to 3 fluorine atoms, or a $C_{3-6}$ cycloalkyloxy group; $R_2$ is a cyano group, a halogen atom, a $C_{1-6}$ alkyl group optionally substituted with 1 to 3 fluorine atoms, or a $C_{1-6}$ alkoxy group optionally substituted with 1 to 3 fluorine atoms; $R_3$ is a methyl group; $R_4$ is a methyl group optionally substituted with 1 to 3 fluorine atoms, provided that when $R_1$ is an unsubstituted methoxy group, $R_2$ is not a fluorine atom.

Specifically, the tetrahydroimidazo[1,5-d][1,4]oxazepine derivative or a pharmaceutically acceptable acid addition salt thereof according to the present invention is preferably selected from the following compounds:

(R)-3-(4-chloro-3-methoxyphenyl)-1-(2,6-dimethylpyridin-4-yl)-6-methyl-5,6,8,9-tetrahydroimidazo[1,5-d][1,4]oxazepine, (R)-1-(2,6-dimethylpyridin-4-yl)-3-(3-methoxy-4-(trifluoromethyl)phenyl)-6-methyl-5,6,8,9-tetrahydroimidazo[1,5-d][1,4]oxazepine, (R)-6-methyl-3-(3-methyl-4-(trifluoromethoxy)phenyl)-1-(2-methylpyridin-4-yl)-5,6,8,9-tetrahydroimidazo[1,5-d][1,4]oxazepine, (R)-3-(4-(difluoromethoxy)-3-methylphenyl)-1-(2,6-dimethylpyridin-4-yl)-6-methyl-5,6,8,9-tetrahydroimidazo[1,5-d][1,4]oxazepine, (R)-3-(4-(difluoromethoxy)-3-methylphenyl)-6-methyl-1-(2-methylpyridin-4-yl)-5,6,8,9-tetrahydroimidazo[1,5-d][1,4]oxazepine, (S)-1-(2,6-dimethylpyridin-4-yl)-6-(fluoromethyl)-3-(3-methoxy-4-(trifluoromethoxy)phenyl)-5,6,8,9-tetrahydroimidazo[1,5-d][1,4]oxazepine, (S)-6-(fluoromethyl)-3-(3-methoxy-4-(trifluoromethoxy)phenyl)-1-(2-methylpyridin-4-yl)-5,6,8,9-tetrahydroimidazo[1,5-d][1,4]oxazepine, (R)-3-(3-chloro-4-cyclopropoxyphenyl)-1-(2,6-dimethylpyridin-4-yl)-6-methyl-5,6,8,9-tetrahydroimidazo[1,5-d][1,4]oxazepine, (R)-3-(4-cyclopropoxy-3-methylphenyl)-1-(2,6-dimethylpyridin-4-yl)-6-methyl-5,6,8,9-tetrahydroimidazo[1,5-d][1,4]oxazepine, (R)-3-(3-chloro-4-(difluoromethoxy)phenyl)-6-methyl-1-(2-methylpyridin-4-yl)-5,6,8,9-tetrahydroimidazo[1,5-d][1,4]oxazepine, (S)-3-(4-cyclopropoxy-3-methylphenyl)-1-(2,6-dimethylpyridin-4-yl)-6-(fluoromethyl)-5,6,8,9-tetrahydroimidazo[1,5-d][1,4]oxazepine, (R)-3-(3-methoxy-4-(trifluoromethoxy)phenyl)-6-methyl-1-(2-methylpyridin-4-yl)-5,6,8,9-tetrahydroimidazo[1,5-d][1,4]oxazepine, (R)-1-(2,6-dimethylpyridin-4-yl)-3-(3-methoxy-4-(trifluoromethoxy)phenyl)-6-methyl-5,6,8,9-tetrahydroimidazo[1,5-d][1,4]oxazepine, (S)-3-(4-(difluoromethoxy)-3-methylphenyl)-1-(2,6-dimethylpyridin-4-yl)-6-(fluoromethyl)-5,6,8,9-tetrahydroimidazo[1,5-d][1,4]oxazepine, (S)-1-(2,6-dimethylpyridin-4-yl)-6-(fluoromethyl)-3-(3-methoxy-4-(trifluoromethyl)phenyl)-5,6,8,9-tetrahydroimidazo[1,5-d][1,4]oxazepine, (R)-3-(3-chloro-4-(difluoromethoxy)phenyl)-1-(2,6-dimethylpyridin-4-yl)-6-methyl-5,6,8,9-tetrahydroimidazo[1,5-d][1,4]oxazepine, (R)-3-(3-chloro-4-methoxyphenyl)-1-(2,6-dimethylpyridin-4-yl)-6-methyl-5,6,8,9-tetrahydroimidazo[1,5-d][1,4]oxazepine, (R)-3-(3-chloro-4-ethoxyphenyl)-1-(2,6-dimethylpyridin-4-yl)-6-methyl-5,6,8,9-tetrahydroimidazo[1,5-d][1,4]oxazepine, (R)-3-(3-chloro-4-isopropoxyphenyl)-1-(2,6-dimethylpyridin-4-yl)-6-methyl-5,6,8,9-tetrahydroimidazo[1,5-d][1,4]oxazepine, (S)-3-(3-chloro-4-methoxyphenyl)-1-(2,6-dimethylpyridin-4-yl)-6-(fluoromethyl)-5,6,8,9-tetrahydroimidazo[1,5-d][1,4]oxazepine, (S)-3-(3-chloro-4-ethoxyphenyl)-1-(2,6-dimethylpyridin-4-yl)-6-(fluoromethyl)-5,6,8,9-tetrahydroimidazo[1,5-d][1,4]oxazepine, (S)-3-(3-chloro-4-isopropoxyphenyl)-1-(2,6-dimethylpyridin-4-yl)-6-(fluoromethyl)-5,6,8,9-tetrahydroimidazo[1,5-d][1,4]oxazepine, (R)-3-(3-(fluoromethyl)-4-(trifluoromethoxy)phenyl)-6-methyl-1-(2-methylpyridin-4-yl)-5,6,8,9-tetrahydroimidazo[1,5-d][1,4]oxazepine, (S)-3-(4-(difluoromethoxy)-3-methylphenyl)-6-(fluoromethyl)-1-(2-methylpyridin-4-yl)-5,6,8,9-tetrahydroimidazo[1,5-d][1,4]oxazepine, or
(S)-6-(fluoromethyl)-3-(3-methoxy-4-(trifluoromethyl)phenyl)-1-(2-methylpyridin-4-yl)-5,6,8,9-tetrahydroimidazo[1,5-d][1,4]oxazepine.

More preferable examples of tetrahydroimidazo[1,5-d][1,4]oxazepine derivatives or a pharmaceutically acceptable acid addition salt thereof are (R)-3-(4-chloro-3-methoxyphenyl)-1-(2,6-dimethylpyridin-4-yl)-6-methyl-5,6,8,9-tetrahydroimidazo[1,5-d][1,4]oxazepine represented by the following formula:

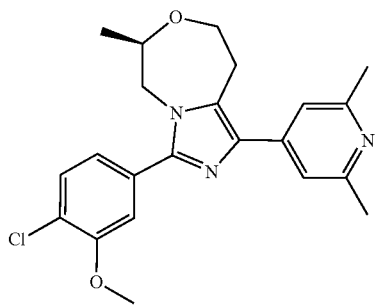 [SMILES: COc1cc(-c2nc(-c3cc(C)nc(C)c3)c3n2C[C@@H](C)OCC3)ccc1Cl]

or a pharmaceutically acceptable acid addition salt thereof, (R)-1-(2,6-dimethylpyridin-4-yl)-3-(3-methoxy-4-(trifluoromethyl)phenyl)-6-methyl-5,6,8,9-tetrahydroimidazo[1,5-d][1,4]oxazepine represented by the following formula:

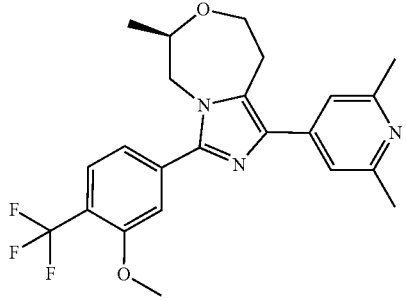 [SMILES: COc1cc(-c2nc(-c3cc(C)nc(C)c3)c3n2C[C@@H](C)OCC3)ccc1C(F)(F)F]

or a pharmaceutically acceptable acid addition salt thereof, (R)-3-(3-methoxy-4-(trifluoromethoxy)phenyl)-6-methyl-1-(2-methylpyridin-4-yl)-5,6,8,9-tetrahydroimidazo[1,5-d][1,4]oxazepine represented by the following formula:

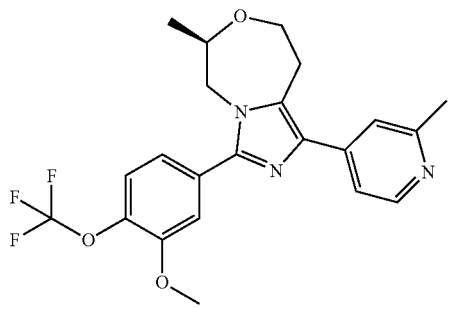 [SMILES: COc1cc(-c2nc(-c3ccnc(C)c3)c3n2C[C@@H](C)OCC3)ccc1OC(F)(F)F]

or a pharmaceutically acceptable acid addition salt thereof, (R)-3-(4-(difluoromethoxy)-3-methylphenyl)-1-(2,6-dimethylpyridin-4-yl)-6-methyl-5,6,8,9-tetrahydroimidazo[1,5-d][1,4]oxazepine represented by the following formula:

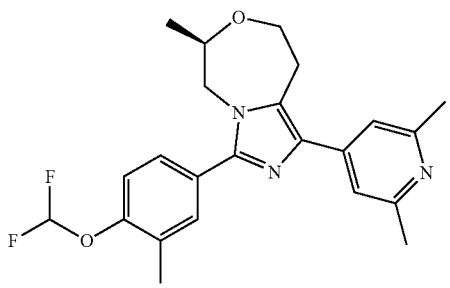 [SMILES: Cc1cc(-c2nc(-c3ccc(OC(F)F)c(C)c3)n3c2CCO[C@H](C)C3)cc(C)n1]

or a pharmaceutically acceptable acid addition salt thereof, (R)-3-(3-chloro-4-(difluoromethoxy)phenyl)-1-(2,6-dimethylpyridin-4-yl)-6-methyl-5,6,8,9-tetrahydro imidazo[1,5-d][1,4]oxazepine represented by the following formula:

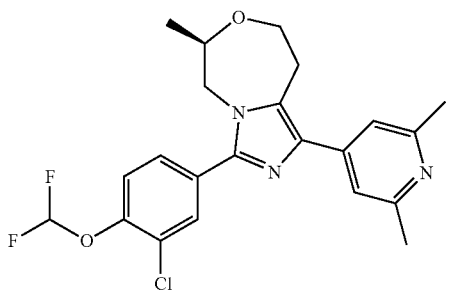 [SMILES: Cc1cc(-c2nc(-c3ccc(OC(F)F)c(Cl)c3)n3c2CCO[C@H](C)C3)cc(C)n1]

or a pharmaceutically acceptable acid addition salt thereof, (S)-3-(4-(difluoromethoxy)-3-methylphenyl)-1-(2,6-dimethylpyridin-4-yl)-6-(fluoromethyl)-5,6,8,9-tetrahydroimidazo[1,5-d][1,4]oxazepine represented by the following formula:

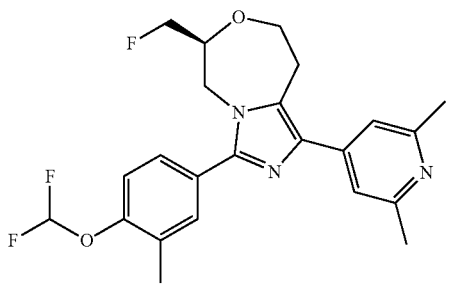 [SMILES: Cc1cc(-c2nc(-c3ccc(OC(F)F)c(C)c3)n3c2CCO[C@H](CF)C3)cc(C)n1]

or a pharmaceutically acceptable acid addition salt thereof, and
(S)-1-(2,6-dimethylpyridin-4-yl)-6-(fluoromethyl)-3-(3-methoxy-4-(trifluoromethyl)phenyl)-5,6,8,9-tetrahydroimidazo[1,5-d][1,4]oxazepine represented by the following formula:

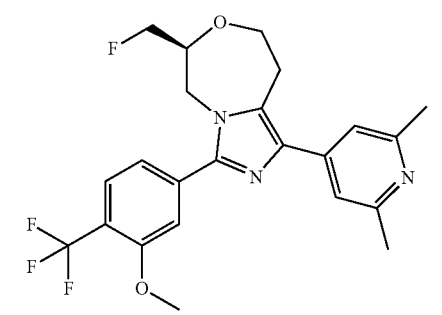 [SMILES: COc1cc(-c2nc(-c3cc(C)nc(C)c3)c3n2C[C@@H](CF)OCC3)ccc1C(F)(F)F]

or a pharmaceutically acceptable acid addition salt thereof.

Next, a method for producing the compound represented by formula (I) (hereinafter referred to as the compound (I), which expression is similarly used for other compounds represented by other formulas) of the present invention or a pharmaceutically acceptable acid addition salt thereof will be described.

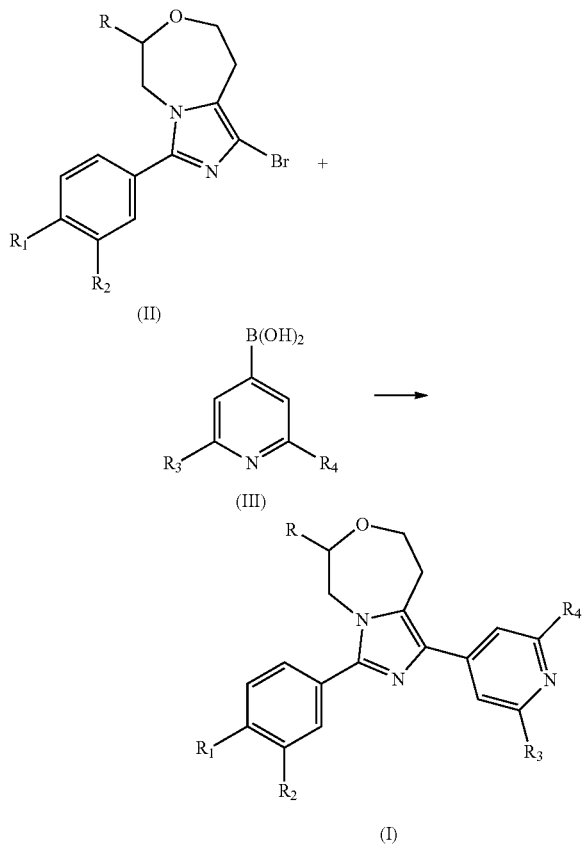

The compound (I) (wherein R, $R_1$, $R_2$, $R_3$ and $R_4$ represent the same as defined above) can be prepared in accordance with Scheme 1 by, for example, the Suzuki-Miyaura reaction of a compound (II) with a compound (III). The Suzuki-Miyaura reaction can be performed by heating the compound (II) and the compound (III) in a solvent in the presence of, for example, a palladium catalyst and a base, with a phosphorus ligand added if necessary. As the palladium catalyst, for example, tetrakis(triphenylphosphine)palladium (0), palladium (II) acetate, $Pd_2DBA_3$ or $(A\text{-taPhos})_2PdCl_2$ can be used. As the base, for example, potassium phosphate, sodium hydroxide, potassium hydroxide, barium hydroxide, sodium carbonate or cesium carbonate can be used. Besides, as the phosphorus ligand, for example, triphenylphosphine, butyl di(1-adamantyl)phosphine or 2-dicyclohexylphosphino-2',4',6'-triisopropyl biphenyl can be used. The solvent used in the reaction is not especially limited as long as it is an inert solvent, and for example, THF, DME, DMF, 1,4-dioxane, water or a mixed solvent of these can be used. The reaction is accelerated by heating, but is generally performed at a temperature ranging from room temperature to the reflux temperature of the solution, and heating by microwaves can be employed as occasion demands.

When $R_4$ is, for example, a hydroxymethyl group, the compound can be also produced from a compound in which $R_4$ is methyl by oxidation with mCPBA or the like, rearrangement reaction with acetic anhydride or the like, and alkaline hydrolysis.

When $R_2$ is, for example, a hydroxymethyl group, the compound can be also produced by deprotecting a corresponding compound in which a hydroxymethyl group is protected by MOM or the like.

When $R_1$ or $R_2$ is, for example, an alkoxy group, the compound can be also produced by alkylating a compound, which is obtained by deprotecting a corresponding alcohol compound protected by MOM, benzyl, methyl or the like, with alkyl bromide, alkyl iodide, alkyl triflate or the like, in a solvent such as DMF or THF in the presence of a base such as potassium carbonate or cesium carbonate. This reaction is generally performed at a temperature ranging from room temperature to the reflux temperature of the solution.

When $R_4$ or $R_2$ is, for example, a fluoromethyl group, the compound can be produced by fluorination of a hydroxymethyl group with DAST, BAST or the like.

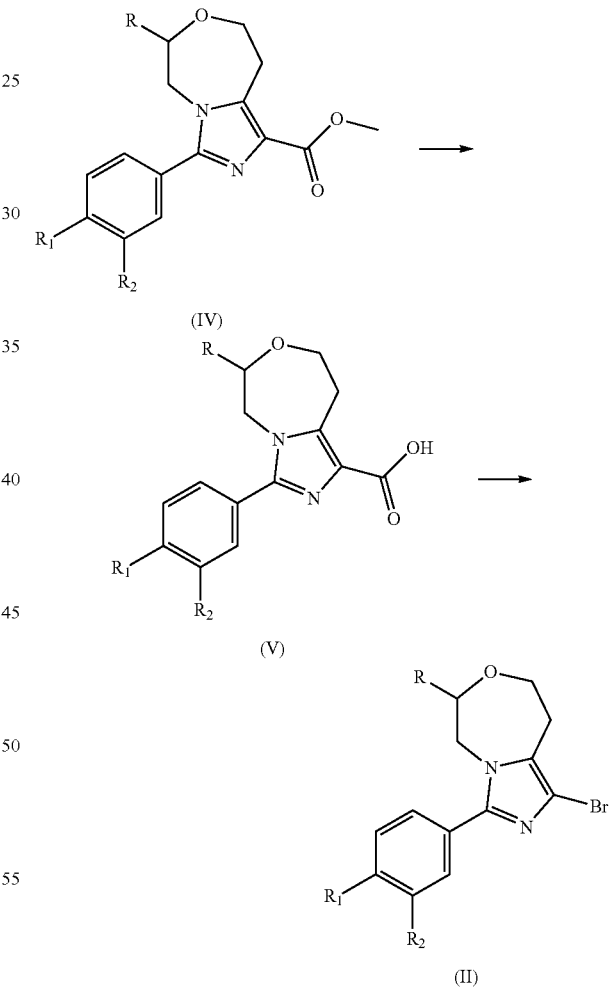

The compound (II) (wherein R, $R_1$ and $R_2$ represent the same as defined above) can be prepared in accordance with Scheme 2 by, for example, ester hydrolysis of a compound (IV) and decarboxylative bromination of a resulting compound (V). A solvent used in the ester hydrolysis of the compound (IV) is not especially limited as long as it is an inert solvent, and for example, methanol, ethanol, THF or a hydrous solvent thereof can be used. Besides, as a base, for example, sodium hydroxide or potassium hydroxide can be used. This reaction is accelerated by heating, but is generally performed at a temperature ranging from room temperature to the reflux temperature of the solution. A solvent used in the decarboxylative bromination of the compound (V) is not especially limited, and for example, DMF, ethanol or a mixed solvent of DMF and ethanol can be used. Furthermore, a bromine source can be, for example, NBS. If potassium carbonate or the like is used as the base, the reaction is accelerated, and the reaction is generally performed at a temperature ranging from room temperature to the reflux temperature of the solution.

When $R_1$ or $R_2$ is, for example, an alkoxy group, the compound can be also produced by alkylating a compound, which is obtained by deprotecting a corresponding alcohol compound protected by MOM, benzyl, methyl or the like, with alkyl bromide, alkyl iodide, alkyl triflate or the like in a solvent such as DMF or THF in the presence of a base such as potassium carbonate or cesium carbonate. This reaction is generally performed at a temperature ranging from room temperature to the reflux temperature of the solution.

compounds (VI) and (VII) is not especially limited as long as it is an inert solvent, and for example, toluene, THF, DME or a mixed solvent of these can be used. The reaction is accelerated by heating, but is generally performed at a temperature ranging from room temperature to the reflux temperature of the solution, and heating with microwaves can be employed as occasion demands. A solvent used in the treatment of the compound (VIII) with a base is not especially limited as long as it is an inert solvent, and for example, methanol can be used. The base can be, for example, sodium methoxide. The reaction is accelerated by heating, but is generally performed at a temperature ranging from room temperature to the reflux temperature of the solution, and heating with microwaves can be employed as occasion demands.

When $R_1$ or $R_2$ is, for example, an alkoxy group, the compound can be also produced by alkylating a compound, which is obtained by deprotecting a corresponding alcohol compound protected by MOM, benzyl, methyl or the like, with alkyl bromide, alkyl iodide, alkyl triflate or the like in a solvent such as DMF or THF in the presence of a base such as potassium carbonate or cesium carbonate. This reaction is generally performed at a temperature ranging from room temperature to the reflux temperature of the solution.

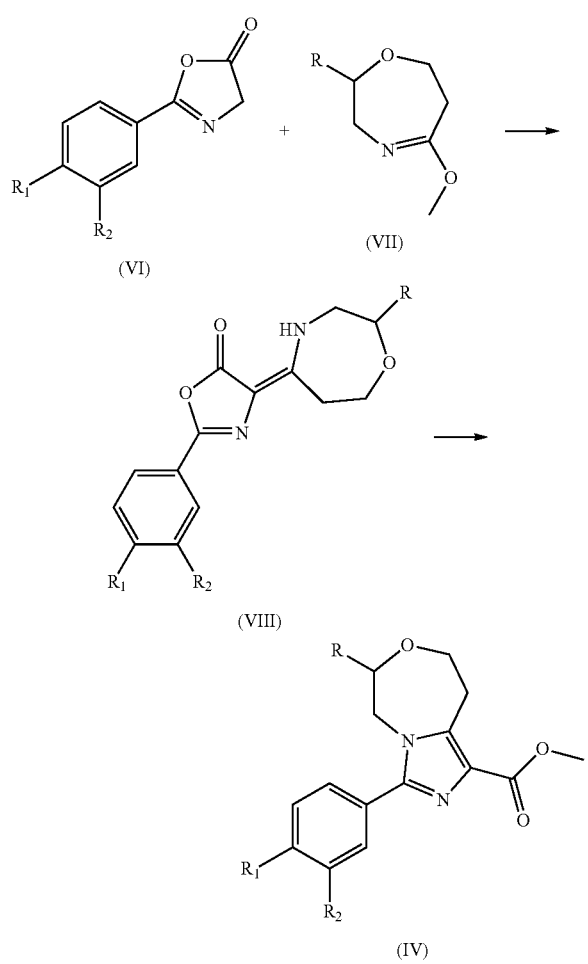

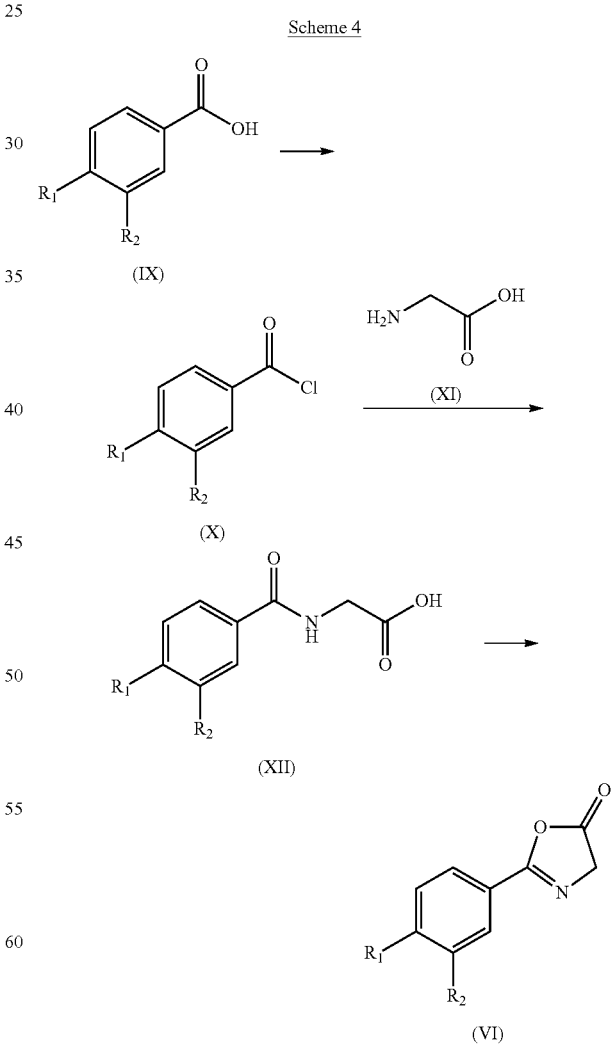

The compound (IV) (wherein R, $R_1$ and $R_2$ represent the same as defined above) can be prepared in accordance with Scheme 3 by, for example, condensing a compound (VI) with a compound (VII) and treating a resulting compound (VIII) with a base. A solvent used in the condensation of the The compound (VI) (wherein $R_1$ and $R_2$ represent the same as defined above) can be prepared in accordance with Scheme 4 by, for example, acid chloridization of a compound (IX), amidation of a resulting compound (X) and a compound (XI) under basic conditions, and cyclization of a resulting compound (XII). A solvent used in the acid chloridization of the compound (IX) is not especially limited as long as it is an inert solvent, and for example, toluene or DCM can be used. Furthermore, for example, oxalyl chloride or thionyl chloride can be used for the reaction, and the reaction is accelerated by addition of DMF. The reaction is accelerated by heating, but is generally performed at a temperature ranging from an ice cooling temperature to the reflux temperature of the solution. A solvent used in the amidation of the compounds (X) and (XI) is not especially limited as long as it is an inert solvent, and for example, toluene, THF, DCM, water or a mixed solvent of these can be used. Furthermore, as a base, for example, sodium hydroxide or potassium hydroxide can be used. This reaction is generally performed at a temperature ranging from an ice cooling temperature to the reflux temperature of the solution. A solvent used in the cyclization of the compound (XII) is not especially limited as long as it is an inert solvent, and for example, toluene or THF can be used. Besides, methyl chloroformate, isopropyl chloroformate, DCC or the like can be used for the cyclization. This reaction is generally performed at a temperature ranging from −78° C. to the reflux temperature of the solution.

potassium hydroxide, barium hydroxide, sodium carbonate or cesium carbonate can be used. Besides, as the phosphorus ligand, for example, triphenylphosphine, butyl di(1-adamantyl)phosphine or 2-dicyclohexylphosphino-2',4',6'-triisopropyl biphenyl can be used. The solvent used in the reaction is not especially limited as long as it is an inert solvent, and for example, THF, DME, DMF, 1,4-dioxane or benzene can be used. The reaction is accelerated by heating, but is generally performed at a temperature ranging from room temperature to the reflux temperature of the solution, and heating by microwaves can be employed as occasion demands.

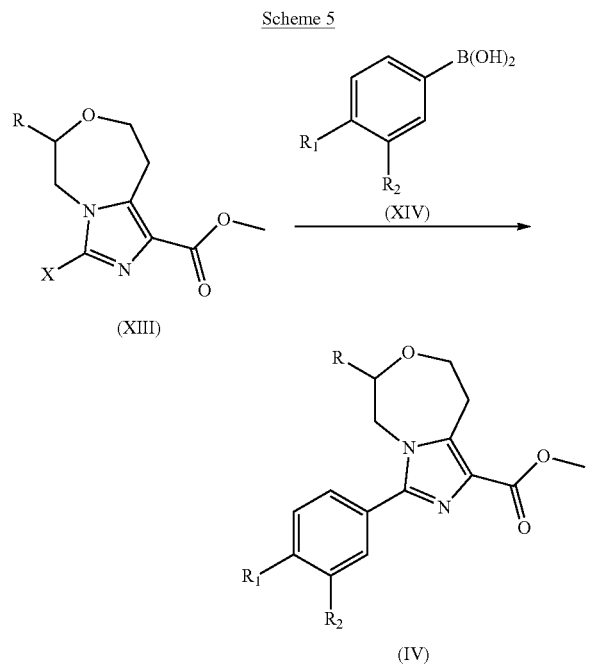

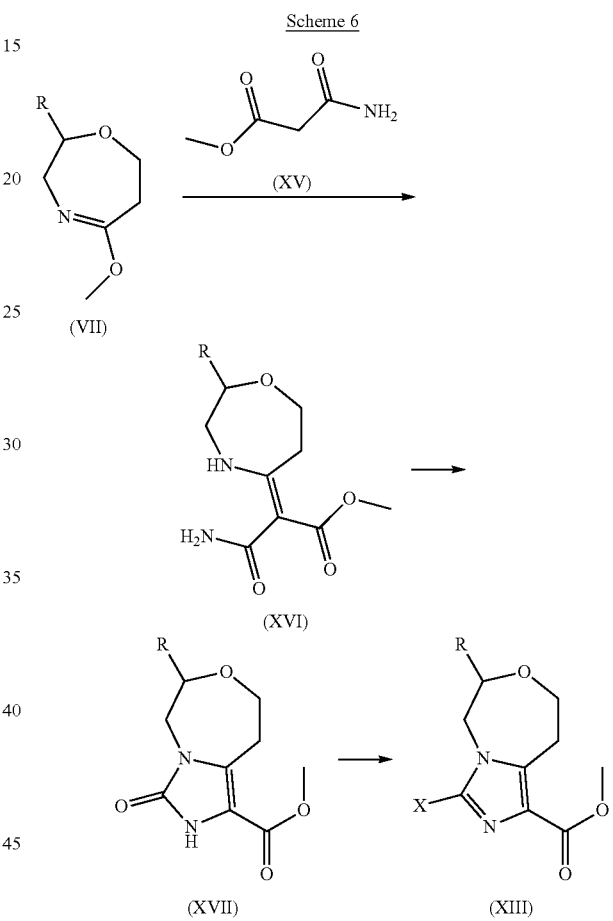

The compound (XIII) (wherein R is the same as defined above and X is halogen) can be prepared in accordance with Scheme 6 by, for example, condensation of the compound (VII) with a compound (XV), a Hofmann rearrangement reaction of a resulting compound (XVI), and halogenation of a resulting compound (XVII). A solvent used in the condensation of the compounds (VII) and (XV) is not especially limited as long as it is an inert solvent, and for example, toluene, THF, DMF, DME or a mixed solvent of these can be used. The reaction is accelerated by heating, but is generally performed at a temperature ranging from room temperature to the reflux temperature of the solution, and heating with microwaves can be employed as occasion demands. A solvent used in the rearrangement reaction of the compound (XVI) is not especially limited as long as it is an inert solvent, and for example, toluene, THF, DME or a mixed solvent of these can be used. Furthermore, iodobenzene diacetate or the like can be used in the reaction. The The compound (IV) (wherein R, R₁ and R₂ represent the same as defined above) can be prepared also in accordance with Scheme 5 by, for example, the Suzuki-Miyaura reaction of a compound (XIII) (wherein X is halogen) and a compound (XIV). The Suzuki-Miyaura reaction can be performed by heating the compound (XIII) and the compound (XIV) in a solvent in the presence of, for example, a palladium catalyst and a base, with a phosphorus ligand added if necessary. As the palladium catalyst, for example, tetrakis(triphenylphosphine)palladium (0), palladium (II) acetate, Pd₂DBA₃ or (A-taPhos)₂PdCl₂ can be used. As the base, for example, potassium phosphate, sodium hydroxide, reaction is generally performed at a temperature ranging from room temperature to the reflux temperature of the solution. A solvent used in the halogenation of the compound (XVII) is not especially limited as long as it is an inert solvent, and for example, toluene can be used. Furthermore, phosphorus oxychloride or phosphorus oxybromide can be used in the reaction. The reaction is accelerated by heating, but is generally performed at a temperature ranging from room temperature to the reflux temperature of the solution.

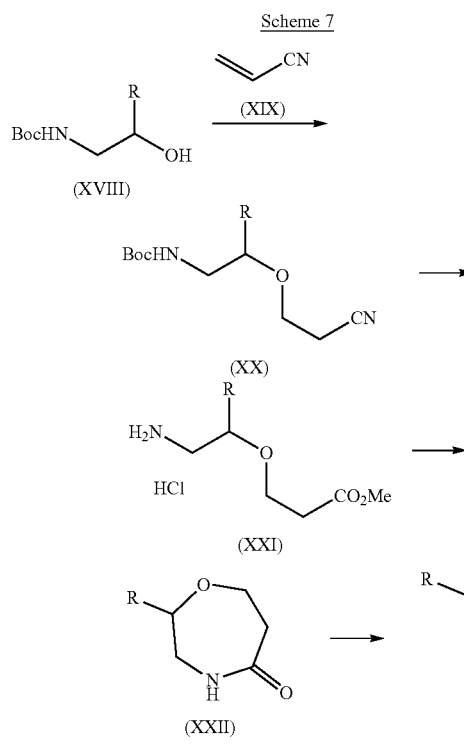

The compound (VII) (wherein R is the same as defined above) can be prepared in accordance with Scheme 7 by, for example, four steps of a 1,4-addition reaction of a compound (XVIII) and a compound (XIX), alcoholysis of a resulting compound (XX) under acidic conditions, cyclization of a resulting compound (XXI) under basic conditions, and O-alkylation of a resulting compound (XXII). In the 1,4-addition reaction of the compound (XVIII), the compound (XIX) can be used as a solvent. As a base, DBU, TEA, DIPEA or the like can be used. This reaction is generally performed at a temperature ranging from an ice cooling temperature to the reflux temperature of the solution. A solvent used in the alcoholysis of the compound (XX) is not especially limited as long as it is an inert solvent, and for example, 1,4-dioxane can be used. As an acid, hydrogen chloride or the like can be used. This reaction is accelerated by heating, but is generally performed at a temperature ranging from room temperature to the reflux temperature of the solution. A solvent used in the cyclization of the compound (XXI) is not especially limited as long as it is an inert solvent, and for example, methanol or the like can be used. As a base, DBU, TEA, potassium carbonate or cesium carbonate can be used. This reaction is accelerated by heating, but is generally performed at a temperature ranging from room temperature to the reflux temperature of the solution. A solvent used in the O-alkylation of the compound (XXII) is not especially limited as long as it is an inert solvent, and for example, DCM or toluene can be used. As an alkylating agent, trimethyloxonium tetrafluoroborate, dimethyl sulfate or the like can be used. This reaction is generally performed at a temperature ranging from an ice cooling temperature to the reflux temperature of the solution.

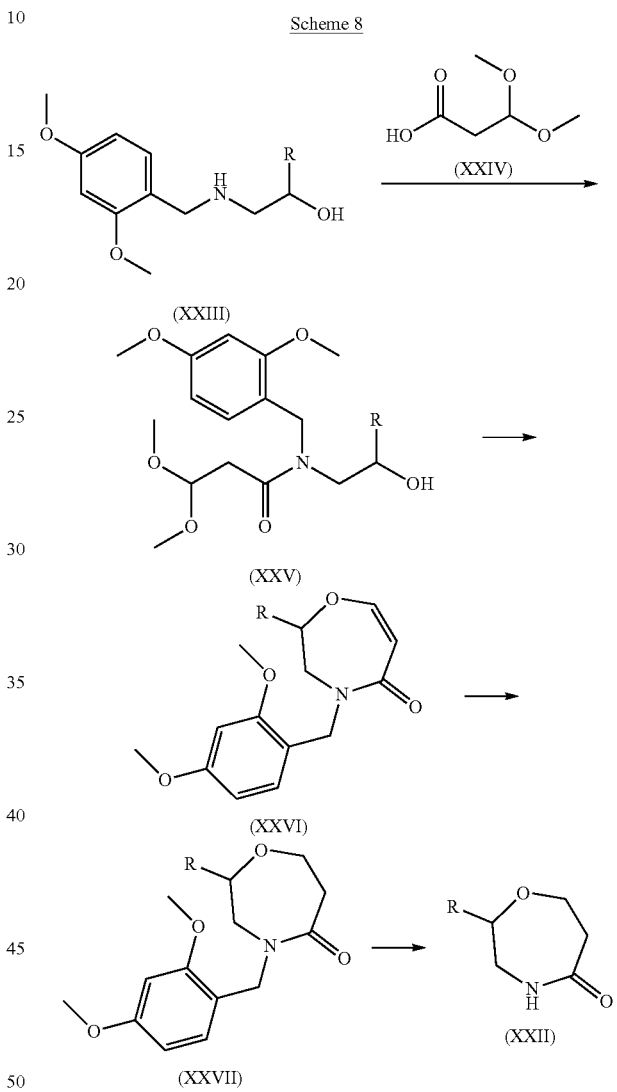

The compound (XXII) (wherein R is the same as defined above) can also be prepared in accordance with Scheme 8 by, for example, four steps of dehydrative condensation of a compound (XXIII) with a compound (XXIV), cyclization of a resulting compound (XXV) performed under acidic conditions, hydrogenation of a resulting compound (XXVI), and deprotection of a resulting compound (XXVII). A solvent used in the dehydrative condensation of the compound (XXIII) with the compound (XXIV) is not especially limited as long as it is an inert solvent, and for example, THF, DMF or DCM can be used. Besides, a condensation agent can be DCC, EDC, HOBt, HATU, HBTU or a combination of any of these. Furthermore, DIPEA, TEA or the like can be used as an additive in the reaction. This reaction is generally performed at a temperature ranging from an ice cooling temperature to the reflux temperature of the solution. A solvent used in the cyclization of the compound (XXV) is not especially limited as long as it is an inert solvent, and for example, THF, acetonitrile, toluene or xylene can be used. Besides, an acid can be, for example, PTS or PPTS. The reaction is accelerated by heating, but is generally performed at a temperature ranging from room temperature to the reflux temperature of the solution. A solvent used in the hydrogenation of the compound (XXVI) is not especially limited as long as it is an inert solvent, and for example, methanol, ethanol or THF can be used. As a catalyst, palladium/carbon, palladium hydroxide/carbon, platinum oxide or the like can be used. This reaction is generally performed at a temperature ranging from room temperature to the reflux temperature of the solution. The deprotection of the compound (XXVII) can be performed, for example, in a solvent such as TFA. As an additive, for example, a scavenger such as a triethyl silane can be used. This reaction is accelerated by heating, but is generally performed at a temperature ranging from room temperature to the reflux temperature of the solution.

The compound (I) of the present invention thus obtained can be prepared into a pharmaceutically acceptable salt by a conventional method as occasion demands. The preparation method can be an appropriate combination of, for example, methods conventionally employed in the field of synthetic organic chemistry. A specific example of the method includes neutralization titration of a solution of the free form of the present compound with an acid solution. Furthermore, the compound (I) of the present invention can be changed into a solvate by a known solvate forming reaction as occasion demands.

Representative examples of the method for producing the compound (I) have been described so far, and material compounds and various reagents used in the production method for the compound (I) may be in the form of a salt or a hydrate, and are different depending upon starting materials, solvents to be used and the like, and hence are not especially limited as long as the reactions are not retarded. Also the solvents to be used differ depending upon the starting materials, reagents and the like, and needless to say, are not especially limited as long as they do not retard the reactions and they dissolve starting materials to some extent. When the compound (I) is obtained in the form of a free form, it can be changed, by a conventional method, into the form of a salt that can be formed by the compound (I). Similarly, when the compound (I) is obtained in the form of a salt of the compound (I), it can be changed, by a conventional method, into a free form of the compound (I). Furthermore, various isomers (such as a geometric isomer, an optical isomer based on asymmetric carbon, a stereoisomer and a tautomer) obtained as the compound (I) can be purified and isolated by general separation means such as recrystallization, a diastereomeric salt formation method, enzymatic resolution, and various types of chromatography (including thin layer chromatography, column chromatography and gas chromatography).

A term "composition" used herein includes a product that contains a specific ingredient in a particular amount, and any product directly or indirectly prepared by a combination of particular ingredients in particular amounts. Such a term used in regard to a pharmaceutical composition is used to intend to include: a product containing an active ingredient and an inactive ingredient forming a carrier; and all products directly or indirectly prepared by combination, complexation or aggregation of any two or more ingredients, or dissociation, another type of reaction, or interaction of one or more ingredients. Accordingly, the pharmaceutical composition of the present invention includes all compositions prepared by mixing the tetrahydroimidazo[1,5-d][1,4]oxazepine derivative of the present invention with any of pharmaceutically acceptable carriers. The term "pharmaceutically acceptable" means that a carrier, a diluent or an excipient should be compatible with other ingredients of the formulation and should not be harmful to those who take the composition.

The compounds of the present invention mostly have, as binding ability to the group II metabotropic glutamate receptors, an IC50 value of 100 nM or less, and have an IC50 value of preferably 30 nM or less and more preferably 10 nM or less.

The tetrahydroimidazo[1,5-d][1,4]oxazepine derivative of the present invention or a pharmaceutically acceptable acid addition salt thereof has an antagonistic action against the group II metabotropic glutamate receptors. Accordingly, it is applicable as a therapeutic agent for diseases in which the antagonistic action against the group II metabotropic glutamate receptors effectively works. Examples of the diseases in which the antagonistic action against the group II metabotropic glutamate receptors effectively works include Alzheimer's disease.

The tetrahydroimidazo[1,5-d][1,4]oxazepine derivative of the present invention or a pharmaceutically acceptable acid addition salt thereof can be formulated by a general method, and the dosage form can be, for example, an oral formulation (such as a tablet, a granule, a powder, a capsule or a syrup), an injection formulation (for intravenous administration, intramuscular administration, subcutaneous administration, intraperitoneal administration or the like), or an external formulation (such as a transdermal absorbable drug (including an ointment, a patch and the like), an eye dropper, nasal drops or a suppository).

For producing an oral solid formulation, an excipient, a binder, a disintegrator, a lubricant, a colorant and the like can be added, if necessary, to the tetrahydroimidazo[1,5-d][1,4] oxazepine derivative of the present invention or a pharmaceutically acceptable acid addition salt thereof, and the resulting mixture can be prepared by a conventional method into tablets, granules, powders or capsules. Furthermore, the tablets, granules, powders or capsules can be coated with a film if necessary.

Examples of the excipient include lactose, corn starch and crystalline cellulose, examples of the binder include hydroxypropyl cellulose and hydroxypropylmethyl cellulose, examples of the disintegrator include carboxymethylcellulose calcium and croscarmellose sodium, examples of the lubricant include magnesium stearate and calcium stearate, an example of the colorant includes titanium oxide, and examples of a film-coating agent include hydroxypropyl cellulose, hydroxypropylmethyl cellulose and methyl cellulose, and it goes without saying that these ingredients are not limited to the aforementioned examples.

The solid formulation such as a tablet, a capsule, a granule or a powder may contain the tetrahydroimidazo[1,5-d][1,4] oxazepine derivative of the present invention, a pharmaceutically acceptable salt thereof, or a solvate thereof in a content of generally 0.001 to 99.5% by weight, preferably 0.001 to 90% by weight, and the like.

For producing an injection formulation (for intravenous administration, intramuscular administration, subcutaneous administration, intraperitoneal administration or the like), a pH adjuster, a buffer, a suspending agent, a solubilizing agent, an antioxidant, a preservative (an antiseptic agent), a tonicity adjusting agent and the like are added, if necessary, to the tetrahydroimidazo[1,5-d][1,4]oxazepine derivative of the present invention or a pharmaceutically acceptable acid addition salt thereof, and the resulting mixture can be prepared into an injection formulation by a conventional method. Furthermore, the resultant can be freeze-dried to be used as a lyophilized product to be dissolved before use.

Examples of the pH adjuster and the buffer include organic acids, inorganic acids and/or salts thereof, examples of the suspending agent include methyl cellulose, Polysorbate 80 and carboxymethyl cellulose sodium, examples of the solubilizing agent include Polysorbate 80 and polyoxyethylene sorbitan monolaurate, an example of the antioxidant includes α-tocopherol, examples of the preservative include methyl paraoxybenzoate and ethyl paraoxybenzoate, and examples of the tonicity adjusting agent include glucose, sodium chloride and mannitol, and it goes without saying that these ingredients are not limited to the aforementioned examples.

Such an injection formulation can contain the tetrahydroimidazo[1,5-d][1,4]oxazepine derivative of the present invention, a pharmaceutically acceptable salt thereof or a solvate thereof in a content of generally 0.000001 to 99.5% by weight, preferably 0.000001 to 90% by weight, and the like.

For producing an external formulation, a base material is added to the tetrahydroimidazo[1,5-d][1,4]oxazepine derivative or a pharmaceutically acceptable acid addition salt thereof of the present invention, and if necessary, for example, a preservative, a stabilizer, a pH adjuster, an antioxidant, a colorant and the like described above are further added thereto, and the resulting mixture is prepared by a conventional method into, for example, a transdermal absorbable drug (such as an ointment or a patch), an eye dropper, nasal drops or a suppository.

As the base material to be used, various materials usually used for, for example, medicines, quasi-drugs and cosmetics can be used. Specific examples of the material include animal and vegetable oils, mineral oils, ester oils, waxes, emulsifiers, higher alcohols, fatty acids, silicone oils, surfactants, phospholipids, alcohols, polyalcohols, water soluble polymers, clay minerals and purified water.

Such an external formulation can contain the tetrahydroimidazo[1,5-d][1,4]oxazepine derivative of the present invention, or a pharmaceutically acceptable salt thereof or a solvate thereof in a content of generally 0.000001 to 99.5% by weight, preferably 0.000001 to 90% by weight, and the like.

A dosage of the tetrahydroimidazo[1,5-d][1,4]oxazepine derivative of the present invention or a pharmaceutically acceptable acid addition salt thereof depends upon the level of symptom severity, the patient's age, sex and weight, the administration form and the kind of salt, a specific kind of disease and the like, and in an adult patient, it is administered, once or dividedly several times per day, at a dose for oral administration of generally approximately 30 μg to 10 g, preferably 100 μg to 5 g and more preferably 100 μg to 1 g, or a dose for injection administration of generally approximately 30 μg to 1 g, preferably 100 μg to 500 mg, and more preferably 100 μg to 300 mg.

The compound of the present invention can be used as a chemical probe for capturing a target protein of a biologically active low molecular weight compound. Specifically, the compound of the present invention can be transformed into an affinity chromatography probe, a photo-affinity probe or the like by introducing a labeling group, a linker or the like into a portion other than a structural portion indispensable to activity expression of the compound by a method described in J. Mass Spectrum. Soc. Jpn. Vol. 51, No. 5, 2003, p. 492-498, WO2007/139149 or the like.

Examples of the labeling group, the linker or the like used in such a chemical probe include groups belonging to the following groups (1) to (5):

(1) protein labeling groups such as photoaffinity labeling groups (such as a benzoyl group, a benzophenone group, an azido group, a carbonyl azide group, a diaziridine group, an enone group, a diazo group and a nitro group), and chemical affinity groups (such as a ketone group in which an alpha carbon atom is substituted with a halogen atom, a carbamoyl group, an ester group, an alkylthio group, a Michael receptor of α,β-unsaturated ketone, ester or the like, and an oxirane group);

(2) cleavable linkers such as —S—S—, —O—Si—O—, a monosaccharide (such as a glucose group or a galactose group) and a disaccharide (such as lactose), and oligopeptide linkers that can be cleaved by an enzyme reaction;

(3) fishing tag groups such as biotin and a 3-(4,4-difluoro-5,7-dimethyl-4H-3a,4a-diaza-4-bora-s-indacen-3-yl)propionyl group;

(4) radioactive labeling groups such as $^{125}$I, $^{32}$P, $^{3}$H and $^{14}$C; fluorescence labeling groups such as fluorescein, rhodamine, dansyl, umbelliferone, 7-nitrofurazanyl, and a 3-(4,4-difluoro-5,7-dimethyl-4H-3a,4a-diaza-4-bora-s-indacen-3-yl) propionyl group; chemiluminescent groups such as lumiferin and luminol; and detectable markers such as heavy metal ions such as lanthanoid metal ions and radium ions; and (5) groups to be bonded to a solid phase carrier such as glass beads, a glass bed, a microtiter plate, agarose beads, an agarose bed, polystyrene beads, a polystyrene bed, nylon beads and a nylon bed.

A probe prepared by introducing, into the compound of the present invention, a labeling group or the like selected from the above-described groups (1) to (5) by the method described in any of the aforementioned literatures or the like can be used as a chemical probe for identifying a marker protein useful for research of a novel potential drug target or the like.

Hereinafter, the present invention will be described in detail with reference to Examples, Production Examples, and Test Examples. However, the present invention is not limited to them. In addition, abbreviations used in Examples are commonly used abbreviations well known to the person skilled in the art, and some of the abbreviations will be described below.

(A-taPhos)$_2$PdCl$_2$: bis(di-tert-butyl(4-dimethylaminophenyl)phosphine)dichloropalladium(II)
BAST: bis(2-methoxyethyl)aminosulfurtrifluoride
Bn: benzyl
Boc: tert-butoxycarbonyl
CSA: camphorsulfonic acid
DAST: diethylaminosulfurtrifluoride
DBN: 1,5-diazabicyclo[4.3.0]non-5-ene
DBU: 1,8-diazabicyclo[5.4.0]undec-7-ene
DCC: 1,3-dicyclohexylcarbodiimide
DCE: 1,2-dichloroethane
DCM: dichloromethane
DIPEA: diisopropylethylamine
DME: dimethoxyethane
DMF: N,N-dimethylformamide
DMPI: Dess-Martin Periodinane
DMSO: dimethylsulfoxide
EDC: 1-ethyl-3-(3-dimethylaminopropyl)carbodiimide hydrochloride HATU: O-(7-azabenzotriazol-1-yl)-N,N,N',N'-tetramethyl-uronium hexafluorophosphate
HBTU: O-benzotriazole-N,N,N',N'-tetramethyluronium hexafluorophosphate
HFIP: 1,1,1,3,3,3-hexafluoro-2-propanol
HOBT: 1-hydroxybenzotriazole
mCPBA: 3-chloroperbenzoic acid
MOM: methoxymethyl
n-: normal
NBS: N-bromosuccinimide
NMM: N-methylmorpholine
Pd(dppf)Cl$_2$.CH$_2$Cl$_2$: (1,1'-bis(diphenylphosphino)ferrocene-dichloropalladium-dichloromethane complex
Pd$_2$DBA$_3$: tris(dibenzylideneacetone)dipalladium
PPTS: pyridinium paratoluenesulfonate
PTS: paratoluenesulfonic acid
tert-: tertiary
TBAF: tetrabutylammonium fluoride
TBS: tert-butyldimethylsilyl
TBSCl: tert-butyldimethylsilyl chloride
TBME: tert-butyl methyl ether
TEA: triethylamine
TFA: trifluoroacetic acid
THF: tetrahydrofuran
Ts: paratoluenesulfonyl
$^1$H-NMR: proton nuclear magnetic resonance spectrometry Chemical shifts of proton nuclear magnetic resonance spectra are recorded in the unit of δ (ppm) with respect to tetramethylsilane and coupling constants are recorded in the unit of Herz (Hz). Patterns include: s; singlet, d; doublet, t; triplet, q; quartet, br; broad, and sep; septet.

The term "room temperature" in Examples and Production Examples described below usually stands for a temperature in the range of about 10° C. to 35° C. The symbol "%" denotes % by weight, unless otherwise described.

The chemical names of compounds in Examples and Production Examples were determined based on their chemical structures with reference to "E-Notebook", version 12 (PerkinElmer Inc.).

Production Example 1

Synthesis of (R)-5-methoxy-2-methyl-2,3,6,7-tetrahydro-1,4-oxazepine

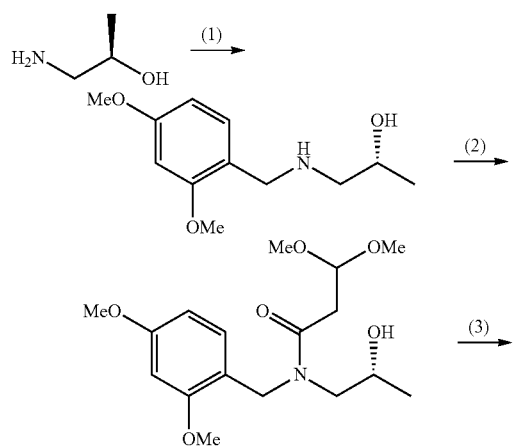

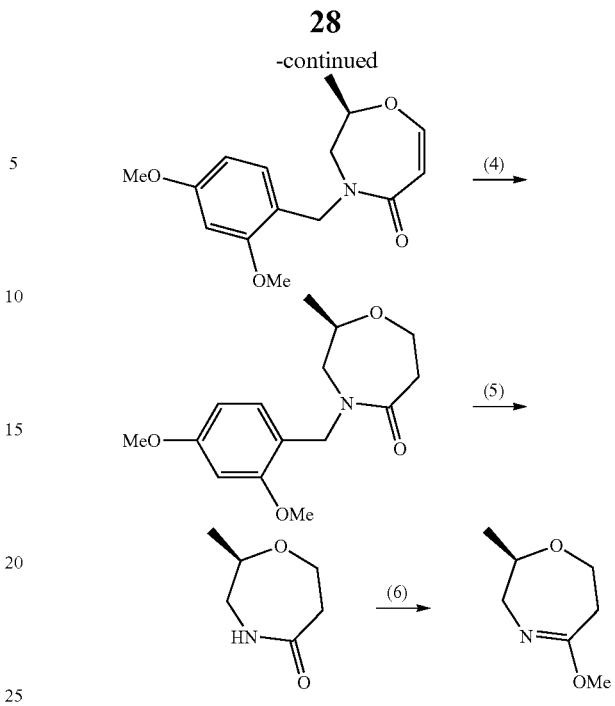

(1) Synthesis of (R)-1-((2,4-dimethoxybenzyl)amino)propan-2-ol 2,4-Dimethoxybenzaldehyde (CAS No. 613-45-65; 55.8 g, 336 mmol) was added to a solution of (R)-(−)-1-amino-2-propanol (CAS No. 2799-16-8; 24.0 g, 320 mmol) and acetic acid (40.2 mL, 703 mmol) in THF (440 mL) at room temperature, and the mixture was stirred at room temperature for 1 hour. Sodium triacetoxyborohydride (102 g, 479 mmol) was added to the reaction liquid at room temperature, and the mixture was stirred for 18 hours. The solvent was concentrated under reduced pressure after the reaction. A 5 N aqueous sodium hydroxide solution (100 mL) and ethyl acetate (500 mL) were added to the resultant residue to separate the organic layer. Chloroform (300 mL) was added to the resultant water layer to separate the organic layer. The resultant organic layers were combined, and the resultant was washed with a saturated aqueous sodium chloride solution and then dried over anhydrous magnesium sulfate. The drying agent was filtered off, and then the solvent was evaporated under reduced pressure. The resultant residue was filtered through NH silica gel (ethyl acetate) for purification to obtain a crude title compound (72 g).
$^1$H-NMR (400 MHz, CDCl$_3$) δ (ppm): 1.13 (d, J=6.3 Hz, 3H), 2.34 (dd, J=9.4, 12.1 Hz, 1H), 2.68 (dd, J=3.1, 12.1 Hz, 1H), 3.72 (d, J=2.0 Hz, 2H), 3.75-3.79 (m, 1H), 3.80 (s, 3H), 3.82 (s, 3H), 6.39-6.48 (m, 2H), 7.10 (d, J=8.2 Hz, 1H).

(2) Synthesis of (R)—N-(2,4-dimethoxybenzyl)-N-(2-hydroxypropyl)-3,3-dimethoxypropanamide DIPEA (173 mL, 995 mmol) was added to a solution of the compound obtained in Production Example 1-(1) (74.7 g, 332 mmol), 3,3-dimethoxypropionic acid (CAS No. 6191-98-6; 38.5 g, 287 mmol), EDC (95 g, 497 mmol), and HOBT (67.2 g, 497 mmol) in DMF (500 mL) at room temperature, and the mixture was stirred for 14 hours. Water (1 L) and ethyl acetate (1 L) were added to the reaction mixture to separate the organic layer. The resultant organic layer was washed with water (1 L) and a saturated aqueous sodium chloride solution, then dried over anhydrous magnesium sulfate, the drying agent was filtered off, and the solvent was evaporated under reduced pressure. The resultant residue was purified by NH-silica gel column chromatography (n-heptane/ethyl acetate) to obtain a title compound (61 g, 179 mmol).

ESI-MS m/z 342 [M+H]$^+$

(3) Synthesis of (R)-4-(2,4-dimethoxybenzyl)-2-methyl-3,4-dihydro-1,4-oxazepin-5(2H)-one PPTS (19.7 g, 78.4 mmol) was added to a solution of the compound obtained in Production Example 1-(2) (53.5 g, 157 mmol) in toluene (900 mL) at room temperature, and then the mixture was heated under reflux for 7 hours. The reaction mixture was cooled to room temperature and then a saturated aqueous sodium bicarbonate solution and ethyl acetate were added to separate the organic layer. The resultant organic layer was washed with a saturated aqueous sodium chloride solution and then dried over anhydrous magnesium sulfate, the drying agent was filtered off, and then the solvent was evaporated under reduced pressure. The resultant residue was purified by silica gel column chromatography (n-heptane/ethyl acetate) to obtain a title compound (30.5 g, 110 mmol).

$^1$H-NMR (400 MHz, CDCl3) δ (ppm): 1.19 (d, J=6.6 Hz, 3H), 3.39-3.44 (m, 2H), 3.80 (s, 3H), 3.82 (s, 3H), 4.03-4.11 (m, 1H), 4.44 (d, J=14.5 Hz, 1H), 4.73 (d, J=14.5 Hz, 1H), 5.08 (d, J=8.2 Hz, 1H), 6.43-6.48 (m, 3H), 7.24 (d, J=9.0 Hz, 1H).

(4) Synthesis of (R)-4-(2,4-dimethoxybenzyl)-2-methyl-1,4-oxazepan-5-one

20% Palladium hydroxide/carbon (3 g, including 50% water content) was added to a solution of the compound obtained in Production Example 1-(3) (30.5 g, 110 mmol) in methanol (500 mL) at room temperature, and the mixture was stirred under hydrogen atmosphere at 40° C. for 18 hours. The reaction mixture was cooled to room temperature and then was filtered through Celite (trademark), and the filtrate was concentrated under reduced pressure. The resultant residue was purified by silica gel column chromatography (ethyl acetate) to obtain a title compound (29.1 g, 104 mmol).

$^1$H-NMR (400 MHz, CDCl3) δ (ppm): 1.05 (d, J=6.6 Hz, 3H), 2.60 (dd, J=5.1, 15.6 Hz, 1H), 2.92 (ddd, J=2.2, 11.0, 15.4 Hz, 1H), 3.20 (d, J=15.2 Hz, 1H), 3.29-3.38 (m, 1H), 3.40-3.50 (m, 1H), 3.56-3.66 (m, 1H), 3.81 (s, 3H), 3.82 (s, 3H), 3.96 (ddd, J=2.3, 5.5, 12.5 Hz, 1H), 4.37 (d, J=14.5 Hz, 1H), 4.70 (d, J=14.5 Hz, 1H), 6.43-6.48 (m, 2H), 7.21 (d, J=8.6 Hz, 1H).

(5) Synthesis of (R)-2-methyl-1,4-oxazepan-5-one

Triethylsilane (26.2 mL, 164 mmol) was added to a solution of the compound obtained in Production Example 1-(4) (30.5 g, 110 mmol) in TFA (150 mL) at room temperature, and the mixture was stirred at 60° C. for 3 hours. The reaction mixture was cooled to room temperature and then concentrated under reduced pressure. The resultant residue was purified by silica gel column chromatography (ethyl acetate/methanol) to obtain a title compound (12.3 g, 95 mmol).

$^1$H-NMR (400 MHz, CDCl3) δ (ppm): 1.19 (d, J=6.3 Hz, 3H), 2.48-2.58 (m, 1H), 2.89 (ddd, J=2.5, 10.9, 15.4 Hz, 1H), 3.03 (ddd, J=0.9, 7.6, 15.3 Hz, 1H), 3.35 (ddd, J=3.9, 8.4, 15.4 Hz, 1H), 3.57-3.76 (m, 2H), 4.01 (ddd, J=2.5, 5.3, 12.7 Hz, 1H), 5.85-6.07 (m, 1H).

(6) Synthesis of (R)-5-methoxy-2-methyl-2,3,6,7-tetrahydro-1,4-oxazepine

Trimethyloxonium tetrafluoroborate (16.8 g, 114 mmol) was added to a solution of the compound obtained in Production Example 1-(5) (13.4 g, 103 mmol) in DCM (500 mL) at room temperature, and the mixture was stirred for 18 hours. A saturated aqueous sodium bicarbonate solution was added to the reaction mixture, and the organic layer was separated. DCM was added to the resultant water layer, and the organic layer was separated. The resultant organic layers were combined, the resultant was washed with a saturated aqueous sodium chloride solution, then the resultant was dried over anhydrous magnesium sulfate, and then the drying agent was filtered off and the solvent was evaporated under reduced pressure to obtain a title compound (13.7 g, 96 mmol).

$^1$H-NMR (400 MHz, CDCl3) δ (ppm): 1.19 (d, J=6.4 Hz, 3H), 2.42 (ddd, J=1.2, 4.5, 15.6 Hz, 1H), 2.81-2.92 (m, 1H), 3.33-3.42 (m, 1H), 3.47-3.59 (m, 3H), 3.61 (s, 3H), 3.85-3.93 (m, 1H).

Production Example 2

Synthesis of (R)-2-methyl-1,4-oxazepan-5-one

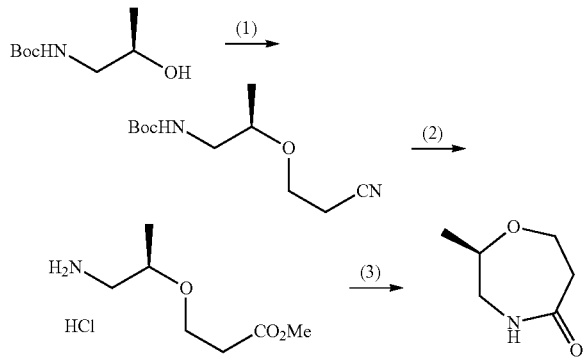

(1) Synthesis of (R)-tert-butyl(2-(2-cyanoethoxy)propyl)carbamate

DBU (27.3 mL, 182 mmol) was added to a solution of (R)-tert-butyl(2-hydroxypropyl)carbamate (CAS No. 119768-44-4; 71.0 g, 405 mmol) in acrylonitrile (400 mL) at room temperature, and the mixture was stirred at the same temperature for 5 hours. Acetic acid (10.4 mL, 182 mmol) was added to the reaction mixture, and the mixture was concentrated under reduced pressure. The resultant residue was purified by silica gel column chromatography (n-heptane/ethyl acetate) to obtain a title compound (63.1 g, 276 mmol).

$^1$H-NMR (400 MHz, CDCl3) δ (ppm): 1.10-1.20 (m, 3H), 1.45 (s, 9H), 2.59 (dd, J=6.3, 6.3 Hz, 2H), 2.96-3.11 (m, 1H), 3.23-3.41 (m, 1H), 3.52-3.66 (m, 1H), 3.61 (td, J=6.3, 9.2 Hz, 1H), 3.75 (td, J=6.3, 9.2 Hz, 1H), 4.88 (brs, 1H).

(2) Synthesis of (R)-methyl 3-((1-aminopropan-2-yl)oxy)propanoate hydrochloride The compound obtained in Production Example 2-(1) (63.1 g, 276 mmol) was dissolved in a 4 M hydrogen chloride/1,4-dioxane solution (691 mL) and a 5 to 10% hydrogen chloride/methanol solution (140 mL), and the mixture was stirred at 50° C. for 3 hours. A 4 M hydrogen chloride/1,4-dioxane solution (311 mL) was further added to the reaction mixture, the mixture was stirred at 50° C. for 3 hours, and then the resultant was concentrated under reduced pressure. Diethyl ether was added to the residue and the resultant was concentrated under reduced pressure to obtain a crude title compound (76.9 g).

ESI-MS m/z 162 [M+H]+

(3) Synthesis of (R)-2-methyl-1,4-oxazepan-5-one

DBU (132 mL, 884 mmol) was added to a solution of the compound obtained in Production Example 2-(2) (76.9 g) in methanol (693 mL) at room temperature, and the mixture was heated under reflux for 16 hours. The reaction mixture was cooled to room temperature and then concentrated under reduced pressure. The resultant residue was purified by silica gel column chromatography (ethyl acetate/methanol) twice to obtain a title compound (21.5 g, 166 mmol).

$^1$H-NMR (400 MHz, CDCl3) δ (ppm): 1.19 (d, J=6.3 Hz, 3H), 2.48-2.58 (m, 1H), 2.89 (ddd, J=2.5, 10.9, 15.4 Hz, 1H), 3.03 (ddd, J=0.9, 7.6, 15.3 Hz, 1H), 3.35 (ddd, J=3.9, 8.4, 15.4 Hz, 1H), 3.57-3.76 (m, 2H), 4.01 (ddd, J=2.5, 5.3, 12.7 Hz, 1H), 5.85-6.07 (m, 1H).

ESI-MS m/z 130 [M+H]+

Production Example 3

Synthesis of (S)-2-(fluoromethyl)-5-methoxy-2,3,6,7-tetrahydro-1,4-oxazepine

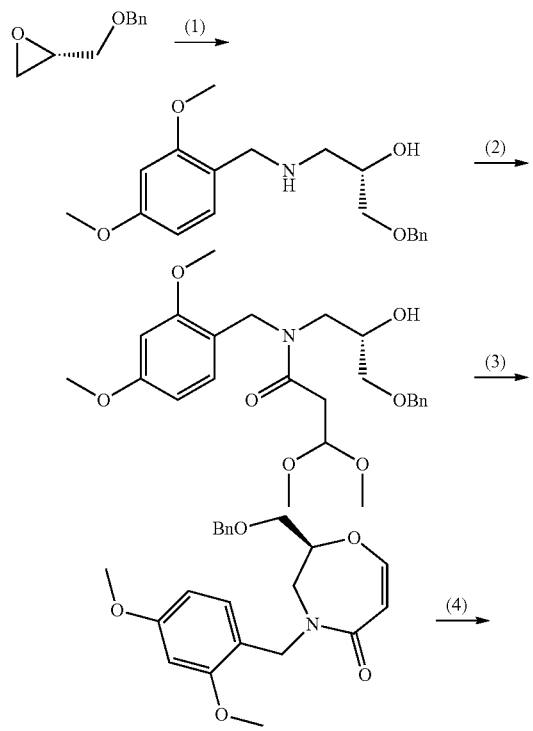

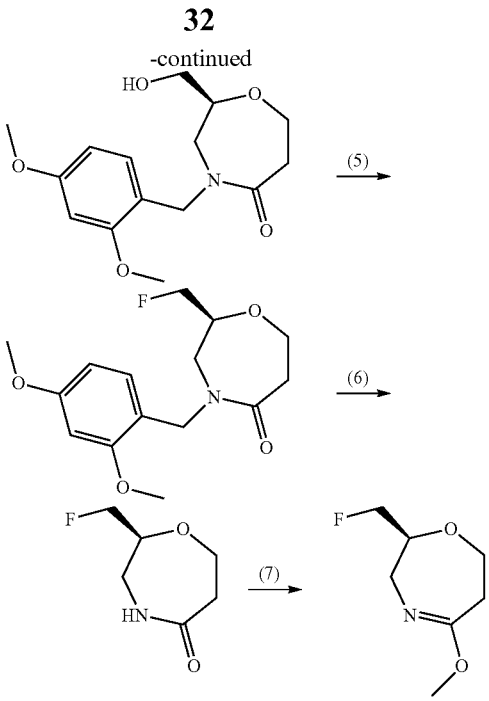

(1) Synthesis of (S)-1-(benzyloxy)-3-((2,4-dimethoxybenzyl)amino)propan-2-ol

Lithium bis(trifluoromethanesulfonyl)imide (87 g, 304.5 mmol) was added to a solution of 2,4-dimethoxybenzylamine (CAS No. 20781-20-8; 46.7 mL, 310.6 mmol) and (S)-(+)-benzyl glycidyl ether (CAS No. 16495-13-9; 50.0 g, 304.5 mmol) in DCM (1.0 L) under water-cooling. The reaction mixture was stirred at room temperature for 20 hours. Water was added to the reaction mixture to separate the organic layer. The organic layers were dried over anhydrous magnesium sulfate. The solvent was evaporated under reduced pressure to obtain a crude title compound (119.4 g).

ESI-MS m/z 332 [M+H]+

(2) Synthesis of (S)—N-(3-(benzyloxy)-2-hydroxypropyl)-N-(2,4-dimethoxybenzyl)-3,3-dimethoxypropanamide EDC (88 g, 456.7 mmol) and HOBT (456.7 mmol) were added to a solution of the compound obtained in Production Example 3-(1) (119.4 g), 3,3-dimethoxypropionic acid (47.0 g, 350.1 mmol), and DIPEA (159 mL) in DMF (800 mL) at room temperature. The reaction mixture was stirred for 16 hours, and then ethyl acetate and a saturated aqueous sodium chloride solution were added. The organic layer was separated and washed with a saturated aqueous sodium chloride solution. The organic layer was dried over anhydrous magnesium sulfate. The organic layer was filtered through a silica gel pad (NH silica gel+silica gel, ethyl acetate). The resultant filtrate was concentrated under reduced pressure to obtain a crude title compound (125.5 g).

ESI-MS m/z 470 [M+Na]+

(3) Synthesis of (S)-2-((benzyloxy)methyl)-4-(2,4-dimethoxybenzyl)-3,4-dihydro-1,4-oxazepin-5(2H)-one A solution of the compound obtained in Production Example 3-(2) (125.5 g) and PPTS (35.2 g, 140.2 mmol) in xylene (1 L) was heated under reflux for 6 hours. The reaction mixture was cooled to room temperature, and ethyl acetate and a saturated aqueous sodium bicarbonate solution were added to the reaction mixture to separate the organic layer. The organic layer was washed with a saturated aqueous sodium chloride solution and then dried over anhydrous magnesium sulfate. The organic layer was concentrated under reduced pressure and the resultant residue was purified by column chromatography (n-heptane/ethyl acetate) to obtain a title compound (57.7 g, 150 mmol).

ESI-MS m/z 384 [M+H]+, 406 [M+Na]+

(4) Synthesis of (S)-4-(2,4-dimethoxybenzyl)-2-(hydroxymethyl)-1,4-oxazepan-5-one A mixture of the compound obtained in Production Example 3-(3) (57.7 g, 150.5 mmol), 20% palladium hydroxide/carbon (6 g, including 50% water content), acetic acid (20 mL), and ethanol (600 mL) was stirred under hydrogen atmosphere at 4 to 5 MPa and 70° C. for 50 hours. The reaction mixture was cooled to room temperature. The insolubles were filtered off through Celite (trademark) and the resultant was washed with ethyl acetate. The filtrate was concentrated under reduced pressure. The resultant residue was purified by silica gel column chromatography (n-heptane/ethyl acetate→ethyl acetate/methanol) to obtain a title compound (33.7 g).

$^1$H-NMR (400 MHz, CDCl3) δ (ppm): 1.83 (dd, J=5.1, 7.0 Hz, 1H), 2.63 (dd, J=5.1, 15.2 Hz, 1H), 2.95 (ddd, J=2.7, 11.3, 15.6 Hz, 1H), 3.22-3.30 (m, 2H), 3.40-3.45 (m, 2H), 3.51 (dd, J=8.2, 16.0 Hz, 1H), 3.62-3.67 (m, 1H), 3.80 (s, 3H), 3.81 (s, 3H), 4.04 (ddd, J=2.3, 5.1, 12.5 Hz, 1H), 4.36 (d, J=14.5 Hz, 1H), 4.73 (d, J=14.5 Hz, 1H), 6.43-6.47 (m, 2H), 7.22 (d, J=8.6 Hz, 1H).

ESI-MS m/z 296 [M+H]+, 318 [M+Na]+

(5) Synthesis of (S)-4-(2,4-dimethoxybenzyl)-2-(fluoromethyl)-1,4-oxazepan-5-one Perfluorobutanesulfonyl fluoride (45.1 mL, 251.0 mmol) was added to a solution of the compound obtained in Production Example 3-(4) (33.7 g, 114.1 mmol), DIPEA (49.2 mL, 285.3 mmol), and tetrabutylammonium difluorotriphenyl silicate (73.9 g, 136.9 mmol) in THF (600 mL) at room temperature. The reaction mixture was stirred at room temperature for 64 hours. The reaction mixture was concentrated under reduced pressure. A mixed solvent of toluene/ethyl acetate (5/1) and a saturated aqueous sodium chloride solution were added to the resultant residue to separate the organic layer. The organic layer was further washed with a saturated aqueous sodium chloride solution twice. The organic layer was concentrated under reduced pressure and the resultant residue was purified serially by silica gel column chromatography (n-heptane/ethyl acetate) and NH silica gel column chromatography (n-heptane/ethyl acetate) to obtain a crude title compound (41 g).

$^1$H-NMR (400 MHz, CDCl3) δ (ppm): 2.62 (dd, J=5.5, 15.2 Hz, 1H), 2.96 (ddd, J=2.3, 11.3, 15.2 Hz, 1H), 3.35-3.68 (m, 4H), 3.80 (s, 3H), 3.81 (s, 3H), 4.00 (ddd, J=2.3, 5.1, 12.5 Hz, 1H), 4.09-4.36 (m, 2H), 4.40 (d, J=14.5 Hz, 1H), 4.74 (d, J=14.5 Hz, 1H), 6.44-6.47 (m, 2H), 7.24 (d, J=8.2 Hz, 1H).

ESI-MS m/z 298 [M+H]+

(6) Synthesis of (S)-2-(fluoromethyl)-1,4-oxazepan-5-one

Triethylsilane (27.4 mL, 171.7 mmol) was added to a solution of the compound obtained in Production Example 3-(5) (41 g) in TFA (300 mL) at room temperature. The reaction mixture was stirred at 60° C. for 3 hours. The reaction mixture was concentrated under reduced pressure. The resultant residue was purified by silica gel column chromatography (n-heptane/ethyl acetate→ethyl acetate/methanol) to obtain a title compound (15 g, 101.94 mmol).

$^1$H-NMR (400 MHz, CDCl3) δ (ppm): 2.54 (ddd, J=2.0, 5.1, 15.6 Hz, 1H), 2.93 (ddd, J=2.7, 11.3, 15.6 Hz, 1H), 3.23-3.31 (m, 1H), 3.46 (ddd, J=3.5, 8.6, 15.2 Hz, 1H), 3.66-3.78 (m, 2H), 4.07 (ddd, J=2.7, 5.1, 12.5 Hz, 1H), 4.24-4.53 (m, 2H), 6.50 (brs, 1H).

(7) Synthesis of (S)-2-(fluoromethyl)-5-methoxy-2,3,6,7-tetrahydro-1,4-oxazepine Trimethyloxonium tetrafluoroborate (17.34 g, 117.2 mmol) was added to a solution of the compound obtained in Production Example 3-(6) (15 g, 101.94 mmol) in DCM (400 mL) at room temperature. The reaction solution was stirred at room temperature for 14 hours. A saturated aqueous sodium bicarbonate solution was added to the reaction mixture, and the mixture was stirred at room temperature for 30 minutes. Chloroform was added to the mixture to separate the organic layer. The organic layer was dried over anhydrous magnesium sulfate. The organic layer was concentrated under reduced pressure to obtain a title compound (14.9 g, 93 mmol).

$^1$H-NMR (400 MHz, CDCl3) δ (ppm): 2.47 (ddd, J=1.2, 4.3, 15.6 Hz, 1H), 2.87-2.96 (m, 1H), 3.45-3.70 (m, 4H), 3.63 (s, 3H), 3.98 (ddd, J=3.1, 4.3, 12.1 Hz, 1H), 4.30-4.50 (m, 2H).

Production Example 4

Synthesis of (S)-2-(fluoromethyl)-1,4-oxazepan-5-one

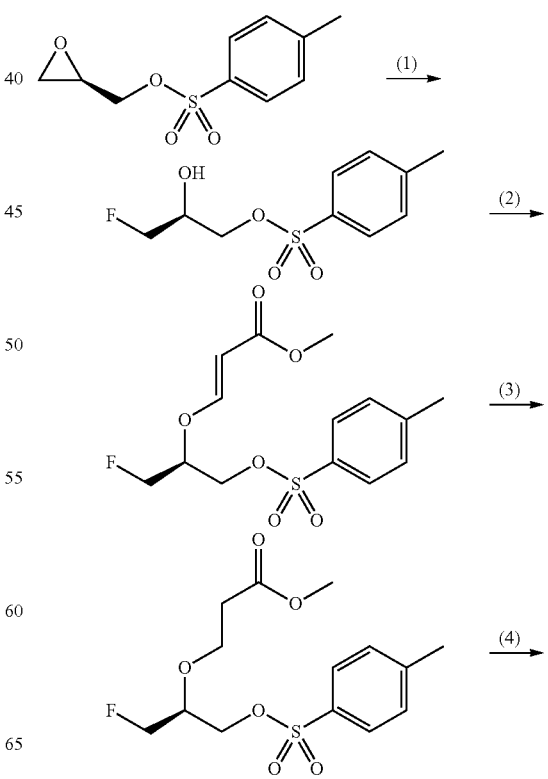

-continued

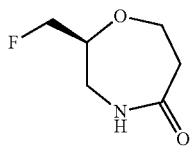

(1) Synthesis of (S)-3-fluoro-2-hydroxypropyl-4-methylbenzene sulfonate

Diethyl ether (1.00 L), (2R)-(–)-glycidyl tosylate (CAS No. 113826-06-5; 50.0 g, 219 mmol), and benzoyl fluoride (33.4 mL, 307 mmol) were added to a mixture of (R,R)-(–)-N,N'-bis(3,5-di-tert-butylsalicylidene)-1,2-cyclohexanediaminocobalt(II) (9.26 g, 15.3 mmol), HFIP (64.4 mL, 613 mmol), and DBN (1.51 mL, 12.3 mmol). The reaction mixture was stirred at room temperature overnight and then a 7 M ammonia/methanol solution (150 mL) was added. The mixture was stirred at room temperature for 2 hours and the solvent was evaporated under reduced pressure. Ethyl acetate (300 mL) was added to the resultant residue, and the resultant was washed serially with water and a saturated aqueous sodium chloride solution. The organic layer was dried over anhydrous magnesium sulfate, and the solvent was evaporated under reduced pressure. The resultant residue was purified by silica gel column chromatography (n-heptane/ethyl acetate) to obtain a title compound (45.5 g, 183 mmol).

$^1$H-NMR (400 MHz, CDCl3) δ (ppm): 2.28-2.42 (m, 1H), 2.46 (s, 3H), 4.03-4.18 (m, 3H), 4.34-4.54 (m, 2H), 7.37 (d, J=8.2 Hz, 2H), 7.81 (d, J=8.2 Hz, 2H).

ESI-MS m/z 271 [M+Na]+

(2) Synthesis of (S,E)-methyl 3-((1-fluoro-3-(tosyloxy)propan-2-yl)oxy)acrylate

A solution of the compound obtained in Production Example 4-(1) (45.5 g, 183 mmol), NMM (12.1 mL, 110 mmol), and methyl propionate (CAS No. 922-67-8; 19.8 mL, 238 mmol) in THF (315 mL) was stirred under ice-cooling for 3 hours. Acetic acid (6.29 mL, 110 mmol) was added to the reaction mixture, and then water and ethyl acetate were added. The organic layer was separated and washed serially with water and a saturated aqueous sodium chloride solution. The organic layer was dried over anhydrous magnesium sulfate and then concentrated under reduced pressure. The resultant residue was purified by silica gel column chromatography (n-heptane/ethyl acetate) to obtain a title compound (49.2 g, 148 mmol).

$^1$H-NMR (400 MHz, CDCl3) δ (ppm): 2.46 (s, 3H), 3.70 (s, 3H), 4.11-4.37 (m, 3H), 4.42-4.66 (m, 2H), 5.26 (d, J=12.5 Hz, 1H), 7.33-7.42 (m, 3H), 7.76-7.83 (m, 2H).

ESI-MS m/z 355 [M+Na]+

(3) Synthesis of (S)-methyl 3-((1-fluoro-3-(tosyloxy)propan-2-yl)oxy)propanoate

A suspension of the compound obtained in Production Example 4-(2) (48.8 g, 147 mmol) and 5% palladium/carbon (6.25 g, including 50% water content) in ethanol (279 mL) was stirred under hydrogen atmosphere at room temperature for 2 hours. The insolubles were removed, and then the filtrate was concentrated under reduced pressure to obtain a crude title compound (45.8 g).

$^1$H-NMR (400 MHz, CDCl3) δ (ppm): 2.46 (s, 3H), 2.53 (t, J=6.3 Hz, 2H), 3.68 (s, 3H), 3.27-3.87 (m, 3H), 4.08 (dt, J=1.6, 5.5 Hz, 2H), 4.29-4.53 (m, 2H), 7.36 (d, J=8.2 Hz, 2H), 7.80 (d, J=8.2 Hz, 2H).

ESI-MS m/z 357 [M+Na]+

(4) Synthesis of (S)-2-(fluoromethyl)-1,4-oxazepan-5-one

A mixture of the compound obtained in Production Example 4-(3) (45.8 g, 137 mmol) and a 7 M ammonia/methanol solution (391 mL, 2.74 mol) was stirred in an autoclave at 130° C. for 2 hours. The reaction mixture was cooled to room temperature, and then the mixture was concentrated under reduced pressure. Methanol (300 mL) and DBU (41.0 mL, 274 mmol) were added to the residue at room temperature. The reaction mixture was stirred at 100° C. for 3 hours. The reaction mixture was cooled to room temperature and then concentrated under reduced pressure. The resultant residue was purified by silica gel column chromatography (n-heptane/ethyl acetate→ethyl acetate/methanol) to obtain a title compound (10.4 g, 70.7 mmol).

$^1$H-NMR (400 MHz, CDCl3) δ (ppm): 2.54 (ddd, J=2.0, 5.1, 15.6 Hz, 1H), 2.93 (ddd, J=2.7, 11.3, 15.6 Hz, 1H), 3.23-3.31 (m, 1H), 3.46 (ddd, J=3.5, 8.6, 15.2 Hz, 1H), 3.66-3.78 (m, 2H), 4.07 (ddd, J=2.7, 5.1, 12.5 Hz, 1H), 4.24-4.53 (m, 2H), 6.50 (brs, 1H).

ESI-MS m/z 295 [M+M+H]+

Production Example 5

Synthesis of (S)-2-(difluoromethyl)-5-methoxy-2,3,6,7-tetrahydro-1,4-oxazepine

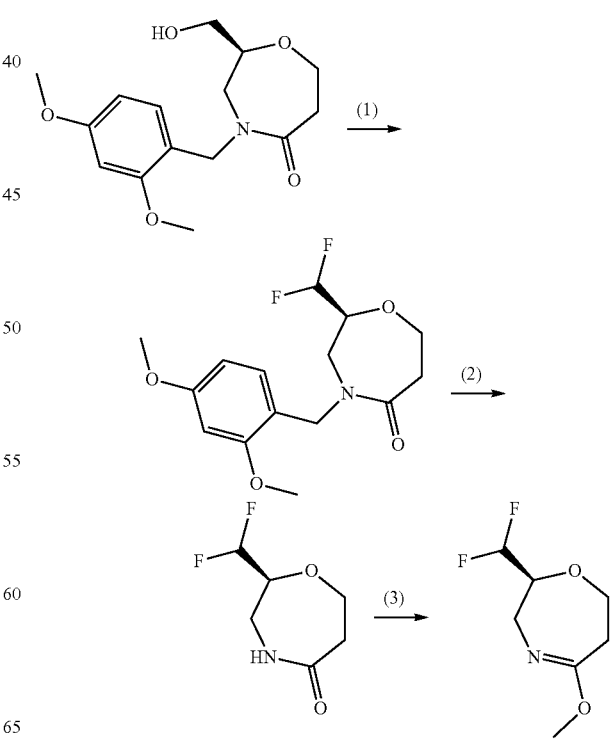

(1) Synthesis of (S)-2-(difluoromethyl)-4-(2,4-dimethoxybenzyl)-1,4-oxazepan-5-one Oxalyl chloride (1.18 mL, 14.0 mmol) was added to a solution of DMSO (1.03 mL, 14.5 mmol) in THF (60 mL) under nitrogen atmosphere at −78° C. The mixture was stirred at −78° C. for 10 minutes and a solution of the compound obtained in Production Example 3-(4) (3.30 g, 11.2 mmol) in THF (40 mL) was added dropwise at the same temperature. After the mixture was stirred at the same temperature for 1 hour, DIPEA (7.79 mL, 44.7 mmol) was added dropwise. After 10 minutes, the reaction mixture was warmed to room temperature and further stirred for 1 hour. An aqueous ammonium chloride solution and ethyl acetate were added to the mixture to separate the organic layer. The organic layer was washed with a saturated aqueous sodium chloride solution and dried over anhydrous magnesium sulfate. The organic layer was concentrated under reduced pressure. The resultant residue was dissolved in DCM (66 mL) and the resultant was cooled to −78° C. BAST (6.18 mL, 33.5 mmol) was added to the mixture at the same temperature, then the resultant was slowly warmed to room temperature and stirred for 15 hours. A saturated aqueous sodium chloride solution and ethyl acetate were added to the reaction mixture to separate the organic layer. The organic layer was washed with a saturated aqueous sodium chloride solution and dried over anhydrous magnesium sulfate. The organic layer was concentrated under reduced pressure. The resultant residue was purified by silica gel column chromatography (n-heptane/ethyl acetate) to obtain a title compound (1.13 g, 3.58 mmol).

$^1$H-NMR (400 MHz, CDCl3) δ (ppm): 2.63 (dd, J=5.1, 15.6 Hz, 1H), 2.97 (ddd, J=2.4, 11.4, 15.6 Hz, 1H), 3.26-3.36 (m, 1H), 3.60 (d, J=4.7 Hz, 2H), 3.77-3.84 (m, 1H), 3.80 (s, 3H), 3.81 (s, 3H), 4.04-4.10 (m, 1H), 4.36 (d, J=14.1 Hz, 1H), 4.75 (d, J=14.1 Hz, 1H), 5.47-5.76 (m, 1H), 6.44-6.47 (m, 2H), 7.24-7.27 (m, 1H).

ESI-MS m/z 316 [M+H]+

(2) Synthesis of (S)-2-(difluoromethyl)-1,4-oxazepan-5-one

Triethylsilane (0.881 mL, 5.52 mmol) was added to a solution of the compound obtained in Production Example 5-(1) (1.16 g, 3.68 mmol) in TFA (10 mL) at room temperature. The reaction mixture was stirred at 60° C. for 3 hours. The reaction mixture was cooled to room temperature and the solvent was evaporated under reduced pressure. The resultant residue was purified by silica gel column chromatography (n-heptane/ethyl acetate→ethyl acetate/methanol) to obtain a title compound (472 mg, 2.86 mmol).

$^1$H-NMR (400 MHz, CDCl3) δ (ppm): 2.57 (ddd, J=1.9, 4.8, 15.7 Hz, 1H), 2.95 (ddd, J=2.7, 11.3, 15.6 Hz, 1H), 3.35 (dd, J=7.8, 15.4 Hz, 1H), 3.54 (ddd, J=3.7, 8.8, 15.5 Hz, 1H), 3.63-3.78 (m, 2H), 4.14 (ddd, J=2.7, 5.0, 12.8 Hz, 1H), 5.63-5.92 (m, 1H), 6.00 (brs, 1H).

(3) Synthesis of (S)-2-(difluoromethyl)-5-methoxy-2,3,6,7-tetrahydro-1,4-oxazepine Trimethyloxonium tetrafluoroborate (597 mg, 4.04 mmol) was added to a solution of the compound obtained in Production Example 5-(2) (580 mg, 3.51 mmol) in DCM (100 mL) under ice-cooling. The reaction mixture was stirred under ice-cooling for 20 minutes, then warmed to room temperature, and further stirred for 14 hours. A saturated aqueous sodium bicarbonate solution was added to the reaction mixture, and the mixture was stirred at room temperature for 30 minutes. Chloroform was added to the mixture to separate the organic layer. The organic layer was dried over anhydrous magnesium sulfate. The organic layer was concentrated under reduced pressure to obtain a title compound (450 mg, 2.51 mmol).

$^1$H-NMR (400 MHz, CDCl3) δ (ppm): 2.47 (ddd, J=1.2, 4.2, 15.6 Hz, 1H), 2.89-2.97 (m, 1H), 3.46-3.61 (m, 3H), 3.64 (s, 3H), 3.77 (d, J=14.5 Hz, 1H), 3.98-4.05 (m, 1H), 5.57-5.86 (m, 1H).

Production Example 6

Synthesis of (R)-2-ethyl-5-methoxy-2,3,6,7-tetrahydro-1,4-oxazepine

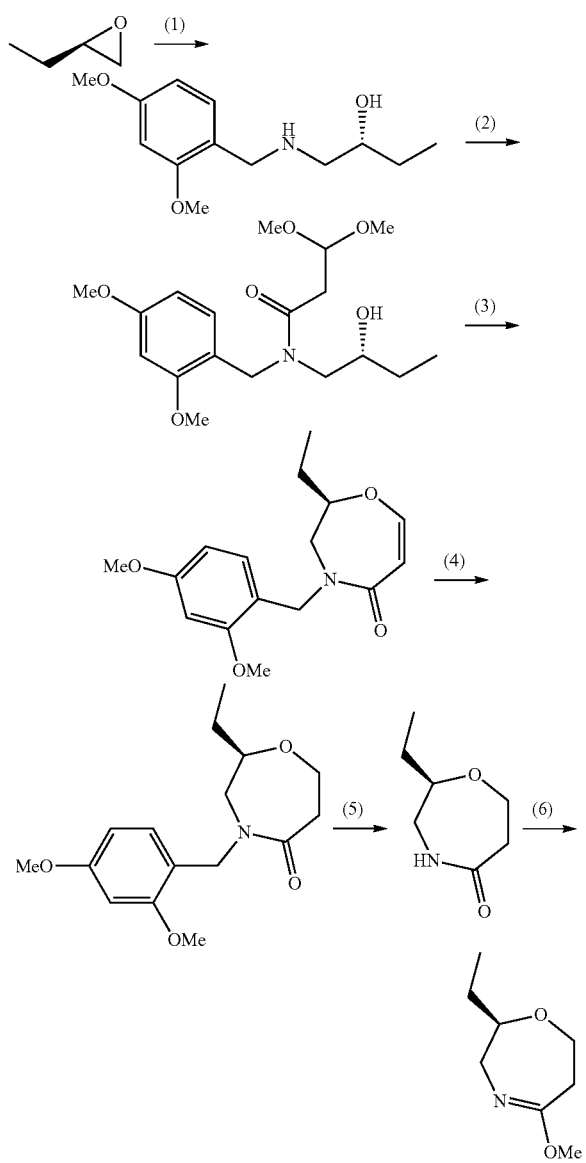

(1) Synthesis of (R)-1-((2,4-dimethoxybenzyl)amino)butan-2-ol

According to the method of Production Example 3-(1), a crude title compound (15.7 g) was obtained from (R)-(+)-

1,2-epoxybutane (CAS No. 3760-95-0; 5.0 g, 69 mmol) and 2,4-dimethoxybenzylamine (15.7 g, 65.8 mmol).
ESI-MS m/z 240 [M+H]+

(2) Synthesis of (R)—N-(2,4-dimethoxybenzyl)-N-(2-hydroxybutyl)-3,3-dimethoxypropanamide According to the method of Production Example 1-(2), a title compound (16.3 g, 45.9 mmol) was obtained from the compound obtained in Production Example 6-(1) (15.7 g) and 3,3-dimethoxypropionic acid (8.80 g, 65.6 mmol).
ESI-MS m/z 378 [M+Na]+

(3) Synthesis of (R)-4-(2,4-dimethoxybenzyl)-2-ethyl-3,4-dihydro-1,4-oxazepin-5(2H)-one According to the method of Production Example 1-(3), a title compound (5.88 g, 20.2 mmol) was obtained from the compound obtained in Production Example 6-(2) (16.3 g, 45.9 mmol).
ESI-MS m/z 292 [M+H]+

(4) Synthesis of (R)-4-(2,4-dimethoxybenzyl)-2-ethyl-1,4-oxazepan-5-one

According to the method of Production Example 1-(4), a title compound (5.92 g, 20.2 mmol) was obtained from the compound obtained in Production Example 6-(3) (5.88 g, 20.2 mmol).
ESI-MS m/z 316 [M+Na]+

(5) Synthesis of (R)-2-ethyl-1,4-oxazepan-5-one

According to the method of Production Example 1-(5), a title compound (2.78 g, 19.4 mmol) was obtained from the compound obtained in Production Example 6-(4) (5.92 g, 20.2 mmol).
$^1$H-NMR (400 MHz, CDCl3) δ (ppm): 0.96 (t, J=7.6 Hz, 3H), 1.38-1.50 (m, 1H), 1.52-1.62 (m, 1H), 2.54 (dd, J=4.5, 15.4 Hz, 1H), 2.82-2.94 (m, 1H), 3.08 (dd, J=7.4, 14.1 Hz, 1H), 3.27-3.41 (m, 2H), 3.63-3.74 (m, 1H), 4.04 (ddd, J=2.3, 5.3, 12.7 Hz, 1H), 6.02-6.22 (m, 1H).

(6) Synthesis of (R)-2-ethyl-5-methoxy-2,3,6,7-tetrahydro-1,4-oxazepine

According to the method of Production Example 1-(6), a title compound (2.51 g, 16.0 mmol) was obtained from the compound obtained in Production Example 6-(5) (2.78 g, 19.4 mmol).
$^1$H-NMR (400 MHz, CDCl3) δ (ppm): 0.95 (t, J=8.0 Hz, 3H), 1.44-1.57 (m, 2H), 2.43 (ddd, J=1.2, 4.5, 15.4 Hz, 1H), 2.87 (ddd, J=3.1, 11.5, 15.0 Hz, 1H), 3.24-3.32 (m, 1H), 3.33-3.41 (m, 1H), 3.47-3.57 (m, 2H), 3.62 (s, 3H), 3.87-3.95 (m, 1H).

Production Example 7

Synthesis of (S)-2-((benzyloxy)methyl)-5-methoxy-2,3,6,7-tetrahydro-1,4-oxazepine

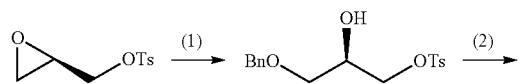

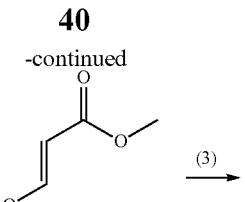

(1) Synthesis of (R)-3-(benzyloxy)-2-hydroxypropyl 4-methylbenzene sulfonate

A boron trifluoride-ethyl ether complex (0.694 mL, 5.48 mmol) was added to a mixture of (2R)-(−)-glycidyl tosylate (25.0 g, 109 mmol), benzyl alcohol (22.7 mL, 219 mmol) and toluene (200 mL) under ice-cooling. The reaction mixture was stirred at room temperature overnight. The reaction mixture was washed with a saturated aqueous sodium bicarbonate solution (50.0 mL) twice and further with water (50.0 mL) twice. Ethanol was added to the organic layer until the suspension became clear. The solvent was evaporated under reduced pressure and the residue was purified by silica gel column chromatography (n-heptane/ethyl acetate) to obtain a title compound (28.0 g, 83.0 mmol).
$^1$H-NMR (400 MHz, CDCl3) δ (ppm): 2.40 (d, J=5.5 Hz, 1H), 2.44 (s, 3H), 3.46-3.57 (m, 2H), 3.96-4.15 (m, 3H), 4.50 (s, 2H), 7.26-7.39 (m, 7H), 7.75-7.82 (m, 2H).

(2) Synthesis of (R,E)-methyl 3-((1-(benzyloxy)-3-(tosyloxy)propan-2-yl)oxy)acrylate A mixture of the compound obtained in Production Example 7-(1) (28.0 g, 83.2 mmol), methyl propiolate (15.3 mL, 183 mmol), NMM (9.15 mL, 83.2 mmol) and THF (280 mL) was stirred at room temperature overnight. The solvent was evaporated under reduced pressure and the residue was purified by silica gel column chromatography (n-heptane/ethyl acetate) to obtain a title compound (34.7 g, 82.5 mmol).
$^1$H-NMR (400 MHz, CDCl3) δ (ppm): 2.44 (s, 3H), 3.57 (dd, J=1.8, 4.9 Hz, 2H), 3.69 (s, 3H), 4.14-4.30 (m, 3H), 4.44-4.55 (m, 2H), 5.20 (d, J=12.5 Hz, 1H), 7.24-7.40 (m, 8H), 7.75-7.78 (m, 2H).

(3) Synthesis of (R)-methyl 3-((1-(benzyloxy)-3-(tosyloxy)propan-2-yl)oxy)propanoate 10% Palladium/carbon (4.39 g, including 50% water content) was added to a solution of the compound obtained in Production Example 7-(2) (34.7 g, 82.5 mmol) in ethanol (347 mL). The reaction mixture was stirred under hydrogen atmosphere for 7 hours. The insolubles were filtered off through Celite (trademark). The solvent was evaporated under reduced pressure to obtain a title compound (34.5 g, 82.0 mmol).

$^1$H-NMR (400 MHz, CDCl3) δ (ppm): 2.44 (s, 3H), 2.51 (t, J=6.3 Hz, 2H), 3.43-3.52 (m, 2H), 3.66 (s, 3H), 3.68-3.72 (m, 1H), 3.74-3.85 (m, 2H), 4.02-4.08 (m, 1H), 4.11-4.18 (m, 1H), 4.46 (s, 2H), 7.21-7.26 (m, 2H), 7.28-7.40 (m, 5H), 7.74-7.82 (m, 2H).

(4) Synthesis of (S)-2-((benzyloxy)methyl)-1,4-oxazepan-5-one

The compound obtained in Production Example 7-(3) (22.0 g, 52.1 mmol) was dissolved in a 7 M ammonia/methanol solution (100 mL, 700 mmol). The reaction mixture was stirred in a sealed tube at 100° C. overnight. The reaction mixture was transferred into an eggplant shaped flask and DBU (24.9 mL, 167 mmol) was added. The reaction mixture was stirred at 80° C. for 6 hours. The resultant was cooled to room temperature and the solvent was evaporated under reduced pressure. The residue was purified by silica gel column chromatography (n-heptane/ethyl acetate) to obtain a title compound (5.56 g, 23.6 mmol).

$^1$H-NMR (400 MHz, CDCl3) δ (ppm): 2.48-2.56 (m, 1H), 2.91 (ddd, J=2.7, 11.0, 15.5 Hz, 1H), 3.24-3.33 (m, 1H), 3.35-3.44 (m, 2H), 3.53 (dd, J=4.7, 9.8 Hz, 1H), 3.61-3.76 (m, 2H), 4.04 (ddd, J=2.7, 5.2, 12.8 Hz, 1H), 4.49-4.60 (m, 2H), 5.92 (brs, 1H), 7.27-7.41 (m, 5H).

(5) Synthesis of (S)-2-((benzyloxy)methyl)-5-methoxy-2,3,6,7-tetrahydro-1,4-oxazepine Trimethyloxonium tetrafluoroborate (1.51 g, 10.2 mmol) was added to a solution of the compound obtained in Production Example 7-(4) (2.00 g, 8.50 mmol) in DCM (40.0 mL) at room temperature, and the mixture was stirred at room temperature for 15 hours. A saturated aqueous sodium bicarbonate solution was added to the reaction mixture, and the mixture was stirred at room temperature for 20 minutes. The organic layer was separated and dried over anhydrous magnesium sulfate. The solvent was evaporated under reduced pressure to obtain a title compound (2.12 g, 8.50 mmol).

$^1$H-NMR (400 MHz, CDCl3) δ (ppm): 2.44 (ddd, 1.2, 4.4, 15.5 Hz, 1H), 2.90 (ddd, J=3.1, 11.6, 15.3 Hz, 1H), 3.41-3.65 (m, 9H), 3.97 (ddd, J=3.1, 4.6, 12.2 Hz, 1H), 4.53-4.60 (m, 2H), 7.27-7.42 (m, 5H).

Production Example 8

Synthesis of (R)-methyl 3-chloro-6-methyl-5,6,8,9-tetrahydroimidazo[1,5-d][1,4]oxazepine-1-carboxylate

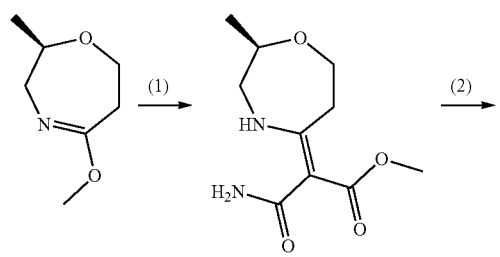

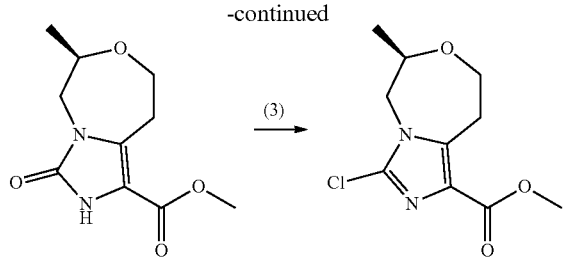

(1) Synthesis of (R)-methyl 3-amino-2-(2-methyl-1,4-oxazepan-5-ylidene)-3-oxopropanoate A solution of the compound obtained in Production Example 1-(6) (16.0 g, 156 mmol) and methyl carbamoyl acetate (CAS No. 51513-29-2; 18.3 g, 156 mmol) in THF (40 mL)/DMF (10 mL) was stirred at 90° C. for 15 hours. The reaction mixture was cooled to room temperature and the solvent was evaporated under reduced pressure. The resultant residue was purified by silica gel chromatography (n-heptane/ethyl acetate→ethyl acetate/methanol) to obtain a title compound (14.2 g, 62.2 mmol).

$^1$H-NMR (400 MHz, CDCl3) δ (ppm): 1.20 (d, J=6.3 Hz, 3H), 2.73-2.81 (m, 1H), 3.33-3.66 (m, 5H), 3.77 (s, 3H), 4.04-4.10 (m, 1H).

(2) Synthesis of (R)-methyl 6-methyl-3-oxo-2,3,5,6,8,9-hexahydroimidazo[1,5-d][1,4]oxazepine-1-carboxylate Iodobenzene diacetate (24.1 g, 74.7 mmol) was added to a solution of the compound obtained in Production Example 8-(1) (14.2 g, 62.2 mmol) in THF (100 mL)/toluene (100 mL), and the mixture was stirred at room temperature for 60 hours. A saturated aqueous sodium bicarbonate solution (60 mL) and a saturated aqueous sodium sulfite solution (60 mL) were added to the reaction mixture, and the mixture was stirred at room temperature for 1 hour. The mixture was extracted with ethyl acetate three times. The combined organic layers were dried over anhydrous magnesium sulfate and concentrated under reduced pressure. The resultant residue was purified by silica gel column chromatography (n-heptane/ethyl acetate→ethyl acetate/methanol) to obtain a title compound (9.97 g, 44.1 mmol).

$^1$H-NMR (400 MHz, CDCl3) δ (ppm): 1.27 (d, J=6.3 Hz, 3H), 2.86 (ddd, J=2.4, 11.0, 16.3 Hz, 1H), 3.45 (dd, J=9.0, 14.7 Hz, 1H), 3.53-3.70 (m, 3H), 3.83 (s, 3H), 4.13-4.19 (m, 1H), 4.29 (d, J=14.7 Hz, 1H), 8.03 (brs, 1H).

ESI-MS m/z 227 [M+H]+

(3) Synthesis of (R)-methyl 3-chloro-6-methyl-5,6,8,9-tetrahydroimidazo[1,5-d][1,4]oxazepine-1-carboxylate A mixture of the compound obtained in Production Example 8-(2) (9.97 g, 44.1 mmol) and phosphorus oxychloride (60 mL) was stirred at 110° C. for 4 hours. The reaction mixture was cooled to room temperature and concentrated under reduced pressure. The resultant residue was purified by NH silica gel column chromatography (n-heptane/ethyl acetate) to obtain a title compound (5.94 g, 24.3 mmol).

$^1$H-NMR (400 MHz, CDCl3) δ (ppm): 1.30 (d, J=6.5 Hz, 3H), 3.02 (ddd, J=2.7, 10.8, 16.4 Hz, 1H), 3.55-3.62 (m, 1H), 3.66-3.74 (m, 1H), 3.87 (s, 3H), 3.88-3.98 (m, 2H), 4.13-4.19 (m, 1H), 4.26-4.31 (m, 1H).

ESI-MS m/z 245 [M+H]+

Production Example 9

Synthesis of (S)-methyl 3-chloro-6-(fluoromethyl)-5,6,8,9-tetrahydroimidazo[1,5-d][1,4]oxazepine-1-carboxylate

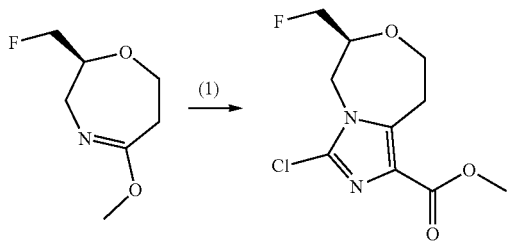 [SMILES: COC1=NC[C@@H](CF)OCC1 ; COC(=O)c1nc(Cl)n2c1CCO[C@H](CF)C2]

According to Production Examples 8-(1), 8-(2), and 8-(3), a title compound (1.77 g, 6.74 mmol) was obtained from the compound obtained in Production Example 3-(7) (9.39 g, 58.3 mmol).

¹H-NMR (400 MHz, CDCl3) δ (ppm): 3.02 (ddd, J=2.7, 11.4, 16.4 Hz, 1H), 3.58-3.65 (m, 1H), 3.71-3.80 (m, 1H), 3.88 (s, 3H), 3.98-4.09 (m, 2H), 4.23-4.28 (m, 1H), 4.33-4.65 (m, 3H).

ESI-MS m/z 263 [M+H]+

Production Example 10

Synthesis of methyl 3-chloro-5,6,8,9-tetrahydroimidazo[1,5-d][1,4]oxazepine-1-carboxylate

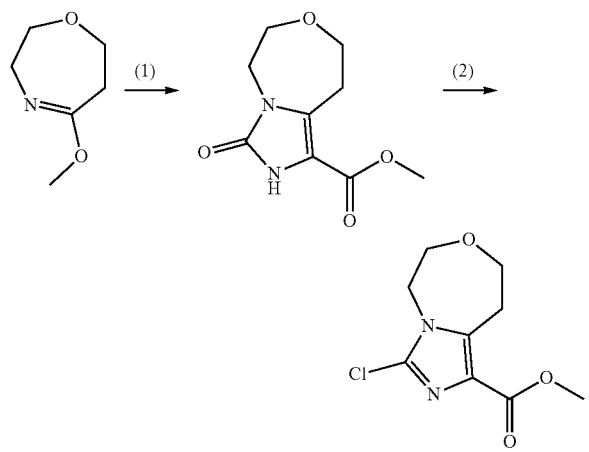

(1) Synthesis of methyl 3-oxo-2,3,5,6,8,9-hexahydroimidazo[1,5-d][1,4]oxazepine-1-carboxylate According to the methods of Production Examples 8-(1) and 8-(2), a title compound (13.0 g, 6.74 mmol) was obtained from 5-methoxy-2,3,6,7-tetrahydro-1,4-oxazepine (CAS No. 384330-36-3; 25.0 g, 194 mmol).

¹H-NMR (400 MHz, CDCl3) δ (ppm): 3.26-3.30 (m, 2H), 3.76-3.85 (m, 4H), 3.83 (s, 3H), 4.00-4.03 (m, 2H), 8.20 (brs, 1H).

ESI-MS m/z 213 [M+H]+

(2) Synthesis of methyl 3-chloro-5,6,8,9-hexahydroimidazo[1,5-d][1,4]oxazepine-1-carboxylate According to the method of Production Example 8-(3), a title compound (7.58 g, 32.9 mmol) was obtained from the compound obtained in Production Example 10-(1) (11 g, 51.8 mmol).

¹H-NMR (400 MHz, CDCl3) δ (ppm): 3.51-3.55 (m, 2H), 3.85-3.89 (m, 4H), 3.89 (s, 3H), 4.25-4.28 (m, 2H).

Production Example 11

Synthesis of methyl 3-bromo-5,6,8,9-tetrahydroimidazo[1,5-d][1,4]oxazepine-1-carboxylate

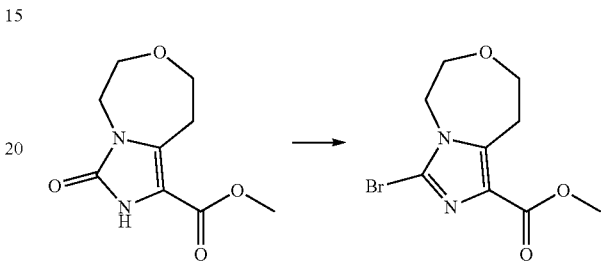

Phosphorus oxybromide (25.0 g, 87.2 mmol) was added to a solution of the compound obtained in Production Example 10-(1) (7.64 g, 36.0 mmol) in toluene (140 mL), and the mixture was stirred and heated under reflux for 24 hours. The reaction mixture was cooled to room temperature, ice and a saturated aqueous sodium bicarbonate solution were added, and the mixture was stirred for 3 hours. The solid was filtered off and the filtrate was extracted with chloroform three times. The resultant organic layer was dried over anhydrous sodium sulfate and then the resultant was concentrated under reduced pressure. The resultant residue was washed with ethyl acetate three times to obtain a title compound (3.18 g, 11.6 mmol). The filtrate was concentrated and the resultant residue was purified by NH silica gel column chromatography (n-heptane/ethyl acetate) to obtain a title compound (0.84 g, 3.1 mmol).

¹H-NMR (400 MHz, CDCl3) δ (ppm): 3.42-3.61 (m, 2H), 3.80-3.89 (m, 4H), 3.86 (s, 3H), 4.25 (t, J=3.5 Hz, 2H).

Production Example 12

Synthesis of (3-chloro-4-cyclopropoxyphenyl)boronic acid

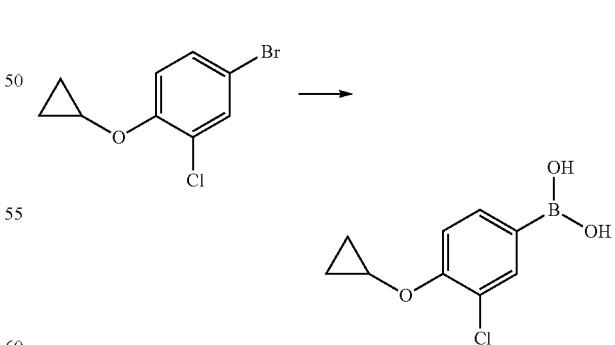

An n-butyl lithium/n-hexane solution (2.69 mol/L, 1.70 mL) was added dropwise into a solution of 4-bromo-2-chloro-1-cyclopropoxybenzene (CAS 869569-68-6; 1.10 g, 4.44 mmol) in THF (8.5 mL) at −78° C., and the mixture was stirred at the same temperature for 30 minutes. Triethyl borate (0.980 mL, 5.79 mmol) was slowly added to the reaction mixture, then the dry ice was removed from the cooling bath, and then the mixture was stirred until the internal temperature rose to 0° C. A saturated aqueous ammonium chloride solution and ethyl acetate were added to the mixture to separate the organic layer. The resultant was washed with a saturated aqueous sodium chloride solution, dried over anhydrous magnesium sulfate, and concentrated under reduced pressure. Ether was added to the resultant residue, and the resultant solid was collected by filtration to obtain a title compound (520 mg, 2.45 mmol).

$^1$H-NMR (400 MHz, CDCl3) δ (ppm): 0.85-0.98 (m, 4H), 3.87-3.98 (m, 1H), 7.43 (d, J=8.2 Hz, 1H), 8.09 (dd, J=1.6, 8.2 Hz, 1H), 8.14 (d, J=1.6 Hz, 1H).

Production Example 13

Synthesis of 2-(3-chloro-4-(methoxymethoxy)phenyl)-4,4,5,5-tetramethyl-1,3,2-dioxaborolane

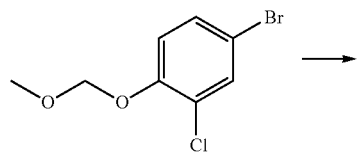

A mixture of 4-bromo-2-chloro-1-(methoxymethoxy)benzene (CAS 1301146-84-8; 4.85 g, 19.3 mmol), bis(pinacolate)diboron (6.87 g, 27.1 mmol), potassium acetate (5.73 g, 58.4 mmol), and Pd(dppf)Cl2.CH2Cl2 (0.788 g, 0.964 mmol) was stirred in DMSO (76 mL) at 80° C. for 5 hours. Water and diethyl ether were added to the reaction mixture to separate the organic layer. The organic layer was washed with a saturated aqueous sodium chloride solution, dried over anhydrous magnesium sulfate, and concentrated under reduced pressure. The resultant residue was purified by silica gel column chromatography (n-heptane/ethyl acetate) to obtain a title compound (4.50 g, 15.1 mmol).

$^1$H-NMR (400 MHz, CDCl3) δ (ppm): 1.33 (s, 12H), 3.51 (s, 3H), 5.28 (s, 2H), 7.15 (d, J=8.2 Hz, 1H), 7.64 (dd, J=1.6, 8.2 Hz, 1H), 7.82 (d, J=1.6 Hz, 1H).

Production Example 14

Synthesis of 2-(4-cyclopropoxy-3-(trifluoromethoxy)phenyl)-4,4,5,5-tetramethyl-1,3,2-dioxaborolane

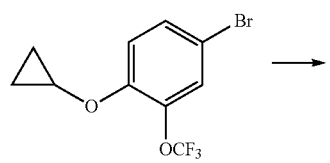

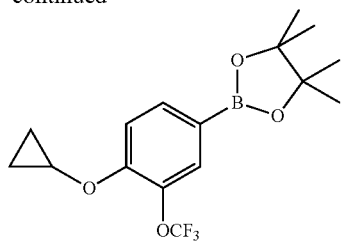

According to the method of Production Example 13, a title compound (1.05 g, 3.05 mmol) was obtained from 4-bromo-1-cyclopropoxy-2-(trifluoromethoxy)benzene (CAS 1337606-89-9; 1.30 g, 4.38 mmol).

$^1$H-NMR (400 MHz, CDCl3) δ (ppm): 0.76-0.84 (m, 4H), 1.33 (s, 12H), 3.76-3.90 (m, 1H), 7.31 (d, J=8.2 Hz, 1H), 7.63 (qd, J=1.3, 1.5 Hz, 1H), 7.70 (dd, J=1.5, 8.2 Hz, 1H).

Production Example 15

Synthesis of 2-(3-chloro-4-cyclopropoxyphenyl)-4,4,5,5-tetramethyl-1,3,2-dioxaborolane

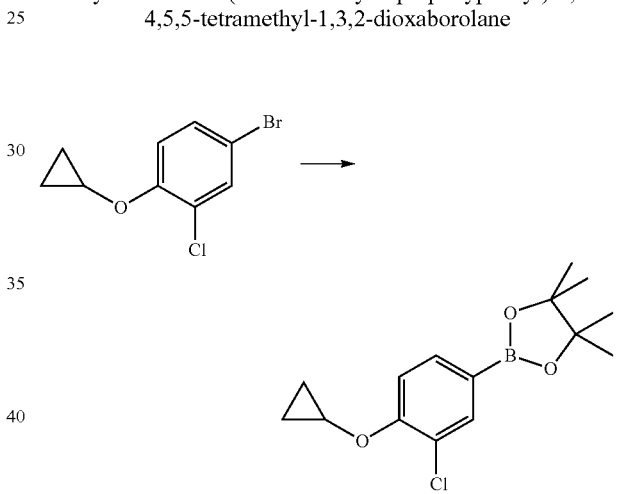

According to the method of Production Example 13, a title compound (1.10 g, 3.73 mmol) was obtained from 4-bromo-2-chloro-1-cyclopropoxybenzene (CAS 869569-68-6; 1.10 g, 4.44 mmol).

$^1$H-NMR (400 MHz, CDCl3) δ (ppm): 0.74-0.96 (m, 4H), 1.33 (s, 12H), 3.71-3.94 (m, 1H), 7.28 (d, J=8.2 Hz, 1H), 7.67 (dd, J=1.6, 8.2 Hz, 1H), 7.78 (d, J=1.6 Hz, 1H).

Production Example 16

Synthesis of 2-(4-cyclopropoxy-3-methylphenyl)-4,4,5,5-tetramethyl-1,3,2-dioxaborolane

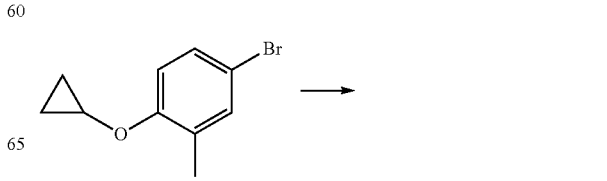

-continued

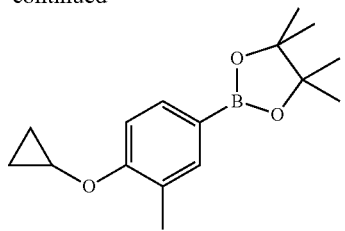

According to the method of Production Example 13, a title compound (1.20 g, 4.38 mmol) was obtained from 4-bromo-1-cyclopropoxy-2-methylbenzene (CAS 1243345-41-6; 2.00 g, 8.81 mmol).

¹H-NMR (400 MHz, CDCl3) δ (ppm): 0.62-0.85 (m, 4H), 1.33 (s, 12H), 2.16 (s, 3H), 3.71-3.81 (m, 1H), 7.19 (d, J=8.2 Hz, 1H), 7.58 (brs, 1H), 7.65 (brd, J=8.2 Hz, 1H).

Production Example 17

Synthesis of 2-(4-(difluoromethoxy)-3-((methoxymethoxy)methyl)phenyl)-4,4,5,5-tetramethyl-1,3,2-dioxaborolane

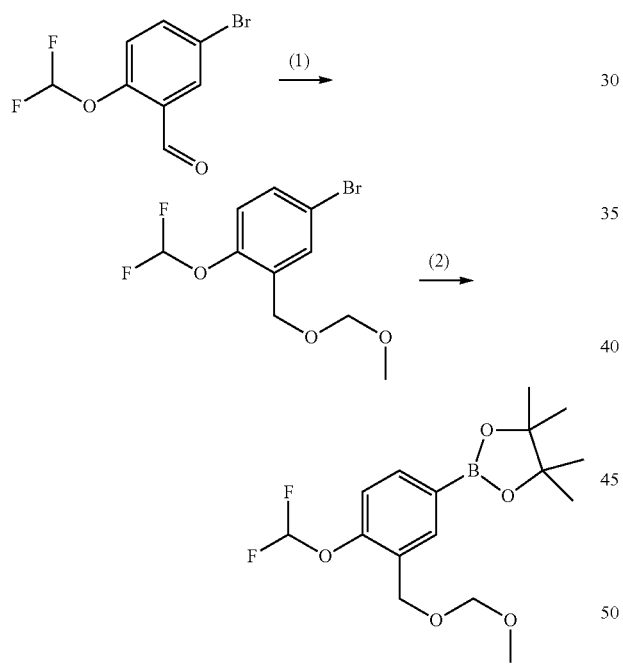

(1) Synthesis of 4-bromo-1-(difluoromethoxy)-2-((methoxymethoxy)methyl)benzene

Sodium borohydride (113 mg, 2.99 mmol) was added to a solution of 5-bromo-2-(difluoromethoxy)benzaldehyde (CAS No. 329269-64-9; 750 mg, 2.99 mmol) in methanol (15 mL) under ice-cooling. The reaction mixture was stirred under ice-cooling for 30 minutes. Acetic acid was added to the reaction mixture, the mixture was warmed to room temperature, and then the solvent was evaporated under reduced pressure. The residue was mixed with methanol for azeotropically evaporation three times and further mixed with chloroform for azeotropically evaporation. The resultant residue was dissolved in DCM. Dimethoxymethane (5.29 mL, 59.8 mmol) was added to the resultant solution. Diphosphorus pentaoxide (4.24 g, 29.9 mmol) was added to the reaction mixture under ice-cooling. The reaction mixture was stirred under ice-cooling for 30 minutes. Potassium carbonate (20 g, 145 mmol) was added to the reaction solution, and then the mixture was warmed to room temperature. The reaction solution was filtered and then the filtrate was concentrated under reduced pressure. The resultant residue was purified by silica gel chromatography (n-heptane/ethyl acetate) to obtain a title compound (622 mg, 2.09 mmol).

¹H-NMR (400 MHz, CDCl3) δ (ppm): 3.42 (s, 3H), 4.62 (s, 2H), 4.74 (s, 2H), 6.50 (t, J=73.8 Hz, 1H) 7.03 (d, J=8.6 Hz, 1H) 7.43 (dd, J=2.3, 8.6 Hz, 1H) 7.65 (d, J=2.3 Hz, 1H).

(2) Synthesis of 2-(4-(difluoromethoxy)-3-((methoxymethoxy)methyl)phenyl)-4,4,5,5-tetramethyl-1,3,2-dioxaborolane Pd(dppf)Cl2.CH2Cl2 (171 mg, 209 μmol) was added to a solution of the compound obtained in Production Example 17-(1) (622 mg, 2.09 mmol), potassium acetate (616 mg, 6.28 mmol), and bis(pinacolate)diboron (1.06 g, 4.19 mmol) in DMF (10 mL) at room temperature. The reaction mixture was stirred at 110° C. for 2 hours and then cooled to room temperature. The reaction solution was diluted with ethyl acetate, then the resultant was washed with water five times and then with a saturated aqueous sodium chloride solution. The organic layer was dried over anhydrous sodium sulfate and the solvent was evaporated under reduced pressure. The resultant residue was purified by silica gel column chromatography (n-heptane/ethyl acetate) to obtain a crude title compound (726 mg).

¹H-NMR (400 MHz, CDCl3) δ (ppm): 1.34 (s, 12H), 3.42 (s, 3H), 4.64 (s, 2H), 4.73, (s, 2H), 6.55 (dt, J=1.2, 74.2 Hz, 1H), 7.11 (d, J=8.2 Hz, 1H), 7.77 (dd, J=1.6, 8.2 Hz, 1H), 7.90 (d, J=1.2 Hz, 1H).

Production Example 18

Synthesis of 5-(4,4,5,5-tetramethyl-1,3,2-dioxaborolan-2-yl)-2-(trifluoromethoxy)benzonitrile

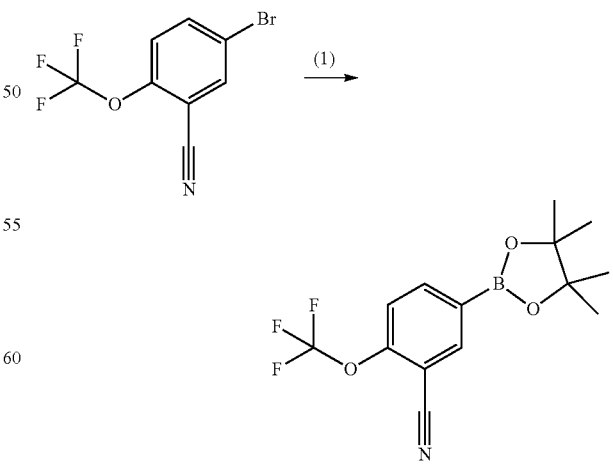

According to the method of Production Example 17-(2), a crude title compound (744 mg) was obtained from 5-bromo-2-(trifluoromethoxy)benzonitrile (CAS No. 1210906-15-2; 500 mg, 1.88 mmol).

¹H-NMR (400 MHz, CDCl3) δ (ppm): 1.35 (s, 12H), 7.37, (qd, J=1.6, 8.6 Hz, 1H), 8.04 (dd, J=1.4, 8.4 Hz, 1H), 8.14 (d, J=1.6 Hz, 1H).

Production Example 19

Synthesis of 2-(3-((methoxymethoxy)methyl)-4-(trifluoromethoxy)phenyl)-4,4,5,5-tetramethyl-1,3,2-dioxaborolane

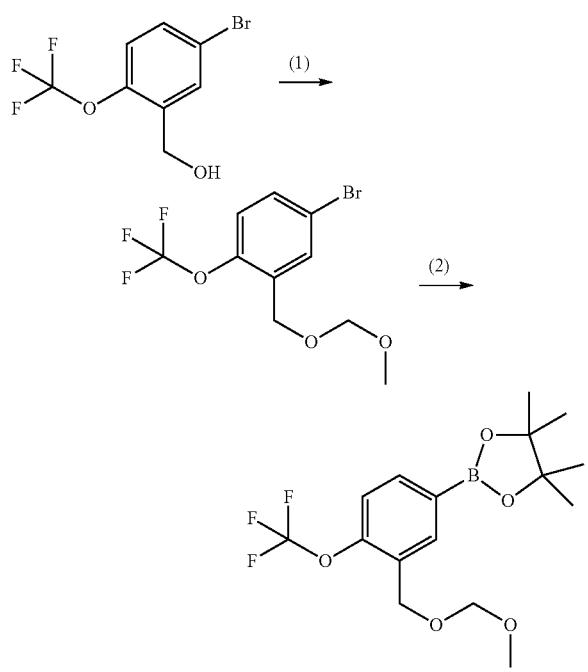

(1) Synthesis of 4-bromo-2-((methoxymethoxy)methyl)-1-(trifluoromethoxy)benzene

Chloromethyl methyl ether (2.80 mL, 36.9 mmol) was added to a solution of (5-bromo-2-(trifluoromethoxy)phenyl)methanol (CAS No. 685126-86-7; 5.00 g, 18.4 mmol) and DIPEA (9.64 mL, 55.3 mmol) in DCM (50 mL) under ice-cooling. The reaction mixture was stirred under ice-cooling for 30 minutes, then warmed to room temperature, and stirred for 13 hours. Water was added to the reaction mixture to separate the organic layer. The organic layer was dried over anhydrous magnesium sulfate and then concentrated under reduced pressure. The resultant residue was purified by silica gel column chromatography (n-heptane/ethyl acetate) to obtain a title compound (5.60 g, 17.8 mmol).

¹H-NMR (400 MHz, CDCl3) δ (ppm): 3.42 (s, 3H), 4.63 (s, 2H), 4.74 (s, 2H), 7.12 (dd, J=1.6, 9.0 Hz, 1H) 7.44 (dd, J=2.5, 8.8 Hz, 1H) 7.70 (d, J=2.0 Hz, 1H).

(2) Synthesis of 2-(3-((methoxymethoxy)methyl)-4-(trifluoromethoxy)phenyl)-4,4,5,5-tetramethyl-1,3,2-dioxaborolane According to the method of Production Example 17-(2), a crude title compound (1.66 g) was obtained from the compound obtained in Production Example 19-(1) (1.12 g, 3.56 mmol).

¹H-NMR (400 MHz, CDCl3) δ (ppm): 1.34 (s, 12H), 3.43 (s, 3H), 4.66 (s, 2H), 4.74, (s, 2H), 7.24 (qd, J=2.0, 8.2 Hz, 1H), 7.78 (dd, J=1.6, 8.2 Hz, 1H), 7.95 (d, 1.6 Hz, 1H).

Production Example 20

Synthesis of 2-(4-chloro-3-((methoxymethoxy)methyl)phenyl)-4,4,5,5-tetramethyl-1,3,2-dioxaborolane

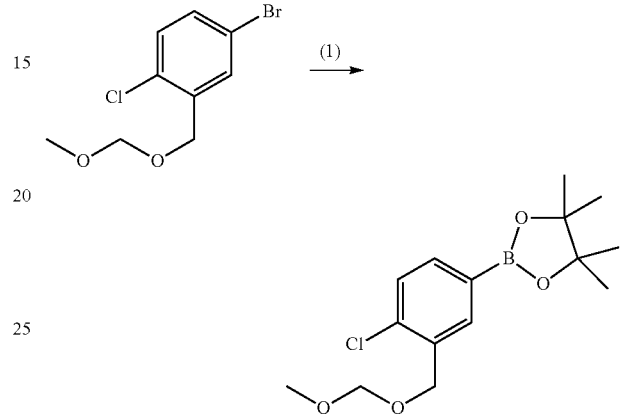

According to the method of Production Example 17-(2), a title compound (3.36 g, 10.8 mmol) was obtained from 4-bromo-1-chloro-2-((methoxymethoxy)methyl)benzene (CAS No. 790228-98-7; 3.95 g, 14.9 mmol).

¹H-NMR (400 MHz, CDCl3) δ (ppm): 1.34 (s, 12H), 3.48 (s, 3H), 4.69 (s, 2H), 4.76 (s, 2H), 7.37 (d, J=7.8 Hz, 1H), 7.67 (dd, J=1.6, 7.8 Hz, 1H), 7.89 (d, J=1.5 Hz, 1H).

Production Example 21

Synthesis of 2-(3-methoxy-4-(trifluoromethoxy)phenyl)-4,4,5,5-tetramethyl-1,3,2-dioxaborolane

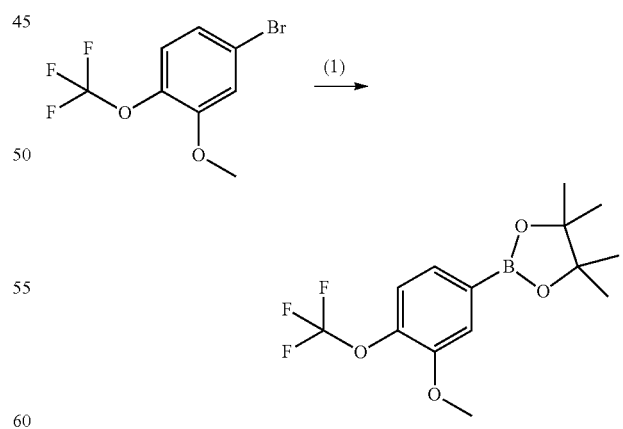

According to the method of Production Example 17-(2), a title compound (4.58 g, 14.4 mmol) was obtained from 4-bromo-2-methoxy-1-(trifluoromethoxy)benzene (CAS No. 672948-65-1; 5.23 g, 19.7 mmol).

¹H-NMR (400 MHz, CDCl3) δ (ppm): 1.35 (s, 12H), 3.92, (s, 3H), 7.23 (qd, J=1.2, 8.2 Hz, 1H), 7.40 (m, 2H).

Production Example 22

Synthesis of 2-(4-chloro-3-(methoxymethoxy)phenyl)-4,4,5,5-tetramethyl-1,3,2-dioxaborolane

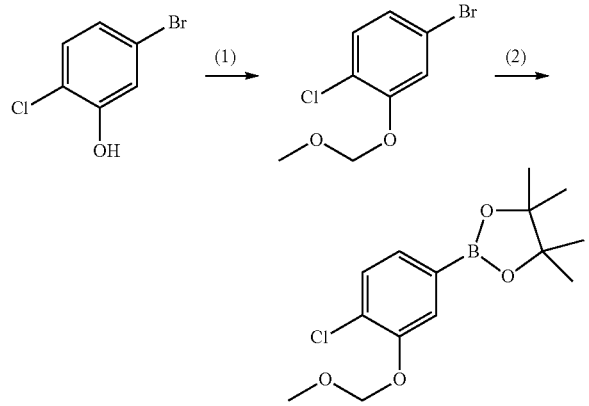

(1) Synthesis of 4-bromo-1-chloro-2-(methoxymethoxy)benzene

Chloromethyl methyl ether (0.44 mL, 5.78 mmol) was added to a mixture of 5-bromo-2-chlorophenol (CAS No. 183802-98-4; 1.00 g, 4.82 mmol), potassium carbonate (2.00 g, 14.5 mmol) and acetone (15.0 mL). The reaction mixture was stirred at room temperature for 2 hours. Water and ethyl acetate were added to the reaction mixture to separate the organic layer. The organic layer was washed serially with water and a saturated aqueous sodium chloride solution and dried over anhydrous magnesium sulfate. The filtrate was concentrated under reduced pressure and the resultant residue was purified by silica gel chromatography (n-heptane/ethyl acetate) to obtain a title compound (1.20 g, 4.77 mmol).

$^1$H-NMR (400 MHz, CDCl3) δ (ppm): 3.52 (s, 3H), 5.23 (s, 2H), 7.08 (dd, J=2.2, 8.4 Hz, 1H), 7.25 (d, J=9.8 Hz, 1H), 7.34-7.38 (m, 2H), 7.53 (s, 1H).

(2) Synthesis of 2-(4-chloro-3-(methoxymethoxy)phenyl)-4,4,5,5-tetramethyl-1,3,2-dioxaborolane According to the method of Production Example 17-(2), a title compound (688 mg, 2.30 mmol) was obtained from the compound obtained in Production Example 22-(1) (1.20 g, 4.77 mmol).

$^1$H-NMR (400 MHz, CDCl3) δ (ppm): 1.34 (s, 12H), 3.54 (s, 3H), 5.29 (s, 2H), 7.34-7.38 (m, 2H), 7.53 (s, 1H)

Production Example 23

Synthesis of (2-(hydroxymethyl)-6-methylpyridin-4-yl)boronic acid hydrochloride

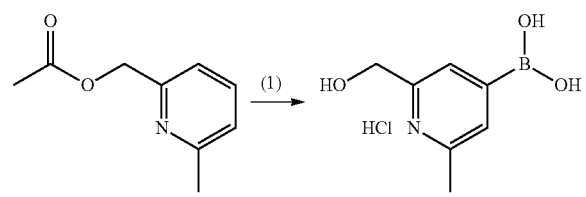

A solution comprising (6-methylpyridin-2-yl)methyl acetate (CAS No. 13287-64-4; 839 mg, 5.08 mmol), bis(pinacolate)diboron (1.29 g, 5.08 mmol), bis(1,5-cyclooctadiene)di-μ-methoxydiiridium(I) (337 mg, 0.508 mmol) and 4,4'-di-tert-butyl-2,2'-dipyridyl (136 mg, 0.508 mmol) in TBME (9.08 mL) was stirred under microwave irradiation at 80° C. for 30 minutes. The reaction mixture was cooled to room temperature and then concentrated under reduced pressure. The residue was dissolved in THF (15.1 mL), and a 5 N hydrochloric acid (5.08 mL) was added to the mixture. The resultant solution was stirred for 48 hours, and THF was evaporated under reduced pressure. The resultant solution was washed with diethyl ether four times and then concentrated under reduced pressure. The resultant solid was washed with DCM to obtain a title compound (514 mg, 2.53 mmol).

$^1$H-NMR (400 MHz, MeOH-d4) δ (ppm): 2.78 (brs, 3H), 4.93 (brs, 2H), 7.95 (brs, 1H), 8.03 (brs, 1H).

Production Example 24

Synthesis of 2-(((tert-butyldimethylsilyl)oxy)methyl)-6-methyl-4-(4,4,5,5-tetramethyl-1,3,2-dioxaborolan-2-yl)pyridine

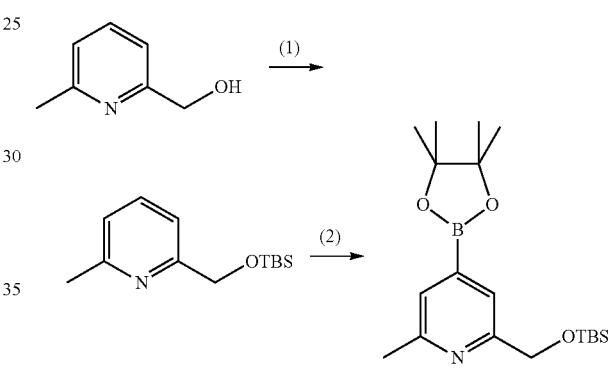

(1) Synthesis of 2-(((tert-butyldimethylsilyl)oxy)methyl)-6-methylpyridine

Imidazole (2.16 g, 31.7 mmol) and TBSCl (4.04 g, 26.8 mmol) were serially added to a solution of 6-methyl-2-pyridinemethanol (CAS No. 1122-71-0; 3.00 g, 24.4 mmol) in DMF (50 mL) under ice-cooling, and the mixture was stirred at room temperature for 30 minutes. Water and n-heptane were added to the reaction mixture to separate the organic layer. The organic layer was washed with a saturated aqueous sodium chloride solution, dried over anhydrous magnesium sulfate, and concentrated under reduced pressure. The resultant residue was purified by silica gel column chromatography (n-heptane/ethyl acetate) to obtain a title compound (4.70 g, 19.8 mmol).

$^1$H-NMR (400 MHz, CDCl3) δ (ppm): 0.12 (s, 6H), 0.96 (s, 9H), 2.52 (s, 3H), 4.81 (s, 2H), 7.00 (d, J=7.7 Hz, 1H), 7.32 (d, J=7.7 Hz, 1H), 7.59 (t, J=7.7 Hz, 1H).

(2) Synthesis of 2-(((tert-butyldimethylsilyl)oxy)methyl)-6-methyl-4-(4,4,5,5-tetramethyl-1,3,2-dioxaborolan-2-yl)pyridine A mixture of the compound obtained in Production Example 24-(1) (2.00 g, 8.42 mmol), bis(pinacolate)diboron (2.14 g, 8.42 mmol), bis(1,5-cyclooctadiene)di-μ-methoxydiiridium(I) (168 mg, 0.253 mmol) and 4,4-di-tert-butyl-2,2-dipyridyl (68 mg, 0.253 mmol) in TBME (20 mL) was stirred at 85° C. for 1.5 hours. The reaction mixture was cooled to room temperature and then concentrated under reduced pressure. The resultant residue was purified by silica gel column chromatography (n-heptane/ethyl acetate→ethyl acetate/methanol) twice to obtain a title compound (450 mg, 1.24 mmol).

$^1$H-NMR (400 MHz, CDCl3) δ (ppm): 0.12 (s, 6H), 0.96 (s, 9H), 1.35 (s, 12H), 2.52 (s, 3H), 4.82 (s, 2H), 7.37 (s, 1H), 7.63 (s, 1H).

Example 1

Synthesis of (R)-3-(4-chloro-3-methoxyphenyl)-1-(2,6-dimethylpyridin-4-yl)-6-methyl-5,6,8,9-tetrahydroimidazo[1,5-d][1,4]oxazepine

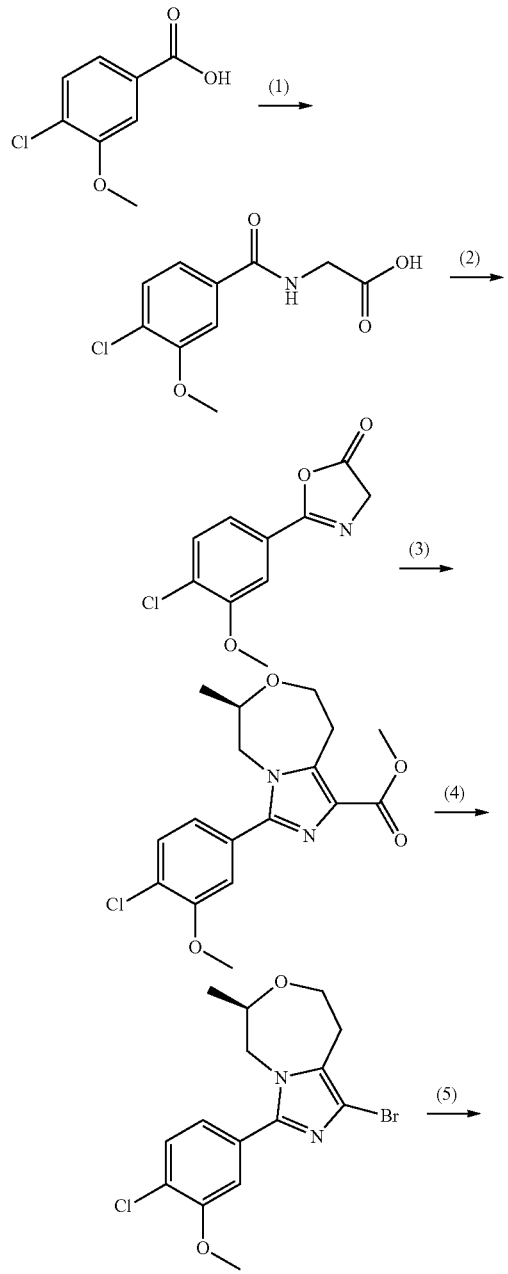

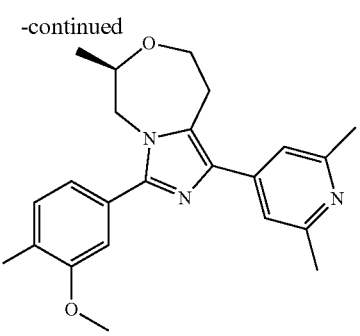

(1) Synthesis of 2-(4-chloro-3-methoxybenzamido)acetic acid

A mixture of 4-chloro-3-methoxybenzoic acid (CAS No. 85740-98-3; 25.0 g, 134 mmol), thionyl chloride (19.6 mL, 268 mmol), and DMF (1.04 mL) was stirred in toluene (428 mL) at 110° C. for 2 hours. The reaction mixture was cooled to room temperature, and then the solvent was evaporated under reduced pressure to obtain crude acid chloride. The resultant crude acid chloride was dissolved in an adequate amount of THF, and glycine (CAS No. 56-40-6; 17.93 g, 161 mmol) was added to the mixture. A 3 N aqueous sodium hydroxide solution (134 mL) was slowly added to the mixture at room temperature, and the reaction mixture was stirred at room temperature for 2 hours. The reaction mixture was acidified with hydrochloric acid, and ethyl acetate was added. The organic layer was separated and the resultant organic layers were washed serially with water and a saturated aqueous sodium chloride solution. The organic layer was dried over anhydrous magnesium sulfate. The organic layers were concentrated under reduced pressure to obtain a title compound (31.1 g, 128 mmol).

$^1$H-NMR (400 MHz, MeOH-d4) δ (ppm): 3.94-3.97 (m, 3H), 4.07-4.12 (m, 2H), 7.40-7.49 (m, 2H), 7.54-7.56 (m, 1H), 8.81 (brs, 1H).

(2) Synthesis of 2-(4-chloro-3-methoxyphenyl)oxazol-5 (4H)-one

A solution of the compound obtained in Example 1-(1) (30.5 g, 125 mmol) and NMM (14.5 mL, 131 mmol) in THF (300 mL) was cooled to −10° C. Methyl chloroformate (10.2 mL, 131 mmol) was added dropwise into the reaction solution at the same temperature. After the addition was complete, the reaction mixture was slowly warmed to room temperature and further stirred for 1 hour at room temperature. The generated insolubles were filtered off and the filtrate was concentrated under reduced pressure. The resultant solid was washed with n-heptane to obtain a title compound (24.3 g, 108 mmol).

$^1$H-NMR (400 MHz, CDCl3) δ (ppm): 3.97 (s, 3H), 4.43 (s, 2H), 7.45-7.55 (m, 3H).

(3) Synthesis of (R)-methyl 3-(4-chloro-3-methoxyphenyl)-6-methyl-5,6,8,9-tetrahydroimidazo[1,5d][1,4]oxazepine-1-carboxylate A solution of the compound obtained in Production Example 1-(6) (1.90 g, 13.3 mmol) and the compound obtained in Example 1-(2) (3.0 g, 13.3 mmol) in THF (24 mL) was heated and stirred under microwave irradiation at 150° C. for 2 hours. The mixture was concentrated under reduced pressure, and the resultant residue was dissolved in methanol (30 mL). Sodium methoxide (718 mg, 13.3 mmol) was added to the mixture and the resultant was stirred at 100° C. for 1 hour. The reaction mixture was cooled to room temperature, and water and ethyl acetate were added. The organic layer was separated and washed serially with water and a saturated aqueous sodium chloride solution. The organic layer was dried over anhydrous magnesium sulfate. The solvent was evaporated under reduced pressure. The resultant residue was purified by silica gel column chromatography (n-heptane/ethyl acetate) to obtain a title compound (3.47 g, 9.89 mmol).

$^1$H-NMR (400 MHz, CDCl3) δ (ppm): 1.22 (d, J=6.3 Hz, 3H), 3.06-3.14 (m, 1H), 3.60-3.75 (m, 2H), 3.90 (s, 3H), 3.94 (s, 3H), 3.93-3.99 (m, 1H), 4.06 (dd, J=4.7, 16.4 Hz, 1H), 4.17-4.24 (m, 2H), 6.87 (dd, J=2.0, 8.2 Hz, 1H), 7.16 (d, J=2.0 Hz, 1H), 7.43 (d, J=8.2 Hz, 1H).

(4) (R)-1-bromo-3-(4-chloro-3-methoxyphenyl)-6-methyl-5,6,8,9-tetrahydroimidazo[1,5][1,4]oxazepine A solution of the compound obtained in Example 1-(3) (3.47 g, 9.89 mmol) and a 5 N aqueous sodium hydroxide solution (9.9 mL, 49.5 mmol) in methanol (20 mL) was stirred at 100° C. for 2 hours. The reaction mixture was cooled to room temperature and acidified with a 5 N hydrochloric acid. The mixture was concentrated under reduced pressure. DMF (20 mL), potassium carbonate (2.32 g, 16.8 mmol), and NBS (1.99 g, 11.2 mmol) were added to the residue, and the mixture was stirred at room temperature for 8 hours. An aqueous sodium thiosulfate solution and ethyl acetate were added to the reaction mixture. The organic layer was separated and washed serially with water and a saturated aqueous sodium chloride solution. The organic layer was dried over anhydrous magnesium sulfate and the solvent was evaporated under reduced pressure. The resultant residue was purified by NH silica gel column chromatography (n-heptane/ethyl acetate) to obtain a title compound (2.42 g, 6.51 mmol).

$^1$H-NMR (400 MHz, CDCl3) δ (ppm): 1.23 (d, J=6.6 Hz, 3H), 2.93-3.11 (m, 2H), 3.57-3.74 (m, 2H), 3.89-3.97 (m, 1H), 3.94 (s, 3H), 4.14-4.26 (m, 2H), 6.85 (dd, J=2.0, 8.2 Hz, 1H), 7.15 (d, J=2.0 Hz, 1H), 7.43 (d, J=8.2 Hz, 1H).

(5) Synthesis of (R)-3-(4-chloro-3-methoxyphenyl)-1-(2,6-dimethylpyridin-4-yl)-6-methyl-5,6,8,9-tetrahydroimidazo[1,5-d][1,4]oxazepine A mixture of the compound obtained in Example 1-(4) (570 mg, 1.53 mmol), 2,6-dimethyl-pyridine-4-boronic acid (CAS No. 846548-44-5; 463 mg, 3.07 mmol), tetrakis(triphenylphosphine)palladium(0) (89 mg, 0.077 mg), an aqueous sodium carbonate solution (2 M, 2.3 mL) and DME (8 mL) was stirred under microwave irradiation at 150° C. for 1 hour. Water and ethyl acetate were added to the mixture. The organic layer was separated, dried over anhydrous magnesium sulfate, and then concentrated under reduced pressure. The resultant residue was purified by silica gel column chromatography (n-heptane/ethyl acetate→ethyl acetate/methanol) to obtain a title compound (388 mg, 0.975 mmol).

$^1$H-NMR (400 MHz, CDCl3) δ (ppm): 1.27 (d, J=6.6 Hz, 3H), 2.56 (s, 6H), 3.19 (ddd, J=2.4, 10.6, 16.0 Hz, 1H), 3.37 (dd, J=3.9, 16.0 Hz, 1H), 3.63-3.70 (m, 1H), 3.75-3.82 (m, 1H), 3.94-4.01 (m, 1H), 3.97 (s, 3H), 4.19-4.28 (m, 2H), 6.93 (dd, J=2.0, 8.2 Hz, 1H), 7.18 (d, J=2.0 Hz, 1H), 7.21 (s, 2H), 7.46 (d, J=8.2 Hz, 1H).

ESI-MS m/z 398 [M+H]+

Example 2

Synthesis of 1-(2,6-dimethylpyridin-4-yl)-3-(3-fluoro-4-(2,2,2-trifluoroethoxy)phenyl)-5,6,8,9-tetrahydroimidazo[1,5-d][1,4]oxazepine

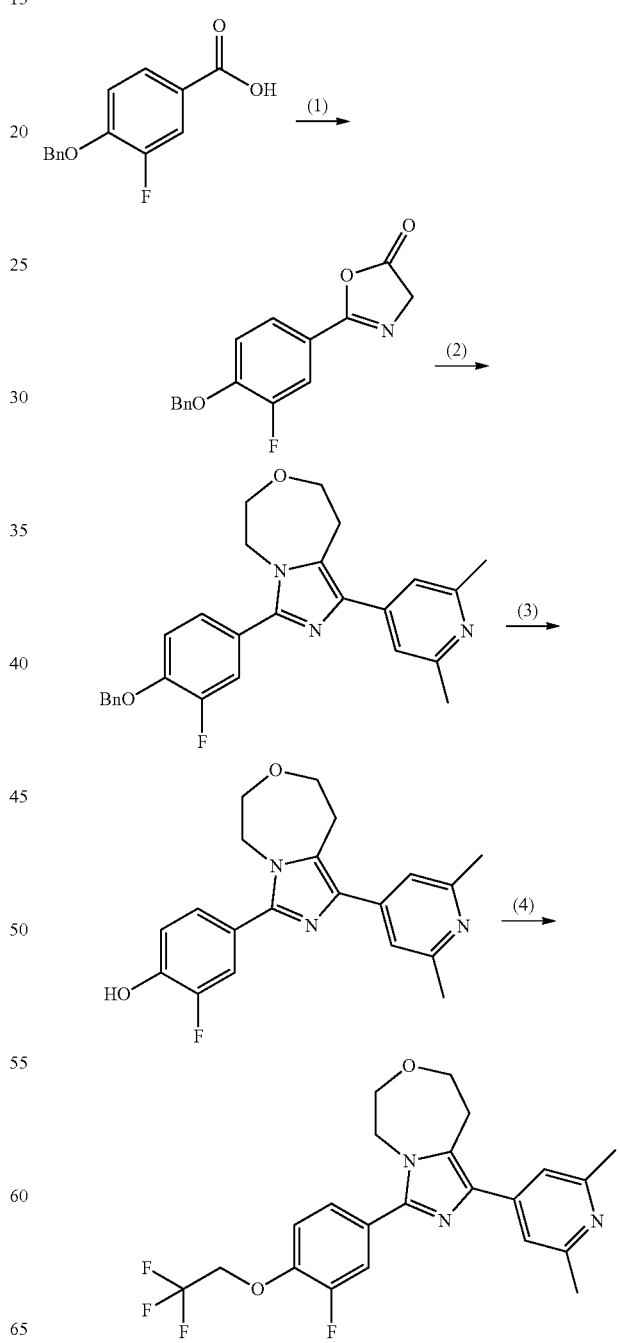

(1) Synthesis of 2-(4-benzyloxy-3-fluorophenyl) oxazol-5 (4H)-one

According to the methods of Examples 1-(1) and 1-(2), a title compound (1.58 g, 5.54 mmol) was obtained from 4-benzyloxy-3-fluorobenzoate (CAS No. 152552-64-2; 2.00 g, 8.12 mmol).

$^1$H-NMR (400 MHz, CDCl3) δ (ppm): 4.39 (s, 2H), 5.22 (s, 2H), 7.03-7.09 (m, 1H), 7.33-7.48 (m, 5H), 7.67-7.78 (m, 2H).

(2) Synthesis of 3-(4-(benzyloxy)-3-fluorophenyl)-1-(2,6-dimethylpyridin-4-yl)-5,6,8,9-tetrahydroimidazo[1,5-d][1,4]oxazepine According to the methods of Examples 1-(3), 1-(4), and 1-(5), a title compound (0.112 g, 0.253 mmol) was obtained from the compound obtained in Example 2-(1) (1.10 g, 3.87 mmol) and 5-methoxy-2,3,6,7-tetrahydro-1,4-oxazepine (0.500 g, 3.87 mmol).

$^1$H-NMR (400 MHz, CDCl3) δ (ppm): 2.55 (s, 6H), 3.27 (dd, J=3.7, 5.7 Hz, 2H), 3.89 (td, J=4.3, 9.0 Hz, 4H), 4.22-4.29 (m, 2H), 5.20 (s, 2H), 7.04-7.10 (m, 1H), 7.15-7.22 (m, 3H), 7.27-7.46 (m, 6H).

(3) Synthesis of 4-(1-(2,6-dimethylpyridin-4-yl)-5,6,8,9-tetrahydroimidazo[1,5-d][1,4]oxazepin-3-yl)-2-fluorophenol A suspension of the compound obtained in Example 2-(2) (105 mg, 0.237 mmol), 5% palladium/carbon (25.2 mg, including 50% water content), and acetic acid (0.014 mL, 0.237 mmol) in ethanol (2.00 mL) was stirred under hydrogen atmosphere at room temperature for 4 hours. The insolubles were removed, then the filtrate was concentrated under reduced pressure and the resultant residue was purified by silica gel column chromatography (n-heptane/ethyl acetate) to obtain a title compound (71.0 mg, 0.201 mmol).

$^1$H-NMR (400 MHz, CDCl3) δ (ppm): 2.55 (s, 6H), 3.26 (dd, J=3.9, 5.5 Hz, 2H), 3.86-3.91 (m, 4H), 4.22-4.29 (m, 2H), 6.90-6.97 (m, 1H), 7.05 (d, J=8.6 Hz, 1H), 7.14-7.23 (m, 1H), 7.21 (s, 2H).
ESI-MS m/z 354 [M+H]+

(4) Synthesis of 1-(2,6-dimethylpyridin-4-yl)-3-(3-fluoro-4-(2,2,2-trifluoroethoxy)phenyl)-5,6,8,9-tetrahydroimidazo[1,5-d][1,4]oxazepine 2-Iodo-1,1,1-trifluoroethane (16.6 mg, 0.079 mmol) was added to a mixture of the compound obtained in Example 2-(3) (14.0 mg, 0.040 mmol), potassium carbonate (16.4 mg, 0.119 mmol) and DMF (500 μL). The reaction mixture was stirred at 100° C. for 3 hours. The reaction mixture was cooled to room temperature and water and ethyl acetate were added. The organic layer was separated, washed serially with water and a saturated aqueous sodium chloride solution, and dried over anhydrous magnesium sulfate. The solvent was evaporated under reduced pressure and the resultant residue was purified by silica gel column chromatography (n-heptane/ethyl acetate→ethyl acetate/methanol) to obtain a title compound (4.88 mg, 0.011 mmol).

$^1$H-NMR (400 MHz, CDCl3) δ (ppm): 2.56 (s, 6H), 3.28 (dd, J=3.7, 5.7 Hz, 2H), 3.84-3.95 (m, 4H), 4.23-4.31 (m, 2H), 4.45-4.52 (m, 2H), 7.09-7.16 (m, 1H), 7.19 (s, 2H), 7.26-7.29 (m, 1H), 7.35 (dd, J=2.2, 11.5 Hz, 1H).
ESI-MS m/z 436 [M+H]+

Example 3

Synthesis of 3-(4-chloro-3-(2,2,2-trifluoroethoxy)phenyl)-1-(2,6-dimethylpyridin-4-yl)-5,6,8,9-tetrahydroimidazo[1,5-d][1,4]oxazepine

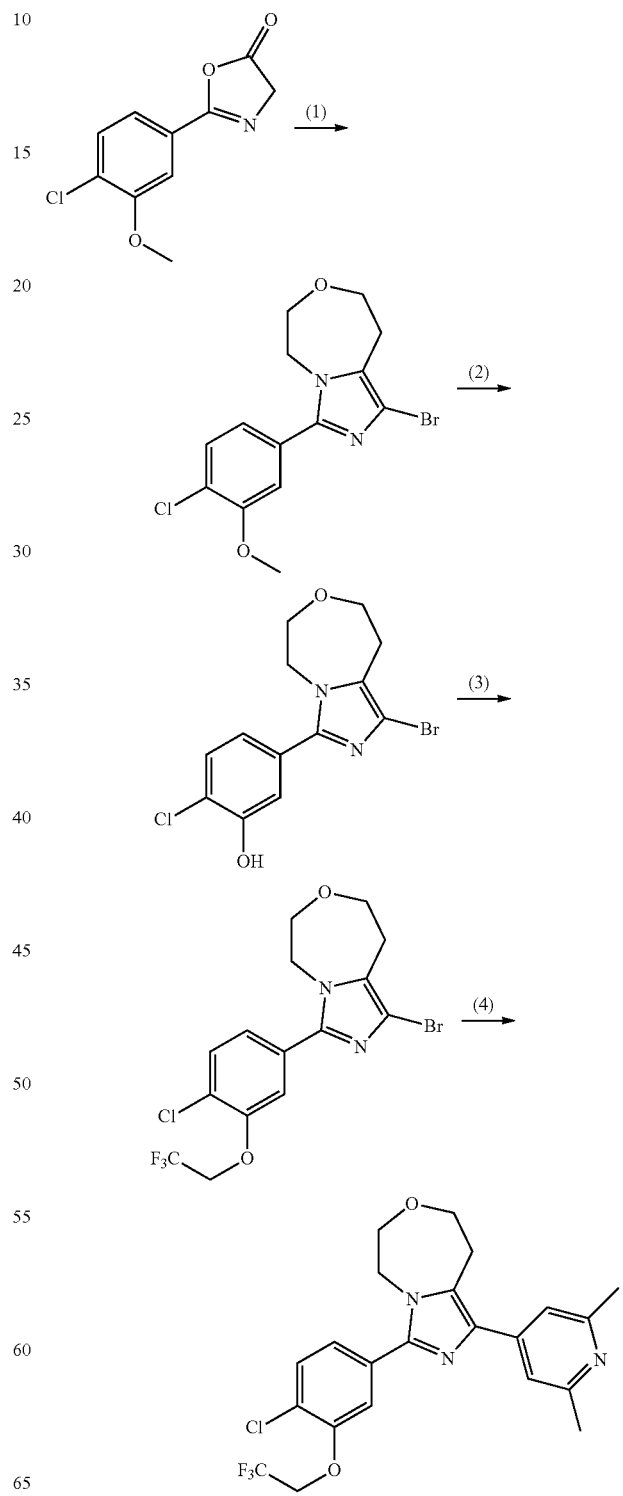

(1) Synthesis of 1-bromo-3-(4-chloro-3-methoxyphenyl)-5,6,8,9-tetrahydroimidazo[1,5-d][1,4]oxazepine According to the methods of Examples 1-(3) and 1-(4), a title compound (73.0 mg, 0.204 mmol) was obtained from the compound obtained in Example 1-(2) (873 mg, 3.87 mmol) and 5-methoxy-2,3,6,7-tetrahydro-1,4-oxazepine (0.500 g, 3.87 mmol).

$^1$H-NMR (400 MHz, CDCl3) δ (ppm): 3.00-3.08 (m, 2H), 3.79-3.90 (m, 4H), 3.94 (s, 3H), 4.22-4.28 (m, 2H), 6.87 (dd, J=1.8, 8.0 Hz, 1H), 7.17 (d, J=1.6 Hz, 1H), 7.41 (d, J=8.2 Hz, 1H).

(2) Synthesis of 5-(1-bromo-5,6,8,9-tetrahydroimidazo[1,5-d][1,4]oxazepin-3-yl)-2-chlorophenol A solution of the compound obtained in Example 3-(1) (68.0 mg, 0.190 mmol) in DCM (3.00 mL) was cooled to −78° C., and a 1 M boron tribromide solution (0.951 mL, 0.951 mmol) in DCM was added dropwise. The reaction mixture was slowly warmed to room temperature and an aqueous ammonia solution was added. Chloroform was added to the mixture to separate the organic layer. The organic layer was washed serially with water and a saturated aqueous sodium chloride solution and then dried over anhydrous magnesium sulfate. The solvent was evaporated under reduced pressure and the resultant residue was purified by silica gel column chromatography (n-heptane/ethyl acetate) to obtain a title compound (41.2 mg, 0.120 mmol).

$^1$H-NMR (400 MHz, CDCl3) δ (ppm): 3.00-3.07 (m, 2H), 3.78-3.90 (m, 4H), 4.20-4.27 (m, 2H), 6.88 (dd, J=2.0, 8.2 Hz, 1H), 7.24 (d, J=2.0 Hz, 1H), 7.36 (d, J=8.2 Hz, 1H).

(3) Synthesis of 1-bromo-3-(4-chloro-3-(2,2,2-trifluoroethoxy)phenyl)-5,6,8,9-tetrahydroimidazo[1,5-d][1,4]oxazepine 2-Iodo-1,1,1-trifluoroethane (69.8 mg, 0.333 mmol) was added to a mixture of the compound obtained in Example 3-(2) (38.1 mg, 0.111 mmol), potassium carbonate (61.3 mg, 0.444 mmol) and DMF (1.00 mL), and the mixture was stirred at 120° C. for 4 hours. The reaction mixture was cooled to room temperature and water and ethyl acetate were added. The organic layer was separated, washed serially with water and a saturated aqueous sodium chloride solution, and dried over anhydrous magnesium sulfate. The solvent was evaporated under reduced pressure and the resultant residue was purified by silica gel column chromatography (n-heptane/ethyl acetate) to obtain a title compound (31.1 mg, 0.073 mmol).

$^1$H-NMR (400 MHz, CDCl3) δ (ppm): 3.01-3.10 (m, 2H), 3.80-3.92 (m, 4H), 4.22-4.30 (m, 2H), 4.44-4.50 (m, 2H), 7.02 (dd, J=2.0, 8.2 Hz, 1H), 7.21 (d, J=1.8 Hz, 1H), 7.47 (d, J=8.2 Hz, 1H).

(4) Synthesis of 3-(4-chloro-3-(2,2,2-trifluoroethoxy)phenyl)-1-(2,6-dimethylpyridin-4-yl)-5,6,8,9-tetrahydroimidazo[1,5-d][1,4]oxazepine According to the method of Example 1-(5), a title compound (7.20 mg, 0.016 mmol) was obtained from the compound obtained in Example 3-(3) (31.0 mg, 0.073 mmol) and 2,6-dimethyl-pyridine-4-boronic acid (22.0 mg, 0.146 mmol).

$^1$H-NMR (400 MHz, CDCl3) δ (ppm): 2.56 (s, 6H), 3.28 (dd, J=3.9, 5.5 Hz, 2H), 3.84-3.95 (m, 4H), 4.24-4.31 (m, 2H), 4.45-4.52 (m, 2H), 7.09 (dd, J=1.8, 8.4 Hz, 1H), 7.19 (s, 2H), 7.25 (d, J=1.6 Hz, 1H), 7.50 (d, J=8.2 Hz, 1H).

ESI-MS m/z 452 [M+H]+

Example 4

Synthesis of 3-(4-bromo-3-methoxyphenyl)-1-(2,6-dimethylpyridin-4-yl)-5,6,8,9-tetrahydroimidazo[1,5-d][1,4]oxazepine

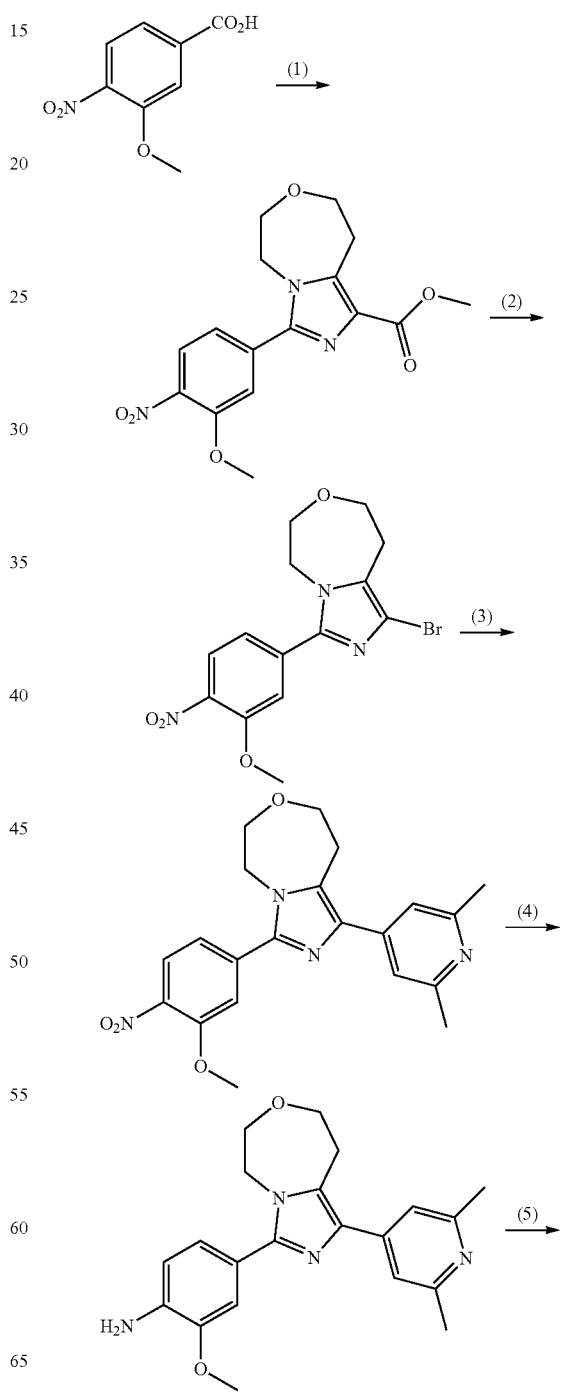

-continued

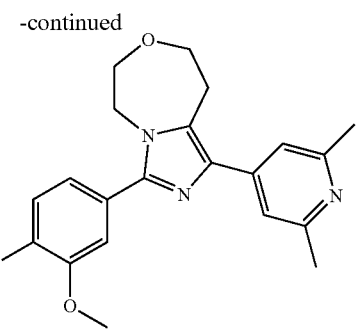

(1) Synthesis of methyl 3-(3-methoxy-4-nitrophenyl)-5,6,8,9-tetrahydroimidazo[1,5-d][1,4]oxazepine-1-carboxylate According to the methods of Examples 1-(1) and 1-(2), an oxazolone compound was obtained from 3-methoxy-4-nitrobenzoic acid (CAS No. 5081-36-7; 3.88 g, 19.7 mmol). According to the method of Example 1-(3), a title compound (1.20 g, 3.46 mmol) was obtained from the oxazolone compound (3.36 g, 14.2 mmol) and 5-methoxy-2,3,6,7-tetrahydro-1,4-oxazepine (1.82 g, 14.2 mmol).

$^1$H-NMR (400 MHz, CDCl3) δ (ppm): 3.60-3.66 (m, 2H), 3.82-3.86 (m, 2H), 3.87-3.93 (m, 2H), 3.92 (s, 3H), 4.02 (s, 3H), 4.26-4.31 (m, 2H), 7.02 (dd, 1.4, 8.0 Hz, 1H), 7.39 (d, J=1.6 Hz, 1H), 7.93 (d, J=8.2 Hz, 1H).

(2) Synthesis of 1-bromo-3-(3-methoxy-4-nitrophenyl)-5,6,8,9-tetrahydroimidazo[1,5-d][1,4]oxazepine According to the method of Example 1-(4), a title compound (83.4 mg, 0.227 mmol) was obtained from the compound obtained in Example 4-(1) (111 mg, 0.320 mmol).

$^1$H-NMR (400 MHz, CDCl3) δ (ppm): 3.08 (dd, J=4.3, 5.9 Hz, 2H), 3.86 (td, J=4.2, 8.0 Hz, 4H), 4.02 (s, 3H), 4.27-4.32 (m, 2H), 7.00 (dd, J=1.6, 8.6 Hz, 1H), 7.38 (d, J=1.6 Hz, 1H), 7.92 (d, J=8.6 Hz, 1H).
ESI-MS m/z 368, 370 [M+H]+390, 392 [M+Na]+

(3) Synthesis of 1-(2,6-dimethylpyridin-4-yl)-3-(3-methoxy-4-nitrophenyl)-5,6,8,9-tetrahydroimidazo[1,5-d][1,4]oxazepine According to the method of Example 1-(5), a crude title compound (101 mg) was obtained from the compound obtained in Example 4-(2) (83 mg, 0.23 mmol) and 2,6-dimethyl-pyridine-4-boronic acid (68 mg, 0.45 mmol).

$^1$H-NMR (400 MHz, CDCl3) δ (ppm): 2.57 (s, 6H), 3.30 (dd, J=3.9, 5.5 Hz, 2H), 3.88-3.95 (m, 4H), 4.04 (s, 3H), 4.30-4.36 (m, 2H), 7.07 (dd, 1.6, 8.2 Hz, 1H), 7.20 (s, 2H), 7.42 (d, J=1.6 Hz, 1H), 7.96 (d, J=8.6 Hz, 1H).
ESI-MS m/z 395 [M+H]+

(4) Synthesis of 4-(1-(2,6-dimethylpyridin-4-yl)-5,6,8,9-tetrahydroimidazo[1,5-d][1,4]oxazepin-3-yl)-2-methoxyaniline A solution of the compound obtained in Example 4-(3) (101 mg) and 10% palladium/carbon (20 mg, including 50% water content) in ethanol (1.0 mL) was stirred under hydrogen atmosphere for 6 hours. The reaction solution was filtered through Celite (trademark), and then the filtrate was concentrated under reduced pressure. The resultant residue was purified by NH silica gel column chromatography (n-heptane/ethyl acetate) to obtain a title compound (39.8 mg, 0.109 mmol).

$^1$H-NMR (400 MHz, CDCl3) δ (ppm): 2.53 (s, 6H), 3.22-3.32 (m, 2H), 3.80-3.94 (m, 4H), 3.89 (s, 3H), 3.99 (brs, 2H), 4.23-4.34 (m, 2H), 6.73 (d, J=7.8 Hz, 1H), 6.82 (dd, J=1.8, 8.0 Hz, 1H), 7.02 (d, J=2.1 Hz, 1H), 7.21 (s, 2H).
ESI-MS m/z 365 [M+H]+

(5) Synthesis of 3-(4-bromo-3-methoxyphenyl)-1-(2,6-dimethylpyridin-4-yl)-5,6,8,9-tetrahydroimidazo[1,5-d][1,4]oxazepine An aqueous sodium nitrite solution (1.0 M, 0.11 mL) was added to a solution of the compound obtained in Example 4-(4) (20 mg, 0.055 mmol), water (0.10 mL), and concentrated sulfuric acid (0.10 mL) in acetonitrile (0.40 mL) under ice-cooling. The mixture was stirred at the same temperature for 10 minutes, then an aqueous copper(I) bromide solution (2.0 M, 0.22 mL) was added, and the mixture was stirred for 1 hour. The reaction mixture was heated to 50° C. and stirred for 5 hours, and then cooled to room temperature. Ethyl acetate was added to the reaction mixture, washed with aqueous ammonia twice, and washed with a saturated aqueous sodium chloride solution. The resultant organic layer was dried over anhydrous sodium sulfate and concentrated under reduced pressure. The resultant residue was purified by silica gel thin layer chromatography (ethyl acetate) to obtain a title compound (16 mg, 0.037 mmol).

$^1$H-NMR (400 MHz, CDCl3) δ (ppm): 2.55 (s, 6H), 3.27 (dd, J=3.9, 5.5 Hz, 2H), 3.84-3.93 (m, 4H), 3.95 (s, 3H), 4.25-4.30 (m, 2H), 6.87 (dd, J=2.0, 8.2 Hz, 1H), 7.16 (d, J=2.0 Hz, 1H), 7.20 (s, 2H), 7.62 (d, J=7.8 Hz, 1H).
ESI-MS m/z 428, 430 [M+H]+

Example 5

Synthesis of (R)-1-(2,6-dimethylpyridin-4-yl)-3-(4-fluoro-3-(2-fluoroethoxy)phenyl)-6-methyl-5,6,8,9-tetrahydroimidazo[1,5-d][1,4]oxazepine

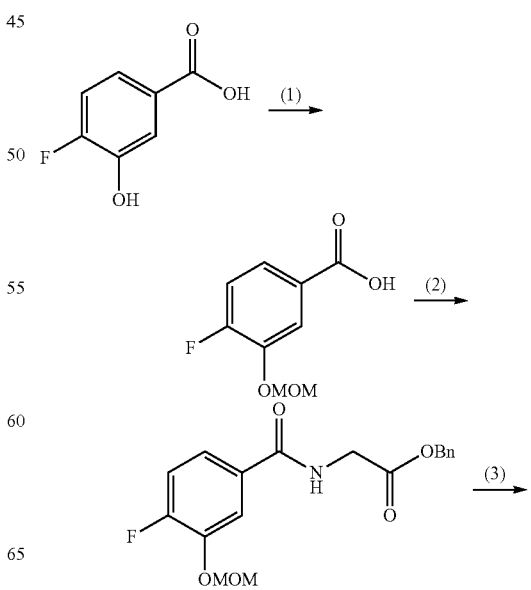

-continued

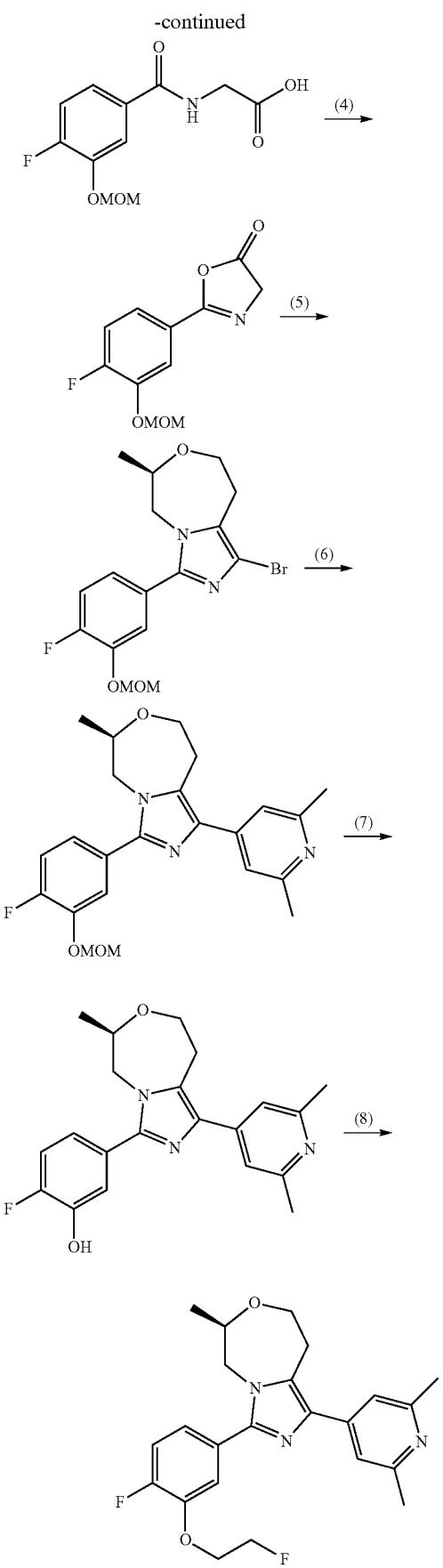

(1) Synthesis of 4-fluoro-3-(methoxymethoxy)benzoic acid

Chloromethyl methyl ether (14.5 mL, 192 mmol) was added to a solution of 4-fluoro-3-hydroxybenzoic acid (CAS No. 51446-31-2; 10.0 g, 64.1 mmol) and TEA (35.7 mL, 256 mmol) in THF (150 mL) under ice-cooling. The reaction mixture was stirred at room temperature for 2 hours. A 1 N hydrochloric acid and ethyl acetate were added to the reaction mixture, the organic layer was separated, and the separated organic layer was filtered through a silica gel pad (silica gel, ethyl acetate/n-heptane). The resultant filtrate was evaporated under reduced pressure. The resultant residue was dissolved in methanol (100 mL), a 5 N aqueous sodium hydroxide solution (38.4 mL) was added, and the mixture was stirred at 80° C. for 1 hour. The reaction mixture was cooled to room temperature, and a 5 N hydrochloric acid and ethyl acetate were added to the reaction mixture to separate the organic layer. The organic layer was washed serially with water and a saturated aqueous sodium chloride solution and dried over anhydrous magnesium sulfate. The solvent was evaporated under reduced pressure to obtain a crude title compound (10.1 g).

$^1$H-NMR (400 MHz, CDCl3) δ (ppm): 3.54 (s, 3H), 5.28 (s, 2H), 7.13-7.22 (m, 1H), 7.78 (ddd, J=2.0, 4.5, 8.4 Hz, 1H), 7.93 (dd, J=2.0, 7.8 Hz, 1H).

(2) Synthesis of benzyl 2-(4-fluoro-3-(methoxymethoxy))benzamido)acetate

EDC (11.1 g, 57.8 mmol) was added to a solution of the compound obtained in Example 5-(1) (8.90 g), glycine benzyl ester p-toluenesulfonate (CAS No. 28607-46-7; 19.5 g; 57.8 mmol), HOBT (7.81 g, 57.8 mmol), and TEA (16.1 mL, 116 mmol) in DCM (100 mL) under ice-cooling. The reaction mixture was stirred overnight, and then a 1 N hydrochloric acid and chloroform were added. The organic layer was separated, washed serially with water and a saturated aqueous sodium chloride solution, and dried over anhydrous magnesium sulfate. The filtrate was concentrated under reduced pressure and the resultant residue was purified by silica gel chromatography (n-heptane/ethyl acetate) to obtain a title compound (14.2 g, 40.9 mmol).

$^1$H-NMR (400 MHz, CDCl3) δ (ppm): 3.52 (s, 3H), 4.27 (d, J=5.1 Hz, 2H), 5.23 (s, 2H), 5.26 (s, 2H), 6.61 (brs, 1H), 7.14 (dd, J=8.4, 10.4 Hz, 1H), 7.30-7.51 (m, 6H), 7.68 (dd, J=2.2, 8.0 Hz, 1H).

(3) Synthesis of 2-(4-fluoro-3-(methoxymethoxy)benzamide)acetic acid

A suspension of the compound obtained in Example 5-(2) (14.2 g, 40.9 mmol) and 5% palladium/carbon (0.44 g, including 50% water content) in ethanol (100 mL) was stirred under hydrogen atmosphere at room temperature for 30 minutes. The palladium catalyst was removed and the solvent was evaporated under reduced pressure to obtain a crude title compound (10.3 g).

$^1$H-NMR (400 MHz, MeOH-d4) δ (ppm): 3.51 (s, 3H), 4.02-4.12 (m, 2H), 5.27 (s, 2H), 7.21 (dd, J=8.4, 10.7 Hz, 1H), 7.51-7.54 (m, 1H), 7.75 (dd, J=2.2, 8.0 Hz, 1H).

(4) Synthesis of 2-(4-fluoro-3-(methoxymethoxy) phenyl)oxazol-5(4H)-one

According to the method of Example 1-(2), a title compound (9.11 g, 26.7 mmol) was obtained from the compound obtained in Example 5-(3) (10.3 g).

¹H-NMR (400 MHz, CDCl3) δ (ppm): 3.54 (s, 3H), 4.42 (s, 2H), 5.28 (s, 2H), 7.20 (dd, J=8.5, 10.5 Hz, 1H), 7.63 (ddd, J=2.1, 4.4, 8.5 Hz, 1H), 7.84 (dd, J=2.1, 7.9 Hz, 1H).

(5) Synthesis of (R)-1-bromo-3-(4-fluoro-3-(methoxymethoxy)phenyl)-6-methyl-5,6,8,9-tetrahydroimidazo[1,5-d][1,4]oxazepine According to the methods of Examples 1-(3) and 1-(4), a title compound (388.0 mg, 1.01 mmol) was obtained from the compound obtained in Example 5-(4) (1.50 g, 6.27 mmol) and the compound obtained in Production Example 1-(6) (0.898 g, 6.27 mmol).
¹H-NMR (400 MHz, CDCl3) δ (ppm): 1.23 (d, J=6.6 Hz, 3H), 2.93-3.10 (m, 2H), 3.52 (s, 3H), 3.58-3.65 (m, 1H), 3.68-3.76 (m, 1H), 3.90 (dd, J=8.4, 14.7 Hz, 1H), 4.14-4.24 (m, 2H), 5.22-5.28 (m, 2H), 7.03-7.07 (m, 1H), 7.16 (dd, J=8.4, 10.6 Hz, 1H), 7.32 (dd, J=2.1, 7.8 Hz, 1H).

(6) Synthesis of (R)-1-(2,6-dimethylpyridin-4-yl)-3-(4-fluoro-3-(methoxymethoxy)phenyl)-6-methyl-5,6,8,9-tetrahydroimidazo[1,5-d][1,4]oxazepine According to the method of Example 1-(5), a title compound (78 mg, 0.190 mmol) was obtained from the compound obtained in Example 5-(5) (330 mg, 0.857 mmol).
¹H-NMR (400 MHz, CDCl3) δ (ppm): 1.27 (d, J=6.4 Hz, 3H), 2.55 (s, 6H), 3.12-3.22 (m, 1H), 3.32-3.38 (m, 1H), 3.53 (s, 3H), 3.63-3.68 (m, 1H), 3.76-3.83 (m, 1H), 3.92-3.98 (m, 1H), 4.18-4.27 (m, 2H), 5.24-5.30 (m, 2H), 7.09-7.13 (m, 1H), 7.17-7.22 (m, 3H), 7.36 (dd, J=2.0, 7.8 Hz, 1H).

(7) Synthesis of (R)-5-(1-(2,6-dimethylpyridin-4-yl)-6-methyl-5,6,8,9-tetrahydroimidazo[1,5-d][1,4]oxazepin-3-yl)-2-fluorophenol hydrochloride A 4 N hydrochloric acid (0.474 mL, 1.90 mmol) was added to a solution of the compound obtained in Example 5-(6) (78 mg, 190 μmol) in methanol, and the mixture was stirred at 80° C. for 4 hours. The reaction mixture was cooled to room temperature and the solvent was evaporated under reduced pressure to obtain a crude title compound (68 mg).
¹H-NMR (400 MHz, MeOH-d4) δ (ppm): 1.26 (d, J=6.3 Hz, 3H), 2.84 (s, 6H), 3.35-3.39 (m, 1H), 3.46-3.51 (m, 1H), 3.74-3.86 (m, 1H), 4.00 (t=6.8 Hz, 1H), 4.22-4.25 (m, 1H), 4.35-4.45 (m, 2H), 7.21 (ddd, J=2.3, 4.1, 8.4 Hz, 1H), 7.29-7.48 (m, 2H), 7.95 (s, 2H).

(8) Synthesis of (R)-1-(2,6-dimethylpyridin-4-yl)-3-(4-fluoro-3-(2-fluoroethoxy)phenyl)-6-methyl-5,6,8,9-tetrahydroimidazo[1,5-d][1,4]oxazepine 2-Fluoroethyl tosylate (24.3 mg, 0.111 mmol) was added to a mixture of the compound obtained in Example 5-(7) (30.0 mg, 0.074 mmol), potassium carbonate (30.8 mg, 0.223 mmol), and DMF (300 μL). The reaction mixture was stirred at 80° C. for 3 hours. The reaction mixture was cooled to room temperature and water and ethyl acetate were added. The organic layer was separated, washed serially with water and a saturated aqueous sodium chloride solution, and dried over anhydrous magnesium sulfate. The solvent was evaporated under reduced pressure and the resultant residue was purified by NH silica gel column chromatography (n-heptane/ethyl acetate) to obtain a title compound (24.3 mg, 0.059 mmol).

¹H-NMR (400 MHz, CDCl3) δ (ppm): 1.24-1.27 (m, 3H), 2.55 (s, 6H), 3.11-3.23 (m, 1H), 3.36 (dd, J=4.3, 16.0 Hz, 1H), 3.60-3.82 (m, 2H), 3.96 (dd, J=8.4, 15.0 Hz, 1H), 4.17-4.27 (m, 2H), 4.29-4.44 (m, 2H), 4.69-4.89 (m, 2H), 7.00-7.02 (m, 1H), 7.14-7.25 (m, 4H).
ESI-MS m/z 414[M+H]+

Example 6

Synthesis of (R)-3-(3-cyclopropylmethoxy-4-fluorophenyl)-1-(2,6-dimethylpyridin-4-yl)-6-methyl-5,6,8,9-tetrahydroimidazo[1,5-d][1,4]oxazepine

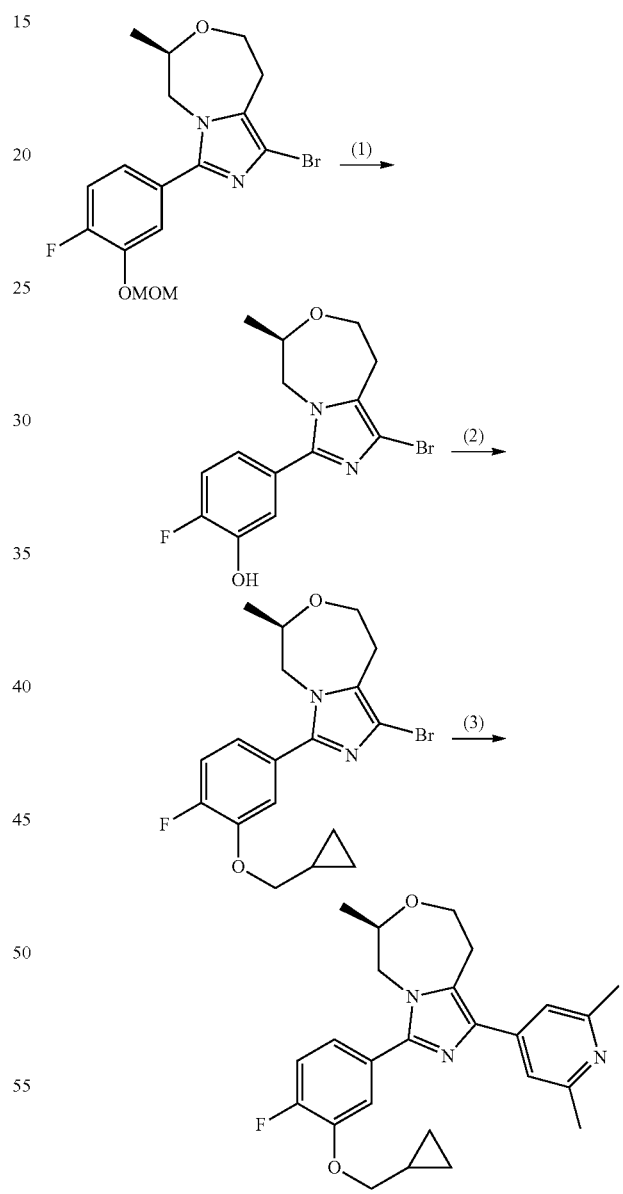

(1) Synthesis of (R)-5-(1-bromo-6-methyl-5,6,8,9-tetrahydroimidazo[1,5-d][1,4]oxazepin-3-yl)-2-fluorophenol hydrochloride A solution of the compound obtained in Example 5-(5) (170 mg, 0.441 mmol) in a 4 M hydrogen chloride/methanol (1.10 mL, 4.41 mmol) was stirred at 80° C. for 2 hours. The reaction mixture was cooled to room temperature and the solvent was evaporated under reduced pressure to obtain a crude title compound (166 mg).

$^1$H-NMR (400 MHz, MeOH-d4) δ (ppm): 1.21 (d, J=6.6 Hz, 3H), 3.07-3.16 (m, 2H), 3.62-3.69 (m, 1H), 3.83-3.89 (m, 1H), 4.13-4.20 (m, 2H), 4.25-4.36 (m, 1H), 7.05-7.10 (m, 1H), 7.19 (d, J=8.2 Hz, 1H), 7.31-7.39 (m, 1H).

(2) Synthesis of (R)-1-bromo-3-(3-(cyclopropyl-methoxy)-4-fluorophenyl)-6-methyl-5,6,8,9-tetrahydroimidazo[1,5-d][1,4]oxazepine Cyclopropylmethyl bromide (64.2 μL, 0.662 mmol) was added to a mixture of the compound obtained in Example 6-(1) (50.0 mg, 0.132 mmol), potassium carbonate (110 mg, 0.794 mmol) and DMF (400 μL), and the mixture was stirred at 120° C. for 5 hours. The reaction mixture was cooled to room temperature, and water and ethyl acetate were added. The organic layer was separated, washed serially with water and a saturated aqueous sodium chloride solution, and dried over anhydrous magnesium sulfate. The solvent was evaporated under reduced pressure and the resultant residue was purified by silica gel column chromatography (n-heptane/ethyl acetate) to obtain a title compound (20.8 mg, 0.053 mmol).

$^1$H-NMR (400 MHz, CDCl3) δ (ppm): 0.28-0.42 (m, 2H), 0.59-0.75 (m 2H), 1.13-1.25 (m, 3H), 1.26-1.40 (m, 1H), 2.87-3.13 (m, 2H), 3.51-3.74 (m, 2H), 3.84-3.96 (m, 3H), 4.10-4.27 (m, 2H), 6.85 (ddd, J=2.0, 4.2, 8.3 Hz, 1H), 7.07-7.20 (m, 2H). δ

(3) Synthesis of (R)-3-(3-cyclopropylmethoxy-4-fluorophenyl)-1-(2,6-dimethylpyridin-4-yl)-6-methyl-5,6,8,9-tetrahydroimidazo[1,5-d][1,4]oxazepine According to the method of Example 1-(5), a title compound (6.80 mg, 0.016 mmol) was obtained from the compound obtained in Example 6-(2) (19.5 mg, 0.049 mmol) and 2,6-dimethyl-pyridine-4-boronic acid (8.94 mg, 0.059 mmol).

$^1$H-NMR (400 MHz, CDCl3) δ (ppm): 0.29-0.42 (m, 2H), 0.62-0.73 (m, 2H), 1.25 (d, J=6.3 Hz, 3H), 1.28-1.38 (m, 1H), 2.55 (s, 6H), 3.19 (dd, J=2.3, 10.5 Hz, 1H), 3.35 (dd, J=3.9, 16.0 Hz, 1H), 3.60-3.82 (m, 2H), 3.88-4.01 (m, 3H), 4.17-4.28 (m, 2H), 6.93 (ddd, J=2.3, 4.1, 8.4 Hz, 1H), 7.11-7.23 (m, 4H).
ESI-MS m/z 422 [M+H]+

Example 7

Synthesis of (R)-1-(2,6-dimethylpyridin-4-yl)-3-(3-methoxy-4-(trifluoromethyl)phenyl)-6-methyl-5,6,8,9-tetrahydroimidazo[1,5-d][1,4]oxazepine

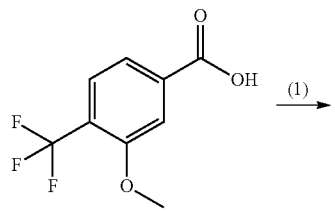

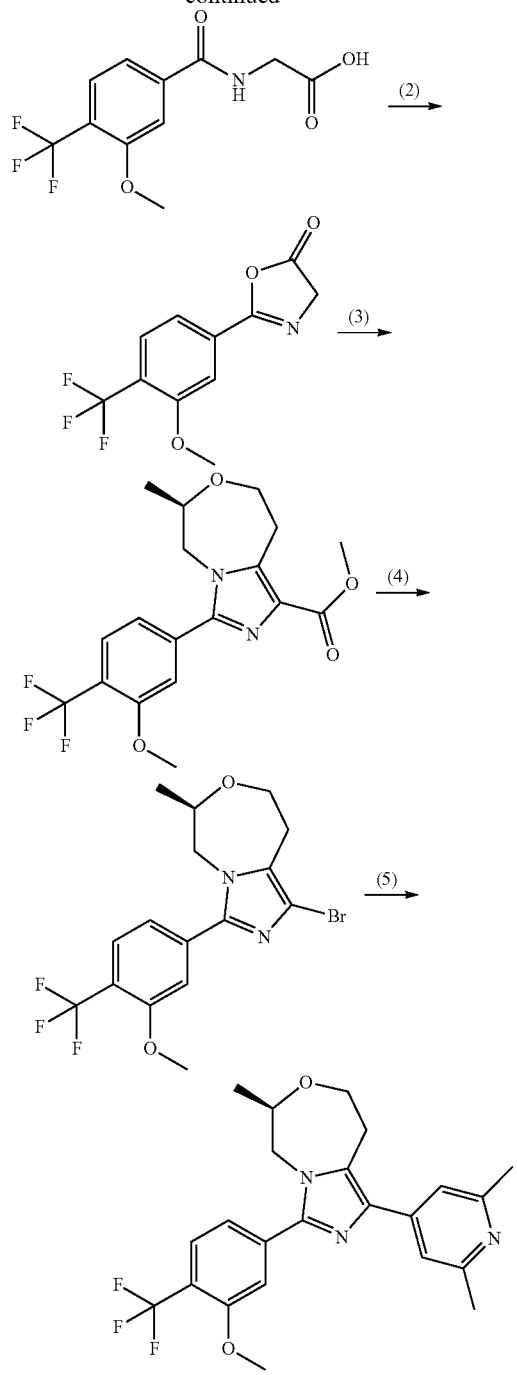

(1) Synthesis of 2-(3-methoxy-4-(trifluoromethyl)benzamido)acetic acid

Oxalyl chloride (9.59 mL, 112 mmol) was added dropwise into a suspension of 3-methoxy-4-(trifluoromethyl)benzoic acid (CAS No. 276861-63-3; 20.5 g, 93.1 mmol) and DMF (0.205 mL, 2.65 mmol) in THF (41 mL)/DCM (164 mL) under ice-cooling. The reaction mixture was warmed to room temperature and further stirred for 2 hours. The solvent was evaporated under reduced pressure to obtain corresponding crude acid chloride. A solution of crude acid chloride in THF (40 mL) was added dropwise into a mixture of glycine (8.39 g, 112 mmol), a 2 N aqueous sodium hydroxide solution (93 mL) and THF (200 mL) over a period of 15 minutes under ice-cooling. The reaction mixture was stirred at room temperature for 3 days. The reaction mixture was acidified with a 5 N hydrochloric acid under ice-cooling. Ethyl acetate was added to the mixture to separate the organic layer. The resultant organic layer was dried over anhydrous magnesium sulfate and the solvent was evaporated under reduced pressure to obtain a title compound (25.6 g, 92.0 mmol).

$^1$H-NMR (400 MHz, DMSO-d6) δ (ppm): 3.94 (s, 2H), 3.96 (s, 3H), 7.57 (d, J=8.2 Hz, 1H), 7.67 (s, 1H), 7.75 (d, J=8.2 Hz, 1H), 9.05 (brs, 1H).

(2) Synthesis of 2-(3-methoxy-4-(trifluoromethyl)phenyl)oxazol-5(4H)-one

Methyl chloroformate (2.34 mL, 30.3 mmol) was added into a solution of the compound obtained in Example 7-(1) (8.00 g, 28.9 mmol) and NMM (3.33 mL, 30.3 mmol) in THF (150 mL) at −10° C. The reaction mixture was stirred at −10° C. for 1 hour and then stirred for 2 hours while slowly warming it to room temperature. The resultant solid was separated by filtration through Celite (trademark). The filtrate was concentrated under reduced pressure to obtain a title compound (7.48 g, 28.9 mmol).

$^1$H-NMR (400 MHz, CDCl3) δ (ppm): 3.95 (s, 3H), 4.44 (s, 2H), 7.32-7.39 (m, 1H), 7.58-7.63 (m, 3H).

(3) Synthesis of (R)-methyl 3-(3-methoxy-4-(trifluoromethyl)phenyl)-6-methyl-5,6,8,9-tetrahydroimidazo[1,5-d][1,4]oxazepine-1-carboxylate A solution of the compound obtained in Example 7-(2) (4.16 g, 16.1 mmol) and the compound obtained in Production Example 1-(6) (2.00 g, 14.0 mmol) in toluene (25 mL) was heated under reflux for 6 hours. The reaction mixture was cooled to room temperature and the solvent was evaporated under reduced pressure. The resultant residue was dissolved in methanol (30 mL). Sodium methoxide (755 mg, 14.0 mmol) was added to the mixture, then the resultant was heated under reflux. After 3 hours, the reaction mixture was cooled to room temperature and ethyl acetate and a saturated aqueous ammonium chloride solution were added. The organic layer was separated, washed with a saturated aqueous sodium chloride solution, and dried over anhydrous magnesium sulfate. The insolubles were separated through filtration, and the filtrate was concentrated under reduced pressure. The resultant residue was purified by NH silica gel column chromatography (n-heptane/ethyl acetate) to obtain a title compound (3.18 g, 8.27 mmol).

$^1$H-NMR (400 MHz, CDCl3) δ (ppm): 1.24 (d, J=6.6 Hz, 3H), 3.11 (ddd, J=2.4, 10.9, 16.4 Hz, 1H), 3.61-3.74 (m, 2H), 3.91 (s, 3H), 3.96 (s, 3H), 3.96-4.03 (m, 1H), 4.07 (dd, J=4.7, 16.4 Hz, 1H), 4.17-4.25 (m, 2H), 6.97 (d, J=8.2 Hz, 1H), 7.25 (s, 1H), 7.64 (d, J=8.2 Hz, 1H).
ESI-MS m/z 385 [M+H]+

(4) Synthesis of (R)-1-bromo-3-(3-methoxy-4-(trifluoromethyl)phenyl)-6-methyl-5,6,8,9-tetrahydroimidazo[1,5-d][1,4]oxazepine A 2 N aqueous sodium hydroxide solution (3.31 mL) was added to a solution of the compound obtained in Example 7-(3) (3.18 g, 8.23 mmol) in ethanol (40 mL). The reaction mixture was heated under reflux for 2 hours. The reaction mixture was cooled to room temperature and acidified with a 5 N hydrochloric acid. The mixture was concentrated under reduced pressure. Ethanol (50 mL) was added to the resultant residue and the insolubles were separated through filtration. The resultant filtrate was concentrated under reduced pressure and dissolved in ethanol (5 mL) and DMF (50 mL). Potassium carbonate (2.86 g, 20.7 mmol) and NBS (2.21 g, 12.4 mmol) were added to the reaction mixture, and the mixture was stirred at room temperature for 14 hours. Water and ethyl acetate were added to the mixture to separate the organic layer. The resultant organic layer was washed with a saturated aqueous sodium chloride solution and dried over anhydrous magnesium sulfate. The insolubles were separated through filtration and the filtrate was concentrated. The residue was purified by NH silica gel column chromatography (n-heptane/ethyl acetate) to obtain a title compound (2.73 g, 6.74 mmol).

$^1$H-NMR (400 MHz, CDCl3) δ (ppm): 1.24 (d, J=6.3 Hz, 3H), 2.95-3.12 (m, 2H), 3.57-3.65 (m, 1H), 3.67-3.75 (m, 1H), 3.92-4.00 (m, 1H), 3.95 (s, 3H), 4.16-4.28 (m, 2H), 6.95 (d, J=8.2 Hz, 1H), 7.24 (s, 1H), 7.63 (d, J=8.2 Hz, 1H).
ESI-MS m/z 405, 407 [M+H]+

(5) Synthesis of (R)-1-(2,6-dimethylpyridin-4-yl)-3-(3-methoxy-4-(trifluoromethyl)phenyl)-6-methyl-5,6,8,9-tetrahydroimidazo[1,5-d][1,4]oxazepine A mixture of the compound obtained in Example 7-(4) (900 mg, 2.22 mmol), 2,6-dimethyl-pyridine-4-boronic acid (402 mg, 2.67 mmol), (A-taPhos)$_2$PdCl$_2$ (79 mg, 0.111 mmol), an aqueous sodium carbonate solution (1 M, 5.55 mL) and DMF (20 mL) was stirred at 130° C. for 2.5 hours. The reaction mixture was cooled to room temperature, and then ethyl acetate and water were added to the mixture to separate the organic layer. The organic layer was washed with a saturated aqueous sodium chloride solution and dried over anhydrous magnesium sulfate. The organic layer was concentrated under reduced pressure. The resultant residue was purified serially by silica gel column chromatography (n-heptane/ethyl acetate→ethyl acetate/methanol) and NH silica gel column chromatography (n-heptane/ethyl acetate) to obtain a title compound (750 mg, 1.74 mmol).

$^1$H-NMR (400 MHz, CDCl3) δ (ppm): 1.28 (d, J=6.6 Hz, 3H), 2.56 (s, 6H), 3.20 (ddd, J=2.4, 10.5, 16.0 Hz, 1H), 3.38 (dd, J=4.3, 16.0 Hz, 1H), 3.64-3.71 (m, 1H), 3.76-3.84 (m, 1H), 3.96-4.05 (m, 1H), 3.97 (s, 3H), 4.20-4.31 (m, 2H), 7.03 (d, J=8.2 Hz, 1H), 7.21 (s, 2H), 7.28 (s, 1H), 7.67 (d, J=8.2 Hz, 1H).
ESI-MS m/z 432 [M+H]+

Example 8

Synthesis of (R)-3-(3-methoxy-4-(trifluoromethyl)phenyl)-6-methyl-1-(2-methylpyridin-4-yl)-5,6,8,9-tetrahydroimidazo[1,5-d][1,4]oxazepine

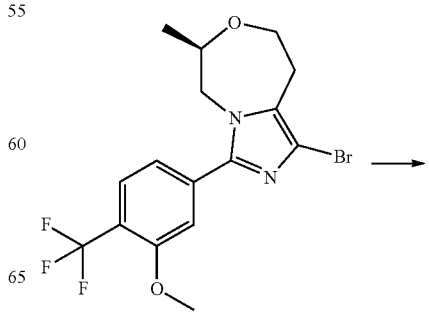

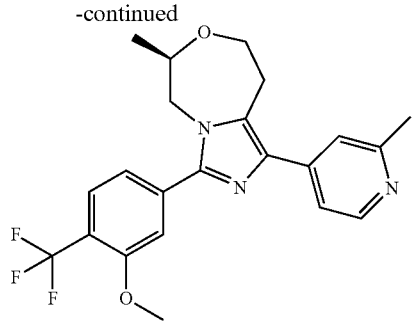

According to the method of Example 7-(5), a title compound (8.0 mg, 0.019 mmol) was obtained from the compound obtained in Example 7-(4) (18 mg, 0.044 mmol) and 2-picoline-4-boronic acid (CAS No. 579476-63-4; 18 mg, 0.13 mmol).

$^1$H-NMR (400 MHz, CDCl3) δ (ppm): 1.28 (d, J=6.6 Hz, 3H), 2.60 (s, 3H), 3.21 (ddd, J=2.3, 10.5, 16.4 Hz, 1H), 3.38 (dd, J=3.9, 15.6 Hz, 1H) 3.64-3.72 (m, 1H), 3.76-3.85 (m, 1H), 3.98 (s, 3H), 4.02 (dd, J=8.6, 14.8 Hz, 1H), 4.23 (ddd, J=2.3, 4.7, 12.1 Hz, 1H), 4.28 (d, J=14.8 Hz, 1H), 7.04 (d, J=7.8 Hz, 1H) 7.28 (s, 1H), 7.30 (dd, J=1.6, 5.1 Hz, 1H), 7.46 (s, 1H), 7.67 (d, J=7.8 Hz, 1H), 8.50 (d, J=5.1 Hz, 1H).

ESI-MS m/z 418 [M+H]+

Example 9

Synthesis of (R)-6-methyl-3-(3-methyl-4-(trifluoromethoxy)phenyl)-1-(2-methylpyridin-4-yl)-5,6,8,9-tetrahydroimidazo[1,5-d][1,4]oxazepine

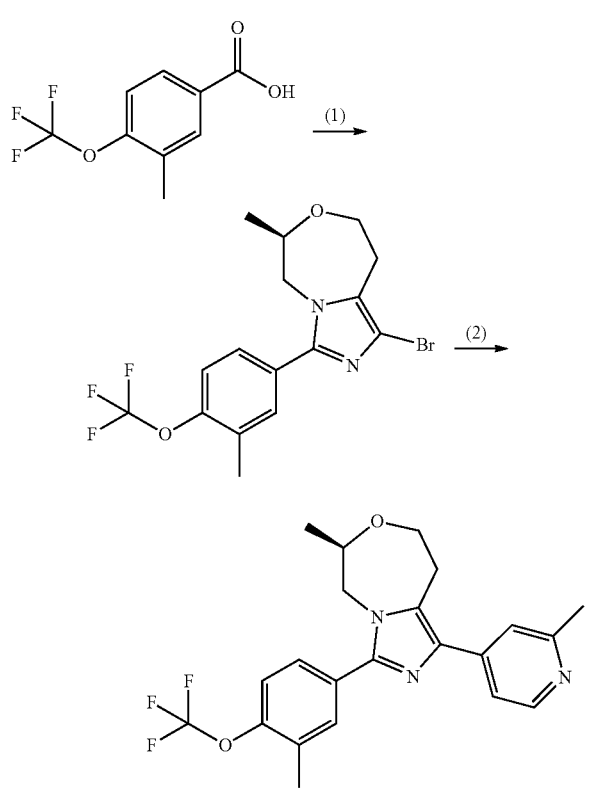

(1) Synthesis of (R)-1-bromo-6-methyl-3-(3-methyl-4-(trifluoromethoxy)phenyl)-5,6,8,9-tetrahydroimidazo[1,5-d][1,4]oxazepine According to the methods of Examples 7-(1) and 7-(2), an oxazolone compound was obtained from 3-methyl-4-(trifluoromethoxy)benzoic acid. According to the methods of Examples 7-(3) and 7-(4), a title compound (44.0 mg, 0.151 mmol) was obtained from the oxazolone compound (300 mg, 1.16 mmol) and the compound obtained in Production Example 1-(6) (166 mg, 1.16 mmol).

ESI-MS m/z 407 [M+H]+

(2) Synthesis of (R)-6-methyl-3-(3-methyl-4-(trifluoromethoxy)phenyl)-1-(2-methylpyridin-4-yl)-5,6,8,9-tetrahydroimidazo[1,5-d][1,4]oxazepine According to the method of Example 7-(5), a title compound (7.20 mg, 0.017 mmol) was obtained from the compound obtained in Example 9-(1) (14.0 mg, 0.0350 mmol) and 2-picoline-4-boronic acid (9.46 mg, 0.069 mmol).

$^1$H-NMR (400 MHz, CDCl3) δ (ppm): 1.28 (d, J=6.3 Hz, 3H), 2.38 (s, 3H), 2.59 (s, 3H), 3.13-3.25 (m, 1H), 3.31-3.42 (m, 1H), 3.62-3.72 (m, 1H), 3.75-3.84 (m, 1H), 3.95-4.04 (m, 1H), 4.18-4.28 (m, 2H), 7.28-7.34 (m, 3H), 7.44-7.52 (m, 2H), 8.47-8.52 (m, 1H).

ESI-MS m/z 418 [M+H]+

Example 10

Synthesis of (R)-1-(2,6-dimethylpyridin-4-yl)-3-(4-ethyl-3-methoxyphenyl)-6-methyl-5,6,8,9,-tetrahydroimidazo[1,5-d][1,4]oxazepine

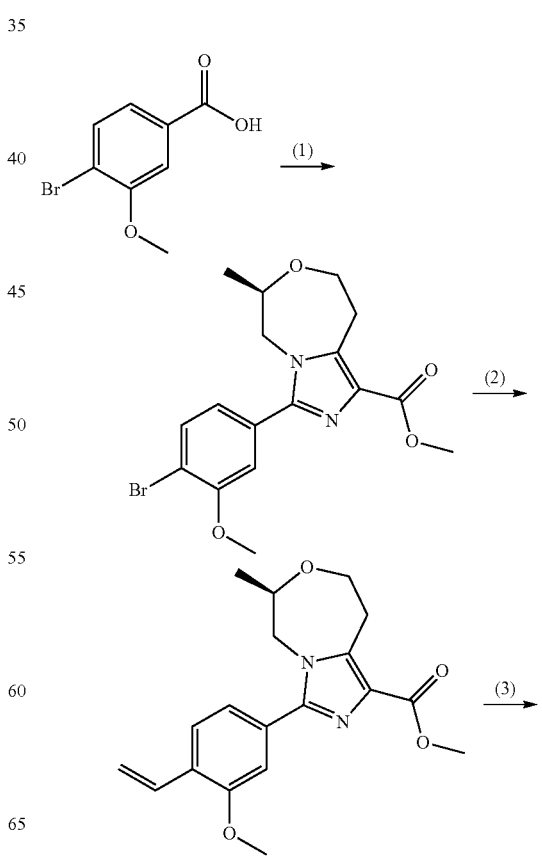

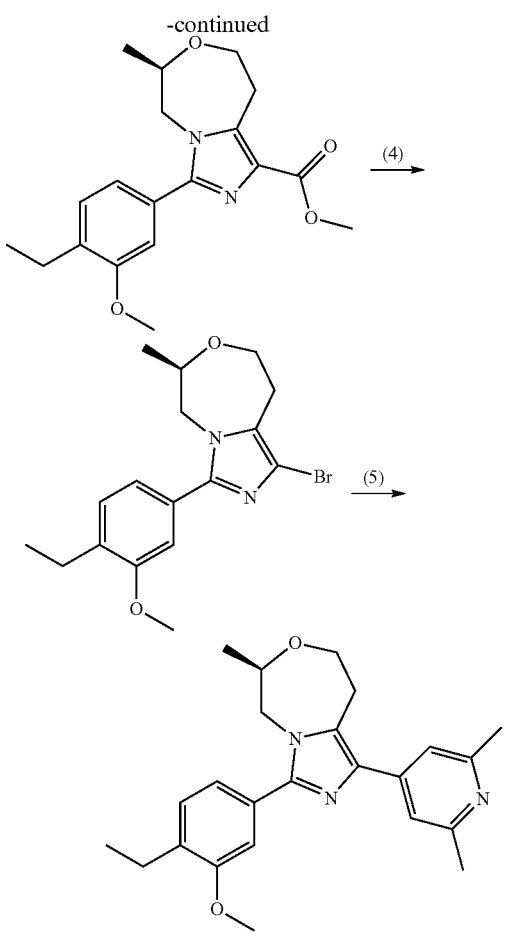

(1) Synthesis of (R)-methyl 3-(4-bromo-3-methoxyphenyl)-6-methyl-5,6,8,9-tetrahydroimidazo[1,5-d][1,4]oxazepine-1-carboxylate According to the methods of Examples 7-(1), 7-(2), and 7-(3), a title compound (224 mg, 0.567 mmol) was synthesized from 4-bromo-3-methoxybenzoic acid (CAS No. 56256-14-5).
ESI-MS m/z 395 [M+H]+

(2) Synthesis of (R)-methyl 3-(3-methoxy-4-vinylphenyl)-6-methyl-5,6,8,9-tetrahydroimidazo[1,5-d][1,4]oxazepine-1-carboxylate A mixture of the compound obtained in Example 10-(1) (214 mg, 0.541 mmol), tributyl vinyl tin (0.190 mL, 0.65 mmol), tetrakis(triphenylphosphine)palladium(0) (25.0 mg, 0.022 mmol), and DMF (3.00 mL) was stirred at 130° C. for 3 hours. The reaction mixture was cooled to room temperature, then the solvent was concentrated by nitrogen blowing and the residue was purified by silica gel column chromatography (n-heptane/ethyl acetate 1/1 to 0/1) to obtain a crude title compound (190 mg).
ESI-MS m/z 343 [M+H]+

(3) Synthesis of (R)-methyl 3-(4-ethyl-3-methoxyphenyl)-6-methyl-5,6,8,9-tetrahydroimidazo[1,5-d][1,4]oxazepine-1-carboxylate A mixture of a crude product of the compound obtained in Example 10-(2) (182 mg), 10% palladium/carbon (30 mg, including 50% water content), and methanol (3.00 mL) was stirred under hydrogen atmosphere. 10% Palladium/carbon (100 mg, including 50% water content) was further added, and the mixture was stirred under hydrogen atmosphere for 3 days. After the completion of the reaction, the insolubles were filtered off through Celite (trademark). The solvent was evaporated under reduced pressure to obtain a title compound (157 mg, 0.456 mmol).
$^1$H-NMR (400 MHz, CDCl3) δ (ppm): 1.18-1.24 (m, 6H), 2.67 (q, J=7.4 Hz, 2H), 3.05-3.15 (m, 1H), 3.61-3.68 (m, 1H), 3.69-3.74 (m, 1H), 3.86 (s, 3H), 3.90 (s, 3H), 3.94 (dd, J=8.4, 15.0 Hz, 1H), 4.06 (dd, J=4.7, 16.4 Hz, 1H), 4.16-4.24 (m, 1H), 4.29 (d, J=15.2 Hz, 1H), 6.87 (dd, J=1.6, 7.4, 1H), 7.04 (d, J=1.6 Hz, 1H), 7.19 (d, J=7.4 Hz, 1H).
ESI-MS m/z 345 [M+H]+

(4) Synthesis of (R)-1-bromo-3-(4-ethyl-3-methoxyphenyl)-6-methyl-5,6,8,9,-tetrahydroimidazo[1,5-d][1,4]oxazepine According to the method of Example 7-(4), a title compound (90.0 mg, 0.246 mmol) was obtained from the compound obtained in Example 10-(3) (157 mg, 0.456 mmol).
$^1$H-NMR (400 MHz, CDCl3) δ (ppm): 1.18-1.24 (m, 6H), 2.67 (q, J=7.3 Hz, 2H), 2.99 (dd, J=2.6, 10.6 Hz, 1H), 3.03-3.11 (m, 1H), 3.62 (ddd, J=1.5, 10.6, 12.1 Hz, 1H), 3.66-3.76 (m, 1H), 3.82-3.97 (m, 4H), 4.13-4.23 (m, 1H), 4.31 (d, J=14.6 Hz, 1H), 6.85 (dd, J=1.7, 7.5 Hz, 1H), 7.03 (d, J=1.5 Hz, 1H), 7.19 (d, J=7.7 Hz, 1H).
ESI-MS m/z 367 [M+H]+

(5) Synthesis of (R)-1-(2,6-dimethylpyridin-4-yl)-3-(4-ethyl-3-methoxyphenyl)-6-methyl-5,6,8,9,-tetrahydroimidazo[1,5-d][1,4]oxazepine According to the method of Example 7-(5) (DME was used as the solvent), a title compound (22.8 mg, 0.058 mmol) was obtained from the compound obtained in Example 10-(4) (30 mg, 0.082 mmol).
$^1$H-NMR (400 MHz, CDCl3) δ (ppm): 1.22 (t, J=7.6 Hz, 3H), 1.27 (d, J=6.6 Hz, 3H), 2.55 (s, 6H), 2.69 (q, J=7.6 Hz, 2H), 3.14-3.23 (m, 1H), 3.33-3.40 (m, 1H), 3.64-3.71 (m, 1H), 3.76-3.82 (m, 1H), 3.88 (s, 3H), 3.92-4.00 (m, 1H), 4.19-4.25 (m, 1H), 4.33 (d, J=14.7 Hz, 1H), 6.92 (dd, J=1.6, 7.6 Hz, 1H), 7.06 (d, J=1.6 Hz, 1H), 7.22 (d, J=7.6 Hz, 1H), 7.24 (s, 2H).
ESI-MS m/z 392 [M+H]+

Example 11

Synthesis of (S)-3-(4-chloro-3-methoxyphenyl)-1-(2,6-dimethylpyridin-4-yl)-6-fluoromethyl-5,6,8,9-tetrahydroimidazo[1,5-d][1,4]oxazepine

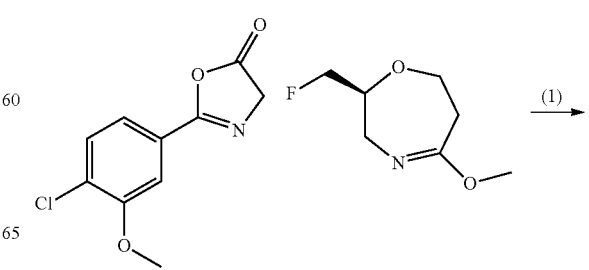

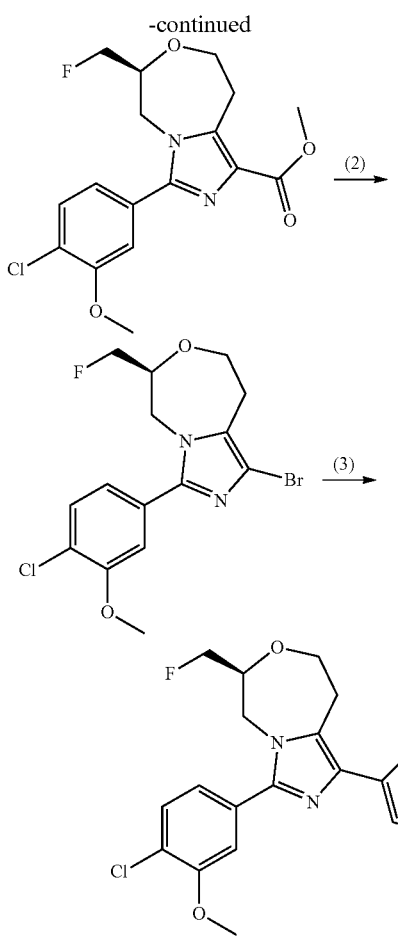

(1) Synthesis of (S)-methyl 3-(4-chloro-3-methoxyphenyl)-6-fluoromethyl-5,6,8,9-tetrahydroimidazo[1,5-d][1,4]oxazepine-1-carboxylate According to the method of Example 1-(3), a title compound (1.10 g, 2.98 mmol) was obtained from the compound obtained in Example 1-(2) (1.39 g, 6.18 mmol) and the compound obtained in Production Example 3-(7) (830 mg, 5.15 mmol).

¹H-NMR (400 MHz, CDCl3) δ (ppm): 3.04-3.14 (m, 1H), 3.68 (t, J=11.9 Hz, 1H), 3.76-3.86 (m, 1H), 3.91 (s, 3H), 3.94 (s, 3H), 4.03 (dd, J=8.6, 14.8 Hz, 1H), 4.17 (dd, J=4.3, 16.4 Hz, 1H), 4.23-4.57 (m, 4H), 6.94 (dd, J=1.8, 8.0 Hz, 1H), 7.14 (d, J=2.0 Hz, 1H), 7.44 (d, J=8.2 Hz, 1H).

(2) Synthesis of (S)-1-bromo-3-(4-chloro-3-methoxyphenyl)-6-fluoromethyl-5,6,8,9-tetrahydroimidazo[1,5-d][1,4]oxazepine According to the method of Example 1-(4), a title compound (858 mg, 2.20 mmol) was obtained from the compound obtained in Example 11-(1) (1.10 g, 2.98 mmol).

¹H-NMR (400 MHz, CDCl3) δ (ppm): 2.94-3.06 (m, 1H), 3.08-3.16 (m, 1H), 3.65 (ddd, J=1.4, 10.9, 12.3 Hz, 1H), 3.74-3.87 (m, 1H), 3.94 (s, 3H), 3.99 (dd, J=8.4, 14.6 Hz, 1H), 4.23-4.40 (m, 2H), 4.43-4.60 (m, 2H), 6.91 (dd, J=2.0, 8.2 Hz, 1H), 7.13 (d, J=2.0 Hz, 1H), 7.43 (d, J=8.2 Hz, 1H).

(3) Synthesis of (S)-3-(4-chloro-3-methoxyphenyl)-1-(2,6-dimethylpyridin-4-yl)-6-fluoromethyl-5,6,8,9-tetrahydroimidazo[1,5-d][1,4]oxazepine According to the method of Example 1-(5), a title compound (364 mg, 1.28 mmol) was obtained from the compound obtained in Example 11-(2) (500 mg, 1.28 mmol) and 2,6-dimethyl-pyridine-4-boronic acid (232 mg, 1.54 mmol).

¹H-NMR (400 MHz, CDCl3) δ (ppm): 2.56 (s, 6H), 3.15-3.26 (m, 1H), 3.38 (d, J=3.9 Hz, 1H), 3.69 (t, J=11.7 Hz, 1H), 3.89 (d, J=7.0 Hz, 1H), 3.95 (s, 3H), 4.03 (d, J=15.2 Hz, 1H), 4.27-4.42 (m, 2H), 4.47-4.65 (m, 2H), 6.99 (dd, J=1.8, 8.0 Hz, 1H), 7.16 (d, J=2.0 Hz, 1H), 7.21 (s, 2H), 7.46 (d, J=7.8 Hz, 1H).

ESI-MS m/z 416 [M+H]+

Example 12

Synthesis of (R)-3-(4-chloro-3-methoxyphenyl)-1-(2-(fluoromethyl)pyridin-4-yl)-6-methyl-5,6,8,9-tetrahydroimidazo[1,5-d][1,4]oxazepine

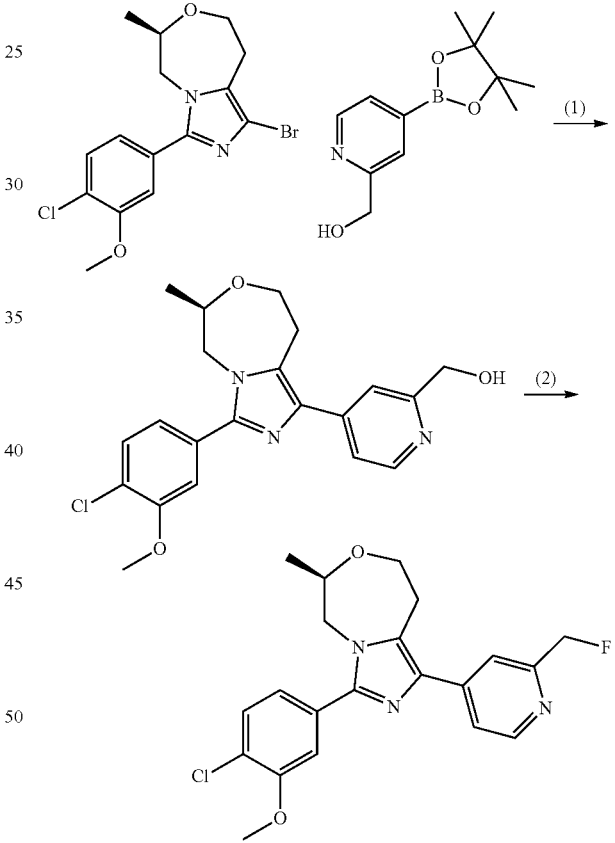

(1) Synthesis of (R)-(4-(3-(4-chloro-3-methoxyphenyl)-6-methyl-5,6,8,9-tetrahydroimidazo[1,5-d][1,4]oxazepin-1-yl)pyridin-2-yl)methanol According to the method of Example 1-(5), a title compound (53.0 mg, 0.133 mmol) was obtained from the compound obtained in Example 1-(4) (100 mg, 0.269 mmol) and 4-(4,4,5,5-tetramethyl-1,3,2-dioxaborolan-2-yl)pyridin-2-yl)methanol (CAS No. 1314135-84-6; 76.0 mg, 0.323 mmol).

ESI-MS m/z 400 [M+H]+

(2) Synthesis of (R)-3-(4-chloro-3-methoxyphenyl)-1-(2-(fluoromethyl)pyridin-4-yl)-6-methyl-5,6,8,9-tetrahydroimidazo[1,5-d][1,4]oxazepine BAST (32.0 μL, 175 μmol) was added to a solution of the compound obtained in Example 12-(1) (50.0 mg, 125 μmol) in DCM (2 mL) under ice-cooling. The reaction mixture was warmed to room temperature and further stirred for 13 hours. A saturated aqueous sodium bicarbonate solution and DCM were added to the reaction mixture to separate the organic layer. The organic layer was dried over anhydrous magnesium sulfate and the solvent was evaporated under reduced pressure. The resultant residue was purified by silica gel column chromatography (n-heptane/ethyl acetate) to obtain a title compound (9.5 mg, 24 μmol).

$^1$H-NMR (400 MHz, CDCl3) δ (ppm): 1.27 (d, J=6.2 Hz, 3H), 3.17-3.26 (m, 1H), 3.34-3.41 (m, 1H), 3.63-3.71 (m, 1H), 3.75-3.83 (m, 1H), 3.95-4.03 (m, 1H), 3.97 (s, 3H), 4.20-4.30 (m, 2H), 5.52 (d, J=46.9 Hz, 2H), 6.94 (dd, J=2.0, 8.0 Hz, 1H), 7.19 (d, J=2.0 Hz, 1H), 7.45-7.52 (m, 2H), 7.70 (s, 1H), 8.58 (d, J=5.2 Hz, 1H).

ESI-MS m/z 402 [M+H]+

Example 13

Synthesis of (R)-3-(4-chloro-3-methoxyphenyl)-1-(2-(fluoromethyl)-6-methylpyridin-4-yl)-6-methyl-5,6,8,9-tetrahydroimidazo[1,5-d][1,4]oxazepine

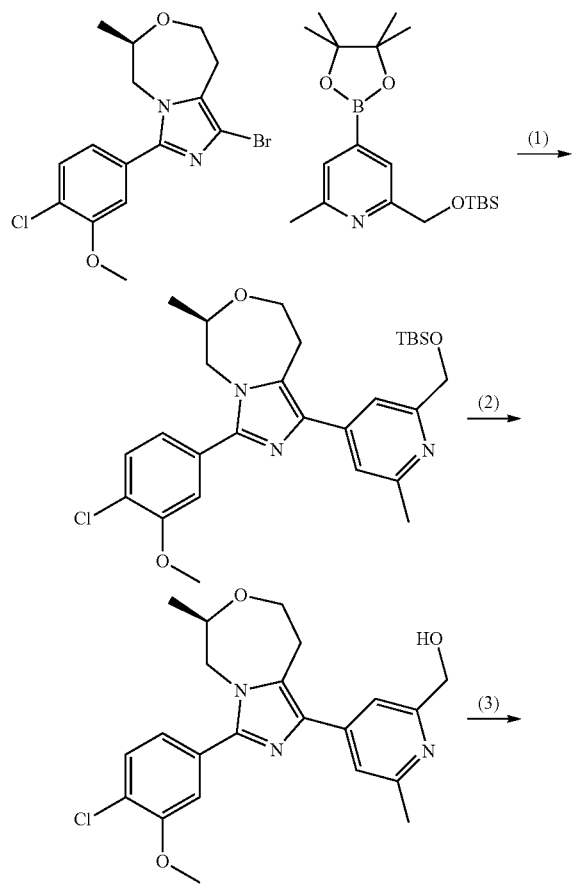

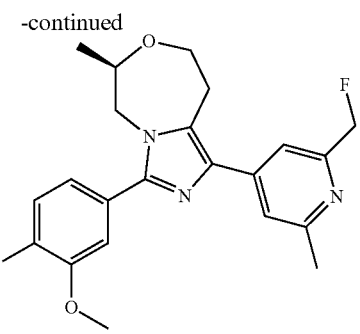

(1) Synthesis of (R)-1-(2-(((tert-butyldimethylsilyl)oxy)methyl)-6-methylpyridin-4-yl)-3-(4-chloro-3-methoxyphenyl)-6-methyl-5,6,8,9-tetrahydroimidazo[1,5-d][1,4]oxazepine According to the method of Example 1-(5), a title compound (283 mg, 0.536 mmol) was obtained from the compound obtained in Example 1-(4) (300 mg, 0.807 mmol) and the compound obtained in Production Example 24 (440 mg, 1.21 mmol).

$^1$H-NMR (400 MHz, CDCl3) δ (ppm): 0.10-0.16 (m, 6H), 0.92-1.02 (m, 9H), 1.26 (d, J=6.6 Hz, 3H), 2.54 (s, 3H), 3.10-3.24 (m, 1H), 3.42 (dd, J=4.7, 16.4 Hz, 1H), 3.61-3.72 (m, 1H), 3.74-3.84 (m, 1H), 3.92-4.04 (m, 1H), 3.96 (s, 3H), 4.15-4.30 (m, 2H), 4.83 (s, 2H), 6.91-6.97 (m, 1H), 7.20 (d, J=1.6 Hz, 1H), 7.41-7.50 (m, 3H).

(2) Synthesis of (R)-(4-(3-(4-chloro-3-methoxyphenyl)-6-methyl-5,6,8,9-tetrahydroimidazo[1,5-d][1,4]oxazepin-1-yl)-6-methylpyridin-2-yl)methanol TBAF (a 1 M THF solution, 0.818 mL, 0.818 mmol) was slowly added to a solution of the compound obtained in Example 13-(1) (360 mg, 0.682 mmol) in THF (5.00 mL) at room temperature. The reaction mixture was stirred at room temperature for 1 hour and an aqueous ammonium chloride solution was added. Ethyl acetate was added to the mixture to separate the organic layer. The organic layer was washed serially with water and a saturated aqueous sodium chloride solution, dried over anhydrous magnesium sulfate, and then concentrated under reduced pressure. The resultant residue was purified by silica gel column chromatography (n-heptane/ethyl acetate→ethyl acetate/methanol) to obtain a title compound (228 mg, 0.551 mmol).

$^1$H-NMR (400 MHz, CDCl3) δ (ppm): 1.26 (d, J=6.3 Hz, 3H), 2.58 (s, 3H), 3.19 (ddd, J=2.3, 10.6, 16.3 Hz, 1H), 3.30-3.40 (m, 1H), 3.60-3.71 (m, 1H), 3.73-3.82 (m, 1H), 3.88 (s, 3H), 3.88-4.03 (m, 1H), 4.15-4.30 (m, 2H), 4.74 (s, 2H), 6.92 (dd, J=1.8, 8.0 Hz, 1H), 7.17 (d, J=1.6 Hz, 1H), 7.26 (s, 1H), 7.33 (s, 1H), 7.46 (d, J=8.2 Hz, 1H).

ESI-MS m/z 414 [M+H]+

(3) Synthesis of (R)-3-(4-chloro-3-methoxyphenyl)-1-(2-(fluoromethyl)-6-methylpyridin-4-yl)-6-methyl-5,6,8,9-tetrahydroimidazo[1,5-d][1,4]oxazepine BAST (97.0 μL, 0.524 mmol) was added to a solution of the compound obtained in Example 13-(2) (31 mg, 75 μmol) in DCM (2 mL) at room temperature. The reaction mixture was stirred for 13 hours and a saturated aqueous sodium bicarbonate solution and DCM were added to the reaction mixture. The organic layer was separated and dried over anhydrous magnesium sulfate. The organic layer was concentrated under reduced pressure. The resultant residue was purified by silica gel column chromatography (n-heptane/ ethyl acetate→ethyl acetate/methanol) and NH silica gel column chromatography (n-heptane/ethyl acetate) to obtain a title compound (3.5 mg, 8.4 μmol).

¹H-NMR (400 MHz, CDCl3) δ (ppm): 1.27 (d, J=6.2 Hz, 3H), 2.58 (s, 3H), 3.16-3.25 (m, 1H), 3.34-3.41 (m, 1H), 3.63-3.71 (m, 1H), 3.75-3.83 (m, 1H), 3.95-4.02 (m, 1H), 3.97 (s, 3H), 4.20-4.29 (m, 2H), 5.50 (d, J=47.1 Hz, 2H), 6.94 (dd, J=1.8, 7.9 Hz, 1H), 7.19 (d, J=1.8 Hz, 1H), 7.42-7.48 (m, 3H).

ESI-MS m/z 416 [M+H]+

Example 13-A

An Alternative Method of Example 13

Synthesis of (R)-3-(4-chloro-3-methoxyphenyl)-1-(2-(fluoromethyl)-6-methylpyridin-4-yl)-6-methyl-5,6,8,9-tetrahydroimidazo[1,5-d][1,4]oxazepine (Example 13)

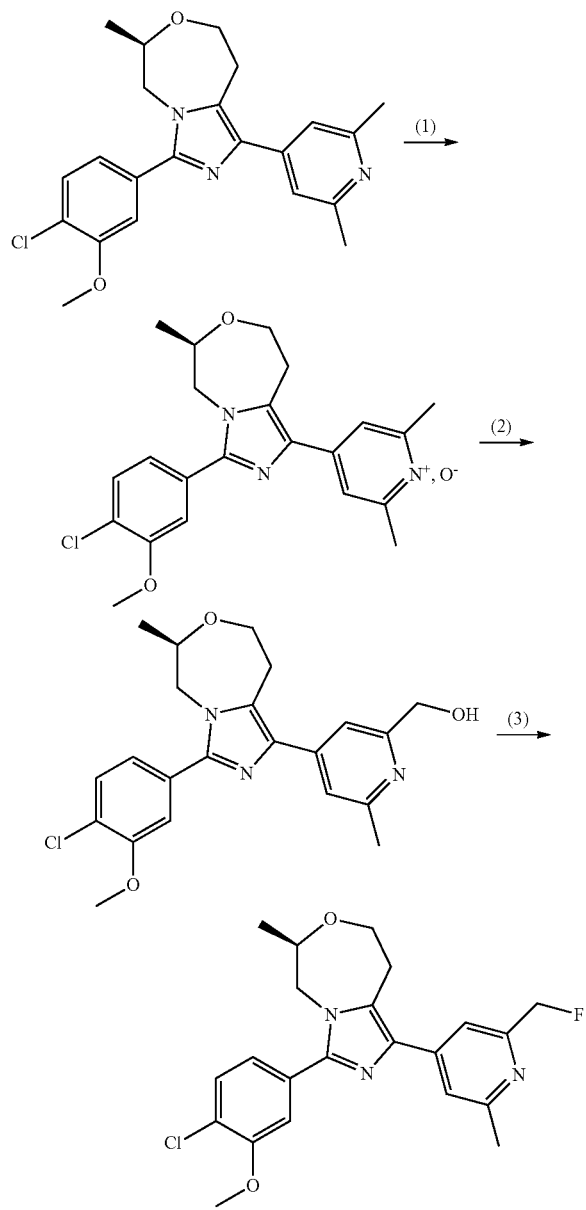

(1) Synthesis of (R)-4-(3-(4-chloro-3-methoxyphenyl)-6-methyl-5,6,8,9-tetrahydroimidazo[1,5-d][1,4]oxazepin-1-yl)-2,6-dimethylpyridine 1-oxide mCPBA (75% by weight, 24.0 mg, 0.138 mmol) was added to a solution of the compound obtained in Example 1-(5) (50.0 mg, 0.126 mmol) in DCM (2 mL), and the mixture was stirred at room temperature for 15 hours. The mixture was purified by NH silica gel column chromatography (n-heptane/ethyl acetate→ethyl acetate/methanol) to obtain a title compound (45.0 mg, 0.109 mmol).

ESI-MS m/z 414 [M+H]+

(2) Synthesis of (R)-(4-(3-(4-chloro-3-methoxyphenyl)-6-methyl-5,6,8,9-tetrahydroimidazo[1,5-d][1,4]oxazepin-1-yl)-6-methylpyridin-2-yl)methanol A solution of the compound obtained in Example 13-A-(1) (45.0 mg, 109 μmol) in acetic anhydride (2 mL) was stirred at 100° C. for 3 hours. The reaction mixture was cooled to room temperature and concentrated under reduced pressure. Chloroform and a saturated aqueous sodium bicarbonate solution were added to the resultant residue to separate the organic layer. The organic layer was dried over anhydrous magnesium sulfate and the solvent was evaporated under reduced pressure. The resultant residue was dissolved in methanol (3 mL) and potassium carbonate (45.1 mg, 326 μmol) was added. The reaction mixture was stirred at 80° C. for 3 hours and then cooled to room temperature. Ethyl acetate and a saturated aqueous sodium bicarbonate solution were added to the reaction mixture to separate the organic layer. The organic layer was dried over anhydrous magnesium sulfate and the solvent was evaporated under reduced pressure. The resultant residue was purified serially by NH silica gel column chromatography (n-heptane/ethyl acetate→ethyl acetate/methanol) and NH silica gel column chromatography (n-heptane/ethyl acetate) to obtain a title compound (3.5 mg, 8.4 μmol).

ESI-MS m/z 414 [M+H]+

(3) Synthesis of (R)-3-(4-chloro-3-methoxyphenyl)-1-(2-(fluoromethyl)-6-methylpyridin-4-yl)-6-methyl-5,6,8,9-tetrahydroimidazo[1,5-d][1,4]oxazepine BAST (97.0 μL, 0.524 mmol) was added to a solution of the compound obtained in Example 13-A-(2) (31 mg, 75 μmol) in DCM (2 mL) at room temperature. The reaction mixture was stirred for 13 hours and then a saturated aqueous sodium bicarbonate solution and DCM were added to the reaction mixture. The organic layer was separated and dried over anhydrous magnesium sulfate. The organic layer was concentrated under reduced pressure. The resultant residue was purified serially by NH silica gel column chromatography (n-heptane/ethyl acetate) and silica gel column chromatography (n-heptane/ethyl acetate) to obtain a title compound (3.5 mg, 8.4 μmol).

¹H-NMR (400 MHz, CDCl3) δ (ppm): 1.27 (d, J=6.2 Hz, 3H), 2.58 (s, 3H), 3.16-3.25 (m, 1H), 3.34-3.41 (m, 1H), 3.63-3.71 (m, 1H), 3.75-3.83 (m, 1H), 3.95-4.02 (m, 1H), 3.97 (s, 3H), 4.20-4.29 (m, 2H), 5.50 (d, J=47.1 Hz, 2H), 6.94 (dd, J=1.8, 7.9 Hz, 1H), 7.19 (d, J=1.8 Hz, 1H), 7.42-7.48 (m, 3H).

ESI-MS m/z 416 [M+H]+

Example 14

Synthesis of (R)-3-(4-(difluoromethoxy)-3-methyl-phenyl)-1-(2,6-dimethylpyridin-4-yl)-6-methyl-5,6,8,9-tetrahydroimidazo[1,5-d][1,4]oxazepine

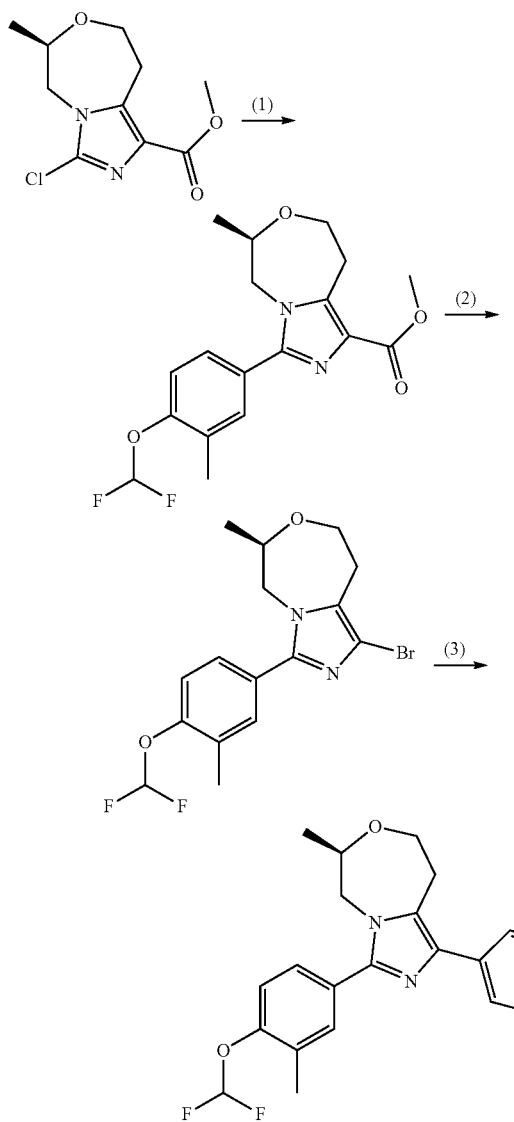

(1) Synthesis of (R)-methyl 3-(4-(difluoromethoxy)-3-methylphenyl)-6-methyl-5,6,8,9-tetrahydroimidazo[1,5-d][1,4]oxazepine-1-carboxylate A mixture of the compound obtained in Production Example 8-(3) (300 mg, 1.23 mmol), 4-difluoromethoxy-3-methyl-benzeneboronic acid (CAS No. 958451-72-4; 297 mg, 1.47 mmol), tetrakis(triphenylphosphine)palladium(0) (142 mg, 0.123 mmol), an aqueous sodium carbonate solution (1 M, 2.45 mL, 2.45 mmol) and DME (6 mL) was stirred under microwave irradiation at 130° C. for 30 minutes. The reaction mixture was cooled to room temperature and ethyl acetate and a saturated aqueous ammonium chloride solution were added. The organic layer was separated, washed with a saturated aqueous sodium chloride solution and dried over anhydrous magnesium sulfate. The insolubles were separated through filtration and the filtrate was concentrated under reduced pressure. The resultant residue was purified by NH silica gel column chromatography (n-heptane/ethyl acetate) to obtain a title compound (290 mg, 0.792 mmol).

ESI-MS m/z 367 [M+H]+

(2) Synthesis of (R)-1-bromo-3-(4-(difluoromethoxy)-3-methylphenyl)-6-methyl-5,6,8,9-tetrahydroimidazo[1,5-d][1,4]oxazepine A 2 N aqueous sodium hydroxide solution (0.317 mL) was added to a solution of the compound obtained in Example 14-(1) (290 mg, 0.792 mmol) in ethanol (4 mL). The reaction mixture was heated under reflux for 2 hours. The reaction mixture was cooled to room temperature and acidified with a 5 N hydrochloric acid. The mixture was concentrated under reduced pressure and DMF (4 mL) was added to the residue. Potassium carbonate (273 mg, 1.98 mmol) and NBS (211 mg, 1.19 mmol) were added to the reaction mixture, and the mixture was stirred at room temperature for 14 hours. Water and ethyl acetate were added to the mixture to separate the organic layer. The resultant organic layer was washed with a saturated aqueous sodium chloride solution and dried over anhydrous magnesium sulfate. The insolubles were separated through filtration and the filtrate was concentrated. The residue was purified by NH silica gel column chromatography (n-heptane/ethyl acetate) to obtain a title compound (135 mg, 0.349 mmol).

$^1$H-NMR (400 MHz, CDCl3) δ (ppm): 1.22 (d, J=6.5 Hz, 3H), 2.32 (s, 3H), 2.97-3.10 (m, 2H), 3.57-3.74 (m, 2H), 3.92 (dd, J=8.4, 14.7 Hz, 1H), 4.14-4.23 (m, 2H), 6.55 (t, J=73.4 Hz, 1H), 7.14 (d, J=8.4 Hz, 1H), 7.23 (dd, J=2.3, 8.4 Hz, 1H), 7.40 (d, J=2.0 Hz, 1H).

ESI-MS m/z 387 [M+H]+

(3) Synthesis of (R)-3-(4-(difluoromethoxy)-3-methylphenyl)-1-(2,6-dimethylpyridin-4-yl)-6-methyl-5,6,8,9-tetrahydroimidazo[1,5-d][1,4]oxazepine A mixture of the compound obtained in Example 14-(2) (135 mg, 0.349 mmol), 2,6-dimethyl-pyridine-4-boronic acid (73.7 mg, 0.488 mmol), tetrakis(triphenylphosphine) palladium(0) (20.1 mg, 0.017 mmol), an aqueous sodium carbonate solution (1 M, 0.697 mL), and DME (3.00 mL) was stirred under microwave irradiation at 150° C. for 1 hour. The reaction mixture was cooled to room temperature and then purified serially by silica gel column chromatography (n-heptane/ethyl acetate→ethyl acetate/methanol) and NH silica gel column chromatography (n-heptane/ethyl acetate) to obtain a title compound (104 mg, 0.252 mmol).

$^1$H-NMR (400 MHz, CDCl3) δ (ppm): 1.26 (d, J=6.7 Hz, 3H), 2.35 (s, 3H), 2.55 (s, 6H), 3.14-3.22 (m, 1H), 3.32-3.39 (m, 1H), 3.63-3.70 (m, 1H), 3.74-3.82 (m, 1H), 3.94-4.01 (m, 1H), 4.19-4.26 (m, 2H), 6.55 (t, J=73.5 Hz, 1H), 7.18 (d, J=8.4 Hz, 1H), 7.21 (s, 2H), 7.28 (dd, J=2.3, 8.4 Hz, 1H), 7.46 (d, J=1.9 Hz, 1H).

ESI-MS m/z 414 [M+H]+

Example 15

Synthesis of (R)-3-(4-(difluoromethoxy)-3-methylphenyl)-6-methyl-1-(2-methylpyridin-4-yl)-5,6,8,9-tetrahydroimidazo[1,5-d][1,4]oxazepine

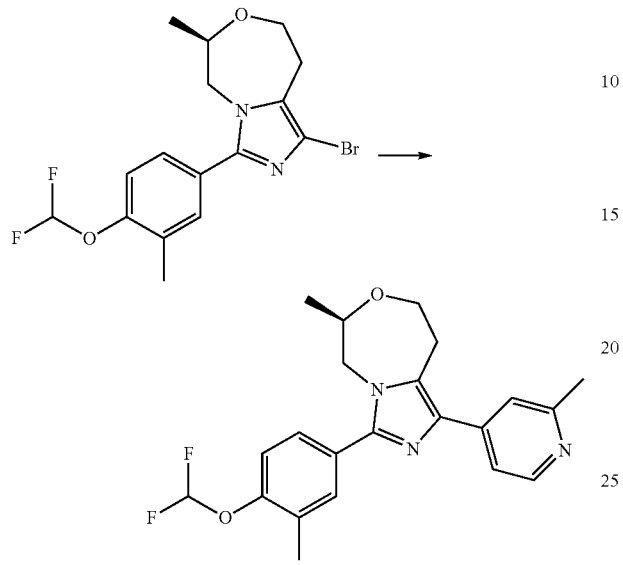

According to the method of Example 8, a title compound (8.1 mg, 0.020 mmol) was obtained from the compound obtained in Example 14-(2) (24 mg, 0.062 mmol).

$^1$H-NMR (400 MHz, CDCl3) δ (ppm): 1.26 (d, J=6.2 Hz, 3H), 2.35 (s, 3H), 2.58 (s, 3H), 3.19 (ddd, J=2.3, 10.5, 16.0 Hz, 1H), 3.36 (dd, J=3.9, 16.0 Hz, 1H), 3.62-3.71 (m, 1H), 3.74-3.84 (m, 1H), 3.98 (dd, J=8.4, 14, 6 Hz, 1H), 4.22 (ddd, J=2.3, 5.1, 12.1 Hz, 1H), 4.24 (d, J=14.4 Hz, 1H) 6.56 (t, J=73.8 Hz, 1H), 7.15-7.22 (m, 1H), 7.26-7.32 (m, 2H), 7.44-7.48 (m, 2H), 8.47-8.50 (m, 1H).

ESI-MS m/z 400 [M+H]+

Example 16

Synthesis of (S)-1-(2,6-dimethylpyridin-4-yl)-6-(fluoromethyl)-3-(3-methoxy-4-(trifluoromethoxy)phenyl)-5,6,8,9-tetrahydroimidazo[1,5-d][1,4]oxazepine

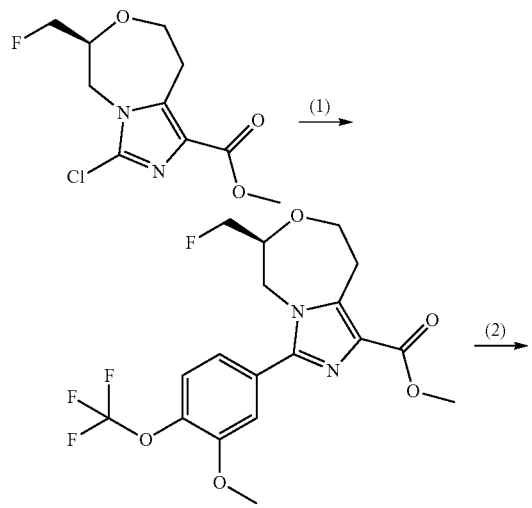

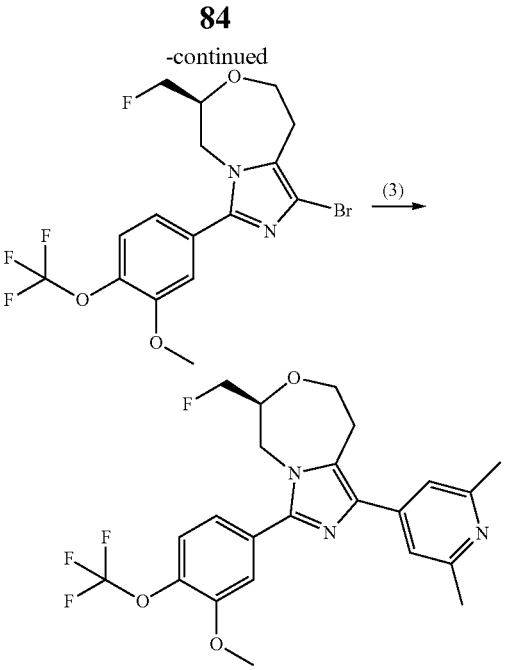

(1) Synthesis of (S)-methyl 6-(fluoromethyl)-3-(3-methoxy-4-(trifluoromethoxy)phenyl)-5,6,8,9-tetrahydroimidazo[1,5-d][1,4]oxazepine-1-carboxylate According to the method of Example 14-(1), a crude title compound (319 mg) was obtained from the compound obtained in Production Example 9 (200 mg, 0.761 mmol) and the compound obtained in Production Example 21 (484 mg, 1.52 mmol).

ESI-MS m/z 419 [M+H]+.

(2) Synthesis of (S)-1-bromo-6-(fluoromethyl)-3-(3-methoxy-4-(trifluoromethoxy)phenyl)-5,6,8,9-tetrahydroimidazo[1,5-d][1,4]oxazepine According to the method of Example 1-(4), a title compound (138 mg, 0.314 mmol) was obtained from the compound obtained in Example 16-(1) (319 mg).

$^1$H-NMR (400 MHz, CDCl3) δ (ppm): 2.98-3.17 (m, 2H), 3.62-3.70 (m, 1H), 3.78-3.88 (m, 1H), 3.92 (s, 3H), 3.98-4.06 (m, 1H), 4.24-4.63 (m, 4H), 6.96 (dd, J=2.0, 8.2 Hz, 1H), 7.20 (d, J=2.0 Hz, 1H), 7.28-7.33 (m, 1H).

(3) Synthesis of (S)-1-(2,6-dimethylpyridin-4-yl)-6-(fluoromethyl)-3-(3-methoxy-4-(trifluoromethoxy)phenyl)-5,6,8,9-tetrahydroimidazo[1,5-d][1,4]oxazepine According to the method of Example 1-(5), a title compound (42 mg, 0.09 mmol) was obtained from the compound obtained in Example 16-(2) (69.0 mg, 0.157 mmol) and 2,6-dimethyl-pyridine-4-boronic acid (35.6 mg, 0.236 mmol).

$^1$H-NMR (400 MHz, CDCl3) δ (ppm): 2.56 (s, 6H), 3.24 (dd, J=2.3, 10.9 Hz, 1H), 3.42 (dd, J=3.9, 16.4 Hz, 1H), 3.71 (t, J=11.5 Hz, 1H), 3.84-3.97 (m, 1H), 3.93 (s, 3H), 4.06 (dd, J=8.6, 14.8 Hz, 1H), 4.28-4.66 (m, 4H), 7.04 (dd, J=2.0, 8.2 Hz, 1H), 7.22 (s, 2H), 7.24 (d, J=2.0 Hz, 1H), 7.34 (m, 1H).

ESI-MS m/z 466 [M+H]+

Example 17

Synthesis of (S)-6-(fluoromethyl)-3-(3-methoxy-4-(trifluoromethoxy)phenyl)-1-(2-methylpyridin-4-yl)-5,6,8,9-tetrahydroimidazo[1,5-d][1,4]oxazepine

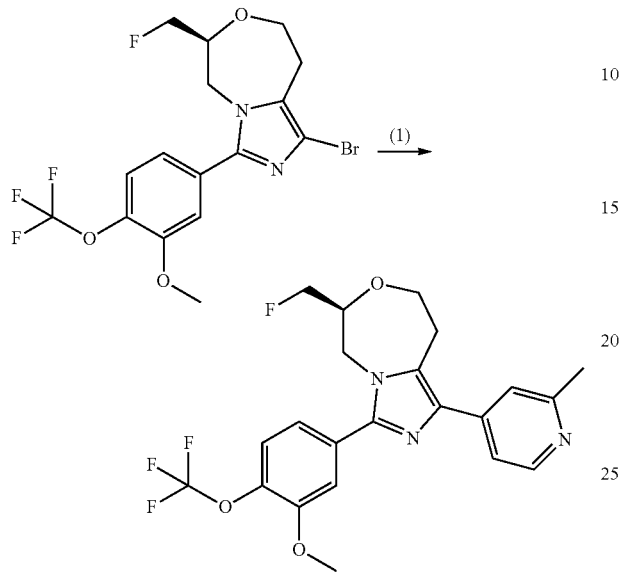

According to the method of Example 1-(5), a title compound (36 mg, 0.08 mmol) was obtained from the compound obtained in Example 16-(2) (69 mg, 0.157 mmol) and 2-picoline-4-boronic acid (32 mg, 0.24 mmol).

$^1$H-NMR (400 MHz, CDCl3) δ (ppm): 2.59 (s, 3H), 3.23 (ddd, J=2.5, 11.1, 16.4 Hz, 1H), 3.37-3.46 (m, 1H), 3.72 (t, J=11.3 Hz, 1H), 3.85-3.95 (m, 1H), 3.94 (s, 3H), 4.07 (dd, J=9.0, 14.8 Hz, 1H), 4.29-4.66 (m, 4H), 7.04 (dd, J=2.0, 8.2 Hz, 1H), 7.24 (d, J=2.0 Hz, 1H), 7.29 (dd, J=1.2, 5.1 Hz, 1H), 7.34 (dq, J=1.3, 8.4 Hz, 1H), 7.45-7.48 (m, 1H), 8.51 (d, J=4.7 Hz, 1H).

Example 18

Synthesis of (R)-1-(2,6-dimethylpyridin-4-yl)-3-(4-methoxy-3-methylphenyl)-6-methyl-5,6,8,9-tetrahydroimidazo[1,5-d][1,4]oxazepine

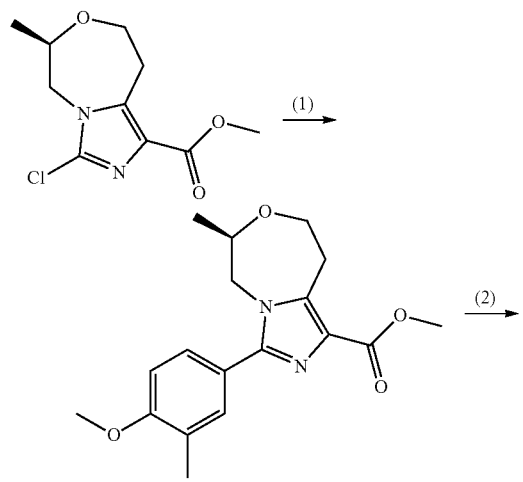

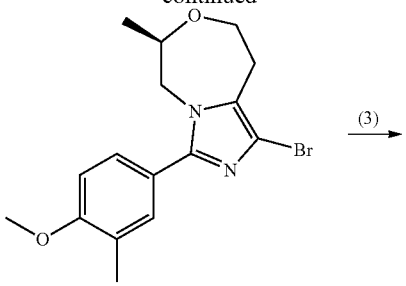

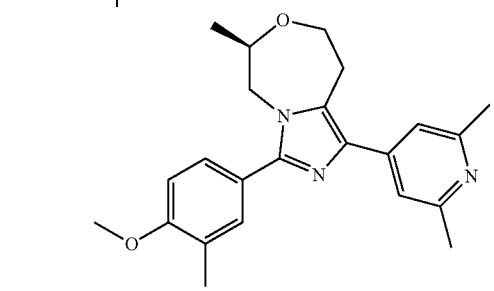

(1) Synthesis of (R)-methyl 3-(4-methoxy-3-methylphenyl)-6-methyl-5,6,8,9-tetrahydroimidazo[1,5-d][1,4]oxazepine-1-carboxylate According to the method of Example 14-(1), a title compound (143 mg, 0.433 mmol) was obtained from the compound obtained in Production Example 8-(3) (150 mg, 0.613 mmol) and 4-methoxy-3-methylphenyl boronic acid (CAS No. 175883-62-2; 122 mg, 0.736 mmol).

$^1$H-NMR (400 MHz, CDCl3) δ (ppm): 1.16-1.24 (m, 3H), 2.24 (s, 3H), 3.01-3.17 (m, 1H), 3.56-3.76 (m, 2H), 3.87 (s, 3H), 3.89 (s, 3H), 3.90-3.98 (m, 1H), 4.00-4.09 (m, 1H), 4.16-4.28 (m, 2H), 6.87 (d, J=8.4 Hz, 1H), 7.24 (dd, J=2.2, 8.4 Hz, 1H), 7.31 (d, J=2.2 Hz, 1H).

(2) Synthesis of (R)-1-bromo-3-(4-methoxy-3-methylphenyl)-6-methyl-5,6,8,9-tetrahydroimidazo[1,5-d][1,4]oxazepine A 5 N aqueous sodium hydroxide solution (433 μL, 2.16 mL) was added to a solution of the compound obtained in Example 18-(1) (143 mg, 0.433 mmol) in methanol (2.0 mL)/THF (2.0 mL), and the mixture was stirred at room temperature for 15 hours. A 5 N hydrochloric acid was added to the reaction mixture for neutralization and the solvent was evaporated under reduced pressure. DMF (2.0 mL) and ethanol (2.0 mL) were added to the residue, and potassium carbonate (59.8 mg, 0.433 mL) and NBS (108 mg, 0.606 mmol) were added to the mixture. The reaction mixture was stirred for 1.5 hours at room temperature, then sodium sulfite (510 mg, 4.04 mL) and water were added to the reaction mixture. The water layer was extracted with ethyl acetate twice. The combined organic layer was washed with a saturated aqueous sodium chloride solution twice and dried over anhydrous magnesium sulfate. The solvent was evaporated under reduced pressure and the residue was purified by NH silica gel column chromatography (n-heptane/ethyl acetate) to obtain and a title compound (81.0 mg, 0.231 mmol).

$^1$H-NMR (400 MHz, CDCl3) δ (ppm): 1.15-1.24 (m, 3H), 2.24 (s, 3H), 2.91-3.11 (m, 2H), 3.55-3.75 (m, 2H), 3.87 (s, 3H), 3.83-3.96 (m, 1H), 4.12-4.30 (m, 2H), 6.87 (d, J=8.4 Hz, 1H), 7.22 (dd, J=22, 8.4 Hz, 1H), 7.28 (d, J=2.2 Hz, 1H).

(3) Synthesis of (R)-1-(2,6-dimethylpyridin-4-yl)-3-(4-methoxy-3-methylphenyl)-6-methyl-5,6,8,9-tetrahydroimidazo[1,5-d][1,4]oxazepine According to the method of Example 14-(3), a title compound (9.1 mg, 0.024 mmol) was obtained from the compound obtained in Example 18-(2) (30.0 mg, 0.085 mmol) and 2,6-dimethyl-pyridine-4-boronic acid (20.6 mg, 0.137 mmol).

$^1$H-NMR (400 MHz, CDCl3) δ (ppm): 1.18-1.32 (m, 3H), 2.26 (s, 3H), 2.55 (s, 6H), 3.09-3.24 (m, 1H), 3.30-3.41 (m, 1H), 3.60-3.71 (m, 1H), 3.73-3.83 (m, 1H), 3.89 (s, 3H), 3.90-4.00 (m, 1H), 4.15-4.32 (m, 2H), 6.90 (d, J=8.4 Hz, 1H), 7.22 (s, 2H), 7.27 (dd, J=2.1, 8.4 Hz, 1H), 7.33 (d, J=2.1 Hz, 1H).

ESI-MS m/z 378 [M+H]+

Example 19

Synthesis of (R)-3-(3-chloro-4-cyclopropoxyphenyl)-1-(2,6-dimethylpyridin-4-yl)-6-methyl-5,6,8,9-tetrahydroimidazo[1,5-d][1,4]oxazepine

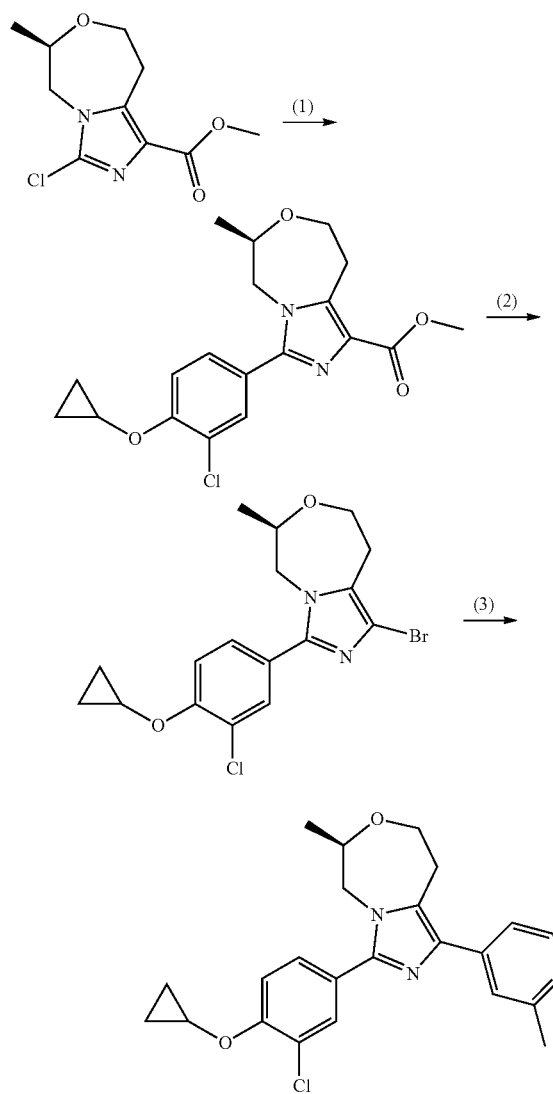

(1) Synthesis of (R)-methyl 3-(3-chloro-4-cyclopropoxyphenyl)-6-methyl-5,6,8,9-tetrahydroimidazo[1,5-d][1,4]oxazepine-1-carboxylate According to the method of Example 14-(1), a title compound (89.0 mg, 0.236 mmol) was obtained from the compound obtained in Production Example 8-(3) (115 mg, 0.470 mmol) and the compound obtained in Production Example 12 (115 mg, 0.541 mmol).

$^1$H-NMR (400 MHz, CDCl3) δ (ppm): 0.84-0.93 (m, 4H), 1.21-1.26 (m, 3H), 3.00-3.21 (m, 1H), 3.56-3.76 (m, 2H), 3.81-3.88 (m, 1H), 3.90 (s, 3H), 3.93-4.10 (m, 2H), 4.16-4.24 (m, 2H), 7.34 (dd, J=1.8, 8.6 Hz, 1H), 7.36 (dd, J=0.6, 8.6 Hz, 1H), 7.51 (dd, J=0.6, 1.8 Hz, 1H).

(2) Synthesis of (R)-1-bromo-3-(3-chloro-4-cyclopropoxyphenyl)-6-methyl-5,6,8,9-tetrahydroimidazo[1,5-d][1,4]oxazepine According to the method of Example 18-(2), a title compound (48.0 mg, 0.121 mmol) was obtained from the compound obtained in Example 19-(1) (89.0 mg, 0.236 mmol).

$^1$H-NMR (400 MHz, CDCl3) δ (ppm): 0.84-0.91 (m, 4H), 1.21-1.26 (m, 3H), 2.88-3.15 (m, 2H), 3.55-3.76 (m, 2H), 3.80-3.88 (m, 1H), 3.89-3.98 (m, 1H), 4.13-4.25 (m, 2H), 7.32 (dd, J=2.0, 8.5 Hz, 1H), 7.36 (d, J=8.5 Hz, 1H), 7.48 (d, J=2.0 Hz, 1H).

(3) Synthesis of (R)-3-(3-chloro-4-cyclopropoxyphenyl)-1-(2,6-dimethylpyridin-4-yl)-6-methyl-5,6,8,9-tetrahydroimidazo[1,5-d][1,4]oxazepine According to the method of Example 1-(5), a title compound (15 mg, 0.035 mmol) was obtained from the compound obtained in Example 19-(2) (25.0 mg, 0.063 mmol) and 2,6-dimethyl-pyridine-4-boronic acid (15.2 mg, 0.101 mmol).

$^1$H-NMR (400 MHz, CDCl3) δ (ppm): 0.85-0.93 (m, 4H), 1.24-1.32 (m, 3H), 2.55 (s, 6H), 3.11-3.24 (m, 1H), 3.28-3.42 (m, 1H), 3.59-3.71 (m, 1H), 3.72-3.90 (m, 2H), 3.92-4.05 (m, 1H), 4.16-4.30 (m, 2H), 7.21 (s, 2H), 7.37-7.40 (m, 2H), 7.52-7.55 (m, 1H).

ESI-MS m/z 424 [M+H]+

Example 20

Synthesis of (R)-3-(4-cyclopropoxy-3-methylphenyl)-1-(2,6-dimethylpyridin-4-yl)-6-methyl-5,6,8,9-tetrahydroimidazo[1,5-d][1,4]oxazepine

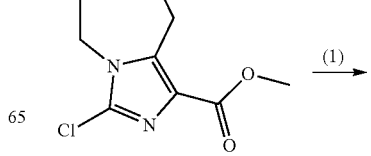

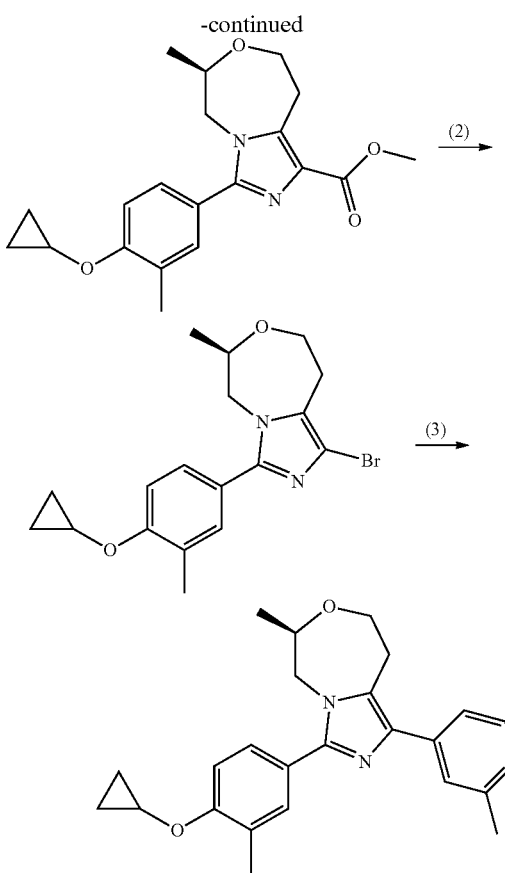

(1) Synthesis of (R)-methyl 3-(4-cyclopropoxy-3-methylphenyl)-6-methyl-5,6,8,9-tetrahydroimidazo[1,5-d][1,4]oxazepine-1-carboxylate According to the method of Example 14-(1), a title compound (248 mg, 0.696 mmol) was obtained from the compound obtained in Production Example 8-(3) (200 mg, 0.817 mmol) and the compound obtained in Production Example 16 (269 mg, 0.981 mmol).

¹H-NMR (400 MHz, CDCl3) δ (ppm): 0.69-0.92 (m, 4H), 1.12-1.33 (m, 3H), 2.19 (s, 3H), 3.00-3.18 (m, 1H), 3.58-3.80 (m, 3H), 3.89 (s, 3H), 3.90-3.98 (m, 1H), 4.00-4.09 (m, 1H), 4.15-4.31 (m, 2H), 7.22-7.25 (m, 2H), 7.28-7.30 (m, 1H).

(2) Synthesis of (R)-1-bromo-3-(4-cyclopropoxy-3-methylphenyl)-6-methyl-5,6,8,9-tetrahydroimidazo[1,5-d][1,4]oxazepine According to the method of Example 18-(2), a title compound (115 mg, 0.305 mmol) was obtained from the compound obtained in Example 20-(1) (248 mg, 0.696 mmol).

¹H-NMR (400 MHz, CDCl3) δ (ppm): 0.73-0.90 (m, 4H), 1.17-1.27 (m, 3H), 2.19 (s, 3H), 2.90-3.01 (m, 1H), 3.02-3.11 (m, 1H), 3.57-3.65 (m, 1H), 3.66-3.81 (m, 2H), 3.84-3.96 (m, 1H), 4.12-4.21 (m, 1H), 4.22-4.32 (m, 1H), 7.17-7.31 (m, 3H).

(3) Synthesis of (R)-3-(4-cyclopropoxy-3-methylphenyl)-1-(2,6-dimethylpyridin-4-yl)-6-methyl-5,6,8,9-tetrahydroimidazo[1,5-d][1,4]oxazepine According to the method of Example 1-(5), a title compound (2.7 mg, 6.7 μmol) was obtained from the compound obtained in Example 20-(2) (30.0 mg, 0.080 mmol) and 2,6-dimethyl-pyridine-4-boronic acid (19.2 mg, 0.127 mmol).

¹H-NMR (400 MHz, CDCl3) δ (ppm): 0.73-0.90 (m, 4H), 1.21-1.32 (m, 3H), 2.21 (s, 3H), 2.55 (s, 6H), 3.11-3.24 (m, 1H), 3.28-3.43 (m, 1H), 3.60-3.72 (m, 1H), 3.73-3.86 (m, 2H), 3.88-4.03 (m, 1H), 4.16-4.35 (m, 2H), 7.22 (s, 2H), 7.25-7.28 (m, 2H), 7.29-7.32 (m, 1H).

ESI-MS m/z 404 [M+H]+

Example 21

Synthesis of (R)-3-(3-chloro-4-(difluoromethoxy)phenyl)-6-methyl-1-(2-methylpyridin-4-yl)-5,6,8,9-tetrahydroimidazo[1,5-d][1,4]oxazepine

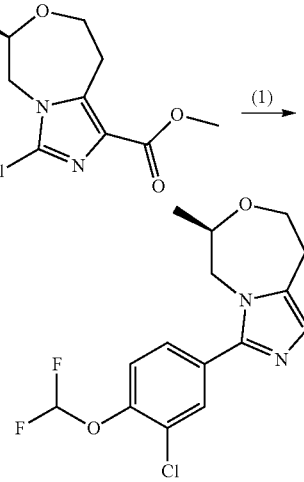

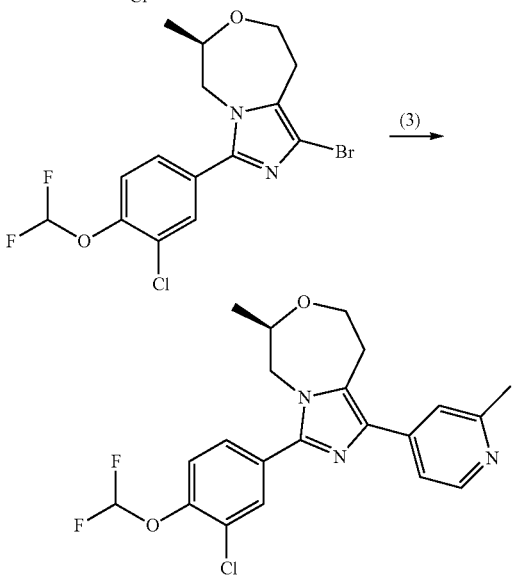

(1) Synthesis of (R)-methyl 3-(3-chloro-4-(difluoromethoxy)phenyl)-6-methyl-5,6,8,9-tetrahydroimidazo[1,5-d][1,4]oxazepine-1-carboxylate According to the method of Example 14-(1), a title compound (177 mg, 0.458 mmol) was obtained from the compound obtained in Production Example 8-(3) (150 mg, 0.613 mmol) and 2-(3-chloro-4-(difluoromethoxy)phenyl)-4,4,5,5-tetramethyl-1,3,2-dioxaborolane (CAS No. 1310949-92-8; 224 mg, 0.736 mmol).

¹H-NMR (400 MHz, CDCl3) δ (ppm): 1.16-1.30 (m, 3H), 3.01-3.22 (m, 1H), 3.59-3.77 (m, 2H), 3.90 (s, 3H), 3.95-4.11 (m, 2H), 4.14-4.28 (m, 2H), 6.60 (t, J=72.8 Hz, 1H), 7.33 (d, J=8.4 Hz, 1H), 7.37 (dd, J=2.0, 8.4 Hz, 1H), 7.66 (d, J=2.0 Hz, 1H).

(2) Synthesis of (R)-1-bromo-3-(3-chloro-4-(difluoromethoxy)phenyl)-6-methyl-5,6,8,9-tetrahydroimidazo[1,5-d][1,4]oxazepine According to the method of Example 18-(2), a title compound (98.0 mg, 0.240 mmol) was obtained from the compound obtained in Example 21-(1) (177 mg, 0.458 mmol).

¹H-NMR (400 MHz, CDCl3) δ (ppm): 1.13-1.34 (m, 3H), 2.91-3.03 (m, 1H), 3.04-3.16 (m, 1H), 3.56-3.79 (m, 2H), 3.89-4.03 (m, 1H), 4.14-4.25 (m, 2H), 6.59 (t, J=72.8 Hz, 1H), 7.32 (d, J=8.4 Hz, 1H), 7.35 (dd, J=1.9, 8.4 Hz, 1H), 7.62 (d, J=1.9 Hz, 1H).

(3) Synthesis of (R)-3-(3-chloro-4-(difluoromethoxy)phenyl)-6-methyl-1-(2-methylpyridin-4-yl)-5,6,8,9-tetrahydroimidazo[1,5-d][1,4]oxazepine According to the method of Example 17, a title compound (13.8 mg, 0.033 mmol) was obtained from the compound obtained in Example 21-(2) (30.0 mg, 0.074 mmol) and 2-picoline-4-boronic acid (15.1 mg, 0.110 mmol).

¹H-NMR (400 MHz, CDCl3) δ (ppm): 1.22-1.38 (m, 3H), 2.59 (s, 3H), 3.12-3.29 (m, 1H), 3.31-3.43 (m, 1H), 3.61-3.72 (m, 1H), 3.74-3.87 (m, 1H), 3.96-4.08 (m, 1H), 4.16-4.28 (m, 2H), 6.60 (t, J=72.9 Hz, 1H), 7.28 (brd, J=5.2 Hz, 1H), 7.36 (brd, J=8.4 Hz, 1H), 7.41 (dd, J=2.0, 8.4 Hz, 1H), 7.44 (brs, 1H), 7.68 (d, J=2.0 Hz, 1H), 8.50 (d, J=5.2 Hz, 1H).
ESI-MS m/z 420 [M+H]+

Example 22

Synthesis of (S)-3-(4-cyclopropoxy-3-methylphenyl)-1-(2,6-dimethylpyridin-4-yl)-6-(fluoromethyl)-5,6,8,9-tetrahydroimidazo[1,5-d][1,4]oxazepine

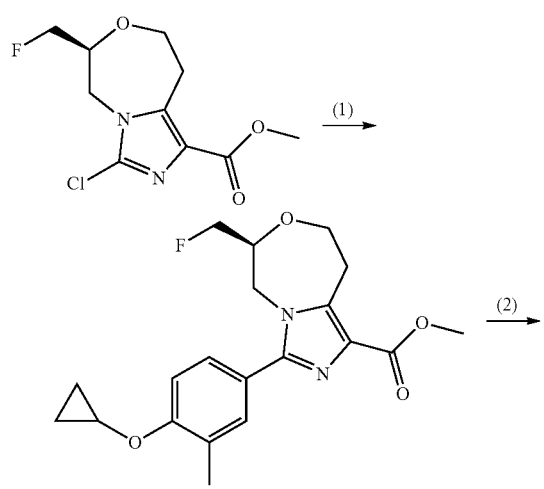

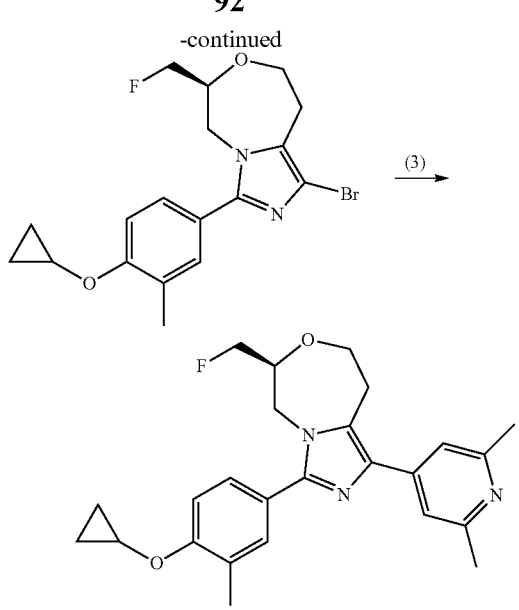

(1) Synthesis of (S)-methyl 3-(4-cyclopropoxy-3-methylphenyl)-6-(fluoromethyl)-5,6,8,9-tetrahydroimidazo[1,5-d][1,4]oxazepine-1-carboxylate According to the method of Example 14-(1), a title compound (107 mg, 0.286 mmol) was obtained from the compound obtained in Production Example 9 (200 mg, 0.761 mmol) and the compound obtained in Production Example 16 (251 mg, 0.914 mmol).

¹H-NMR (400 MHz, CDCl3) δ (ppm): 0.73-0.87 (m, 4H), 2.18 (s, 3H), 2.97-3.19 (m, 1H), 3.63-3.72 (m, 1H), 3.73-3.85 (m, 2H), 3.90 (s, 3H), 3.96-4.06 (m, 1H), 4.12-4.20 (m, 1H), 4.24-4.64 (m, 4H), 7.22-7.27 (m, 2H), 7.29-7.32 (m, 1H).

(2) Synthesis of (S)-1-bromo-3-(4-cyclopropoxy-3-methylphenyl)-6-(fluoromethyl)-5,6,8,9-tetrahydroimidazo[1,5-d][1,4]oxazepine According to the method of Example 18-(2), a title compound (75.0 mg, 0.190 mmol) was obtained from the compound obtained in Example 22-(1) (107 mg, 0.286 mmol).

¹H-NMR (400 MHz, CDCl3) δ (ppm): 0.72-0.87 (m, 4H), 2.18 (d, J=0.8 Hz, 3H), 2.94-3.18 (m, 2H), 3.57-3.70 (m, 1H), 3.71-3.88 (m, 2H), 3.91-4.05 (m, 1H), 4.20-4.63 (m, 4H), 7.24 (d, J=1.4 Hz, 2H), 7.28 (qd, J=0.8, 1.4 Hz, 1H).

(3) Synthesis of (S)-3-(4-cyclopropoxy-3-methylphenyl)-1-(2,6-dimethylpyridin-4-yl)-6-(fluoromethyl)-5,6,8,9-tetrahydroimidazo[1,5-d][1,4]oxazepine According to the method of Example 14-(3), a title compound (12.0 mg, 0.028 mmol) was obtained from the compound obtained in Example 22-(2) (26 mg, 0.066 mmol) and 2,6-dimethylpyridine-4-boronic acid (15.9 mg, 0.105 mmol).

¹H-NMR (400 MHz, CDCl3) δ (ppm): 0.70-0.93 (m, 4H), 2.20 (s, 3H), 2.55 (s, 6H), 3.12-3.29 (m, 1H), 3.33-3.45 (m, 1H), 3.64-3.74 (m, 1H), 3.75-3.94 (m, 2H), 3.97-4.09 (m, 1H), 4.23-4.66 (m, 4H), 7.22 (s, 2H), 7.25-7.35 (m, 3H).
ESI-MS m/z 422 [M+H]+

Example 23

Synthesis of (R)-3-(4-(1,1-difluoroethyl)-3-methoxyphenyl)-1-(2,6-dimethylpyridin-4-yl)-6-methyl-5,6,8,9-tetrahydroimidazo[1,5-d][1,4]oxazepine

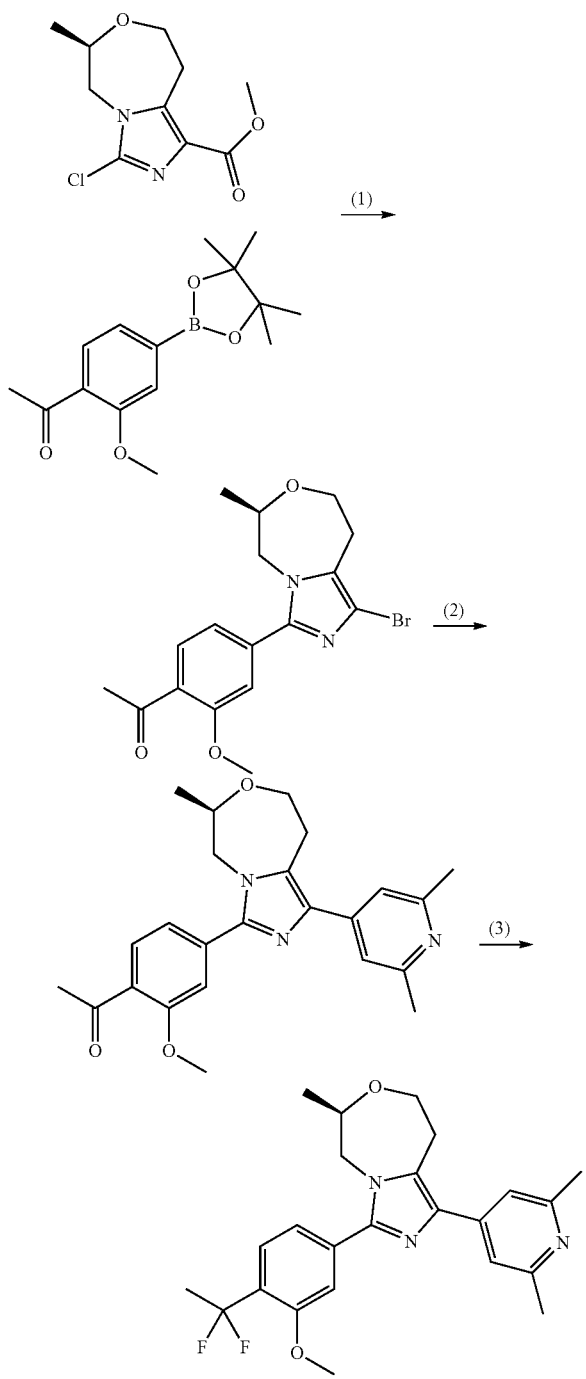

(1) Synthesis of (R)-1-(4-(1-bromo-6-methyl-5,6,8,9-tetrahydroimidazo[1,5-d][1,4]oxazepin-3-yl)-2-methoxyphenyl)ethanone According to the methods of Examples 14-(1) and 18-(2), a title compound (79.4 mg, 0.209 mmol) was obtained from 1-(2-methoxy-4-(4,4,5,5-tetramethyl-1,3,2-dioxaborolan-2-yl)phenyl)ethanone (CAS No. 638214-65-0; 293 mg, 1.06 mmol) and the compound obtained in Production Example 8-(3) (173 mg, 0.707 mmol).

$^1$H-NMR (400 MHz, CDCl3) δ (ppm): 1.23 (d, J=6.2 Hz, 3H), 2.64 (s, 3H), 2.99 (ddd, J=2.7, 10.9, 16.4 Hz, 1H), 3.09 (ddd, J=1.6, 4.3, 16.4 Hz, 1H), 3.62 (ddd, J=1.4, 10.6, 12.2 Hz, 1H), 3.67-3.76 (m, 1H), 3.95 (dd, J=8.2, 14.8 Hz, 1H), 3.97 (s, 3H), 4.19 (ddd, J=2.7, 3.9, 12.5 Hz, 1H), 4.28 (d, J=14.4 Hz, 1H), 6.93 (dd, J=1.6, 7.8 Hz, 1H), 7.24 (d, J=1.2 Hz, 1H), 7.79 (d, J=7.8 Hz, 1H).

ESI-MS m/z 379, 381 [M+H]+401, 403 [M+Na]+

(2) Synthesis of (R)-1-(4-(1-(2,6-dimethylpyridin-4-yl)-6-methyl-5,6,8,9-tetrahydroimidazo[1,5-d][1,4]oxazepin-3-yl)-2-methoxyphenyl)ethanone According to Example 1-(5), a title compound (35 mg, 0.086 mmol) was obtained from the compound obtained in Example 23-(1) (39 mg, 0.10 mmol).

$^1$H-NMR (400 MHz, CDCl3) δ (ppm): 1.27 (d, J=6.6 Hz, 3H), 2.56 (s, 6H), 2.65 (d, J=0.8 Hz, 3H), 3.19 (ddd, J=2.3, 10.9, 16.0 Hz, 1H), 3.37 (dd, J=4.5, 16.2 Hz, 1H), 3.67 (t, J=11.5 Hz, 1H), 3.75-3.85 (m, 1H), 3.96-4.05 (m, 1H), 3.99 (s, 3H), 4.23 (ddd, J=2.3, 4.3, 12.5 Hz, 1H), 4.30 (d, J=14.8 Hz, 1H), 6.96-7.04 (m, 1H), 7.22 (s, 2H), 7.28 (d, J=0.8 Hz, 1H), 7.82 (d, J=7.8 Hz, 1H).

ESI-MS m/z 406 [M+H]+, 428 [M+Na]+

(3) Synthesis of (R)-3-(4-(1,1-difluoroethyl)-3-methoxyphenyl)-1-(2,6-dimethylpyridin-4-yl)-6-methyl-5,6,8,9-tetrahydroimidazo[1,5-d][1,4]oxazepine DAST (23 μL, 0.17 mmol) was added to a solution of the compound obtained in Example 23-(2) (35 mg, 0.073 mmol) in DCM (1.0 mL), at −78° C. The reaction mixture was warmed to room temperature and stirred for 16 hours, and then DCE (1 mL) and BAST (0.080 mL, 0.43 mmol) were added. The reaction mixture was heated to 80° C. and stirred for 2 hours, and then BAST (0.20 mL, 1.1 mmol) was added. The reaction mixture was stirred at 80° C. for 5 hours, and then BAST (0.50 mL, 2.7 mmol) was added. The reaction mixture was stirred at 80° C. for 5 hours, then cooled to room temperature, and then purified by NH silica gel column chromatography (n-heptane/ethyl acetate). The resultant compound was purified serially by silica gel thin layer chromatography (ethyl acetate) and NH silica gel thin layer chromatography (n-heptane/ethyl acetate) to obtain a title compound (3.4 mg, 0.0080 mmol).

$^1$H-NMR (400 MHz, CDCl3) δ (ppm): 1.28 (d, J=6.2 Hz, 3H), 2.03 (t, J=18.7 Hz, 3H), 2.63 (s, 6H), 3.21 (ddd, J=2.3, 10.7, 16.2 Hz, 1H), 3.38 (dd, J=3.9, 16.0 Hz, 1H), 3.68 (t, J=11.1 Hz, 1H), 3.76-3.84 (m, 1H), 3.95 (s, 3H), 4.00 (dd, J=8.2, 14.8 Hz, 1H), 4.24 (ddd, J=2.3, 4.7, 12.1 Hz, 1H), 4.30 (d, J=14.8 Hz, 1H), 7.00 (dd, J=1.6, 7.8 Hz, 1H), 7.21 (s, 1H), 7.30 (s, 2H), 7.62 (d, J=7.8 Hz, 1H).

ESI-MS m/z 428[M+H]+

Example 24

Synthesis of (R)-3-(3-methoxy-4-(trifluoromethoxy)phenyl)-6-methyl-1-(2-methylpyridin-4-yl)-5,6,8,9-tetrahydroimidazo[1,5-d][1,4]oxazepine

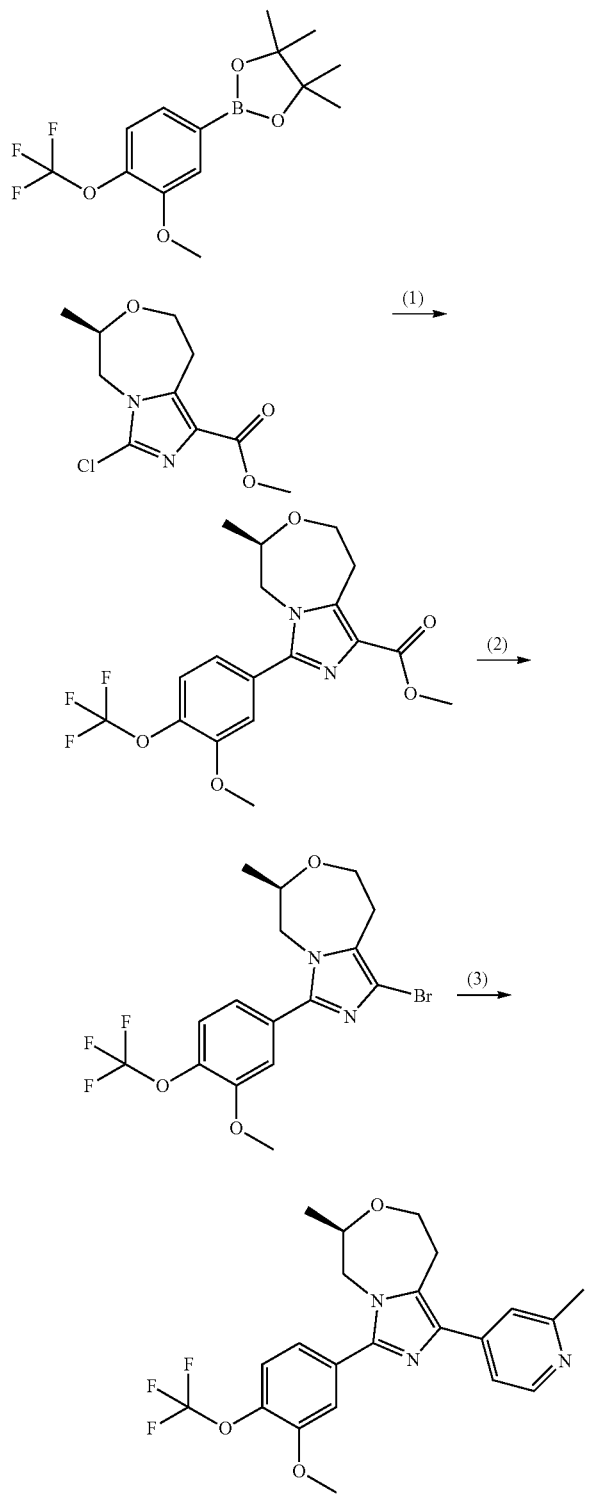

(1) Synthesis of (R)-methyl 3-(3-methoxy-4-(trifluoromethoxy)phenyl)-6-methyl-5,6,8,9-tetrahydroimidazo[1,5-d][1,4]oxazepine-1-carboxylate A mixture of the compound obtained in Production Example 8-(3) (600 mg, 2.45 mmol), the compound obtained in Production Example 21 (1.56 g, 4.90 mmol), tetrakis(triphenylphosphine)palladium(0) (283 mg, 0.245 mmol), an aqueous sodium carbonate solution (2 M, 4.9 mL) and DME (15 mL) was stirred under microwave irradiation at 130° C. for 30 minutes. The reaction mixture was cooled to room temperature, and then ethyl acetate and a saturated aqueous ammonium chloride solution were added. The insolubles were filtered off through Celite (trademark) and the organic layer of the resultant filtrate was separated. The resultant organic layers were washed with a saturated aqueous sodium chloride solution, dried over anhydrous magnesium sulfate, the drying agent was filtered off, and the solvent was evaporated under reduced pressure. The resultant residue was purified by silica gel column chromatography (n-heptane/ethyl acetate) to obtain a title compound (982 mg, 2.45 mmol).

ESI-MS m/z 401 [M+H]+

(2) Synthesis of (R)-1-bromo-3-(3-methoxy-4-(trifluoromethoxy)phenyl)-6-methyl-5,6,8,9-tetrahydroimidazo[1,5-d][1,4]oxazepine A 5 N aqueous sodium hydroxide solution (0.981 mL) was added to a solution of the compound obtained in Example 24-(1) (982 mg, 2.45 mmol) in ethanol (10.0 mL). The reaction mixture was heated and stirred at 45° C. for 4 hours. The reaction mixture was cooled to room temperature, then a 5 N hydrochloric acid (0.98 mL) was added for neutralization. The insolubles were filtered off, then the filtrate was concentrated under reduced pressure, and then DMF (5 mL) was added to the resultant residue. Potassium carbonate (678 mg, 4.91 mmol) and NBS (480 mg, 2.70 mmol) were added to the reaction mixture, and the mixture was stirred at room temperature for 14 hours. Water and ethyl acetate were added to the mixture to separate the organic layer. The resultant organic layers were washed with a saturated aqueous sodium chloride solution, dried over anhydrous magnesium sulfate, the drying agent was filtered off, and then the solvent was evaporated under reduced pressure. The resultant residue was purified by NH silica gel column chromatography (n-heptane/ethyl acetate) to obtain a title compound (640 mg, 1.52 mmol).

$^1$H-NMR (400 MHz, CDCl3) δ (ppm): 1.24 (d, J=6.3 Hz, 3H), 2.94-3.12 (m, 2H), 3.58-3.66 (m, 1H), 3.67-3.76 (m, 1H), 3.93 (s, 3H), 3.94-3.99 (m, 1H), 4.15-4.22 (m, 1H), 4.23-4.30 (m, 1H), 6.83-6.93 (m, 1H), 7.20-7.24 (m, 1H), 7.27-7.33 (m, 1H).

(3) Synthesis of (R)-3-(3-methoxy-4-(trifluoromethoxy)phenyl)-6-methyl-1-(2-methylpyridin-4-yl)-5,6,8,9-tetrahydroimidazo[1,5-d][1,4]oxazepine A mixture of the compound obtained in Example 24-(2) (640 mg, 1.52 mmol), 2-picoline-4-boronic acid (312 mg, 2.28 mmol), tetrakis(triphenylphosphine)palladium(0) (176 mg, 0.152 mmol), an aqueous sodium carbonate solution (2 M, 3.04 mL, 6.08 mmol), and DME (10 mL) was stirred under microwave irradiation at 150° C. for 30 minutes. The reaction mixture was cooled to room temperature and ethyl acetate and a saturated aqueous ammonium chloride solution were added for separation. The resultant organic layer was washed with a saturated aqueous sodium chloride solution, then dried over anhydrous magnesium sulfate, the drying agent was filtered off, and then the solvent was evaporated under reduced pressure. The resultant residue was purified serially by NH silica gel column chromatography (heptane-ethyl acetate) and silica gel column chromatography (methanol-ethyl acetate) to obtain a title compound (152 mg, 0.351 mmol).

¹H-NMR (400 MHz, CDCl3) δ (ppm): 1.28 (d, J=6.3 Hz, 3H), 2.59 (s, 3H), 3.16-3.26 (m, 1H), 3.33-3.42 (m, 1H), 3.64-3.73 (m, 1H), 3.76-3.85 (m, 1H), 3.95 (s, 3H), 3.96-4.05 (m, 1H), 4.19-4.32 (m, 2H), 6.95-7.00 (m, 1H), 7.25-7.36 (m, 3H), 7.45-7.48 (m, 1H), 8.47-8.52 (m, 1H).

ESI-MS m/z 434 [M+H]+.

Example 25

Synthesis of (R)-1-(2,6-dimethylpyridin-4-yl)-3-(3-methoxy-4-(trifluoromethoxy)phenyl)-6-methyl-5,6,8,9-tetrahydroimidazo[1,5-d][1,4]oxazepine

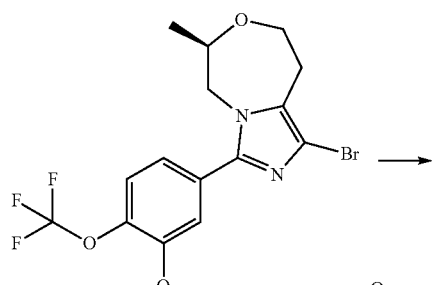

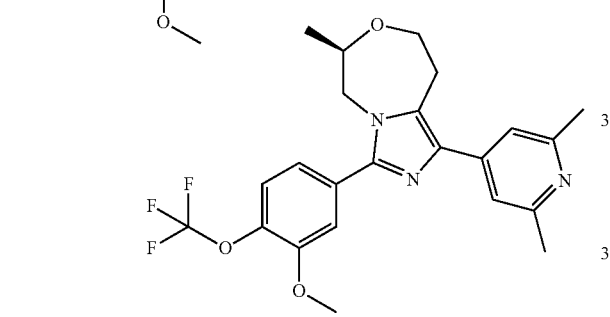

According to the method of Example 7-(5), a title compound (6.7 mg, 0.015 mmol) was obtained from the compound obtained in Example 24-(2) (19 mg, 0.045 mmol) and 2,6-dimethyl-pyridine-4-boronic acid (14 mg, 0.093 mmol).

¹H-NMR (400 MHz, CDCl3) δ (ppm): 1.28 (d, J=6.2 Hz, 3H), 2.56 (s, 6H), 3.19 (ddd, J=2.3, 10.5, 16.0 Hz, 1H), 3.37 (dd, J=3.9, 16.0 Hz, 1H), 3.67 (t, J=11.3 Hz, 1H), 3.75-3.84 (m, 1H), 3.94 (s, 3H), 4.00 (dd, J=8.6, 14.8 Hz, 1H), 4.23 (ddd, J=2.3, 4.7, 12.5 Hz, 1H), 4.27 (d, J=14.8 Hz, 1H), 6.97 (dd, J=2.0, 8.6 Hz, 1H), 7.22 (s, 2H), 7.26 (d, J=2.0 Hz, 1H), 7.33 (d, J=1.2, 8.2 Hz, 1H).

ESI-MS m/z 448 [M+H]+.

Example 26

Synthesis of (S)-3-(4-chloro-3-methoxyphenyl)-6-fluoromethyl-1-(2-methylpyridin-4-yl)-5,6,8,9-tetrahydroimidazo[1,5-d][1,4]oxazepine

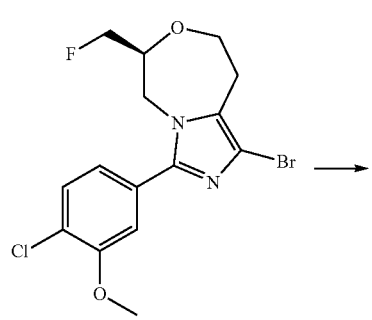

According to the method of Example 1-(5), a title compound (13.3 mg, 0.033 mmol) was obtained from the compound obtained in Example 11-(2) (30.0 mg, 0.077 mmol) and 2-picoline-4-boronic acid (21.1 mg, 0.154 mmol).

¹H-NMR (400 MHz, CDCl3) δ (ppm): 2.59 (s, 3H), 3.15-3.28 (m, 1H), 3.41 (dd, J=4.1, 16.2 Hz, 1H), 3.70 (t, J=11.5 Hz, 1H), 3.84-3.93 (m, 1H), 3.95 (s, 3H), 4.04 (dd, J=9.0, 14.8 Hz, 1H), 4.26-4.44 (m, 2H), 4.47-4.64 (m, 2H), 6.96-7.03 (m, 1H), 7.16 (d, J=2.0 Hz, 1H), 7.30 (d, J=5.1 Hz, 1H), 7.44-7.51 (m, 2H), 8.50 (d, J=5.5 Hz, 1H).

ESI-MS m/z 402 [M+H]+

Example 27

Synthesis of (S)-3-(4-(difluoromethoxy)-3-methylphenyl)-1-(2,6-dimethylpyridin-4-yl)-6-(fluoromethyl)-5,6,8,9-tetrahydroimidazo[1,5-d][1,4]oxazepine

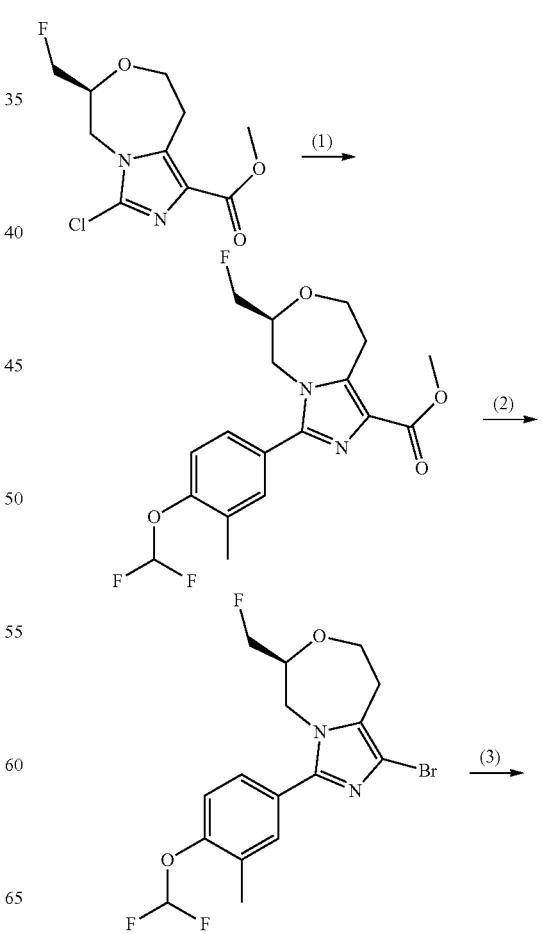

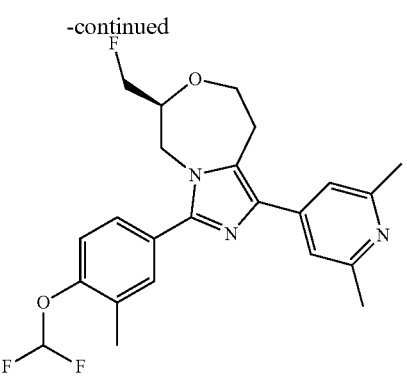

(1) Synthesis of (S)-methyl 3-(4-(difluoromethoxy)-3-methylphenyl)-6-(fluoromethyl)-5,6,8,9-tetrahydroimidazo[1,5-d][1,4]oxazepine-1-carboxylate A mixture of the compound obtained in Production Example 9 (203 mg, 0.773 mmol), 4-difluoromethoxy-3-methyl-benzeneboronic acid (234 mg, 1.16 mmol), tetrakis(triphenylphosphine)palladium(0) (89 mg, 0.077 mmol), and an aqueous sodium carbonate solution (1 M, 1.47 mL) in DME (3.09 mL) was stirred under microwave irradiation at 130° C. for 30 minutes. Ethyl acetate and an aqueous sodium chloride solution were added to the mixture. The organic layer was separated. The water layer was extracted with ethyl acetate three times, then the resultant organic layer was dried over anhydrous sodium sulfate and then concentrated under reduced pressure. The resultant residue was purified by silica gel column chromatography (n-heptane/ethyl acetate) to obtain a title compound (281 mg, 0.731 mmol).

ESI-MS m/z 385 [M+H]+

(2) Synthesis of (S)-1-bromo-3-(4-(difluoromethoxy)-3-methylphenyl)-6-(fluoromethyl)-5,6,8,9-tetrahydroimidazo[1,5-d][1,4]oxazepine A solution of the compound obtained in Example 27-(1) (281 mg, 0.731 mmol) and a 5 N aqueous sodium hydroxide solution (0.731 mL, 3.66 mmol) in THF (1.8 mL)-methanol (1.8 mL) was stirred at room temperature for 2 hours. The reaction mixture was neutralized with hydrochloric acid. The mixture was concentrated under reduced pressure and the resultant residue was azeotroped with toluene. DMF (3.6 mL), ethanol (3.6 mL), potassium carbonate (101 mg, 0.731 mmol), and NBS (260 mg, 1.46 mmol) were added to the residue, and the mixture was stirred at room temperature for 16 hours. Sodium sulfite was added to the reaction mixture and ethanol was evaporated under reduced pressure. Ethyl acetate was added to the resultant solution, and then the mixture was washed with water five times and then with a saturated aqueous sodium chloride solution. The organic layer was dried over anhydrous sodium sulfate and concentrated under reduced pressure. The resultant residue was purified by silica gel column chromatography (n-heptane/ethyl acetate) to obtain a title compound (140 mg, 0.346 mmol).

$^1$H-NMR (400 MHz, CDCl3) δ (ppm): 2.33 (s, 3H), 3.02 (ddd, J=2.7, 10.9, 16.4 Hz, 1H), 3.12 (ddd, J=1.2, 3.5, 16.4 Hz, 1H), 3.65 (dt, J=1.2, 11.7 Hz, 1H), 3.74-3.86 (m, 1H), 4.00 (dd, J=8.8, 14.6 Hz, 1H), 4.23-4.30 (m, 1H), 4.40 (ddd, J=6.6, 9.4, 46.9 Hz, 1H) 4.51 (ddd, J=4.7, 9.8, 46.1 Hz, 1H), 4.53 (d, J=14.8 Hz, 1H), 6.55 (t, J=73.4 Hz, 1H), 7.15 (d, J=8.6 Hz, 1H), 7.27 (dd, J=2.0, 8.2 Hz, 1H), 7.41 (d, J=2.0 Hz, 1H).

ESI-MS m/z 405, 407 [M+H]+ 427, 429 [M+Na]+

(3) Synthesis of (S)-3-(4-(difluoromethoxy)-3-methylphenyl)-1-(2,6-dimethylpyridin-4-yl)-6-(fluoromethyl)-5,6,8,9-tetrahydroimidazo[1,5-d][1,4]oxazepine A mixture of the compound obtained in Example 27-(2) (28 mg, 0.069 mmol), 2,6-dimethyl-pyridine-4-boronic acid (20.9 mg, 0.138 mmol), tetrakis(triphenylphosphine)palladium(0) (8.0 mg, 0.0069 mmol), an aqueous sodium carbonate solution (1 M, 0.35 mL), and DME (0.70 mL) was stirred under microwave irradiation at 150° C. for 30 minutes. Ethyl acetate was added to the mixture, then the mixture was filtered through a silica gel pad (NH silica gel), and then the filtrate was concentrated under reduced pressure. The resultant residue was purified by silica gel thin layer chromatography (ethyl acetate) to obtain a title compound (21.0 mg, 0.049 mmol).

$^1$H-NMR (400 MHz, CDCl3) δ (ppm): 2.35 (s, 3H), 2.56 (s, 6H), 3.21 (ddd, J=2.7, 11.3, 16.4 Hz, 1H), 3.41 (dd, J=3.9, 16.0 Hz, 1H), 3.70 (t, J=11.3 Hz, 1H), 3.83-3.94 (m, 1H), 4.05 (d, J=9.0, 14.8 Hz, 1H), 4.28-4.46 (m, 2H), 4.55 (ddd, J=5.1, 9.8, 46.5 Hz, 1H), 4.55 (d, J=14.8 Hz, 1H), 6.56 (t, J=73.4 Hz, 1H), 7.17-7.21 (m, 1H), 7.21 (s, 2H), 7.33 (d, J=2.1, 8.4 Hz, 1H), 7.47 (d, J=2.0 Hz, 1H).

ESI-MS m/z 432 [M+H]+

Example 28

Synthesis of (S)-3-(4-(difluoromethyl)-3-methoxyphenyl)-1-(2,6-dimethylpyridin-4-yl)-6-(fluoromethyl)-5,6,8,9-tetrahydroimidazo[1,5-d][1,4]oxazepine

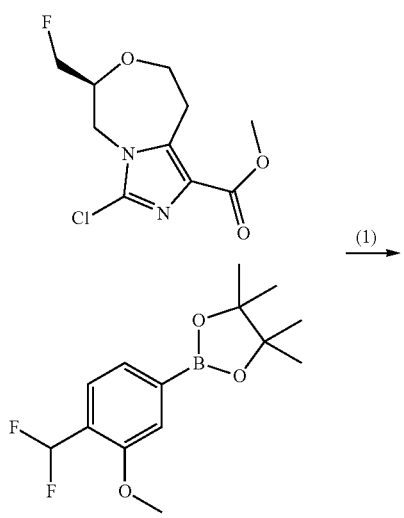

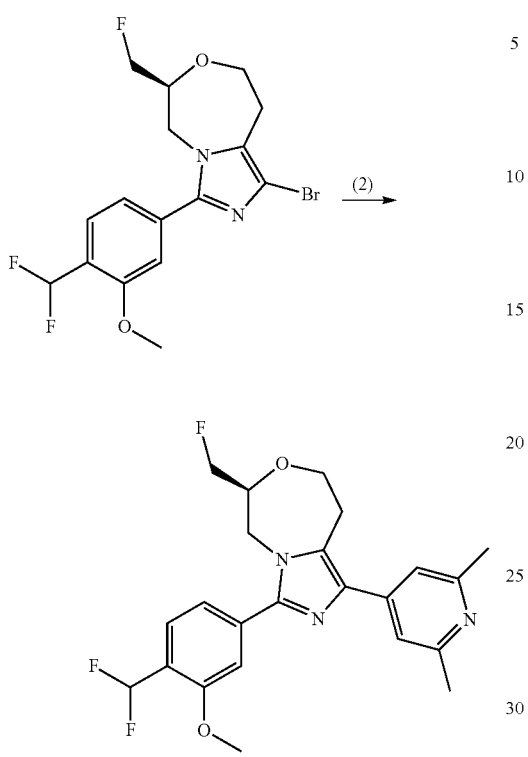

(1) Synthesis of (S)-1-bromo-3-(4-(difluoromethyl)-3-methoxyphenyl)-6-(fluoromethyl)-5,6,8,9-tetrahydroimidazo[1,5-d][1,4]oxazepine According to the methods of Examples 27-(1) and 27-(2), a title compound (107 mg, 0.264 mmol) was obtained from the compound obtained in Production Example 9 (140 mg, 0.533 mmol) and 2-(4-(difluoromethyl)-3-methoxyphenyl)-4,4,5,5-tetramethyl-1,3,2-dioxaborolane (CAS No. 1310949-77-9; 267 mg, 0.940 mmol).

ESI-MS m/z 405, 407 [M+H]+427, 429 [M+Na]+

(2) Synthesis of (S)-3-(4-(difluoromethyl)-3-methoxyphenyl)-1-(2,6-dimethylpyridin-4-yl)-6-(fluoromethyl)-5,6,8,9-tetrahydroimidazo[1,5-d][1,4]oxazepine According to the method of Example 27-(3), a title compound (16 mg, 0.037 mmol) was obtained from the compound obtained in Example 28-(1) (21 mg, 0.052 mmol).

$^1$H-NMR (400 MHz, CDCl3) δ (ppm): 2.57 (s, 6H), 3.22 (ddd, J=2.3, 10.9, 16.4 Hz, 1H), 3.42 (dd, J=3.7, 16.2 Hz, 1H), 3.71 (t, J=11.3 Hz, 1H), 3.84-3.96 (m, 1H), 3.93 (s, 3H), 4.06 (dd, J=8.6, 14.8, 1H), 4.28-4.66 (m, 4H), 6.98 (t, J=55.5 Hz, 1H), 7.10-7.25 (m, 4H), 7.67 (d, J=7.8 Hz, 1H).

ESI-MS m/z 432 [M+H]+

Example 29

Synthesis of (S)-1-(2,6-dimethylpyridin-4-yl)-6-(fluoromethyl)-3-(3-methoxy-4-(trifluoromethyl)phenyl)-5,6,8,9-tetrahydroimidazo[1,5-d][1,4]oxazepine

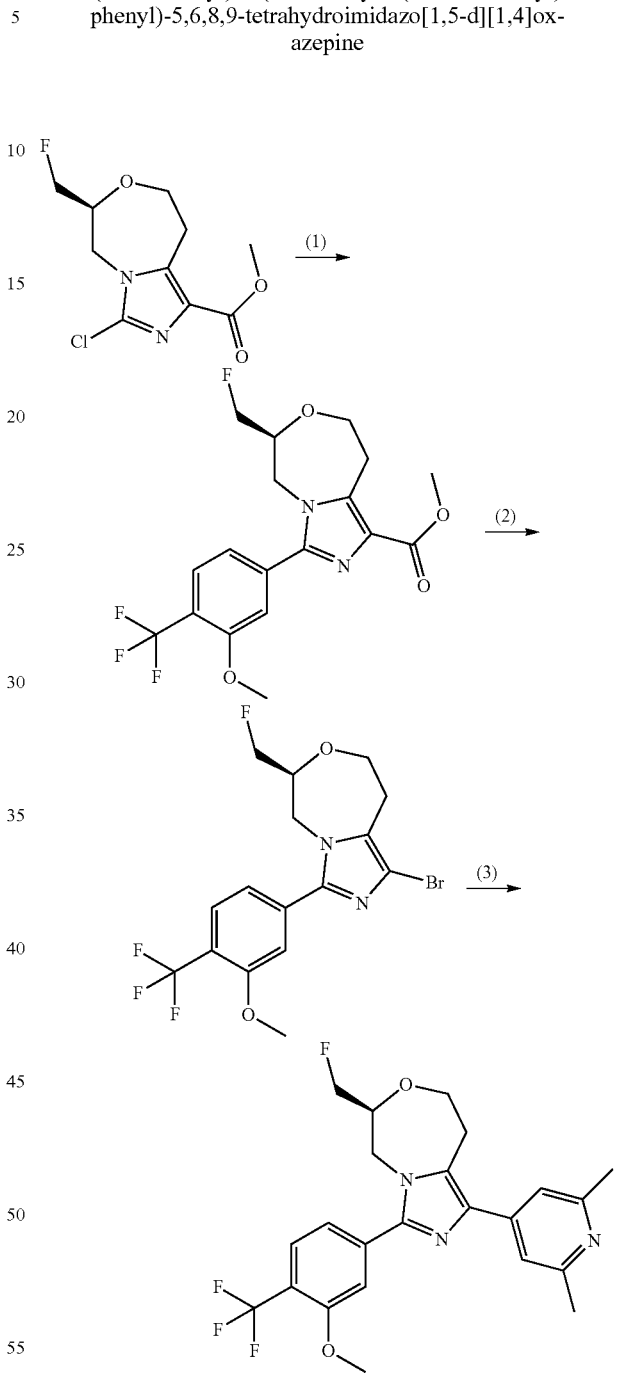

(1) Synthesis of (S)-methyl 6-(fluoromethyl)-3-(3-methoxy-4-(trifluoromethyl)phenyl)-5,6,8,9-tetrahydroimidazo[1,5-d][1,4]oxazepine-1-carboxylate A mixture of the compound obtained in Production Example 9 (202 mg, 0.769 mmol), 2-(3-methoxy-4-(trifluoromethyl)phenyl)-4,4,5,5-tetramethyl-1,3,2-dioxaborolane (CAS No. 1004775-33-0; 465 mg, 1.54 mmol), tetrakis(triphenylphosphine)palladium(0) (89 mg, 0.077 mmol), and an aqueous sodium carbonate solution (1 M, 1.46 mL) in DME (3.08 mL) was stirred under microwave irradiation at 130° C. for 30 minutes. Ethyl acetate and sodium chloride were added to the mixture. The organic layer was separated. The aqueous layer was extracted with ethyl acetate four times, and then the resultant organic layer was dried over anhydrous sodium sulfate and concentrated under reduced pressure. The resultant residue was purified by silica gel column chromatography (n-heptane/ethyl acetate) to obtain a crude title compound (391 mg).

ESI-MS m/z 403 [M+H]+

(2) Synthesis of (S)-1-bromo-6-(fluoromethyl)-3-(3-methoxy-4-(trifluoromethyl)phenyl)-5,6,8,9-tetrahydroimidazo[1,5-d][1,4]oxazepine A solution of the compound obtained in Example 29-(1) (391 mg) and a 5 N aqueous sodium hydroxide solution (0.972 mL) in THF (2.4 mL)/methanol (2.4 mL) was stirred at room temperature for 3 hours. The reaction mixture was neutralized with hydrochloric acid. The mixture was concentrated under reduced pressure and the resultant residue was azeotroped with toluene. DMF (2.4 mL), ethanol (2.4 mL), potassium carbonate (134 mg, 0.972 mmol), and NBS (346 mg, 1.94 mmol) were added to the residue at room temperature. The reaction mixture was stirred at room temperature for 20 hours. NBS (346 mg, 1.94 mmol) was added to the reaction mixture and then the mixture was stirred for 5 hours. Sodium sulfite was added to the reaction mixture and ethanol was evaporated under reduced pressure. Ethyl acetate was added to the resultant solution and the mixture was washed with water five times and then with a saturated aqueous sodium chloride solution. The organic layer was dried over anhydrous sodium sulfate and concentrated under reduced pressure. The resultant residue was purified by silica gel column chromatography to obtain a title compound (179 mg, 0.423 mmol).

¹H-NMR (400 MHz, CDCl3) δ (ppm): 3.06 (ddd, J=2.7, 10.9, 16.0 Hz, 1H), 3.14 (ddd, J=1.6, 3.9, 16.4 Hz, 1H), 3.66 (ddd, J=1.4, 10.9, 12.3 Hz, 1H), 3.79-3.89 (m, 1H), 3.95 (s, 3H), 4.02 (dd, J=8.6, 14.8 Hz, 1H), 4.25-4.42 (m, 2H), 4.53 (ddd, J=4.7, 9.4, 46.1 Hz, 1H), 4.59 (d, J=15.6 Hz, 1H), 7.03 (d, J=7.8 Hz, 1H), 7.22 (s, 1H), 7.64 (d, J=7.8 Hz, 1H).

ESI-MS m/z 423, 425 [M+H]+445, 447 [M+Na]+

(3) Synthesis of (S)-1-(2,6-dimethylpyridin-4-yl)-6-(fluoromethyl)-3-(3-methoxy-4-(trifluoromethyl)phenyl)-5,6,8,9-tetrahydroimidazo[1,5-d][1,4]oxazepine A mixture of the compound obtained in Example 29-(2) (26 mg, 0.061 mmol), 2,6-dimethyl-pyridine-4-boronic acid (18.6 mg, 0.123 mmol), tetrakis(triphenylphosphine)palladium(0) (7.1 mg, 0.0061 mmol), an aqueous sodium carbonate solution (1 M, 0.40 mL), and DME (0.80 mL) was stirred under microwave irradiation at 150° C. for 30 minutes. Ethyl acetate was added to the mixture, and then the mixture was filtered through a silica gel pad (NH silica gel) and concentrated under reduced pressure. The resultant residue was purified by silica gel thin layer chromatography (ethyl acetate) to obtain a title compound (17.3 mg, 0.038 mmol).

¹H-NMR (400 MHz, CDCl3) δ (ppm): 2.57 (s, 6H), 3.21 (ddd, J=2.7, 11.3, 16.4 Hz, 1H) 3.42 (dd, J=4.1, 16.2 Hz, 1H), 3.71 (t, J=11.7 Hz, 1H), 3.87-3.99 (m, 1H), 3.97 (s, 3H), 4.07 (dd, J=9.0, 14.8 Hz, 1H), 4.28-4.47 (m, 2H), 4.57 (ddd, J=4.5, 9.6, 46.1 Hz, 1H), 4.62 (d, J=14.4 Hz, 1H), 7.10 (d, J=7.8 Hz, 1H), 7.21 (s, 2H), 7.26 (s, 1H), 7.67 (d, J=7.8 Hz, 1H).

ESI-MS m/z 450 [M+H]+

Example 30

Synthesis of (R)-1-(2-(fluoromethyl)-6-methylpyridin-4-yl)-3-(3-methoxy-4-(trifluoromethoxy)phenyl)-6-methyl-5,6,8,9-tetrahydroimidazo[1,5-d][1,4]oxazepine

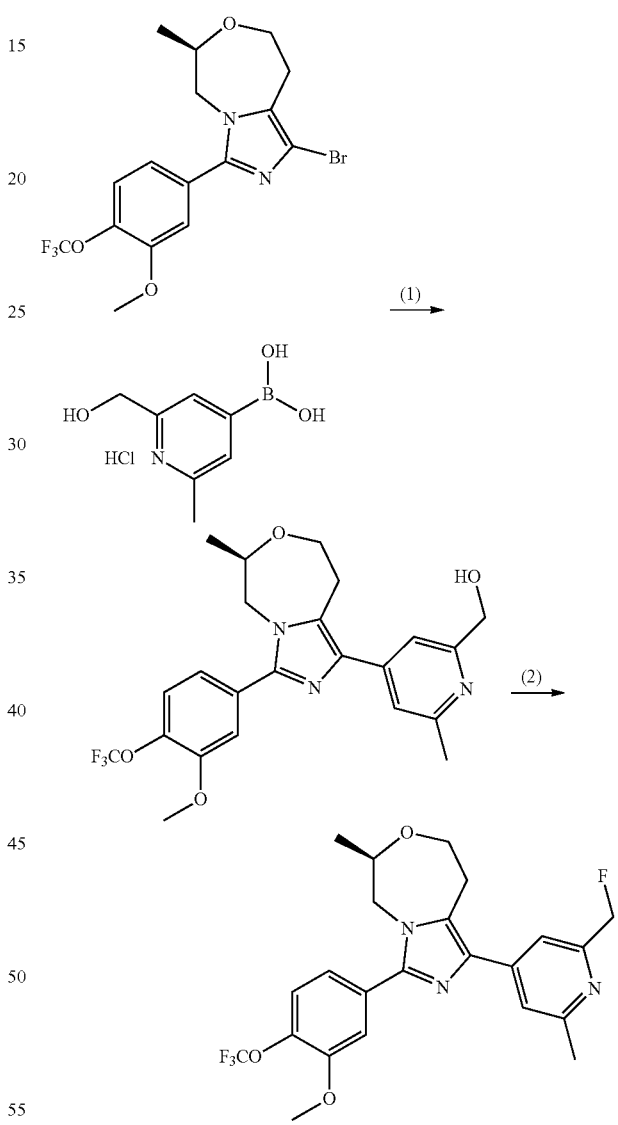

(1) Synthesis of (R)-(4-(3-(3-methoxy-4-(trifluoromethoxy)phenyl)-6-methyl-5,6,8,9-tetrahydroimidazo[1,5-d][1,4]oxazepin-1-yl)-6-methylpyridin-2-yl)methanol According to the method of Example 1-(5), a title compound (7.1 mg, 0.015 mmol) was obtained from the compound obtained in Example 24-(2) (39 mg, 0.093 mmol) and the compound obtained in Production Example 23 (37.7 mg, 0.185 mmol).

$^1$H-NMR (400 MHz, CDCl3) δ (ppm): 1.28 (d, J=6.6 Hz, 3H), 2.59 (s, 3H), 3.20 (ddd, J=2.3, 10.5, 16.0 Hz, 1H), 3.37 (dd, J=4.1, 16.2 Hz, 1H), 3.67 (t, J=11.3 Hz, 1H), 3.76-3.84 (m, 1H), 3.95 (s, 3H), 4.00 (dd, J=8.6, 14.8 Hz, 1H), 4.23 (ddd, J=2.3, 5.1, 12.5 Hz, 1H), 4.28 (d, J=14.8 Hz, 1H), 4.75 (s, 2H), 6.97 (dd, 2.0, 8.2 Hz, 1H), 7.25 (d, J=1.6 Hz, 1H), 7.26-7.29 (m, 1H), 7.31-7.40 (m, 2H).

ESI-MS m/z 464 [M+H]+

(2) Synthesis of (R)-1-(2-(fluoromethyl)-6-methyl-pyridin-4-yl)-3-(3-methoxy-4-(trifluoromethoxy)phenyl)-6-methyl-5,6,8,9-tetrahydroimidazo[1,5-d][1,4]oxazepine DAST (12 μL, 0.091 mmol) was added to a solution of the compound obtained in Example 30-(1) (7.1 mg, 0.015 mmol) in DCM (1.0 mL) at −78° C. The reaction solution was warmed to room temperature, stirred for 16 hours, and then filtered through a silica gel pad (NH silica gel). The filtrate was concentrated under reduced pressure, and then the resultant residue was purified by silica gel thin layer chromatography (ethyl acetate) to obtain a title compound (3.5 mg, 0.0075 mmol).

$^1$H-NMR (400 MHz, CDCl3) δ (ppm): 1.28 (d, J=6.6 Hz, 3H), 2.58 (s, 3H), 3.22 (ddd, J=2.3, 10.7, 16.2 Hz, 1H), 3.38 (dd, J=4.7, 16.4 Hz, 1H), 3.68 (dd, J=10.5, 11.7 Hz, 1H), 3.75-3.84 (m, 1H), 3.95 (s, 3H), 4.01 (dd, J=8.2, 14.8 Hz, 1H), 4.24 (ddd, J=2.3, 4.7, 12.1 Hz, 1H), 4.28 (d, J=14.4 Hz, 1H), 5.49 (d, J=46.9 Hz, 2H), 6.98 (dd, 2.0, 8.6 Hz, 1H), 7.24-7.27 (m, 1H), 7.31-7.36 (m, 1H), 7.43 (s, 1H), 7.46 (s, 1H).

ESI-MS m/z 466 [M+H]+488 [M+Na]+

Example 31

Synthesis of (S)-1-(2-(difluoromethyl)-6-methyl-pyridin-4-yl)-6-(fluoromethyl)-3-(3-methoxy-4-(trifluoromethyl)phenyl)-5,6,8,9-tetrahydroimidazo[1,5-d][1,4]oxazepine

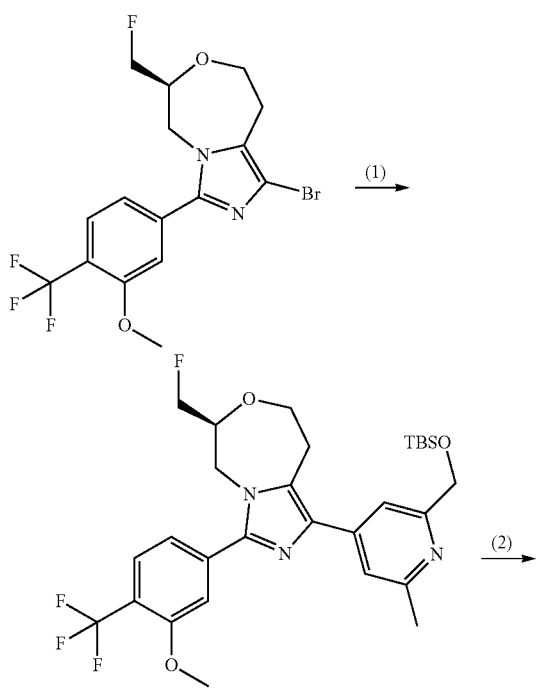

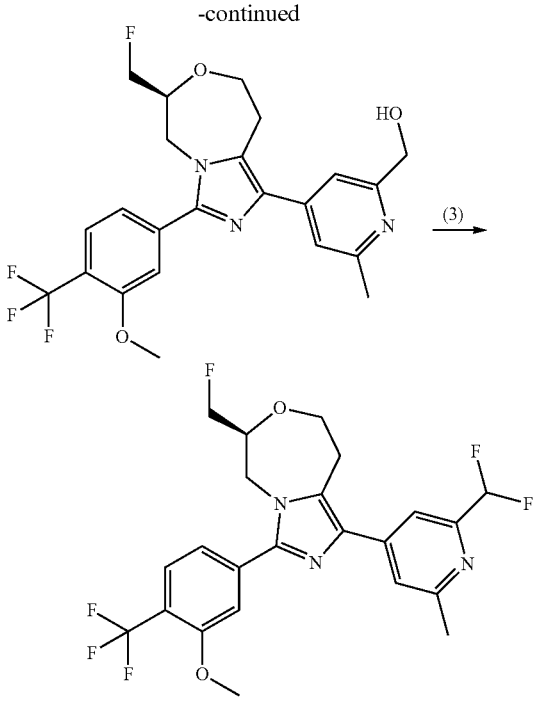

(1) Synthesis of (S)-1-(2-(((tert-butyldimethylsilyl)oxy)methyl)-6-methylpyridin-4-yl)-6-(fluoromethyl)-3-(3-methoxy-4-(trifluoromethyl)phenyl)-5,6,8,9-tetrahydroimidazo[1,5-d][1,4]oxazepine According to the method of Example 1-(5), a crude title compound (148 mg, 0.255 mmol) was obtained from the compound obtained in Example 29-(2) (140 mg, 0.331 mmol) and the compound obtained in Production Example 24-(2) (162 mg, 0.446 mmol).

ESI-MS m/z 580 [M+H]+

(2) Synthesis of (S)-(4-(6-(fluoromethyl)-3-(3-methoxy-4-(trifluoromethyl)phenyl)-5,6,8,9-tetrahydroimidazo[1,5-d][1,4]oxazepin-1-yl)-6-methylpyridin-2-yl)methanol TBAF (a 1 M THF solution, 0.373 mL, 0.373 mmol) was added to a solution of the compound obtained in Example 31-(1) (144 mg, 0.248 mmol) in THF (3 mL) at room temperature. The mixture was stirred at room temperature for 30 minutes, then ethyl acetate and water were added to separate the organic layer. The resultant organic layer was washed with a saturated aqueous sodium chloride solution and then dried over anhydrous magnesium sulfate. The drying agent was filtered off and then the solvent was evaporated under reduced pressure. The resultant residue was purified by NH silica gel column chromatography (ethyl acetate) to obtain a title compound (88.0 mg, 0.189 mmol).

$^1$H-NMR (400 MHz, CDCl3) δ (ppm): 2.60 (s, 3H), 3.17-3.29 (m, 1H), 3.42 (dd, J=4.0, 16.0 Hz, 1H), 3.71 (t, J=12.0 Hz, 1H), 3.84-3.95 (m, 2H), 3.97 (s, 3H), 4.08 (dd, J=8.0, 16.0 Hz, 1H), 4.28-4.66 (m, 4H), 4.76 (s, 2H), 7.10 (d, J=7.8 Hz, 1H), 7.24 (s, 1H), 7.27 (s, 1H), 7.33 (s, 1H), 7.68 (d, J=7.8 Hz, 1H).

(3) Synthesis of (S)-1-(2-(difluoromethyl)-6-methyl-pyridin-4-yl)-6-(fluoromethyl)-3-(3-methoxy-4-(trifluoromethyl)phenyl)-5,6,8,9-tetrahydroimidazo[1,5-d][1,4]oxazepine DMPI (82.0 mg, 0.193 mmol) was added to a solution of the compound obtained in Example 31-(2) (60.0 mg, 0.129 mmol) in DCM (2.5 mL) at room temperature. The reaction mixture was stirred at room temperature for 1 hour and then a saturated aqueous sodium thiosulfate solution, a saturated aqueous sodium bicarbonate solution and ethyl acetate were added to separate the organic layer. The resultant organic layer was washed with a saturated aqueous sodium chloride solution, dried over anhydrous magnesium sulfate, the drying agent was filtered off, and then the solvent was evaporated under reduced pressure. The resultant residue was dissolved in DCM (2.5 mL), and DAST (0.043 mL, 0.32 mmol) was added dropwise thereto at −20° C. The mixture was slowly warmed to room temperature, stirred for 3 hours, and then ice water, a saturated aqueous sodium bicarbonate solution, and ethyl acetate were added to the reaction mixture to separate the organic layer. The resultant organic layer was washed with a saturated aqueous sodium chloride solution and then dried over anhydrous magnesium sulfate, the drying agent was filtered off, and then the solvent was evaporated under reduced pressure. The resultant residue was purified by NH silica gel column chromatography (n-heptane/ethyl acetate) to obtain a title compound (55.3 mg, 0.114 mmol).

$^1$H-NMR (400 MHz, CDCl3) δ (ppm): 2.63 (s, 3H), 3.22-3.32 (m, 1H), 3.42 (dd, J=4.0, 16.0 Hz, 1H), 3.72 (t, J=11.1 Hz, 1H), 3.87-3.96 (m, 1H), 3.97 (s, 3H), 4.09 (dd, J=8.6, 14.8 Hz, 1H), 4.29-4.66 (m, 4H), 6.64 (t, J=56.0 Hz, 1H), 7.09-7.13 (m, 1H), 7.25 (s, 1H), 7.58 (s, 1H), 7.63 (s, 1H), 7.68 (d, J=8.2 Hz, 1H).

ESI-MS m/z 486 [M+H]+.

Example 32

Synthesis of (R)-3-(3-chloro-4-(difluoromethoxy)phenyl)-1-(2,6-dimethylpyridin-4-yl)-6-methyl-5,6,8,9-tetrahydroimidazo[1,5-d][1,4]oxazepine

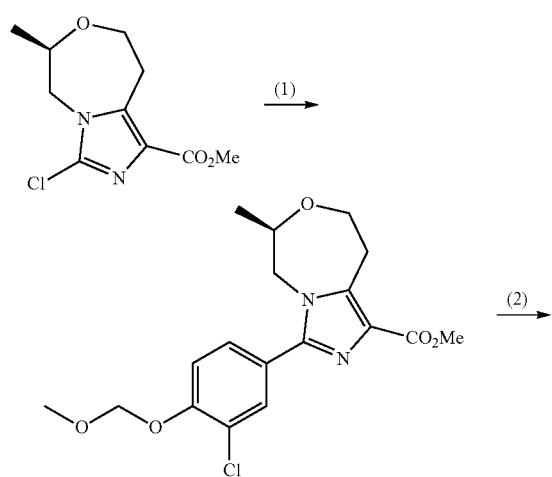

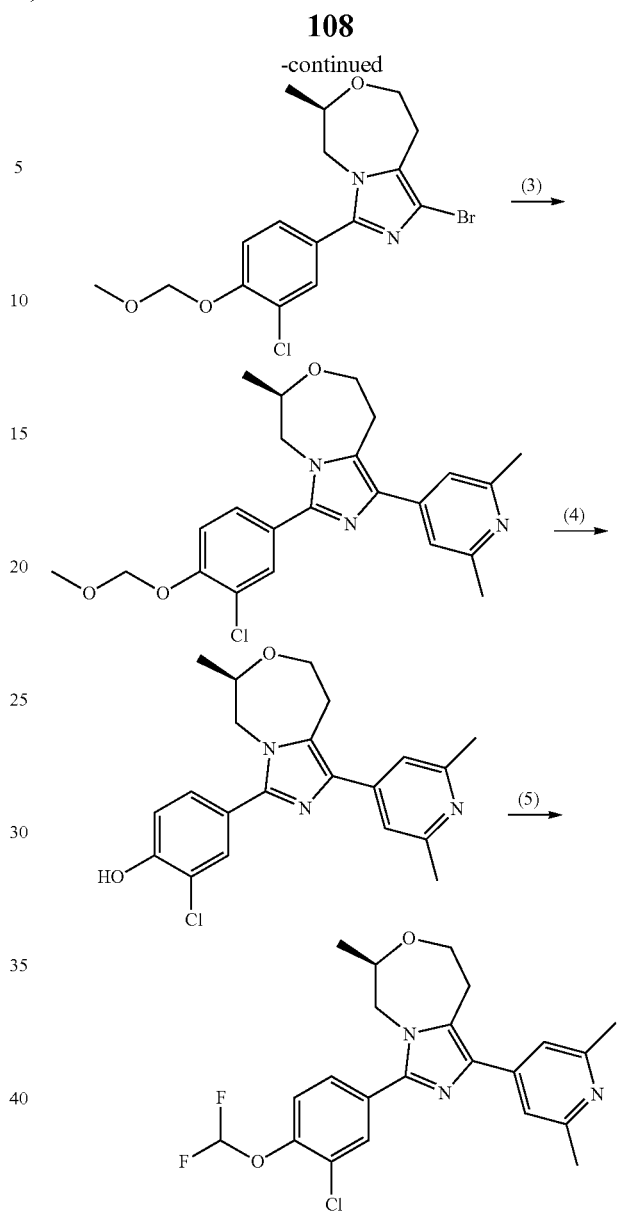

(1) Synthesis of (R)-methyl 3-(3-chloro-4-(methoxymethoxy)phenyl)-6-methyl-5,6,8,9-tetrahydroimidazo[1,5-d][1,4]oxazepine-1-carboxylate A mixture of the compound obtained in Production Example 8-(3) (470 mg, 1.92 mmol), the compound obtained in Production Example 13 (688 mg, 2.31 mmol), tetrakis(triphenylphosphine)palladium(0) (166 mg, 0.144 mmol), an aqueous sodium carbonate solution (2 M, 1.92 mL) and DME (7.5 mL) was stirred under microwave irradiation at 130° C. for 2 hours. The reaction mixture was cooled to room temperature and ethyl acetate and water were added to separate the organic layer. The organic layer was washed with a saturated aqueous sodium chloride solution, dried over anhydrous magnesium sulfate, and concentrated under reduced pressure. The resultant residue was purified by silica gel column chromatography (n-heptane/ethyl acetate) to obtain a title compound (460 mg, 1.21 mmol).

$^1$H-NMR (400 MHz, CDCl3) δ (ppm): 1.20-1.26 (m, 3H), 3.02-3.17 (m, 1H), 3.54 (s, 3H), 3.59-3.77 (m, 2H), 3.90 (s, 3H), 3.92-4.09 (m, 2H), 4.16-4.24 (m, 2H), 5.31 (s, 2H), 7.25 (d, J=8.6 Hz, 1H), 7.30 (dd, J=2.1, 8.6 Hz, 1H), 7.57 (d, J=2.1 Hz, 1H).

(2) Synthesis of (R)-1-bromo-3-(3-chloro-4-(methoxymethoxy)phenyl)-6-methyl-5,6,8,9-tetrahydroimidazo[1,5-d][1,4]oxazepine The compound obtained in Example 32-(1) (460 mg, 1.21 mmol) was dissolved in THF (5 mL) and methanol (5 mL), and a 5 N aqueous sodium hydroxide solution (1.21 mL, 6.04 mmol) was added. The mixture was stirred at room temperature for 15 hours, neutralized with a 5 N hydrochloric acid, and concentrated under reduced pressure. The resultant residue was dissolved in ethanol (5 mL) and DMF (5 mL), potassium carbonate (167 mg, 1.21 mmol) and NBS (301 mg, 1.69 mmol) were added, and the mixture was stirred at room temperature for 2 hours. Sodium sulfite (1.22 g, 9.66 mmol), water, and ethyl acetate were added to the reaction mixture to separate the organic layer. The resultant organic layer was washed with a saturated aqueous sodium chloride solution, dried over anhydrous magnesium sulfate, and concentrated under reduced pressure. The residue was purified by NH silica gel column chromatography (n-heptane/ethyl acetate) to obtain a title compound (240 mg, 0.597 mmol).

$^{1}$H-NMR (400 MHz, CDCl3) δ (ppm): 1.20-1.26 (m, 3H), 2.91-3.01 (m, 1H), 3.02-3.14 (m, 1H), 3.54 (s, 3H), 3.56-3.77 (m, 2H), 3.84-4.01 (m, 1H), 4.10-4.28 (m, 2H), 5.30 (s, 2H), 7.24 (d, J=8.6 Hz, 1H), 7.28 (dd, J=2.0, 8.6 Hz, 1H), 7.53 (d, J=2.0 Hz, 1H).

(3) Synthesis of (R)-3-(3-chloro-4-(methoxymethoxy)phenyl)-1-(2,6-dimethylpyridin-4-yl)-6-methyl-5,6,8,9-tetrahydroimidazo[1,5-d][1,4]oxazepine A mixture of the compound obtained in Example 32-(2) (200 mg, 0.498 mmol), 2,6-dimethylpyridine-4-boronic acid (120 mg, 0.797 mmol), tetrakis(triphenylphosphine)palladium(0) (43.2 mg, 0.0370 mmol), an aqueous sodium carbonate solution (2 M, 0.80 mL) and DME (1.7 mL) was stirred under microwave irradiation at 120° C. for 1 hour. The reaction mixture was cooled to room temperature and water and ethyl acetate were added to separate the organic layer. The resultant organic layer was washed with a saturated aqueous sodium chloride solution, dried over anhydrous magnesium sulfate, and concentrated under reduced pressure. The resultant residue was purified by NH silica gel column chromatography (n-heptane/ethyl acetate). The resultant was further purified by silica gel chromatography (ethyl acetate/methanol) to obtain a title compound (175 mg, 0.409 mmol).

$^{1}$H-NMR (400 MHz, CDCl3) δ (ppm): 1.23-1.32 (m, 3H), 2.55 (s, 6H), 3.10-3.25 (m, 1H), 3.29-3.40 (m, 1H), 3.55 (s, 3H), 3.60-3.71 (m, 1H), 3.73-3.85 (m, 1H), 3.91-4.04 (m, 1H), 4.17-4.28 (m, 2H), 5.31 (s, 2H), 7.20 (s, 2H), 7.27 (d, J=8.6 Hz, 1H), 7.33 (dd, J=2.0, 8.6 Hz, 1H), 7.59 (d, J=2.0 Hz, 1H).

(4) Synthesis of (R)-2-chloro-4-[1-(2,6-dimethylpyridin-4-yl)-6-methyl-5,6,8,9-tetrahydroimidazo[1,5-d][1,4]oxazepin-3-yl]phenol The compound obtained in Example 32-(3) (175 mg, 0.409 mmol) was dissolved in methanol (8 mL), a 5 N hydrochloric acid (0.818 mL, 4.09 mmol) was added at room temperature, and the mixture was stirred at 70° C. for 3 hours. The reaction mixture was cooled to room temperature, and then a saturated aqueous sodium bicarbonate solution was added, and then the methanol was evaporated under reduced pressure. Ethyl acetate and water were added to the residue and the resultant solid was collected by filtration. The resultant solid was dried under reduced pressure to obtain a crude title compound (360 mg).

$^{1}$H-NMR (400 MHz, CDCl3) δ (ppm): 1.23-1.29 (m, 3H), 2.55 (s, 6H), 3.10-3.24 (m, 1H), 3.29-3.40 (m, 1H), 3.59-3.85 (m, 2H), 3.90-4.04 (m, 1H), 4.16-4.27 (m, 2H), 7.10 (d, J=8.2 Hz, 1H), 7.20 (s, 2H), 7.27 (dd, J=2.0, 8.2 Hz, 1H), 7.56 (d, J=2.0 Hz, 1H).

(5) Synthesis of (R)-3-(3-chloro-4-(difluoromethoxy)phenyl)-1-(2,6-dimethylpyridin-4-yl)-6-methyl-5,6,8,9-tetrahydroimidazo[1,5-d][1,4]oxazepine A mixture of a crude product of the compound obtained in Example 32-(4) (69 mg), sodium chlorodifluoroacetate (29.8 mg, 0.195 mmol), cesium carbonate (33.1 mg, 0.102 mmol), and water (35.2 μL, 1.95 mmol) in DMF (0.30 mL) was stirred at 80° C. for 4 hours. The reaction mixture was cooled to room temperature and then water and ethyl acetate were added to separate the organic layer. The organic layer was dried over anhydrous magnesium sulfate and the solvent was concentrated under reduced pressure. The resultant residue was purified serially by NH silica gel column chromatography (n-heptane/ethyl acetate) and silica gel thin layer chromatography (ethyl acetate/methanol) to obtain a title compound (6.7 mg, 0.015 mmol).

$^{1}$H-NMR (400 MHz, CDCl3) δ (ppm): 1.22-1.35 (m, 3H), 2.56 (s, 6H), 3.11-3.28 (m, 1H), 3.29-3.43 (m, 1H), 3.60-3.72 (m, 1H), 3.73-3.88 (m, 1H), 3.93-4.08 (m, 1H), 4.14-4.29 (m, 2H), 6.60 (t, J=73.0 Hz, 1H), 7.19 (s, 2H), 7.35 (d, J=8.4 Hz, 1H), 7.40 (dd, J=2.0, 8.4 Hz, 1H), 7.68 (d, J=2.0 Hz, 1H).

ESI-MS m/z 434 [M+H]+

Example 33

Synthesis of (R)-3-(3-chloro-4-methoxyphenyl)-1-(2,6-dimethylpyridin-4-yl)-6-methyl-5,6,8,9-tetrahydroimidazo[1,5-d][1,4]oxazepine

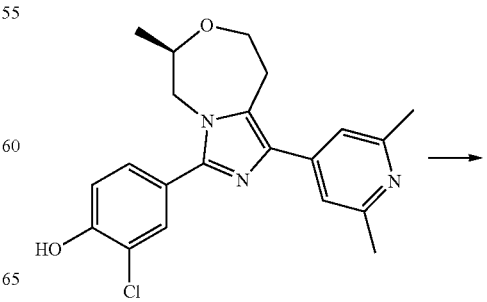

-continued

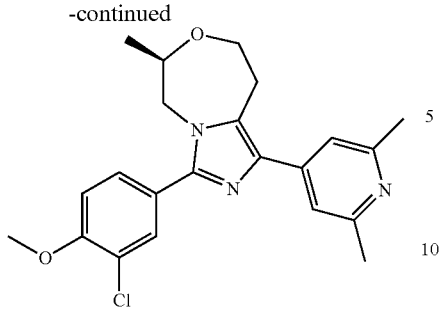

Cesium carbonate (34.0 mg, 0.104 mmol) was added to a mixture of the compound obtained in Example 32-(4) (46 mg), dimethyl sulfate (9.86 μL, 0.104 mmol) and DMF (0.3 mL), and the mixture was stirred at room temperature for 1 hour. The reaction mixture was diluted with DCM and the resultant solid was separated through filtration. The filtrate was concentrated under reduced pressure and the resultant residue was purified by NH silica gel column chromatography (n-heptane/ethyl acetate) to obtain a title compound (8.1 mg, 0.020 mmol).

$^1$H-NMR (400 MHz, CDCl3) δ (ppm): 1.23-1.35 (m, 3H), 2.55 (s, 6H), 3.10-3.24 (m, 1H), 3.28-3.42 (m, 1H), 3.59-3.71 (m, 1H), 3.72-3.85 (m, 1H), 3.89-4.05 (m, 1H), 3.97 (s, 3H), 4.16-4.29 (m, 2H), 7.02 (d, J=8.4 Hz, 1H), 7.20 (s, 2H), 7.38 (dd, J=2.1, 8.4 Hz, 1H), 7.56 (d, J=2.1 Hz, 1H).

ESI-MS m/z 398 [M+H]+

Example 34

Synthesis of (R)-3-(3-chloro-4-ethoxyphenyl)-1-(2,6-dimethylpyridin-4-yl)-6-methyl-5,6,8,9-tetrahydroimidazo[1,5-d][1,4]oxazepine

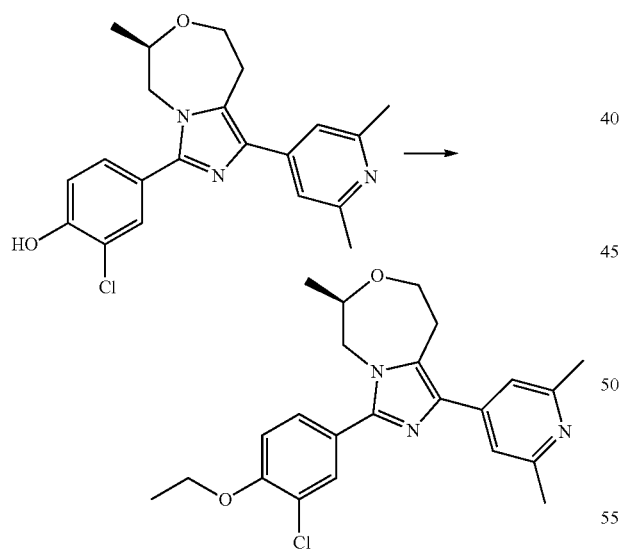

According to the method of Example 33, a title compound (10.6 mg, 0.026 mmol) was obtained from the compound obtained in Example 32-(4) (46 mg) and iodoethane (8.33 μL, 0.104 mmol).

$^1$H-NMR (400 MHz, CDCl3) δ (ppm): 1.22-1.33 (m, 3H), 1.51 (0=7.0 Hz, 3H), 2.55 (s, 6H), 3.10-3.25 (m, 1H), 3.29-3.42 (m, 1H), 3.59-3.72 (m, 1H), 3.72-3.84 (m, 1H), 3.91-4.04 (m, 1H), 4.17 (q, J=7.0 Hz, 2H), 4.17-4.28 (m, 2H), 7.00 (d, J=8.5 Hz, 1H), 7.20 (s, 2H), 7.35 (dd, J=2.1, 8.5 Hz, 1H), 7.55 (d, J=2.1 Hz, 1H).

ESI-MS m/z 412 [M+H]+

Example 35

Synthesis of (R)-3-(3-chloro-4-isopropoxyphenyl)-1-(2,6-dimethylpyridin-4-yl)-6-methyl-5,6,8,9-tetrahydroimidazo[1,5-d][1,4]oxazepine

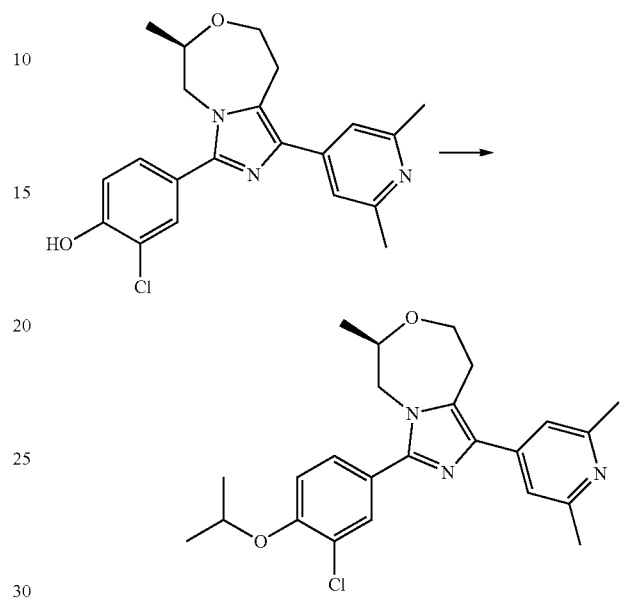

Cesium carbonate (50.9 mg, 0.156 mmol) was added to a mixture of the compound obtained in Example 32-(4) (46 mg), 2-bromopropane (9.78 μL, 0.104 mmol) and DMF (0.3 mL). The reaction mixture was stirred at 100° C. for 2 hours. The reaction mixture was cooled to room temperature and then diluted with DCM. The generated insolubles were separated through filtration and the filtrate was concentrated under reduced pressure. The resultant residue was purified by NH silica gel column chromatography (n-heptane/ethyl acetate) to obtain a title compound (12.0 mg, 0.028 mmol).

$^1$H-NMR (400 MHz, CDCl3) δ (ppm): 1.24-1.30 (m, 3H), 1.42 (d, J=6.1 Hz, 6H), 2.55 (s, 6H), 3.09-3.25 (m, 1H), 3.29-3.42 (m, 1H), 3.59-3.71 (m, 1H), 3.72-3.86 (m, 1H), 3.88-4.04 (m, 1H), 4.15-4.29 (m, 2H), 4.63 (sep, J=6.1 Hz, 1H), 7.03 (d, J=8.5 Hz, 1H), 7.21 (s, 2H), 7.35 (dd, J=2.1, 8.5 Hz, 1H), 7.53 (d, J=2.1 Hz, 1H).

ESI-MS m/z 426 [M+H]+

Example 36

Synthesis of (S)-3-(3-chloro-4-methoxyphenyl)-1-(2,6-dimethylpyridin-4-yl)-6-(fluoromethyl)-5,6,8,9-tetrahydroimidazo[1,5-d][1,4]oxazepine

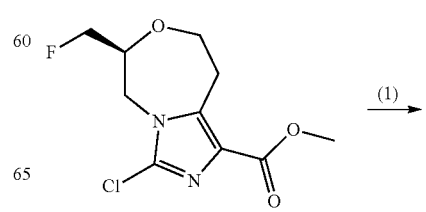

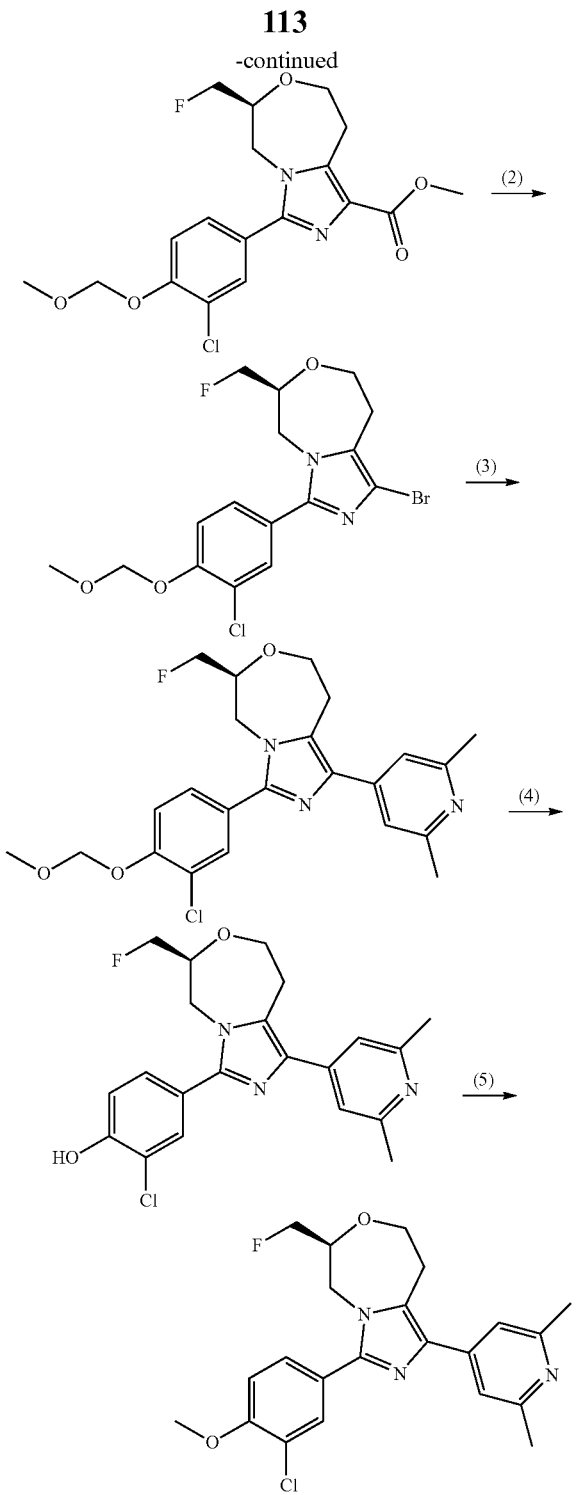

(1) Synthesis of (S)-methyl 3-(3-chloro-4-(methoxymethoxy)phenyl)-6-(fluoromethyl)-5,6,8,9-tetrahydroimidazo[1,5-d][1,4]oxazepine-1-carboxylate According to the method of Example 32-(1), a title compound (760 mg, 1.91 mmol) was obtained from the compound obtained in Production Example 9 (600 mg, 2.28 mmol) and the compound obtained in Production Example 13 (818 mg, 2.74 mmol).

$^1$H-NMR (400 MHz, CDCl3) δ (ppm): 3.00-3.17 (m, 1H), 3.54 (s, 3H), 3.62-3.72 (m, 1H), 3.73-3.86 (m, 1H), 3.91 (s, 3H), 3.99-4.10 (m, 1H), 4.12-4.21 (m, 1H), 4.23-4.66 (m, 4H), 5.30 (s, 2H), 7.25 (d, J=8.6 Hz, 1H), 7.31 (dd, J=2.1, 8.6 Hz, 1H), 7.60 (d, J=2.1 Hz, 1H).

(2) Synthesis of (S)-1-bromo-3-(3-chloro-4-(methoxymethoxy)phenyl)-6-(fluoromethyl)-5,6,8,9-tetrahydroimidazo[1,5-d][1,4]oxazepine According to the method of Example 32-(2), a title compound (530 mg, 1.26 mmol) was obtained from the compound obtained in Example 36-(1) (760 mg, 1.91 mmol).

$^1$H-NMR (400 MHz, CDCl3) δ (ppm): 2.85-3.18 (m, 2H), 3.54 (s, 3H), 3.59-3.70 (m, 1H), 3.73-3.87 (m, 1H), 3.95-4.09 (m, 1H), 4.19-4.63 (m, 4H), 5.30 (s, 2H), 7.25 (d, J=8.6 Hz, 1H), 7.29 (dd, J=2.1, 8.6 Hz, 1H), 7.56 (d, J=2.1 Hz, 1H).

(3) Synthesis of (S)-3-(3-chloro-4-(methoxymethoxy)phenyl)-1-(2,6-dimethylpyridin-4-yl)-6-(fluoromethyl)-5,6,8,9-tetrahydroimidazo[1,5-d][1,4]oxazepine According to the method of Example 32-(3), a title compound (154 mg, 0.345 mmol) was obtained from the compound obtained in Example 36-(2) (200 mg, 0.477 mmol) and 2,6-dimethylpyridine-4-boronic acid (115 mg, 0.762 mmol).

$^1$H-NMR (400 MHz, CDCl3) δ (ppm): 2.56 (s, 6H), 3.11-3.30 (m, 1H), 3.33-3.48 (m, 1H), 3.55 (s, 3H), 3.62-3.77 (m, 1H), 3.79-3.95 (m, 1H), 3.99-4.11 (m, 1H), 4.24-4.69 (m, 4H), 5.31 (s, 2H), 7.20 (s, 2H), 7.28 (d, J=8.6 Hz, 1H), 7.35 (dd, J=2.2, 8.6 Hz, 1H), 7.61 (d, J=2.2 Hz, 1H).

(4) Synthesis of (S)-2-chloro-4-(1-(2,6-dimethyl-pyridin-4-yl)-6-(fluoromethyl)-5,6,8,9-tetrahydroimidazo[1,5-d][1,4]oxazepin-3-yl)phenol According to the method of Example 32-(4), a crude title compound (330 mg) was obtained from the compound obtained in Example 36-(3) (154 mg, 0.345 mmol).

$^1$H-NMR (400 MHz, CDCl3) δ (ppm): 2.56 (s, 6H), 3.14-3.28 (m, 1H), 3.34-3.47 (m, 1H), 3.62-3.76 (m, 1H), 3.78-3.94 (m, 1H), 3.98-4.09 (m, 1H), 4.24-4.67 (m, 4H), 7.10 (d, J=8.4 Hz, 1H), 7.20 (s, 2H), 7.30 (dd, J=2.1, 8.4 Hz, 1H), 7.58 (d, J=2.1 Hz, 1H).

(5) Synthesis of (S)-3-(3-chloro-4-methoxyphenyl)-1-(2,6-dimethylpyridin-4-yl)-6-(fluoromethyl)-5,6,8,9-tetrahydroimidazo[1,5-d][1,4]oxazepine According to the method of Example 33, a title compound (5.1 mg, 0.012 mmol) was obtained from the compound obtained in Example 36-(4) (48 mg) and dimethyl sulfate (9.42 μL, 0.100 mmol).

$^1$H-NMR (400 MHz, CDCl3) δ (ppm): 2.56 (s, 6H), 3.14-3.29 (m, 1H), 3.33-3.44 (m, 1H), 3.62-3.76 (m, 1H), 3.79-3.92 (m, 1H), 3.97 (s, 3H), 4.00-4.10 (m, 1H), 4.25-4.67 (m, 4H), 7.03 (d, J=8.6 Hz, 1H), 7.20 (s, 2H), 7.39 (dd, J=2.1, 8.6 Hz, 1H), 7.60 (d, J=2.1 Hz, 1H).

ESI-MS m/z 416 [M+H]+

Example 37

Synthesis of (S)-3-(3-chloro-4-ethoxyphenyl)-1-(2,6-dimethylpyridin-4-yl)-6-(fluoromethyl)-5,6,8,9-tetrahydroimidazo[1,5-d][1,4]oxazepine

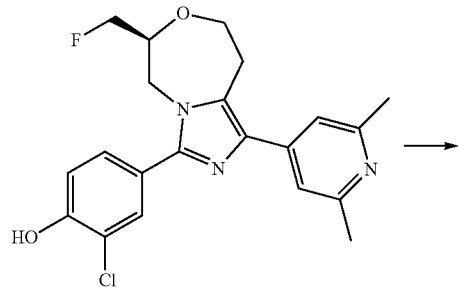

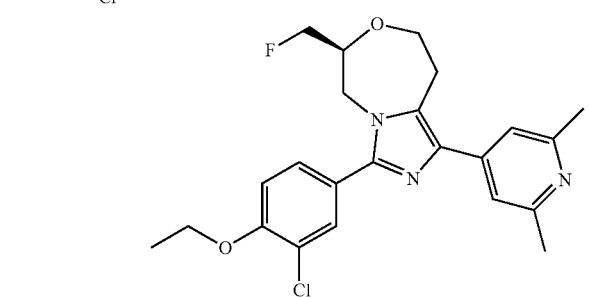

According to the method of Example 33, a title compound (8.8 mg, 0.020 mmol) was obtained from the compound obtained in Example 36-(4) (48 mg) and iodoethane (7.96 µL, 0.100 mmol).

$^1$H-NMR (400 MHz, CDCl3) δ (ppm): 1.51 (t, J=7.0 Hz, 3H), 2.56 (s, 6H), 3.11-3.29 (m, 1H), 3.33-3.46 (m, 1H), 3.60-3.77 (m, 1H), 3.79-3.94 (m, 1H), 3.98-4.10 (m, 1H), 4.17 (q, J=7.0 Hz, 2H), 4.24-4.66 (m, 4H), 7.01 (d, J=8.6 Hz, 1H), 7.20 (s, 2H), 7.36 (dd, J=2.1, 8.6 Hz, 1H), 7.59 (d, J=2.1 Hz, 1H).

ESI-MS m/z 430 [M+H]+

Example 38

Synthesis of 3-chloro-4-isopropoxyphenyl)-1-(2,6-dimethylpyridin-4-yl)-6-(fluoromethyl)-5,6,8,9-tetrahydroimidazo[1,5-d][1,4]oxazepine

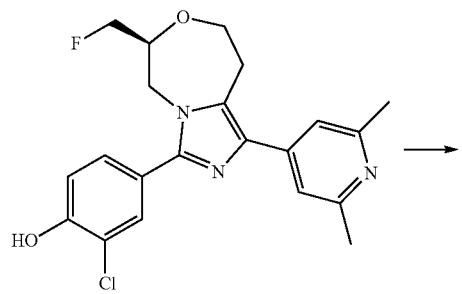

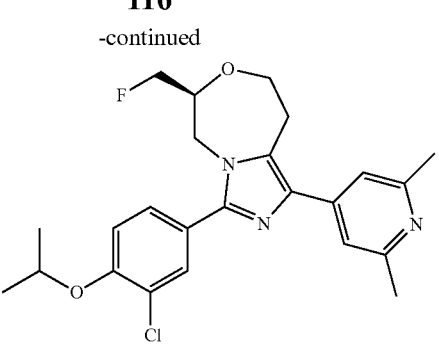

According to the method of Example 35, a title compound (14.0 mg, 0.032 mmol) was obtained from the compound obtained in Example 36-(4) (48 mg) and 2-bromopropane (9.35 µL, 0.100 mmol).

$^1$H-NMR (400 MHz, CDCl3) δ (ppm): 1.42 (d, J=6.1 Hz, 6H), 2.56 (s, 6H), 3.11-3.29 (m, 1H), 3.33-3.48 (m, 1H), 3.63-3.75 (m, 1H), 3.78-3.95 (m, 1H), 3.98-4.11 (m, 1H), 4.24-4.63 (m, 4H), 4.64 (sep, J=6.1 Hz, 1H), 7.03 (d, J=8.6 Hz, 1H), 7.20 (s, 2H), 7.36 (dd, J=2.2, 8.6 Hz, 1H), 7.57 (d, J=2.2 Hz, 1H).

ESI-MS m/z 444 [M+H]+

Example 39

Synthesis of (R)-3-(3-(fluoromethyl)-4-(trifluoromethoxy)phenyl)-6-methyl-1-(2-methylpyridin-4-yl)-5,6,8,9-tetrahydroimidazo[1,5-d][1,4]oxazepine

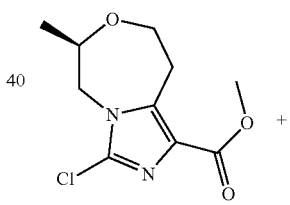

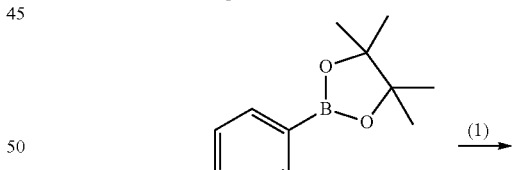

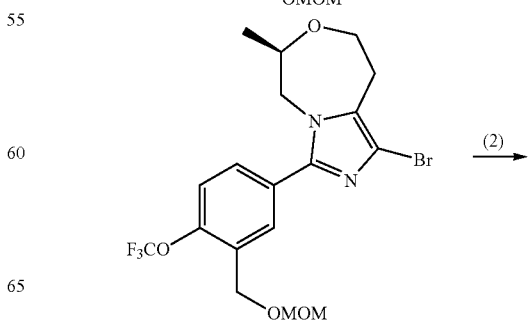

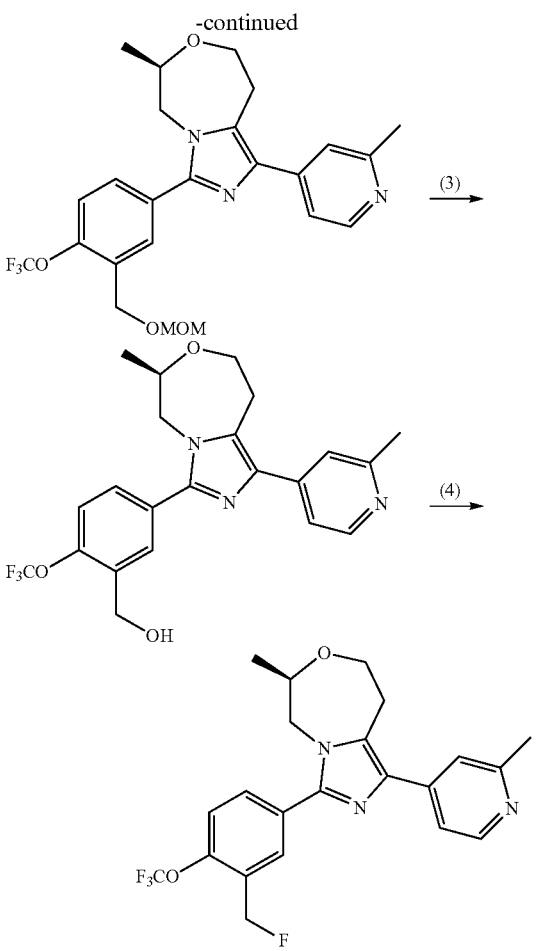

(1) Synthesis of (R)-1-bromo-3-(3-((methoxymethoxy)methyl)-4-(trifluoromethoxy)phenyl)-6-methyl-5,6,8,9-tetrahydroimidazo[1,5-d][1,4]oxazepine According to the methods of Examples 27-(1) and 18-(2), a title compound (101 mg, 0.217 mmol) was obtained from the compound obtained in Production Example 19 (370 mg, 1.02 mmol) and the compound obtained in Production Example 8-(3) (125 mg, 0.511 mmol).

¹H-NMR (400 MHz, CDCl3) δ (ppm): 1.23 (d, J=6.6 Hz, 3H), 2.97 (ddd, J=2.7, 10.5, 16.0 Hz, 1H), 3.07 (ddd, J=1.2, 3.9, 16.0 Hz, 1H), 3.40 (s, 3H), 3.61 (ddd, J=1.6, 10.5, 12.5 Hz, 1H), 3.67-3.79 (m, 1H), 3.94 (dd, J=8.4, 14.6 Hz, 1H), 4.14-4.27 (m, 2H), 4.63-4.73 (m, 2H), 4.74 (s, 2H), 7.28-7.37 (m, 1H), 7.43 (dd, J=2.3, 8.6 Hz, 1H), 7.67 (d, J=2.0 Hz, 1H).
ESI-MS m/z 465, 467 [M+H]+487, 489 [M+Na]+

(2) Synthesis of (R)-3-(3-((methoxymethoxy)methyl)-4-(trifluoromethoxy)phenyl)-6-methyl-1-(2-methylpyridin-4-yl)-5,6,8,9-tetrahydroimidazo[1,5-d][1,4]oxazepine According to the method of Example 1-(5), a title compound (46.8 mg, 0.098 mmol) was obtained from the compound obtained in Example 39-(1) (50.0 mg, 0.107 mmol) and 2-picoline-4-boronic acid (29.4 mg, 0.215 mmol).
ESI-MS m/z 478 [M+H]+

(3) Synthesis of (R)-(5-(6-methyl-1-(2-methylpyridin-4-yl)-5,6,8,9-tetrahydroimidazo[1,5-d][1,4]oxazepin-3-yl)-2-(trifluoromethoxy)phenyl)methanol A solution of the compound obtained in Example 39-(2) (46.8 mg, 0.098 mmol) and CSA (68.3 mg, 0.294 mmol) in methanol (1.0 mL) was stirred and heated under reflux for 4 hours. The reaction mixture was cooled to room temperature, TEA (0.1 mL) was added, and then the mixture was concentrated under reduced pressure. The resultant residue was filtered through a silica gel pad (NH silica gel) and then the eluate was concentrated under reduced pressure. The resultant residue was purified by NH silica gel thin layer chromatography (ethyl acetate) to obtain a title compound (25.2 mg, 0.058 mmol).

¹H-NMR (400 MHz, CDCl3) δ (ppm): 1.26 (d, J=6.6 Hz, 3H), 2.59 (s, 3H), 3.20 (ddd, J=2.3, 10.5, 16.4 Hz, 1H), 3.36 (dd, J=3.9, 15.6, 1H), 3.59-3.73 (m, 1H), 3.74-3.87 (m, 1H), 4.00 (dd, J=8.6, 14.8 Hz, 1H), 4.18-4.32 (m, 2H), 4.80 (s, 2H), 7.29-7.38 (m, 2H), 7.43-7.52 (m, 2H), 7.77 (d, J=2.3 Hz, 1H), 8.49 (d, J=4.7 Hz, 1H).
ESI-MS m/z 434 [M+H]+

(4) Synthesis of (R)-3-(3-(fluoromethyl)-4-(trifluoromethoxy)phenyl)-6-methyl-1-(2-methylpyridin-4-yl)-5,6,8,9-tetrahydroimidazo[1,5-d][1,4]oxazepine DAST (0.033 mL, 0.25 mmol) was added to a solution of the compound obtained in Example 39-(3) (21.3 mg, 0.049 mmol) and TEA (69 μL, 0.50 mmol) in DCM (1.0 mL) under ice-cooling. The reaction solution was warmed to room temperature, stirred for 20 hours, and then filtered through a silica gel pad (NH silica gel). The resultant solution was concentrated under reduced pressure and the residue was purified serially by silica gel thin layer chromatography (ethyl acetate) and NH silica gel thin layer chromatography (n-heptane/ethyl acetate) to obtain a title compound (3.0 mg, 0.0069 mmol).

¹H-NMR (400 MHz, CDCl3) δ (ppm): 1.28 (d, J=6.6 Hz, 3H), 2.59 (s, 3H), 3.21 (ddd, J=2.3, 10.5, 16.0 Hz, 1H), 3.37 (dd, J=4.3, 16.0 Hz, 1H), 3.68 (t, J=11.1 Hz, 1H), 3.76-3.87 (m, 1H), 4.03 (dd, J=8.6, 14.8 Hz, 1H), 4.19-4.28 (m, 2H), 5.55 (d, J=46.9 Hz, 2H), 7.29 (dd, J=1.4, 5.3 Hz, 1H), 7.37-7.43 (m, 1H), 7.45 (s, 1H), 7.58 (dd, J=1.8, 8.4 Hz, 1H), 7.71 (d, J=2.0 Hz, 1H), 8.50 (d, J=5.1 Hz, 1H).
ESI-MS m/z 436 [M+H]+

Example 40

Synthesis of (S)-3-(4-(difluoromethoxy)-3-methylphenyl)-6-(fluoromethyl)-1-(2-methylpyridin-4-yl)-5,6,8,9-tetrahydroimidazo[1,5-d][1,4]oxazepine

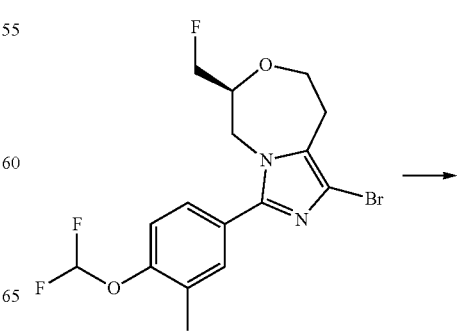

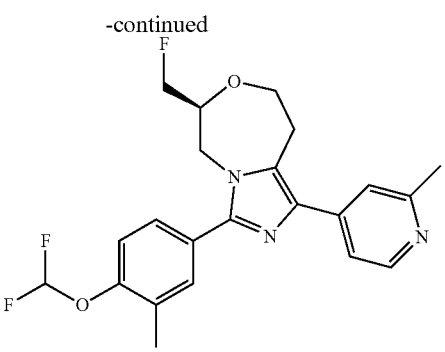

According to the method of Example 39-(2), a title compound (18 mg, 0.043 mmol) was obtained from the compound obtained in Example 27

(2) (28 mg, 0.069 mmol)

¹H-NMR (400 MHz, CDCl3) δ (ppm): 2.35 (s, 3H), 2.59 (s, 3H), 3.22 (ddd, J=2.3, 10.9, 16.0 Hz, 1H), 3.41 (dd, J=3.7, 16.2 Hz, 1H), 3.66-3.75 (m, 1H), 3.83-3.95 (m, 1H), 4.06 (dd, J=8.6, 14.8 Hz, 1H), 4.28-4.46 (m, 2H), 4.55 (ddd, J=4.7, 9.8, 46.1 Hz, 1H), 4.56 (d, J=14.8 Hz, 1H), 6.57 (t, J=73.4 Hz, 1H), 7.19 (d, J=8.2 Hz, 1H), 7.29 (dd, J=1.4, 4.9 Hz, 1H), 7.33 (dd, J=2.3, 8.6 Hz, 1H), 7.45-7.48 (m, 2H), 8.50 (d, J=5.1 Hz, 1H).
ESI-MS m/z 418 [M+H]+

Example 41

Synthesis of (S)-6-(fluoromethyl)-3-(3-methoxy-4-(trifluoromethyl)phenyl)-1-(2-methylpyridin-4-yl)-5,6,8,9-tetrahydroimidazo[1,5-d][1,4]oxazepine

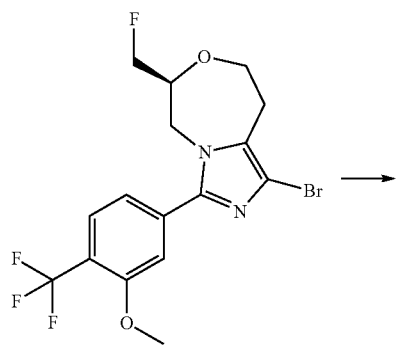

→

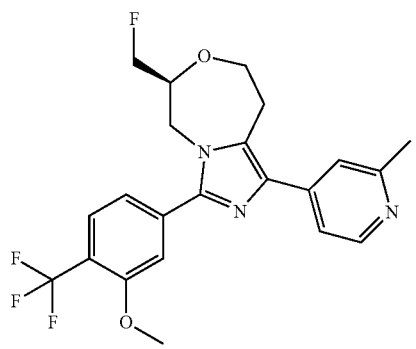

According to the method of Example 39-(2), a title compound (13 mg, 0.030 mmol) was obtained from the compound obtained in Example 29-(2) (26 mg, 0.061 mmol).

¹H-NMR (400 MHz, CDCl3) δ (ppm): 2.60 (s, 3H) 3.19-3.29 (m, 1H) 3.42 (dd, J=4.3, 16.4 Hz, 1H), 3.72 (t, J=11.9 Hz, 1H), 3.86-4.00 (m, 4H) 4.08 (dd, J=9.0, 14.8 Hz, 1H), 4.28-4.47 (m, 2H), 4.48-4.66 (m, 2H), 7.11 (d, J=8.2 Hz, 1H), 7.26 (d, J=4.7 Hz, 1H), 7.30 (d, J=5.1 Hz, 1H), 7.46 (s, 1H), 7.68 (d, J=8.2 Hz, 1H), 8.52 (d, J=5.1 Hz, 1H).
ESI-MS m/z 436 [M+H]+

Each compound illustrated in Tables 1 to 7 was synthesized according to the method(s) of any of Examples described above.

TABLE 1

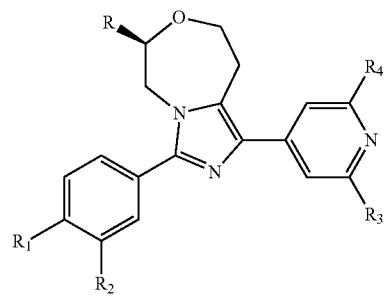

| Example No. | R | R₁ | R₂ | R₃ | R₄ | ESI-MS [M + H]⁺ |
|---|---|---|---|---|---|---|
| 42 | H | OCF₃ | H | CH₃ | CH₃ | 404 |
| 43 | H | OCF₃ | H | H | CH₃ | 390 |
| 44 | H | Cl | OCH₃ | CH₃ | CH₃ | 384 |
| 45 | H | F | OCF₃ | CH₃ | CH₃ | 422 |
| 46 | H | CH₃ | OCH₃ | CH₃ | CH₃ | 364 |
| 47 | CH₃ | Cl | OCH₃ | H | CH₂OH | 400 |
| 48 | H | Cl | OCF₃ | CH₃ | CH₃ | 438 |
| 49 | H | OBn | F | CH₃ | CH₃ | 444 |
| 50 | CH₃ | OCF₃ | H | H | CH₃ | 404 |
| 51 | CH₃ | OCF₃ | H | CH₃ | CH₃ | 418 |
| 52 | CH₃ | Cl | CH₃ | CH₃ | CH₃ | 382 |
| 53 | CH₃ | CH₃ | OCH₃ | CH₃ | CH₃ | 378 |
| 54 | CH₃ | Cl | CH₃ | H | CH₃ | 368 |
| 55 | CH₃ | CH₃ | OCH₃ | H | CH₃ | 364 |
| 56 | CH₃ | Cl | F | CH₃ | CH₃ | 386 |
| 57 | CH₃ | Cl | OCH₃ | CH₃ | OCH₃ | 414 |
| 58 | CH₃ | Cl | F | H | CH₃ | 372 |
| 59 | CH₃ | OCH₃ | F | CH₃ | CH₃ | 382 |
| 60 | CH₃ | OCH₃ | F | H | CH₃ | 368 |
| 61 | CH₃ | Cl | H | CH₃ | CH₃ | 368 |
| 62 | CH₃ | H | Cl | CH₃ | CH₃ | 368 |
| 63 | CH₃ | H | Cl | H | CH₃ | 354 |
| 64 | CH₃ | H | OCF₃ | CH₃ | CH₃ | 418 |
| 65 | CH₃ | Cl | Cl | CH₃ | CH₃ | 402 |
| 66 | CH₃ | Cl | Cl | H | CH₃ | 388 |
| 67 | CH₃ | OCF₃ | CH₃ | CH₃ | CH₃ | 432 |
| 68 | CH₃ | Cl | OCF₃ | CH₃ | CH₃ | 452 |
| 69 | CH₂F | OCF₃ | H | CH₃ | CH₃ | 436 |
| 70 | CH₂F | OCF₃ | H | H | CH₃ | 422 |

TABLE 2

| Example No. | R | R₁ | R₂ | R₃ | R₄ | ESI-MS [M + H]⁺ |
|---|---|---|---|---|---|---|
| 71 | CH₂F | CH₃ | OCH₃ | CH₃ | CH₃ | 396 |
| 72 | CH₂F | CH₃ | OCH₃ | H | CH₃ | 382 |
| 73 | CH₂F | Cl | CH₃ | CH₃ | CH₃ | 400 |
| 74 | CH₂F | Cl | CH₃ | H | CH₃ | 386 |
| 75 | CH₂F | Cl | Cl | H | CH₃ | 406 |

TABLE 2-continued

| Example No. | R | R₁ | R₂ | R₃ | R₄ | ESI-MS [M + H]⁺ |
|---|---|---|---|---|---|---|
| 76 | CH₂F | Cl | Cl | CH₃ | CH₃ | 420 |
| 77 | CH₂CH₃ | Cl | OCH₃ | CH₃ | CH₃ | 412 |
| 78 | CH₂CH₃ | Cl | OCH₃ | H | CH₃ | 398 |
| 79 | CHF₂ | Cl | OCH₃ | CH₃ | CH₃ | 434 |
| 80 | CH₃ | CH₃ | OCH₃ | CH₃ | CHF₂ | 414 |
| 81 | CH₂F | CH₃ | OCH₃ | CH₃ | CHF₂ | 432 |
| 82 | CH₃ | CF₃ | OCH₂CH₃ | CH₃ | CH₃ | 446 |
| 83 | CH₃ | CF₃ | OCH₂CH₃ | H | CH₃ | 432 |
| 84 | H | Cl | OCH₃ | CH₃ | CH₂F | 402 |
| 85 | CH₃ | OCF₃ | H | H | CH₂F | 422 |
| 86 | CH₃ | OCF₃ | H | CH₃ | CH₂F | 436 |
| 87 | CH₃ | Cl | F | CH₃ | CH₂F | 404 |
| 88 | CH₃ | Cl | CH₃ | CH₃ | CH₂F | 400 |
| 89 | CH₃ | Cl | Cl | CH₃ | CH₂F | 420 |
| 90 | CH₃ | CH₃ | OCH₃ | CH₃ | CH₂F | 396 |
| 91 | CH₂F | Cl | OCH₃ | CH₃ | CH₂F | 434 |
| 92 | H | F | OCH₂CHF₂ | CH₃ | CH₃ | 418 |
| 93 | H | F | OCH₂CF₃ | CH₃ | CH₃ | 436 |
| 94 | H | F | O-CH₂-cyclopropyl | CH₃ | CH₃ | 408 |
| 95 | H | F | OCH₂CH(CH₃)₂ | CH₃ | CH₃ | 410 |
| 96 | H | F | OCH₂CH₂CH₃ | CH₃ | CH₃ | 396 |
| 97 | H | F | O-CH₂-cyclobutyl | CH₃ | CH₃ | 422 |
| 98 | CH₃ | F | O-CH₂-cyclobutyl | CH₃ | CH₃ | 436 |
| 99 | CH₃ | F | O-CH₂-(3-methyl-oxetan-3-yl) | CH₃ | CH₃ | 452 |
| 100 | CH₃ | F | O-CH₂-cyclobutyl | H | CH₃ | 422 |
| 101 | CH₃ | CH₂CH₃ | OCH₃ | H | CH₃ | 378 |
| 102 | H | Cl | OCH₂CH₃ | CH₃ | CH₃ | 398 |

TABLE 3

| Example No. | R | R₁ | R₂ | R₃ | R₄ | ESI-MS [M + H]⁺ |
|---|---|---|---|---|---|---|
| 103 | H | Cl | Cl | CH₃ | CH₃ | 388 |
| 104 | H | OCF₃ | CH₃ | CH₃ | CH₃ | 418 |
| 105 | H | Cl | F | CH₃ | CH₃ | 372 |
| 106 | H | OCF₃ | F | CH₃ | CH₃ | 422 |
| 107 | H | CF₃ | F | CH₃ | CH₃ | 406 |
| 108 | H | Cl | CF₃ | CH₃ | CH₃ | 422 |
| 109 | H | CF₃ | Cl | CH₃ | CH₃ | 422 |
| 110 | H | Cl | CH₃ | CH₃ | CH₃ | 368 |
| 111 | H | Cl | CN | CH₃ | CH₃ | 379 |
| 112 | H | OCF₃ | Cl | CH₃ | CH₃ | 438 |
| 113 | H | CF₃ | CH₃ | CH₃ | CH₃ | 402 |
| 114 | CH₃ | Cl | OCH₃ | CH₃ | CH₃ | 384 |
| 115 | H | OCF₃ | CH₃ | H | F | 408 |
| 116 | H | OCF₃ | CN | CH₃ | CH₃ | 429 |
| 117 | H | OCF₃ | OCH₃ | CH₃ | CH₃ | 434 |
| 118 | H | OCF₃ | CH₃ | CH₃ | CH₃ | 404 |
| 119 | H | OCHF₂ | F | CH₃ | CH₃ | 404 |
| 120 | H | OCHF₂ | F | H | CH₃ | 390 |
| 121 | H | CHF₂ | OCH₃ | CH₃ | CH₃ | 400 |
| 122 | H | CF₃ | OCH₃ | CH₃ | CH₃ | 418 |
| 123 | H | CF₃ | OCH₃ | H | CH₃ | 404 |

TABLE 3-continued

| Example No. | R | R₁ | R₂ | R₃ | R₄ | ESI-MS [M + H]⁺ |
|---|---|---|---|---|---|---|
| 124 | CH₃ | CF₃ | CH₃ | CH₃ | CH₃ | 416 |
| 125 | H | Cl | CHF₂ | CH₃ | CH₃ | 404 |
| 126 | H | Cl | CHF₂ | H | CH₃ | 390 |
| 127 | H | OCHF₂ | OCH₃ | CH₃ | CH₃ | 416 |
| 128 | CH₃ | CHF₂ | OCH₃ | CH₃ | CH₃ | 414 |
| 129 | CH₃ | CF₃ | Cl | CH₃ | CH₃ | 436 |
| 130 | CH₃ | Cl | CN | CH₃ | CH₃ | 393 |
| 131 | CH₃ | Cl | CHF₂ | CH₃ | CH₃ | 418 |
| 132 | CH₃ | CF₃ | Cl | H | CH₃ | 422 |
| 133 | CH₃ | OCF₃ | Cl | CH₃ | CH₃ | 452 |
| 134 | CH₃ | CF₃ | F | CH₃ | CH₃ | 420 |
| 135 | H | cyclopropyl-O | Cl | CH₃ | CH₃ | 410 |
| 136 | CH₃ | F | OCH₃ | CH₃ | CH₃ | 382 |
| 137 | H | CHF₂ | Cl | CH₃ | CH₃ | 404 |
| 138 | CH₃ | F | Cl | CH₃ | CH₃ | 386 |
| 139 | CH₃ | CF₃ | F | H | CH₃ | 406 |

TABLE 4

| Example No. | R | R₁ | R₂ | R₃ | R₄ | ESI-MS [M + H]⁺ |
|---|---|---|---|---|---|---|
| 140 | CH₃ | Cl | CF₃ | CH₃ | CH₃ | 436 |
| 141 | CH₃ | F | OCH₃ | H | CH₃ | 368 |
| 142 | CH₃ | CF₃ | H | CH₃ | CH₃ | 402 |
| 143 | CH₃ | F | CF₃ | CH₃ | CH₃ | 420 |
| 144 | H | cyclopropyl-O | OCF₃ | CH₃ | CH₃ | 460 |
| 145 | CH₃ | F | Cl | H | CH₃ | 372 |
| 146 | CH₃ | CHF₂ | Cl | CH₃ | CH₃ | 418 |
| 147 | CH₃ | OCF₃ | F | CH₃ | CH₃ | 436 |
| 148 | CH₃ | OCHF₂ | OCH₃ | CH₃ | CH₃ | 430 |
| 149 | CH₃ | OCHF₂ | OCH₃ | H | CH₃ | 416 |
| 150 | CH₃ | OCF₃ | F | H | CH₃ | 422 |
| 151 | CH₃ | F | CF₃ | H | CH₃ | 406 |
| 152 | CH₃ | Cl | CF₃ | H | CH₃ | 422 |
| 153 | CH₃ | OCF₃ | Cl | H | CH₃ | 438 |
| 154 | CH₃ | OCH₃ | OCF₃ | CH₃ | CH₃ | 448 |
| 155 | CH₃ | OCH₃ | OCF₃ | H | CH₃ | 434 |
| 156 | CH₂F | CF₃ | OCH₃ | CH₃ | CH₂OH | 466 |
| 157 | CH₃ | F | OCF₃ | CH₃ | CH₃ | 436 |
| 158 | CH₃ | F | OCF₃ | H | CH₃ | 422 |
| 159 | CH₃ | cyclopropyl-O | Cl | H | CH₃ | 410 |
| 160 | CH₂F | CHF₂ | OCH₃ | H | CH₃ | 418 |
| 161 | CH₂F | OCF₃ | CH₃ | CH₃ | CH₃ | 450 |
| 162 | CH₂F | OCF₃ | CH₃ | H | CH₃ | 436 |
| 163 | CH₂F | OCHF₂ | OCH₃ | CH₃ | CH₃ | 448 |
| 164 | CH₂F | OCHF₂ | OCH₃ | H | CH₃ | 434 |
| 165 | CH₂F | OCF₃ | F | CH₃ | CH₃ | 454 |
| 166 | CH₂F | OCF₃ | F | H | CH₃ | 440 |
| 167 | CH₂F | cyclopropyl-O | Cl | CH₃ | CH₃ | 442 |
| 168 | CH₃ | OCF₃ | CN | CH₃ | CH₃ | 443 |
| 169 | CH₃ | OCF₃ | CN | H | CH₃ | 429 |
| 170 | CH₂F | OCF₃ | F | CH₃ | CH₂OH | 470 |
| 171 | CH₂F | F | Cl | CH₃ | CH₃ | 404 |
| 172 | CH₂F | F | Cl | H | CH₃ | 390 |
| 173 | CH₂F | F | CF₃ | CH₃ | CH₃ | 438 |

TABLE 5

| Example No. | R | R₁ | R₂ | R₃ | R₄ | ESI-MS [M + H]⁺ |
|---|---|---|---|---|---|---|
| 174 | CH₂F | F | CF₃ | H | CH₃ | 424 |
| 175 | CH₂F | OCH₃ | OCF₃ | CH₃ | CH₃ | 466 |
| 176 | CH₂F | Cl | OCH₃ | CH₃ | CHF₂ | 452 |
| 177 | CH₃ | OCHF₂ | CH₃ | CH₃ | CH₂OH | 430 |
| 178 | CH₃ | OCH₃ | CH₃ | CH₃ | CHF₂ | 414 |
| 179 | CH₃ | OCF₃ | CH₃ | CH₃ | CH₂OH | 448 |
| 180 | CH₃ | OCF₃ | F | CH₃ | CH₂OH | 452 |
| 181 | CH₃ | OCHF₂ | F | CH₃ | CH₃ | 418 |
| 182 | CH₃ | OCHF₂ | F | H | CH₃ | 404 |
| 183 | CH₃ | CH₃ | CF₃ | CH₃ | CH₃ | 416 |
| 184 | CH₃ | F | OCHF₂ | CH₃ | CH₃ | 418 |
| 185 | CH₃ | F | OCHF₂ | H | CH₃ | 404 |
| 186 | CH₂F | CF₃ | CH₃ | CH₃ | CH₃ | 434 |
| 187 | CH₂F | CF₃ | CH₃ | H | CH₃ | 420 |
| 188 | CH₂F | OCHF₂ | CH₃ | CH₃ | CHF₂ | 468 |
| 189 | CH₃ | CHF₂ | OCH₃ | CH₃ | CHF₂ | 450 |
| 190 | CH₃ | OCH₃ | Cl | CH₃ | CHF₂ | 434 |
| 191 | CH₂F | OCH₂F | CH₃ | CH₃ | CH₂OH | 448 |
| 192 | CH₃ | OCHF₂ | OCH₃ | CH₃ | CHF₂ | 466 |
| 193 | CH₂F | OCHF₂ | OCH₃ | CH₃ | CHF₂ | 484 |
| 194 | CH₂F | OCHF₂ | OCH₃ | CH₃ | CH₂OH | 464 |
| 195 | CH₂F | OCF₃ | CN | CH₃ | CH₃ | 461 |
| 196 | CH₂F | OCF₃ | CN | H | CH₃ | 447 |
| 197 | CH₂F | CHF₂ | Cl | CH₃ | CH₃ | 436 |
| 198 | H | OCF₃ | CH₃ | CH₃ | CH₂F | 436 |
| 199 | CH₃ | OCHF₂ | CH₃ | CH₃ | CH₂F | 432 |
| 200 | CH₃ | CF₃ | OCH₃ | CH₃ | CH₂F | 450 |
| 201 | CH₂F | CF₃ | OCH₃ | CH₃ | CH₂F | 468 |
| 202 | CH₂F | OCF₃ | F | CH₃ | CH₂F | 472 |
| 203 | CH₃ | OCF₃ | CN | CH₃ | CH₂F | 461 |
| 204 | CH₃ | OCF₃ | CH₃ | CH₃ | CH₂F | 450 |
| 205 | CH₃ | [cyclopropylmethoxy] | Cl | CH₃ | CH₂F | 442 |
| 206 | CH₃ | OCF₃ | F | CH₃ | CH₂F | 454 |
| 207 | CH₂F | OCHF₂ | CH₃ | CH₃ | CH₂F | 450 |

TABLE 6

| Example No. | R | R₁ | R₂ | R₃ | R₄ | ESI-MS [M + H]⁺ |
|---|---|---|---|---|---|---|
| 208 | CH₃ | [cyclopropylmethoxy] | CH₃ | CH₃ | CH₂F | 422 |
| 209 | CH₂F | OCHF₂ | OCH₃ | CH₃ | CH₂F | 466 |
| 210 | CH₃ | OCH₃ | OCF₃ | CH₃ | CH₂F | 466 |
| 211 | H | OCF₃ | CH₂F | CH₃ | CH₃ | 436 |
| 212 | H | Cl | OCHF₂ | CH₃ | CH₃ | 420 |
| 213 | H | CH₂CH₃ | OCH₂CH₃ | CH₃ | CH₃ | 392 |
| 214 | H | CH₂CH₃ | OCH₂CH₃ | H | CH₃ | 378 |
| 215 | H | OCHF₂ | Cl | CH₃ | CH₃ | 420 |
| 216 | H | OCH₂CH₃ | Cl | CH₃ | CH₃ | 398 |
| 217 | H | [cyclopropylmethoxy] | Cl | CH₃ | CH₃ | 424 |
| 218 | H | OCH₂CHF₂ | Cl | CH₃ | CH₃ | 434 |
| 219 | CH₃ | CH₂CH₃ | OCH₂CH₃ | H | CH₃ | 392 |
| 220 | CH₃ | CH₂CH₃ | OCH₂CH₃ | CH₃ | CH₃ | 406 |
| 221 | CH₃ | CH₂CH₃ | [cyclopropylmethoxy] | H | CH₃ | 418 |
| 222 | CH₃ | CH₂CH₃ | [cyclopropylmethoxy] | CH₃ | CH₃ | 432 |
| 223 | CH₃ | CH₃ | OCH₂CH₃ | H | CH₃ | 378 |
| 224 | CH₃ | CH₃ | [cyclopropylmethoxy] | H | CH₃ | 404 |
| 225 | CH₃ | CH₃ | OCH₂CH₃ | CH₃ | CH₃ | 392 |
| 226 | CH₃ | CH₃ | [cyclopropylmethoxy] | CH₃ | CH₃ | 418 |
| 227 | CH₃ | CH₃ | OCH₂CH(CH₃)₂ | CH₃ | CH₃ | 420 |
| 228 | CH₃ | CH₃ | [(tetrahydropyran-4-yl)methoxy] | CH₃ | CH₃ | 462 |
| 229 | CH₃ | OCF₃ | CH₂OH | CH₃ | CH₃ | 448 |
| 230 | CH₃ | OCF₃ | CH₂OH | H | CH₃ | 434 |
| 231 | CH₃ | OCF₃ | CH₂F | CH₃ | CH₃ | 450 |
| 232 | CH₃ | [oxetan-3-yloxy] | Cl | CH₃ | CH₃ | 440 |
| 233 | CH₂F | OCHF₂ | Cl | CH₃ | CH₃ | 452 |
| 234 | CH₃ | OCHF₂ | CH₂F | CH₃ | CH₃ | 432 |
| 235 | CH₃ | OCHF₂ | CH₂OH | CH₃ | CH₃ | 430 |

TABLE 7

| Example No. | R | R₁ | R₂ | R₃ | R₄ | ESI-MS [M + H]⁺ |
|---|---|---|---|---|---|---|
| 236 | CH₃ | OCHF₂ | CH₂F | H | CH₃ | 418 |
| 237 | CH₃ | OCHF₂ | CH₂OH | H | CH₃ | 416 |
| 238 | CH₃ | Cl | CH₂F | CH₃ | CH₃ | 400 |
| 239 | CH₃ | OCH₂CH₂F | Cl | CH₃ | CH₃ | 430 |
| 240 | CH₃ | CF₂CH₃ | OCH₃ | H | CH₃ | 414 |
| 241 | CH₃ | OCH₂CH₃ | CH₃ | CH₃ | CH₃ | 392 |
| 242 | CH₃ | OCH(CH₃)₂ | CH₃ | CH₃ | CH₃ | 406 |
| 243 | CH₂F | OCH₂CH₃ | CH₃ | CH₃ | CH₃ | 410 |
| 244 | CH₂F | OCH(CH₃)₂ | CH₃ | CH₃ | CH₃ | 424 |
| 245 | CH₂F | OCH₃ | CH₃ | CH₃ | CH₃ | 396 |

Test Example 1

Affinity to mGluR2

(Preparation of Cell Membrane Fraction of HEK293 Cells Stably Expressing Human Metabotropic Glutamate Receptor 2 (mGluR2))

HEK293 cells stably expressing human mGluR2 and human glutamate transporter SLC1A3 were cultured in a Dulbecco's modified Eagle's medium with 10% fetal bovine serum (50 units/mL of penicillin, 50 μg/mL of streptomycin, 60 μg/mL of geneticin, 400 μg/mL of hygromycin B and 2 mM of glutamine) at 37° C. under 5% CO₂. Confluent cell cultures were washed twice with PBS(−), and then scraped off with a cell scraper, and subjected to centrifugal separation at 4° C. and 1500 rpm for 5 minutes for collecting cells.

The centrifuged sediment (cell pellet) was homogenized in a 20 mM HEPES buffer containing 10 mM EDTA (pH 7.4) by using sonicator and centrifuged at 4° C. and 1500×g for 30 minutes. The supernatant (soluble fraction) was subjected to the centrifugal separation at 4° C. and 40,000×g for 30 minutes, and thus, insoluble fraction was obtained. After additional centrifugally washing the obtained fraction with 20 mM HEPES buffer containing 10 mM EDTA (pH 7.4), the pellet was centrifugally suspended with a 20 mM HEPES buffer containing 0.1 mM EDTA, and the cell membrane fraction was obtained by the centrifugal separation at 4° C. and 40,000×g for 30 minutes. The thus obtained cell membrane fraction was suspended in a 20 mM HEPES buffer containing 0.1 mM EDTA in a protein concentration of 3 mg/mL, which was stored at −80° C.

([$^{35}$S]GTPγS Binding Assay)

The frozen cell membrane fraction prepared as described above was thawed before use, and the resultant was diluted with a buffer for a binding assay (final concentrations: 20 mM HEPES, 100 mM NaCl, 1 mM MgCl$_2$, 3 μM GDP, 300 μg/mL saponin, 0.1% BSA). The compound of each example was added to a cell membrane fraction containing 1.8 to 3 μg/assay of membrane protein on a plate, followed by incubation at room temperature for 30 minutes. Thereafter, with glutamic acid (in a final concentration of 10 μM) added thereto, incubation was performed at room temperature for 15 minutes, and thereafter, [$^{35}$S]GTPγS (in a final concentration of 0.8 kBq) and 588 μg WGA-SPA beads were added thereto, followed by incubation at room temperature for 1 hour. After the incubation, the plate was subjected to the centrifugal separation at 2,500 rpm and room temperature, and then, membrane cell binding radioactivity was measured with a top count.

A [$^{35}$S]GTPγS binding amount obtained by performing the above-described reaction in the absence of glutamic acid was defined as nonspecific binding, and a difference from a [$^{35}$S]GTPγS binding amount obtained in the presence of glutamic acid was defined as specific binding. On the basis of ratios of inhibiting the specific binding at various concentrations of the compounds of the respective examples, inhibition curves were obtained. Concentrations of the compounds of the respective examples at which the specific [$^{35}$S]GTPγS binding amount was suppressed by 50% (IC50 values) were calculated on the basis of the inhibition curves and shown in Tables 8 and 9.

TABLE 8

| Example No. | GTPγS binding assay IC$_{50}$ (nM) |
|---|---|
| 1 | 10.0 |
| 2 | 97.4 |
| 3 | 13.9 |
| 4 | 31.9 |
| 5 | 26.5 |
| 6 | 13.0 |
| 7 | 4.2 |
| 8 | 13.2 |
| 9 | 1.9 |
| 10 | 4.2 |
| 11 | 11.4 |
| 12 | 28.3 |
| 13 | 5.7 |
| 14 | 5.6 |
| 15 | 7.4 |
| 16 | 2.7 |

TABLE 8-continued

| Example No. | GTPγS binding assay IC$_{50}$ (nM) |
|---|---|
| 17 | 3.8 |
| 18 | 12.3 |
| 19 | 3.0 |
| 20 | 3.4 |
| 21 | 7.5 |
| 22 | 4.1 |
| 23 | 19.4 |
| 24 | 4.8 |
| 25 | 3.2 |
| 26 | 13.5 |
| 27 | 3.5 |
| 28 | 16.2 |
| 29 | 3.8 |
| 30 | 5.2 |
| 31 | 7.9 |
| 32 | 2.8 |
| 33 | 5.0 |
| 34 | 2.8 |
| 35 | 2.7 |
| 36 | 10.0 |
| 37 | 6.0 |
| 38 | 5.4 |
| 39 | 2.5 |
| 40 | 4.7 |
| 41 | 4.1 |
| 42 | 45.3 |
| 43 | 90.0 |
| 44 | 22.3 |
| 45 | 73.9 |
| 46 | 65.6 |
| 47 | 242.5 |
| 48 | 40.0 |
| 49 | 11.4 |
| 50 | 14.2 |
| 51 | 7.8 |
| 52 | 20.5 |
| 53 | 21.3 |
| 54 | 19.4 |
| 55 | 21.9 |
| 56 | 21.9 |
| 57 | 28.5 |
| 58 | 41.8 |
| 59 | 96.3 |
| 60 | 119.3 |
| 61 | 21.7 |
| 62 | 37.7 |
| 63 | 78.6 |
| 64 | 31.2 |
| 65 | 14.0 |
| 66 | 12.6 |
| 67 | 4.7 |
| 68 | 13.2 |
| 69 | 20.9 |
| 70 | 25.5 |
| 71 | 18.9 |
| 72 | 29.4 |
| 73 | 24.8 |
| 74 | 35.3 |
| 75 | 31.0 |
| 76 | 20.9 |
| 77 | 11.5 |
| 78 | 3.8 |
| 79 | 30.4 |
| 80 | 6.3 |
| 81 | 7.1 |
| 82 | 1.1 |
| 83 | 1.7 |
| 84 | 25.3 |
| 85 | 29.7 |
| 86 | 4.4 |
| 87 | 22.0 |
| 88 | 16.7 |
| 89 | 13.2 |
| 90 | 12.7 |

TABLE 8-continued

| Example No. | GTPγS binding assay IC$_{50}$ (nM) |
|---|---|
| 91 | 16.1 |
| 92 | 95.8 |
| 93 | 28.7 |
| 94 | 34.9 |
| 95 | 49.5 |
| 96 | 59.8 |
| 97 | 25.4 |
| 98 | 3.1 |
| 99 | 103.4 |
| 100 | 25.3 |
| 101 | 7.6 |
| 102 | 22.7 |
| 103 | 26.0 |
| 104 | 19.4 |
| 105 | 92.1 |
| 106 | 20.9 |
| 107 | 54.0 |
| 108 | 19.2 |
| 109 | 9.1 |
| 110 | 64.2 |
| 111 | 25.2 |
| 112 | 17.9 |
| 113 | 27.0 |
| 114 | 19.2 |
| 115 | 61.7 |
| 116 | 33.8 |
| 117 | 22.0 |
| 118 | 10.9 |
| 119 | 31.8 |
| 120 | 47.2 |
| 121 | 40.9 |
| 122 | 22.1 |
| 123 | 36.0 |
| 124 | 4.5 |
| 125 | 16.5 |
| 126 | 8.4 |
| 127 | 12.1 |
| 128 | 9.1 |
| 129 | 15.7 |
| 130 | 26.0 |
| 131 | 25.5 |
| 132 | 33.3 |
| 133 | 4.4 |
| 134 | 27.8 |
| 135 | 36.9 |
| 136 | 33.9 |
| 137 | 18.7 |
| 138 | 21.2 |
| 139 | 47.5 |
| 140 | 5.7 |

TABLE 9

| Example No. | GTPγS binding assay IC$_{50}$ (nM) |
|---|---|
| 141 | 51.9 |
| 142 | 20.2 |
| 143 | 13.6 |
| 144 | 27.7 |
| 145 | 45.5 |
| 146 | 22.2 |
| 147 | 10.5 |
| 148 | 9.6 |
| 149 | 18.9 |
| 150 | 18.1 |
| 151 | 26.4 |
| 152 | 14.5 |

TABLE 9-continued

| Example No. | GTPγS binding assay IC$_{50}$ (nM) |
|---|---|
| 153 | 3.0 |
| 154 | 6.7 |
| 155 | 19.2 |
| 156 | 7.3 |
| 157 | 12.7 |
| 158 | 44.6 |
| 159 | 5.0 |
| 160 | 24.1 |
| 161 | 4.0 |
| 162 | 5.0 |
| 163 | 15.8 |
| 164 | 36.8 |
| 165 | 9.4 |
| 166 | 15.2 |
| 167 | 1.8 |
| 168 | 4.2 |
| 169 | 4.6 |
| 170 | 43.1 |
| 171 | 26.7 |
| 172 | 38.3 |
| 173 | 19.2 |
| 174 | 24.3 |
| 175 | 18.5 |
| 176 | 38.8 |
| 177 | 29.4 |
| 178 | 17.8 |
| 179 | 17.9 |
| 180 | 100.5 |
| 181 | 16.1 |
| 182 | 19.3 |
| 183 | 7.4 |
| 184 | 13.7 |
| 185 | 19.5 |
| 186 | 19.3 |
| 187 | 19.3 |
| 188 | 20.8 |
| 189 | 15.1 |
| 190 | 42.2 |
| 191 | 30.3 |
| 192 | 5.0 |
| 193 | 9.0 |
| 194 | 108.5 |
| 195 | 3.7 |
| 196 | 3.8 |
| 197 | 15.1 |
| 198 | 13.2 |
| 199 | 5.2 |
| 200 | 4.4 |
| 201 | 2.4 |
| 202 | 14.0 |
| 203 | 4.9 |
| 204 | 4.0 |
| 205 | 5.3 |
| 206 | 18.7 |
| 207 | 6.0 |
| 208 | 4.7 |
| 209 | 5.1 |
| 210 | 4.7 |
| 211 | 27.1 |
| 212 | 72.5 |
| 213 | 10.7 |
| 214 | 21.0 |
| 215 | 58.1 |
| 216 | 48.0 |
| 217 | 60.6 |
| 218 | 78.8 |
| 219 | 7.9 |
| 220 | 5.9 |
| 221 | 26.7 |
| 222 | 17.2 |
| 223 | 16.7 |
| 224 | 50.4 |
| 225 | 3.9 |
| 226 | 10.5 |

TABLE 9-continued

| Example No. | GTPγS binding assay IC$_{50}$ (nM) |
|---|---|
| 227 | 22.0 |
| 228 | 82.0 |
| 229 | 18.0 |
| 230 | 19.8 |
| 231 | 2.4 |
| 232 | 9.7 |
| 233 | 2.0 |
| 234 | 1.9 |
| 235 | 21.7 |
| 236 | 2.9 |
| 237 | 30.3 |
| 238 | 36.8 |
| 239 | 11.9 |
| 240 | 46.9 |
| 241 | 2.9 |
| 242 | 2.4 |
| 243 | 1.7 |
| 244 | 1.8 |
| 245 | 5.2 |

Test Example 2

Novel Object Recognition (NOR) Test in Rats

Six-week old male Long-Evans rats were used for this test. For 2 days before starting the test, the rats were acclimated to experimental operations such as administration and a test device (that is, a black or gray plastic cage with a width of 40 cm, a depth of 30 cm and a height of 45 cm). Each test compound was dissolved in a 0.1 N hydrochloric acid to be orally administered. Thirty minutes after the administration, scopolamine hydrobromide was intraperitoneally administered at a 0.3 mg/kg dose, so as to induce cognitive impairment. After another 30 minutes, each rat was acclimated in the test device for 3 minutes, and thereafter, two blocks in the same shape were put in the test device as acquisition trial, and exploring time for each block was measured for 5 minutes. Two hours after the acquisition trial, the rat was acclimated in the test device for 3 minutes, and thereafter, the same block as those used in the acquisition trial and a new block in a different shape were put in the cage for retention trial. The exploring time for each block was measured for 3 minutes, and a ratio of the exploring time for the newly used block to the sum of the exploring times for the respective blocks was calculated as a discrimination index. The thus obtained discrimination indexes were compared among a group of rats to which a medium alone was administered (medium group), a group of rats to which scopolamine alone was administered (scopolamine alone group) and a group of rats to which both the test compound and scopolamine were administered, so as to evaluate the action of the test compound on the novel object recognition function (cognitive function) of the rats.

Each discrimination index was shown as an average and a standard error. The statistical significance between the medium group and the scopolamine alone group was analyzed by the independent t-test. The statistical significance between the scopolamine alone group and each sample group was analyzed by one-way analysis of variance and then by Dunnett's multiple comparison test. The significance level was set to 5% on both sides. If the discrimination index was significantly lower in the scopolamine alone group than in the medium group, it was determined that the cognitive impairment was sufficiently induced, and hence, the test compound was evaluated in the corresponding group. The analysis was carried out by using Prism 5 for Windows for Japanese, ver. 5.03.

A minimum effective dose at which a statistically significant difference was found between a group suffering from the cognitive impairment induced by scopolamine and a group treated with each compound is shown in Table 10.

TABLE 10

| Example No. | Test dose (mg/kg, p.o.) | Minimum effective dose (mg/kg, p.o.) |
|---|---|---|
| 1 | 0.3, 1, 3 | 3 |
| 7 | 0.3, 1 | 0.3 |
| 11 | 0.3, 1 | >1* |
| 14 | 1, 3 | 1 |
| 24 | 0.3, 1 | 1 |
| 44 | 0.3, 1, 3, 10 | 1 |
| 87 | 1, 3 | 3 |

*No statistically significant difference was found at the test dose.

INDUSTRIAL APPLICABILITY

As described above, the tetrahydroimidazo[1,5-d][1,4]oxazepine derivative of the present invention or a pharmaceutically acceptable acid addition salt thereof is an antagonist against group II metabotropic glutamate receptor and showed an action to suppress downstream signaling of the mGluR2. Furthermore, the compound of the present invention showed an action to improve the novel object recognition function in rats suffering from cognitive impairment induced by scopolamine. Accordingly, the compound of the present invention is applicable as a therapeutic agent for neurological disorders related to glutamate dysfunction and diseases involving the mGluR2, that is, a subtype of the metabotropic receptors, such as Alzheimer's disease.

What is claimed is:

1. A compound represented by the following formula (I) or a pharmaceutically acceptable acid addition salt thereof:

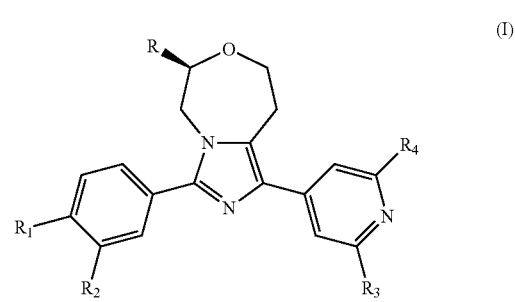

(I)

wherein R is a hydrogen atom or a $C_{1-6}$ alkyl group optionally substituted with 1 to 3 fluorine atoms, wherein when R is a hydrogen atom, $R_1$ is a chlorine atom, a bromine atom, a trifluoromethyl group, an ethyl group, a trifluoromethoxy group, a methoxy group substituted with a phenyl group, a methoxy group substituted with a $C_{3-8}$ cycloalkyl group, an ethoxy group optionally substituted with 1 to 3 fluorine atoms, or $C_{3-8}$ cycloalkyloxy group, $R_2$ is a fluorine atom, a chlorine atom, a methyl group optionally substituted with 2 to 3 fluorine atoms, a methoxy group optionally substituted with 1 to 3 fluorine atoms, or an ethoxy group optionally substituted with 1 to 3 fluorine atoms, $R_3$ is a hydrogen atom or a methyl group, and $R_4$ is a fluorine atom or a methyl group optionally substituted with 1 to 3 fluorine atoms, or when R is a $C_{1-6}$ alkyl group optionally substituted with 1 to 3 fluorine atoms, $R_1$ is a hydrogen atom, a halogen atom, a $C_{1-6}$ alkyl group optionally substituted with 1 to 3 fluorine atoms, a $C_{1-6}$ alkoxy group optionally substituted with 1 to 3 substituents selected from a fluorine atom and a $C_{3-8}$ cycloalkyl group, a $C_{3-8}$ cycloalkyloxy group, or a 4- to 6-membered heterocycloalkyloxy group, $R_2$ is a hydrogen atom, a cyano group, a halogen atom, a $C_{1-6}$ alkyl group optionally substituted with 1 to 3 substituents selected from a fluorine atom and a hydroxyl group, or a $C_{1-6}$ alkoxy group optionally substituted with 1 to 3 substituents selected from a fluorine atom, a $C_{3-8}$ cycloalkyl group and a 4- to 6-membered heterocycloalkyl group, $R_3$ is a hydrogen atom or a $C_{1-6}$ alkyl group, and $R_4$ is a $C_{1-6}$ alkyl group optionally substituted with 1 to 3 substituents selected from a fluorine atom and a hydroxyl group, or a $C_{1-6}$ alkoxy group.

2. The compound or a pharmaceutically acceptable acid addition salt thereof according to claim 1, wherein R is a $C_{1-6}$ alkyl group optionally substituted with 1 to 3 fluorine atoms, $R_1$ is a hydrogen atom, a halogen atom, a $C_{1-6}$ alkyl group optionally substituted with 1 to 3 fluorine atoms, a $C_{1-6}$ alkoxy group optionally substituted with 1 to 3 substituents selected from a fluorine atom and a $C_{3-8}$ cycloalkyl group, a $C_{3-8}$ cycloalkyloxy group, or a 4- to 6-membered heterocycloalkyloxy group, $R_2$ is a hydrogen atom, a cyano group, a halogen atom, a $C_{1-6}$ alkyl group optionally substituted with 1 to 3 substituents selected from a fluorine atom and a hydroxyl group, or a $C_{1-6}$ alkoxy group optionally substituted with 1 to 3 substituents selected from a fluorine atom, a $C_{3-8}$ cycloalkyl group and a 4- to 6-membered heterocycloalkyl group, $R_3$ is a hydrogen atom or a $C_{1-6}$ alkyl group, and $R_4$ is a $C_{1-6}$ alkyl group optionally substituted with 1 to 3 substituents selected from a fluorine atom and a hydroxyl group, or a $C_{1-6}$ alkoxy group.

3. The compound or a pharmaceutically acceptable acid addition salt thereof according to claim 2, wherein R is a methyl group, an ethyl group, a fluoromethyl group or a difluoromethyl group.

4. The compound or a pharmaceutically acceptable acid addition salt thereof according to claim 3, wherein $R_1$ is a hydrogen atom, a fluorine atom, a chlorine atom, a methyl group, a fluoromethyl group, a difluoromethyl group, a trifluoromethyl group, an ethyl group, a 1,1-difluoroethyl group, a methoxy group, a fluoromethoxy group, a difluoromethoxy group, a trifluoromethoxy group, an ethoxy group, a 2-fluoroethoxy group, a 2-propyloxy group, a cyclopropylmethoxy group, a cyclopropyloxy group or an (oxetan-3-yl)oxy group.

5. The compound or a pharmaceutically acceptable acid addition salt thereof according to claim 4, wherein $R_2$ is a hydrogen atom, a cyano group, a fluorine atom, a chlorine atom, a methyl group, a fluoromethyl group, a difluoromethyl group, a trifluoromethyl group, a hydroxymethyl group, an ethyl group, a methoxy group, a fluoromethoxy group, a difluoromethoxy group, a trifluoromethoxy group, an ethoxy group, a 2-fluoroethoxy group, a 2-propyloxy group, a cyclopropylmethoxy group, a cyclobutylmethoxy group or a (tetrahydro-2H-pyran-4-yl)methoxy group.

6. The compound or a pharmaceutically acceptable acid addition salt thereof according to claim 5, wherein $R_3$ is a hydrogen atom or a methyl group.

7. The compound or a pharmaceutically acceptable acid addition salt thereof according to claim 6, wherein $R_4$ is a methyl group, a fluoromethyl group, a difluoromethyl group, a hydroxymethyl group or a methoxy group.

8. The compound or a pharmaceutically acceptable acid addition salt thereof according to claim 2, wherein R is a methyl group optionally substituted with 1 to 2 fluorine atoms, $R_1$ is a hydrogen atom, a chlorine atom, a methyl group optionally substituted with 1 to 3 fluorine atoms, an ethyl group, a $C_{1-6}$ alkoxy group optionally substituted with 1 to 3 fluorine atoms, or a $C_{3-6}$ cycloalkyloxy group, $R_2$ is a cyano group, a chlorine atom, a $C_{1-6}$ alkyl group optionally substituted with 1 to 3 fluorine atoms, or a $C_{1-6}$ alkoxy group optionally substituted with 1 to 3 fluorine atoms, $R_3$ is a hydrogen atom or a methyl group, and $R_4$ is a methyl group optionally substituted with 1 to 3 fluorine atoms.

9. A compound selected from the group consisting of the following compounds or a pharmaceutically acceptable acid addition salt thereof:

(R)-3-(4-chloro-3-methoxyphenyl)-1-(2,6-dimethylpyridin-4-yl)-6-methyl-5,6,8,9-tetrahydroimidazo[1,5-d][1,4]oxazepine, (R)-1-(2,6-dimethylpyridin-4-yl)-3-(3-methoxy-4-(trifluoromethyl)phenyl)-6-methyl-5,6,8,9-tetrahydroimidazo[1,5-d][1,4]oxazepine, (R)-6-methyl-3-(3-methyl-4-(trifluoromethoxy)phenyl)-1-(2-methylpyridin-4-yl)-5,6,8,9-tetrahydroimidazo[1,5-d][1,4]oxazepine, (R)-3-(4-(difluoromethoxy)-3-methylphenyl)-1-(2,6-dimethylpyridin-4-yl)-6-methyl-5,6,8,9-tetrahydroimidazo[1,5-d][1,4]oxazepine, (R)-3-(4-(difluoromethoxy)-3-methylphenyl)-6-methyl-1-(2-methylpyridin-4-yl)-5,6,8,9-tetrahydroimidazo[1,5-d][1,4]oxazepine, (S)-1-(2,6-dimethylpyridin-4-yl)-6-(fluoromethyl)-3-(3-methoxy-4-(trifluoromethoxy)phenyl)-5,6,8,9-tetrahydroimidazo[1,5-d][1,4]oxazepine, (S)-6-(fluoromethyl)-3-(3-methoxy-4-(trifluoromethoxy)phenyl)-1-(2-methylpyridin-4-yl)-5,6,8,9-tetrahydroimidazo[1,5-d][1,4]oxazepine, (R)-3-(3-chloro-4-cyclopropoxyphenyl)-1-(2,6-dimethylpyridin-4-yl)-6-methyl-5,6,8,9-tetrahydroimidazo[1,5-d][1,4]oxazepine, (R)-3-(4-cyclopropoxy-3-methylphenyl)-1-(2,6-dimethylpyridin-4-yl)-6-methyl-5,6,8,9-tetrahydroimidazo[1,5-d][1,4]oxazepine, (R)-3-(3-chloro-4-(difluoromethoxy)phenyl)-6-methyl-1-(2-methylpyridin-4-yl)-5,6,8,9-tetrahydroimidazo[1,5-d][1,4]oxazepine, (S)-3-(4-cyclopropoxy-3-methylphenyl)-1-(2,6-dimethylpyridin-4-yl)-6-(fluoromethyl)-5,6,8,9-tetrahydroimidazo[1,5-d][1,4]oxazepine,
(R)-3-(3-methoxy-4-(trifluoromethoxy)phenyl)-6-methyl-1-(2-methylpyridin-4-yl)-5,6,8,9-tetrahydroimidazo[1,5-d][1,4]oxazepine,
(R)-1-(2,6-dimethylpyridin-4-yl)-3-(3-methoxy-4-(trifluoromethoxy)phenyl)-6-methyl-5,6,8,9-tetrahydroimidazo[1,5-d][1,4]oxazepine,
(S)-3-(4-(difluoromethoxy)-3-methylphenyl)-1-(2,6-dimethylpyridin-4-yl)-6-(fluoromethyl)-5,6,8,9-tetrahydroimidazo[1,5-d][1,4]oxazepine,
(S)-1-(2,6-dimethylpyridin-4-yl)-6-(fluoromethyl)-3-(3-methoxy-4-(trifluoromethyl)phenyl)-5,6,8,9-tetrahydroimidazo[1,5-d][1,4]oxazepine,
(R)-3-(3-chloro-4-(difluoromethoxy)phenyl)-1-(2,6-dimethylpyridin-4-yl)-6-methyl-5,6,8,9-tetrahydroimidazo[1,5-d][1,4]oxazepine,
(R)-3-(3-chloro-4-methoxyphenyl)-1-(2,6-dimethylpyridin-4-yl)-6-methyl-5,6,8,9-tetrahydroimidazo[1,5-d][1,4]oxazepine,
(R)-3-(3-chloro-4-ethoxyphenyl)-1-(2,6-dimethylpyridin-4-yl)-6-methyl-5,6,8,9-tetrahydroimidazo[1,5-d][1,4]oxazepine,
(R)-3-(3-chloro-4-isopropoxyphenyl)-1-(2,6-dimethylpyridin-4-yl)-6-methyl-5,6,8,9-tetrahydroimidazo[1,5-d][1,4]oxazepine,
(S)-3-(3-chloro-4-methoxyphenyl)-1-(2,6-dimethylpyridin-4-yl)-6-(fluoromethyl)-5,6,8,9-tetrahydroimidazo[1,5-d][1,4]oxazepine,
(S)-3-(3-chloro-4-ethoxyphenyl)-1-(2,6-dimethylpyridin-4-yl)-6-(fluoromethyl)-5,6,8,9-tetrahydroimidazo[1,5-d][1,4]oxazepine,
(S)-3-(3-chloro-4-isopropoxyphenyl)-1-(2,6-dimethylpyridin-4-yl)-6-(fluoromethyl)-5,6,8,9-tetrahydroimidazo[1,5-d][1,4]oxazepine,
(R)-3-(3-(fluoromethyl)-4-(trifluoromethoxy)phenyl)-6-methyl-1-(2-methylpyridin-4-yl)-5,6,8,9-tetrahydroimidazo[1,5-d][1,4]oxazepine,
(S)-3-(4-(difluoromethoxy)-3-methylphenyl)-6-(fluoromethyl)-1-(2-methylpyridin-4-yl)-5,6,8,9-tetrahydroimidazo[1,5-d][1,4]oxazepine, and
(S)-6-(fluoromethyl)-3-(3-methoxy-4-(trifluoromethyl)phenyl)-1-(2-methylpyridin-4-yl)-5,6,8,9-tetrahydroimidazo[1,5-d][1,4]oxazepine.

10. The compound or a pharmaceutically acceptable acid addition salt thereof according to claim 9, which is (R)-3-(4-chloro-3-methoxyphenyl)-1-(2,6-dimethylpyridin-4-yl)-6-methyl-5,6,8,9-tetrahydroimidazo[1,5-d][1,4]oxazepine represented by the following formula:

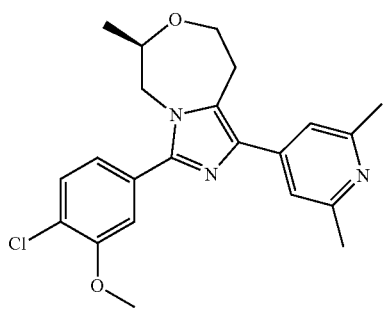 [SMILES: COc1cc(-c2nc(-c3cc(C)nc(C)c3)c3n2C[C@@H](C)OCC3)ccc1Cl]

or a pharmaceutically acceptable acid addition salt thereof.

11. The compound or a pharmaceutically acceptable acid addition salt thereof according to claim 9, which is (R)-1-(2,6-dimethylpyridin-4-yl)-3-(3-methoxy-4-(trifluoromethyl)phenyl)-6-methyl-5,6,8,9-tetrahydroimidazo[1,5-d][1,4]oxazepine represented by the following formula:

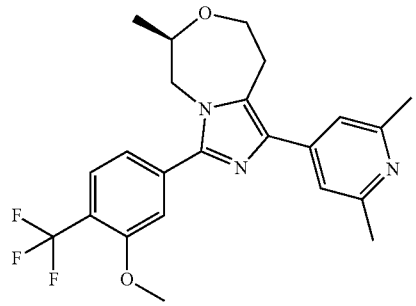 [SMILES: COc1cc(-c2nc(-c3cc(C)nc(C)c3)c3n2C[C@@H](C)OCC3)ccc1C(F)(F)F]

or a pharmaceutically acceptable acid addition salt thereof.

12. The compound or a pharmaceutically acceptable acid addition salt thereof according to claim 9, which is (R)-3-(3-methoxy-4-(trifluoromethoxy)phenyl)-6-methyl-1-(2-methylpyridin-4-yl)-5,6,8,9-tetrahydroimidazo[1,5-d][1,4]oxazepine represented by the following formula:

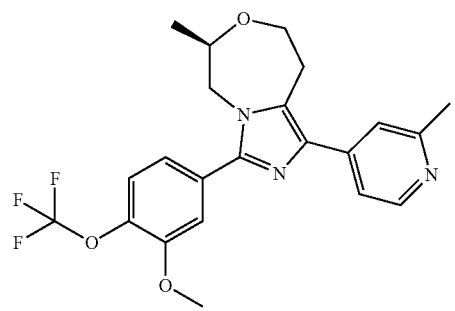 [SMILES: COc1cc(-c2nc(-c3ccnc(C)c3)c3n2C[C@@H](C)OCC3)ccc1OC(F)(F)F]

or a pharmaceutically acceptable acid addition salt thereof.

13. The compound or a pharmaceutically acceptable acid addition salt thereof according to claim 9, which is (R)-3-(4-(difluoromethoxy)-3-methylphenyl)-1-(2,6-dimethylpyridin-4-yl)-6-methyl-5,6,8,9-tetrahydroimidazo[1,5-d][1,4]oxazepine represented by the following formula:

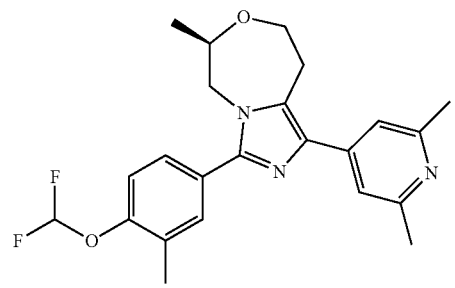 [SMILES: Cc1cc(-c2nc(-c3ccc(OC(F)F)c(C)c3)n3c2CCO[C@H](C)C3)cc(C)n1]

or a pharmaceutically acceptable acid addition salt thereof.

14. The compound or a pharmaceutically acceptable acid addition salt thereof according to claim 9, which is (R)-3-(3-chloro-4-(difluoromethoxy)phenyl)-1-(2,6-dimethylpyridin-4-yl)-6-methyl-5,6,8,9-tetrahydroimidazo[1,5-d][1,4]oxazepine represented by the following formula:

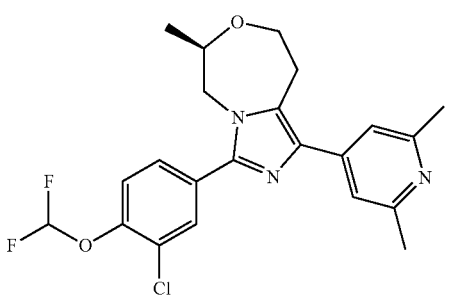 [SMILES: Cc1cc(-c2nc(-c3ccc(OC(F)F)c(Cl)c3)n3c2CCO[C@H](C)C3)cc(C)n1]

or a pharmaceutically acceptable acid addition salt thereof.

15. The compound or a pharmaceutically acceptable acid addition salt thereof according to claim 9, which is (S)-3-(4-(difluoromethoxy)-3-methylphenyl)-1-(2,6-dimethylpyridin-4-yl)-6-(fluoromethyl)-5,6,8,9-tetrahydroimidazo[1,5-d][1,4]oxazepine represented by the following formula:

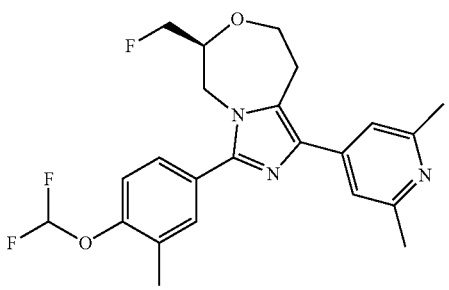 [SMILES: Cc1cc(-c2nc(-c3ccc(OC(F)F)c(C)c3)n3c2CCO[C@H](CF)C3)cc(C)n1]

or a pharmaceutically acceptable acid addition salt thereof.

16. The compound or a pharmaceutically acceptable acid addition salt thereof according to claim 9, which is (S)-1-(2,6-dimethylpyridin-4-yl)-6-(fluoromethyl)-3-(3-methoxy-4-(trifluoromethyl)phenyl)-5,6,8,9-tetrahydroimidazo[1,5-d][1,4]oxazepine represented by the following formula:

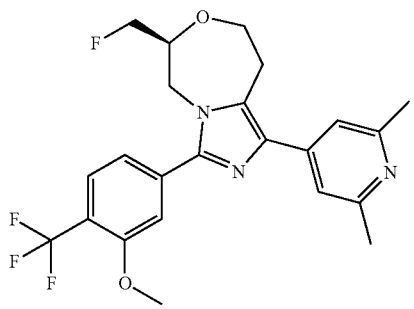 [SMILES: COc1cc(-c2nc(-c3cc(C)nc(C)c3)c3n2C[C@@H](CF)OCC3)ccc1C(F)(F)F]

or a pharmaceutically acceptable acid addition salt thereof.

17. A pharmaceutical composition comprising the compound or a pharmaceutically acceptable acid addition salt according to claim 1, and one or more pharmaceutically acceptable excipients.

18. A method for treating cognitive impairment, comprising administering the compound or a pharmaceutically acceptable acid addition salt according to claim 1 to a subject in need thereof.

19. A method for treating Alzheimer's disease, comprising administering the compound or a pharmaceutically acceptable acid addition salt according to claim 1 to a subject in need thereof.

20. A pharmaceutical composition comprising the compound or a pharmaceutically acceptable acid addition salt according to claim 9, and one or more pharmaceutically acceptable excipients.

21. A method for treating cognitive impairment, comprising administering the compound or a pharmaceutically acceptable acid addition salt according to claim 9 to a subject in need thereof.

22. A method for treating Alzheimer's disease, comprising administering the compound or a pharmaceutically acceptable acid addition salt according to claim 9 to a subject in need thereof.

23. The compound or a pharmaceutically acceptable acid addition salt thereof according to claim 9, which is (R)-3-(3-chloro-4-cyclopropoxyphenyl)-1-(2,6-dimethylpyridin-4-yl)-6-methyl-5,6,8,9-tetrahydroimidazo[1,5-d][1,4]oxazepine represented by the following formula:

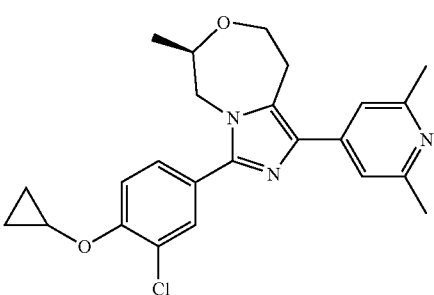 [SMILES: Cc1cc(-c2nc(-c3ccc(OC4CC4)c(Cl)c3)n3c2CCO[C@H](C)C3)cc(C)n1]

or a pharmaceutically acceptable acid addition salt thereof.

24. The compound or a pharmaceutically acceptable acid addition salt thereof according to claim 1, which is (S)-3-(3-chloro-4-(difluoromethoxy)phenyl)-1-(2,6-dimethylpyridin-4-yl)-6-(fluoromethyl)-5,6,8,9-tetrahydroimidazo[1,5-d][1,4]oxazepine represented by the following formula:

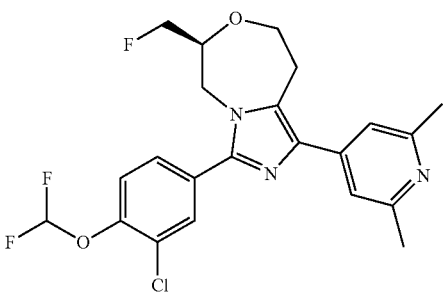 [SMILES: Cc1cc(-c2nc(-c3ccc(OC(F)F)c(Cl)c3)n3c2CCO[C@H](CF)C3)cc(C)n1]

or a pharmaceutically acceptable acid addition salt thereof.

25. The compound or a pharmaceutically acceptable acid addition salt thereof according to claim 1, which is (R)-3-(4-chloro-3-fluorophenyl)-1-(2,6-dimethylpyridin-4-yl)-6-methyl-5,6,8,9-tetrahydroimidazo[1,5-d][1,4]oxazepine represented by the following formula:

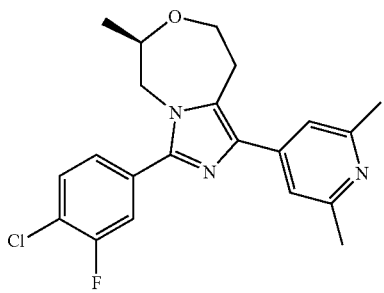 [SMILES: Cc1cc(-c2nc(-c3ccc(Cl)c(Cl)c3)n3c2CCO[C@H](C)C3)cc(C)n1]

or a pharmaceutically acceptable acid addition salt thereof.

26. The compound or a pharmaceutically acceptable acid addition salt thereof according to claim 1, which is (R)-3-(3,4-dichlorophenyl)-1-(2,6-dimethylpyridin-4-yl)-6-methyl-5,6,8,9-tetrahydroimidazo[1,5-d][1,4]oxazepine represented by the following formula:

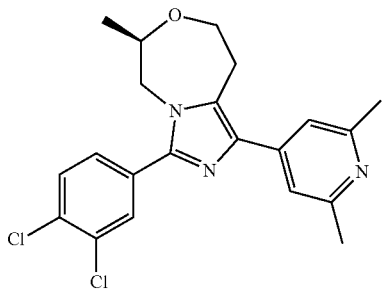

or a pharmaceutically acceptable acid addition salt thereof.

27. The compound or a pharmaceutically acceptable acid addition salt thereof according to claim 1, which is (R)-3-(4-chloro-3 -(difluoromethyl)phenyl)-1-(2,6-dimethylpyridin-4-yl)-6-methyl-5,6,8,9-tetrahydroimidazo[1,5-d][1,4]oxazepine represented by the following formula:

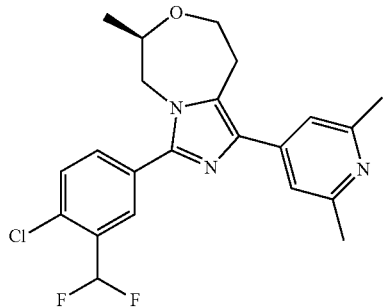 [SMILES: Cc1cc(-c2nc(-c3ccc(Cl)c(C(F)F)c3)n3c2CCO[C@H](C)C3)cc(C)n1]

or a pharmaceutically acceptable acid addition salt thereof.

28. The compound or a pharmaceutically acceptable acid addition salt thereof according to claim 1, which is (S)-3-(3,4-dichlorophenyl)-1-(2,6-dimethylpyridin-4-yl)-6-(fluoromethyl)-5,6,8,9-tetrahydroimidazo[1,5-d][1,4]oxazepine represented by the following formula:

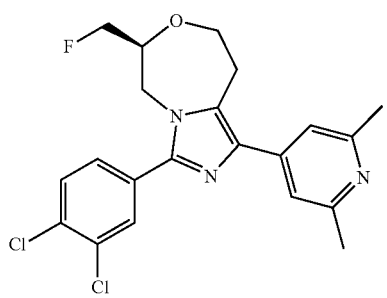 [SMILES: Cc1cc(-c2nc(-c3ccc(Cl)c(Cl)c3)n3c2CCO[C@H](CF)C3)cc(C)n1]

or a pharmaceutically acceptable acid addition salt thereof.

* * * * *